US009606121B2

(12) United States Patent
Yang et al.

(10) Patent No.: US 9,606,121 B2
(45) Date of Patent: Mar. 28, 2017

(54) NICOTINAMIDE ADENINE DINUCLEOTIDE GENE ENCODING FLUORESCENT PROBE, PREPARATION METHOD THEREFOR AND APPLICATION THEREOF

(71) Applicant: East China University of Science and Technology, Shanghai (CN)

(72) Inventors: Yi Yang, Shanghai (CN); Yuzheng Zhao, Shanghai (CN); Jing Jin, Shanghai (CN); Qingxun Hu, Shanghai (CN)

(73) Assignee: East China University of Science and Technology (CN)

( * ) Notice: Subject to any disclaimer, the term of this patent is extended or adjusted under 35 U.S.C. 154(b) by 0 days.

(21) Appl. No.: 14/347,575

(22) PCT Filed: Sep. 26, 2012

(86) PCT No.: PCT/CN2012/081977
§ 371 (c)(1),
(2) Date: Mar. 26, 2014

(87) PCT Pub. No.: WO2013/044792
PCT Pub. Date: Apr. 4, 2013

(65) Prior Publication Data
US 2014/0329718 A1    Nov. 6, 2014

(30) Foreign Application Priority Data
Sep. 26, 2011   (CN) .......................... 2011 1 0288807

(51) Int. Cl.
| | | |
|---|---|---|
| *G01N 33/573* | (2006.01) | |
| *C07K 14/195* | (2006.01) | |
| *C07K 14/32* | (2006.01) | |
| *G01N 33/50* | (2006.01) | |
| *G01N 33/58* | (2006.01) | |

(52) U.S. Cl.
CPC ....... *G01N 33/5735* (2013.01); *C07K 14/195* (2013.01); *C07K 14/32* (2013.01); *G01N 33/5011* (2013.01); *G01N 33/582* (2013.01); *C07K 2319/00* (2013.01); *C07K 2319/60* (2013.01); *G01N 2500/02* (2013.01); *G01N 2800/7028* (2013.01)

(58) Field of Classification Search
None
See application file for complete search history.

(56) References Cited

U.S. PATENT DOCUMENTS 6,469,154 B1   10/2002   Tsien et al.

FOREIGN PATENT DOCUMENTS

CN         1821751 A       8/2006

OTHER PUBLICATIONS

DTU Team Denamark '09 "The REDOXILATOR & The User Fusion Standard"; 2009, Retrieved from < http://2009.igem.org/wiki/index.php?title=Team:DTU_Denmark/testtesttest242&printable=yes > Retrieved on Sep. 1, 2015. From the 2009 International Genetically Engineered Machine competition.*
McLaughlin et al., "Structural Basis for NADH/NAD+ Redox Sensing by a Rex Family Repressor", Molecular Cell 38, 563-575, May 28, 2010.*
Belousov et al., "Genetically encoded fluorescent indicator for intracellular hydrogen peroxide", Nat. Methods, 2006, 4:281-286.*
Jin, Jing, "A novel fluorescent sensor for nicotinamide adenine dinucleotide", Fulltext Database of Selected Chinese M.Sc. Thesis, Fundamental Sciences, May 15, 2012, dissertation in Chinese, with Abstract in English on pp. 3-4 (138 pages).
International Preliminary Report on Patentability in corresponding PCT/CN2012/081977 issued Apr. 1, 2014 (English Translation) (10 pages).
Rich, P.R. et al., "The molecular machinery of Keilin's Respiratory Chain", Biochem Soc Trans. 2003, V.31 (6), pp. 1095-1105 (11 pages).
Belenky, P. et al., "NAD+ metabolism in health and disease" Trends in Biochemical Sciences. Dec. 11, 2006, V.32 (1), pp. 12-19 (8 pages).
Sauve, A. A. et al., "NAD+ and Vitamin B3: From Metabolism to Therapies"; J Pharmacol Exp Ther. 2008, V.324(3), pp. 883-893 (11 pages).
Lin, S. J. et al., "Nicotinamide adenine dinucleotide, a metabolic regulator of transcription, longevity and disease" Current Opinion in Cell Biology. 2003, V.15(2), pp. 241-246 (6 pages).
Zhang, Q. H. et al., "Regulation of Corepressor Function by Nuclear NADH"; Science. 2002, V.295 (5561), pp. 1895-1897 (4 pages).
Heim, R. et al., "Wavelength mutations and posttranslational autoxidation of green fluorescent protein", Proc Natl Acad Sci U S A. 1994, V.91 (26), pp. 12501-12504 (4 pages).
Nagai, T. et al., "Circularly permuted green fluorescent proteins engineered to sense CA2+", Proc Natl Acad Sci U.S.A. 2001, V.98 (6), pp. 3197-3202 (6 pages).

(Continued)

Primary Examiner — Suzanne M Noakes
(74) Attorney, Agent, or Firm — Hovey Williams LLP

(57) ABSTRACT

The invention relates to a genetically encoded fluorescent sensor for nicotinamide adenine dinucleotide, as well as methods of preparation and uses thereof. In one aspect, this invention relates to a sensor for detecting nicotinamide adenine dinucleotide, particularly, a recombinant fluorescent fusion protein sensor for detecting nicotinamide adenine dinucleotide. In one specific aspect, this invention relates to a recombinant fluorescent fusion protein sensor for detecting reduced nicotinamide adenine dinucleotide (NADH); in another specific aspect, this invention relates to a recombinant fluorescent fusion protein sensor for detecting oxidized nicotinamide adenine dinucleotide ($NAD^+$); in yet another aspect, the invention relates to a recombinant fluorescent fusion protein sensor for detecting the ratio of reduced to oxidized nicotinamide adenine dinucleotide. This invention also relates to the method of preparing the sensors, and uses of the sensors in detecting NADH, $NAD^+$, $NADH/NAD^+$ ratio, screening drugs and measuring NADH metabolism.

4 Claims, 9 Drawing Sheets

(56) References Cited

OTHER PUBLICATIONS

Brekasis, D. et al., "A novel sensor of NADH/NAD+ redox poise in Streptomyces coelicolor A3(2)", EMBO J., 2003, V.22 (18), pp. 4856-4865 (10 pages).
Wang, E. et al., "Structure and functional properties of the Bacillus subtilis transcriptional repressor Rex" Mol Microbiol 2008, V.69 (2), pp. 466-478 (13 pages).
Mei et al., "Quantitative detection of NADH by in vitro bacterial luciferase bioluminescent, Acta Microbiologica Sinica", 2009, 49(9): 1223-1228 (A) (English translation of Abstract) (6 pages).
Liu et al., "Determinaton of Human Red Blood Cells' NADH by Enzyme Cycling Fluorimetry", Chinese Journal of Spectroscopy Laboratory, 2010, 27(2): 602-605 (English translation of Abstract) (5 pages).
Office Action dispatched Nov. 12, 2012 in corresponding Chinese Application No. 201110288807.6 (7 pages) and Brief English Translation (3 pages).
Office Action dispatched Apr. 23, 2013 in corresponding Chinese Application No. 201110288807.6 (6 pages) and Brief English Translation (1 page).
Decision on Rejection dispatched Sep. 2, 2013 in corresponding Chinese Application No. 201110288807.6 (4 pages) and Brief English Translation (1 page1).
Office Action dispatched Jul. 14, 2014 in corresponding Chinese Application No. 201110288807.6 (3 pages) and Brief English Translation (1 page).
Yu, Q., et al. "Two-Photon Autofluorescence Dynamics Imaging Reveals Sensitivity of Intracellular NADH Concentration and Conformation to Cell Physiology at the Single-Cell Level", J. Photochem. Photobiol. B., Apr. 2, 2009 (30 pages).
Zhao, Y., et al. "Genetically Encloded Fluorescent Sensors for Intracellular NADH Detection", Cell Metabolism, Oct. 5, 2011, pp. 555-566 (12 pages).
Office Action dated Aug. 22, 2016 in related Chinese application patent Serial No. 201410499267.X filed Sep. 26, 2011 (English translation).
Wang, et al., "Structure and functional properties of the Bacillus subtilis transcriptional repressor Rex," Molecular Microbiology, vol. 69, issue 2, Jun. 2008, pp. 466-478.
Office Action dated Aug. 22, 2016 in related Chinese application patent Serial No. 201110288807.6 filed Sep. 26, 2011 (English translation attached).
Office Action dated Oct. 31, 2016 in related Chinese application Serial No. 201410499305.1, 7 pages (English translation attached).
McLaughlin, et al., "Structural Basis for NADH/NAD+ Redox Sensing by a Rex Family Repressor," Molecular Cell, vol. 38, pp. 563-575, May 2010.

\* cited by examiner

A

B

NICOTINAMIDE ADENINE DINUCLEOTIDE GENE ENCODING FLUORESCENT PROBE, PREPARATION METHOD THEREFOR AND APPLICATION THEREOF

CROSS-REFERENCE TO RELATED APPLICATIONS

The present application is the U.S. National Stage of PCT/CN2012/081977, filed Sep. 26, 2012, which claims the priority benefit of Chinese Application No. 201110288807.6, filed Sep. 26, 2011, incorporated by reference in their entireties herein.

FIELD OF INVENTION

The invention relates to a sensor for detecting nicotinamide adenine dinucleotide, especially, relates to a recombinant fluorescent fusion protein sensor for detecting nicotinamide adenine dinucleotide. In one specific aspect, this invention relates to a recombinant fluorescent fusion protein sensor for detecting reduced nicotinamide adenine dinucleotide (NADH); in another specific aspect, this invention relates to a recombinant fluorescent fusion protein sensor for detecting oxidized nicotinamide adenine dinucleotide (NAD$^+$); in another aspect, the invention further relates to a recombinant fluorescent fusion protein sensor for detecting the ratio of reduced to oxidized nicotinamide adenine dinucleotide. This invention also relates to a process for preparing the sensors, and uses of the sensors in detecting NADH, NAD$^+$ and NADH/NAD$^+$ ratio.

BACKGROUND OF INVENTION

As coenzymes, NAD$^+$ and NADH are important components of the respiratory chain, and involved in the electron transfer process in the respiratory chain (Rich, P. R. et al., Biochem Soc Trans. 2003, V.31 (6), pp. 1095-1105). In redox reactions of the respiratory chain, NAD$^+$ acts as a proton carrier and transforms from its initial oxidation state to reduction state upon reception of an electron from other molecules; NADH, the product of this transformation, can act as a reducing agent providing electron for other molecules (Belenky. P. et al., Trends in Biochemical Sciences. 2007, V.32 (1), pp. 12-19). Recent studies have shown that, NAD(H) is not only involved in energy metabolism, substance synthesis, and antioxidation, but also relates to, inter alia, in vivo calcium homeostasis, gene expression, immunization, cell ageing and death, wherein NAD(H) plays vital roles. Accordingly, NAD(H) itself and numerous enzymes relating to NAD(H) metabolism have become targets for drug design (Sauve, A. A. et al., J Pharmacol Exp Ther. 2008, V.324(3), pp. 883-893).

However, in most living cells, the total amount of NAD (H) is about $10^{-6}$ M~$10^{-3}$ M, while the NAD$^+$/NADH ratio also varies depending on intracellular states (Lin, S. J. et al., Current Opinion in Cell Biology. 2003, V.15(2), pp. 241-246), therefore, it is difficult to determine NAD(H). Earlier detecting methods mainly utilize the characteristic UV absorption of NADH at 340 nm, which leads to the UV spectrophotometry assay. This method has two main flaws: 1, the effective sensitivity is about $10^{-7}$ M, limited by the instrument precision; 2, effective differentiation between NADH and NADPH is not possible in complicated systems. A series of enzymatic assay are later developed based on the characteristic of NAD$^+$ as a coenzyme which accepts an electron during electron transport and transforms to NADH. Other methods, such as HPLC analysis, the electrochemical assay, capillary electrophoresis, fluorescence imaging, etc., are also commonly reported in literatures. However, most of the methods either lack sensitivity towards target molecules in individual cells or lack capacity for localization to subcellular organelles. It is noteworthy that, a major common defect in these available methods is the need of sample processing including lysis, separation, and purification. As NADH itself is prone to oxidization, and errors are readily introduced, the cumbersome operations would lead to experimental results deviated from the bona fide values. In addition, these existing methods can not be applied to living animals or cells and can not detect in real time, which limits the applications in clinical diagnosis and prodrugs research. At present, NADH detection in living animals or cells can only be achieved by using NADH autofluorescence (Zhang, Q. H. et al., Science. 2002, V.295 (5561), pp. 1895-1897), but this traditional method has serious flaws as follows: first, it is known that the regulations of NAD$^+$/NADH and NADP$^+$/NADPH in cells are relatively independent, normally, NAD$^+$/NADH ratio is about 700:1, while NADP$^+$/NADPH ratio is about 1:200; second, the vast different in redox potential between NADH and NADPH indicates the distinct roles in energy metabolism and anabolism played by them; third, with NADH and NADPH autofluorescence being completely indistinguishable, the result obtained through autofluorescence imaging measurement is the sum of NADH and NADPH, and the data essentially indicates the concentration of protein-bound NADPH instead because the content of NADPH is low and mostly presented in protein binding form (Zhang, Q. H. et al., Science. 2002, V.295 (5561), pp. 1895-1897); fourth, since NADH is excited with wavelength in the ultraviolet range (340 nm) and its autofluorescence is weak, sophisticated and expensive equipments such as CritiView for clinical monitoring are required; furthermore, UV light has a rather weak capability of penetrating through tissues and can cause cell damages, so these optical properties severely restrict the application of autofluorescence monitoring.

Therefore, there is an urgent need in the art to develop a specific NADH detecting technique, especially, a specific technique which is suitable for detecting NADH in physiological level and subcellular level.

Relative to traditional detection techniques involving small molecule dye and rapid developing detection techniques using quantom dot, fluorescent protein detection technique has a unique overwhelming advantage in the imaging of most living cells; fluorescent protein can be genetically introduced into cells, tissues, and even whole organs, therefore it can be used as a whole-cell marker or gene activation indicator.

Green fluorescent protein is originally isolated from *Aequorea victoria*, and the wild-type AvGFP is consisted of 238 amino acids and has a molecular weight of about 26 kD. Recent study confirms that, in native GFP protein, three amino acids from 65 to 67, Ser-Tyr-Gly, are able to spontaneously form a fluorescent chromogenic moiety, wherein p-hydroxy-benzylidene-imidazolinone is the main luminous feature. The wild-type AvGFP has rather complex spectral characteristics with its main fluorescent excitation peak at 395 nm, and a secondary peak at 475 nm, whose amplitude intensity is approximately ⅓ of the main peak. Under standard solution condition, 395 nm excitation can produce 508 nm emission, and 475 nm excitation produces maximal emission at 503 nm (Heim, R. et al., Proc Natl Acad Sci USA. 1994, V.91 (26), pp. 12501-12504).

Upon intensive studies on GFP protein mutations, a variety of prominent GFP derivatives have been developed using molecular biotechnology. Through various single-point mutations or combination thereof made to the wild-type GFP, mutants such as enhanced-type GFP (S65T, F64L), YFP (T203Y) and CFP (Y66W) can be obtained. By rearranging GFP protein sequence to shift the original amino acids 145-238 to the N terminal and the amino acids 1-144 to the C terminal of the new protein, and binding the two fragments through a flexible short peptide chain, a space sensitive circular permutation fluorescent protein is formed thereby, and a T203Y point mutation thereupon results in a circular permutation yellow fluorescent protein cpYFP (Nagai, T. et al., Proc Natl Acad Sci U.S.A. 2001, V.98 (6), pp. 3197-3202).

Fluorescence-based analytical techniques have further developed along with the progression in fluorescent protein studies. One example is fluorescent resonance energy transfer (FRET) technique that is routinely adopted nowadays, the key mechanism of which is, when two fluorophores are in sufficiently close proximity, a donor entity absorbs photon of suitable frequency and is excited to a higher energy state returns to the ground state upon transferring energy to nearby acceptor entity via dipole-dipole interaction (that is, the occurrence of resonance energy transfer). FRET is a non-radiation energy transfer through intermolecular dipole-dipole interaction transferring energy from donor in excited state to result in acceptor in excited state, so that the fluorescence intensity of the donor decreases while the acceptor may emit characteristic fluorescence (sensitized fluorescence) which is stronger than its basic fluorescence, or it may emit no fluorescence (fluorescence quenching). Further studies of the green fluorescent protein show that cyan fluorescent protein (CFP) and yellow fluorescent protein (YFP) derived from green fluorescent protein mutants constitute a prominent donor/acceptor pair. Emission spectrum of CFP substantially overlaps absorption spectrum of YFP, when CFP and YFP are in sufficiently close proximity and upon the excitation with the absorption wavelength of CFP, the chromophore of CFP will effectively resonance transfer energy to the chromophore of YFP, so CFP emitted fluorescence will be weakened or disappeared, and the main emission is YFP fluorescence. The efficiency of energy transfer between the two chromophores is inversely proportional to sixth power of the spatial distance between them, and is very sensitive to changes in spatial position. Therefore, existing studies report the use of genetically engineering recombinant methods for expression of a novel fusion protein having both termini of the protein of interest fused with CFP and YFP, respectively, such that spatial change caused by binding of the protein with its specific target molecule will be visualized by the fluorescent change.

So the fluorescent protein sequence used herein may come from *Aequorea victoria* fluorescent protein and its derivatives, including, but not limited to sequences of the following mutants: yellow fluorescent protein (YFP), green fluorescent protein (GFP), cyan fluorescent protein (CFP), and the likes, the sequence of yellow fluorescent protein YFP is preferable, and the sequence of circular permutation yellow fluorescent protein cpYFP is particularly preferable.

The technique described herein involves another protein, YdiH protein (also known as Rex protein), a bacterial transcriptional repressor protein already known in the art, which has a molecular weight of 23 kDa and can regulate fermentation and anaerobic respiration. Generally, YdiH proteins are derived from *Thermus aquaticus* (SEQ ID NO: 1 NCBI GenBank: AF061257.1), *Streptomyces coelicolor* (SEQ ID NO: 2 NCBI GenBank: AL9391.1) or *Bacillus subtilis* (SEQ ID NO: 3 NCBI GenBank: AL009126.3). YdiH protein is initially identified in 2003 from *Streptomyces coelicolor* by Brekasis and Paget et al., which is a redox-sensitive regulatory protein that widely presents in Gram-positive bacteria. The study on YdiH (Rex) protein of *Streptomyces coelicolor* indicates that it is a typical NAD(H) binding protein with Rossmann domain. The key Rossmann domain is a super-secondary protein structure mainly exists in nucleotide binding proteins, and it is a typical cofactor NAD(H) binding domain, represented by various cofactor NAD(H) binding proteins. The structure is essentially comprised of 6 β-pleated sheets linked through two pairs of α-helixes in the form of β-α-β-α-β. Since each Rossmann domain can bind one nucleotide molecule only, there are two Rossmann segments presented pairwise in dinucleotide binding proteins such as these for NAD. Current studies have shown that the *Streptomyces coelicolor* YdiH (Rex) protein can directly probe changes in cytoplasmic NADH/NAD$^+$ ratio, while under aerobic conditions, the YdiH (Rex) protein can inhibit the transcription of its target genes (cydABC, nuoA-D and rexhemACD) when intracellular NADH/NAD$^+$ ratio is at low level, but dissociates from its operon region at elevated NADH/NAD$^+$ ratio, and during this dynamic process, the steric configuration of YdiH (Rex) protein transforms upon environmental change (Brekasis, D. et al., EMBO J., 2003, V.22 (18), pp. 4856-4865). Therefore, Rex protein is a good candidate for intracellular NADH sensor. Meanwhile, Wang et al. recently crystallized the *Bacillus subtilis* YdiH (Rex) protein and investigated its mechanism and function. Their results show that YdiH(Rex) protein from *Bacillus subtilis* is a homodimer protein having two functional domains, wherein the N-terminal domain (residues 1-85) is a DNA-binding domain, while the C-terminal domain (residues 86-215) is a typical Rossmann fold that can bind NADH (Wang, E. et al., Mol Microbiol 2008, V.69 (2), pp. 466-4'78).

Although YdiH (Rex) protein per se is sensitive to the redox state of the environment, the changes thereof are not intuitively exhibited and can not be captured externally. While by means of the fluorescent protein, we can ideally obtain a novel genetically encoded fluorescent sensor by fusioned expression of YdiH (Rex) and fluorescent protein, YdiH (Rex) is utilized for probing environmental redox state change and relaying the change to the fluorescent protein, which will visualize the change in environmental redox state in real-time and intuitively by the presence/absence or the intensity of the fluorescence generated thereby.

In summary, we believe that the use of recombinant fluorescent fusing protein which contains YdiH protein is able to meet the urgent need to detect NADH in physiological level and subcellular level.

The citation or discussion of any reference in this specification should not be construed as an admission that such reference is available as "Prior Art" to the present invention.

SUMMARY OF INVENTION

On one aspect, this invention provides a genetically encoded fluorescent sensor for NADH, comprising a polypeptide which is sensitive to environmental NADH, and a segment that exhibits the environmental NADH by change in its spectral characteristics. In one embodiment, the segment that exhibits the environmental NADH by change in the spectral characteristic is a fluorescent protein sequence or a derivative thereof. In another embodiment, the NADH-sensitive polypeptide is a polypeptide or its functional fragment or NADH binding domains having following characteristics:

(1) comprising Rossman domain with NADH binding feature; and/or (2) derived from an NADH sensitive protein of transcription regulatory factor Rex family.

In a preferred embodiment, the polypeptide sensitive to NADH described herein may have following characteristics:

(1) containing polypeptide derived from bacterial transcription factor Rex protein gene ydiH, wherein the polypeptide may be encoded by a sequence selected from SEQ ID NO: 1, 2 or 3;

(2) a homologous or non-homologous sequence that is 95% identical to the sequence describe in (1) in at least 85 amino acid residues;

(3) any homologous or non-homologous sequence that is 90% identical to the sequence describe in (1) in at least 85 amino acid residues;

(4) any homologous or non-homologous sequence that is 70% identical to the sequence describe in (1) in at least 85 amino acid residues;

(5) any homologous or non-homologous sequence that is 50% identical to the sequence describe in (1) in at least 85 amino acid residues;

(6) any homologous or non-homologous sequence that is 40% identical to the sequence describe in (1) in at least 85 amino acid residues; or (7) any homologous or non-homologous sequence that is 35% identical to the sequence describe in (1) in at least 85 amino acid residues.

In another embodiment, the fluorescent sensor of this invention may contain Rossman domain B characterized by NADH binding property and fluorescent protein sequence A, A1 and/or A2, which may be combined in a form of:

(1) B-A-B;

(2) B-A-B-B;

(3) A1-B-A2, wherein A1 and A2 can be identical or different; A1 can be an amino acid sequence derived from *Aequorea Victoria* fluorescent protein or a derivative thereof, and A2 can be an amino acid sequence derived from another *Aequorea victoria* fluorescent protein or a derivative thereof;

(4) a first portion of B-A-a second portion of B; wherein A is inserted in the flexible region of B such that B is segmented into the first portion and the second portion, while the first portion of B and the second portion of B constitute a complete B domain; or (5) a first portion of B-A-a second portion of B-B; wherein A is inserted in the flexible region of B such that B is segmented into the first portion and the second portion of B, while the first portion of B and the second portion of B constitute a complete B domain.

In yet another embodiment, the fluorescent sensor in this invention may also have the following structure:

$A_1$-$B_1$-$Linker_1$-FM-$Linker_2$-$B_2$, wherein $A_1$ is a first domain of YdiH protein, preferably containing amino acids 1-84 of *Bacillus subtilis* YdiH protein sequence (SEQ ID NO: 14), or amino acids 1-79 of *Thermus aquaticus* YdiH protein sequence (SEQ ID NO: 15), or variant thereof; $B_1$ is a second domain of YdiH protein, preferably containing amino acids 85-194 of *Bacillus subtilis* YdiH protein sequence (SEQ ID NO: 16), or amino acids 80-189 of *Thermus aquaticus* YdiH protein sequence (SEQ ID NO: 17), or variant thereof; $B_2$ is a third domain of YdiH protein, preferably containing amino acids 120-215 of *Bacillus subtilis* YdiH protein sequence (SEQ ID NO: 18), or amino acids 114-211 of *Thermus aquaticus* YdiH protein sequence (SEQ ID NO: 19), or variant thereof;

FM is a fluorophore, and it can be YFP, GFP, CFP and variants derived from these proteins, wherein YFP is preferable, and cpYFP is more preferable;

$Linker_1$ may be present or absent; if present, $Linker_1$ can be any amino acid sequence, preferably not longer than 4 amino acids, for example, it may contain amino acids T, S, A, G, or may be any combination of any 1 to 4 amino acids of them, e.g., amino acid sequence SAG or TS or the likes, but not limited thereto;

$Linker_2$ may be present or absent; if present, $Linker_2$ can be any amino acid sequence, preferably not longer than 3 amino acids, for example, it may contain amino acids G, T, G, or may be any combination of any 1 to 3 amino acids of them, e.g., amino acid sequence GTG, but not limited thereto.

In one embodiment, this invention also provides a fluorescent sensor containing a fluorophore, and a YdiH protein or any one of protein fragments, derivatives or analogs of YdiH. In another embodiment, the invention also provides a fluorescent sensor containing a fluorophore and a YdiH protein variant. The invention also provides a fluorescent sensor containing a fluorophore and a soluble fragment of YdiH protein.

In one embodiment, this invention provides a fluorescent sensor comprising the amino acid sequence of SEQ ID NO: 4, 5, 6, 7 or 8. In a preferred embodiment, this invention provides a fluorescent sensor comprising a homologous and non-homologous sequence having 99%, 95%, 90%, 80%, 70% or 50% identity with amino acid sequence SEQ ID NO: 4, 5, 6, 7 or 8 in at least 85 amino acid residues. In a preferred embodiment, this invention provides a fluorescent sensor comprising a homologous or non-homologous sequence that is substantially similar or identical to amino acid sequence SEQ ID NO: 4, 5, 6, 7 or 8 in at least 85 amino acid residues. In a preferred embodiment, this invention provides a fluorescent sensor comprising a mutant or derivative of amino acid sequence SEQ ID NO: 4, 5, 6, 7 or 8.

In another embodiment, the invention also provides a genetically encoded fluorescent sensor for $NAD^+$, comprising a polypeptide which is sensitive to environmental $NAD^+$, and a segment that exhibits the environmental $NAD^+$ by change in its spectral characteristics. In a specific embodiment, the fluorescent sensor for $NAD^+$ comprises SEQ ID NO: 129.

In another embodiment, the invention also provides a genetically encoded fluorescent sensor for $NADH/NAD^+$ ratio, comprising a polypeptide sensitive to environmental $NADH/NAD^+$ ratio, and a segment that exhibits the environmental $NADH/NAD^+$ ratio by change in its spectral characteristics. In a specific embodiment, the fluorescent sensor for $NADH/NAD^+$ ratio comprises SEQ ID NO: 148.

In another aspect, the invention provides a fusion protein comprising the fluorescent sensor of this invention. In one embodiment, the fusion protein comprises the fluorescent sensor of this invention and various specific signal for subcellular localization, wherein the signal allows localization of a target protein into a specified subcellular organelle.

In another aspect, the invention provides a nucleic acid sequence comprising the nucleotide sequence that encodes the fluorescent sensor or the fusion protein of the invention. In a specific embodiment, the invention provides a nucleic acid sequence comprising the nucleotide sequence encoding a fluorescent protein and a nucleotide sequence encoding a NADH sensitive protein.

In a preferred embodiment, the nucleotide sequence encoding the NADH sensitive protein is a nucleotide sequence encoding a polypeptide or its functional fragments or NADH binding domain having following characteristics:

(1) comprising a Rossman domain with NADH binding feature; and/or (2) derived from an NADH sensitive protein of transcription factor Rex family In another preferred embodiment, the nucleic acid sequence of the invention may comprise a coding sequence b for a Rossman domain having NADH binding feature and coding sequences a, a1 and/or a2 for fluorescent protein(s), in an arrangement of the following:

(1) b-a-b;
(2) b-a-b-b;
(3) a1-b-a2, wherein a1 and a2 can be the identical or not; a1 can be a coding sequence of a fluorescent protein from *Aequorea victoria* or a derivative thereof, a2 can be a coding sequence of another fluorescent protein from *Aequorea victoria* or a derivative thereof;
(4) a first portion of b-a-a second portion of b; wherein a is inserted in the flexible region of b such that b is segmented into the first portion of b and the second portion of b, while the first portion of b and the second portion of b constitute a complete b domain;
(5) a first portion of b-a-a second portion of b-b; wherein a is inserted in the flexible region of b such that b is divided into the first portion of b and the second portion of b, while the first portion of b and the second portion of b constitute a complete b domain.

In another preferred embodiment, the invention provides a nucleic acid sequence comprising nucleotide sequence SEQ ID NO: 9, 10, 11, 12, or 13. In a preferred embodiment, the invention provides a nucleic acid sequence comprising any homologous and non-homologous sequences having 99%, 95%, 90%, 80%, 70% or 50% identity with the nucleotide sequence SEQ ID NO: 9, 10, 11, 12 or 13 in at least 85 bases in length. In another preferred embodiment, the invention provides a nucleic acid sequence comprising nucleotide sequence that is substantially similar or identical to the nucleotide sequence of SEQ ID NO: 9, 10, 11, 12 or 13 in at least 85 bases; in a preferred embodiment, the invention provides a nucleic acid sequence comprising a variant or derivative of the nucleotide sequence of SEQ ID NO: 9, 10, 11, 12 or 13.

The present invention also relates to a complementary sequence and a variant of the aforementioned nucleic acid sequence, which may include a nucleic acid sequence or a complement of the sequences encoding fragments, analogues, derivatives, soluble fragments and variants of the fluorescent sensor or fusion protein of the invention.

In yet another aspect, the invention also provides an expression vector comprising the nucleic acid sequence of the invention operably linked to a expression control sequence. The expression control sequence can be an origin of replication, a promoter, an enhancer, an operon, a terminator, or a ribosome binding sites, etc.

In yet another aspect, the present invention also provides a host cell containing the expression vector of the invention.

In yet another aspect, the present invention also provides a method for preparing the fluorescent sensor or the fusion protein of this invention, comprising the following steps:

a. transferring the expression vector of the invention into a host cell, b. culturing the host cell under conditions suitable for the expression in the host cell, and c. separating the fluorescent sensor or fusion protein from host cells.

The invention also provides uses of the fluorescent sensor or the fusion protein of the invention in detecting NADH. In one embodiment, the invention provides uses of the fluorescent sensor or the fusion protein of the invention in detecting NADH in vitro or in vivo. In one embodiment, the invention provides uses of the fluorescent sensor or the fusion protein of the invention in detecting NADH at subcellular level. In one embodiment, the invention provides uses of the fluorescent sensor or the fusion protein in detecting NADH in situ. In another embodiment, the invention provides uses of the fluorescent sensor or the fusion protein of the invention in drug screening, wherein the drugs may be used to adjust NADH level in a subject. In another embodiment, the invention provides uses of the fluorescent sensor or the fusion protein of the invention in diagnosis of diseases which are associated with the level of NADH.

The invention also provides a kit for NADH detection, which comprises the fluorescent sensor or the fusion protein of the invention. The detection can be conducted in vitro, in vivo, in situ, or at subcellular level. The invention also provides a kit for screening drug which can be used to adjust the NADH level in a subject, wherein the kit comprises an effective amount of fluorescent sensor or fusion protein of the invention. The invention also provides a kit for diagnosing diseases associated with the level of NADH, wherein the kit comprises an effective amount of the fusion protein of the invention. For said uses, one skilled in the art can readily determine the effective amount based on the activity of the fusion protein of the invention.

The protein and nucleic acid sequences of the invention are preferably provided in isolated form, and more preferably purified to homogeneity.

BRIEF DESCRIPTION OF THE FIGURES

The invention is further described with reference to the following figures and examples.

FIG. 8-1 shows the real-time measurements of the NADH change within cells treated with exogenous NADH using a sensor for NADH/NAD$^+$ ratio.

FIG. 8-2 shows the real-time measurements of the NADH change within cells treated with glucose, pyruvic acid, lactic acid using a sensor for NADH/NAD$^+$ ratio.

FIG. 8-3 shows the real-time measurements of the NADH level change within mitochondrias using a sensor for NADH/NAD$^+$ ratio.

FIG. 9-1 shows the detection of cytosolic NAD⁺ change using an NAD sensor.

FIG. 9-2 shows the change of the response of NAD⁺ sensor to NAD⁺ in vitro.

FIG. 9-3 shows the response of NAD⁺ sensor to pyridine nucleotide analogs under simulated physiological conditions in vitro.

FIG. 10-1 shows the characteristics of the sensor for NADH/NAD⁺ ratio in response to the combination of NADH and NAD⁺.

FIG. 10-2 shows the measurement results using the sensor for NADH/NAD⁺ ratio at various NADH/NAD⁺ ratios.

FIG. 10-3 shows the detection of the effect of pyridine nucleotide analogs to the sensor for NADH/NAD⁺ ratio under simulative physiological conditions in vitro.

DESCRIPTION OF THE EMBODIMENTS

I. Definitions

Figure 1:
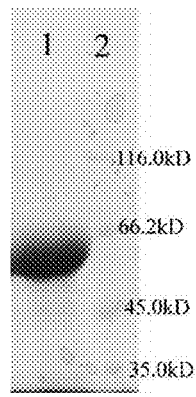
FIG. 1 shows SDS-PAGE characterizing F-rex1 separated and purified from *E. coli*.

When a numerical value or range is indicated, the term "about" used herein means the value or range is within 20%, 10% and 5% of the indicated value or range.

Terms such as "containing", "comprising" and its equivalents used herein shall be read as encompasses the meaning of "having" and "consisting of . . . ", for example, a composition "containing" X may consist exclusively of X or may include other substances, like X+Y.

In the invention, the term "YdiH protein" refers to protein YdiH (also known as Rex protein), which is a bacterial transcriptional inhibiting protein already known in the art. YdiH has a molecular weight of 23 kDa and regulates the fermentation and anaerobic respiration. It is a type of redox-sensitive regulatory protein which widely exists in Gram-positive bacteria, and is a typical NAD(H)-binding protein that containing Rossmann domain. The key Rossmann domain therein is a super secondary protein structure mainly presents in nucleotide binding proteins, a typical region active in binding cofactor NAD(H), and is represented by various cofactor NAD binding proteins. The structure is essentially comprised of 6 β-sheets linked through two pairs of α-helixes in the form of β-α-β-α-β. Since each Rossmann domain could bind one nucleotide molecule only, there are two Rossmann segments presented pairwise in dinucleotide-binding protein domains such as these for NAD. YdiH (Rex) protein can directly probe changes in cytoplasmic NADH/NAD⁺ ratio, but under aerobic conditions, YdiH (Rex) protein can inhibit transcription of its target genes (cydABC, nuoA-D and rexhemACD) when intracellular NADH/NAD⁺ ratio is at low level, while dissociates from its operon region at elevated NADH/NAD⁺ ratio, and the steric configuration of YdiH (Rex) protein transforms upon the environment changes during this dynamic process. The "YdiH protein" involved in the invention may contain amino acid sequence encoded by nucleotide sequence of SEQ ID NO: 1 or SEQ ID NO: 2 or SEQ ID NO: 3. The "flexible region" referred to in the invention means specific structure, such as Loop configuration, presents in advanced protein structure. These structures exhibit better mobility and flexibility than other advanced structures of proteins, and are capable of causing dynamic change of domains, while proteins also exhibit significant tendency of undergo spatial conformational change in such regions. The flexible region referred to in the invention mainly means the V113-G119 region and D188-G192 region of T-rex (the Rex protein from *Thermus aquaticus*).

The term "fluorescent sensor" used herein refers to a polypeptide sensitive to environmental NADH and fused with a fluorescent protein, specifically, the polypeptide sensitive to environmental NADH can be a YdiH protein. The sensor utilizes the conformational changes of the fluorescent protein caused by binding of the NADH-specific binding structure Rossman domain in YdiH with NADH, and thus lead to the generation or reduction of fluorescence, or changes in the generated fluorescence; plotting standard curve based on the fluorescence of fluorescent protein measured under different NADH concentrations would, in turn, allow the detection and analy the presence and/or level of NADH.

The term "fusion protein" is synonymous with the terms "fluorescent fusion protein" and "recombinant fluorescent fusion protein", refers a polypeptide or protein comprising an amino acid sequence of a first polypeptide or protein, or fragment, analog or derivative thereof, and an amino acid sequence of a heterologous polypeptide or protein (that is, a second polypeptide or protein, or fragment, analog or derivative thereof, which differs from the first polypeptide or protein, or fragment, analog or derivative thereof). In one embodiment, the fusion protein comprises a fluorescent protein fused with the heterologous protein, polypeptide or peptide. According to this embodiment, the heterologous protein, polypeptide or peptide may or may not be a fluorescent protein of different type. In one embodiment, the fusion protein maintains or enhances its activity relative to the activity of the original polypeptide or protein prior to the fusion with heterologous protein, polypeptide or peptide. In a specific embodiment, the fusion protein comprises a fluorescent sensor fused with a heterologous protein, polypeptide or peptide, wherein the heterologous protein, polypeptide or peptide can be a specific subcellular localization signal.

The term "fluorophore" used here is synonymous with "fluorescent protein", representing a protein exhibits autofluorescence or emits fluorescence under illumination. Fluorescent proteins are often used as detection means, for instance, green fluorescent protein GFP and BFP, CFP, YFP, etc, derived therefrom GFP are routinely used in the biotechnology arts.

The term "GFP" used herein refers to green fluorescent protein, which is originally isolated from *Aequorea victoria*. The wild type AvGFP is consisted of 238 amino acids and has a molecular weight of about 26 kD, and amino acid sequence SEQ ID No: 20. Recent study confirms that Ser-Tyr-Gly, the three amino acids 65-67 in native GFP protein, are able to spontaneously form a fluorescent chromophore: p-hydroxybenzylideneimidazolinone, which is the primary emitting site. The wild-type AvGFP exhibits very complex spectral characteristics with its main fluorescence excitation peak at 395 nm and a secondary peak at 475 nm, whose amplitude intensity is about ⅓ of the main peak. Under standard solution condition, 395 nm excitation can produce 508 nm emission, and 475 nm excitation produces maximum emission at 503 nm wavelength.

The term "YFP" used herein refers to yellow fluorescent protein, which is derived from green fluorescent protein GFP, the amino acid sequence of which is up to 90% or more homologous to GFP, and the key change of YFP from GFP is that the substitution of amino acid 203 from threonine to tyrosine (T203Y), Compared to original AvGFP, the main excitation peak of YFP is red-shifted to 514 nm wavelength and emission wavelength shifted to 527 nm. Site-directed mutation of amino acid no. 65 of the YFP (S65T) thereupon will obtain the fluorescence enhanced yellow fluorescent protein EYFP, and typical EYFP amino acid sequence is SEQ ID NO: 21. And sequence rearrangement of the EYFP protein by having the original amino acids 145-238 as the N terminus, and the original amino acid 1-144 as the C terminus of the new protein, with the two fragments linked through a short flexible peptide chain VDGGSGGTG (residues 312-320 of SEQ ID NO:5) forms cpYFP (circular permutation yellow fluorescent protein) that is sensitive to spacial changes, and typical cpYFP amino acid sequence is SEQ ID NO: 22.

In this invention, the YdiH protein that fused with fluorophore can be a full length native YdiH protein, or a fragment thereof, isolated from *Bacillus subtilis* or *Thermus aquaticus* or *Streptomyces coelicolor*; amino acids 1-215 of native YdiH protein from *Bacillus subtilis* or amino acids 1-211 of YdiH protein from *Thermus aquaticus*, or amino acids 1-259 of YdiH protein from *Streptomyces coelicolor* are preferable; while amino acids 1-215 of YdiH protein from *Bacillus subtilis* or tamino acids 1-211 of YdiH protein from *Thermus aquaticus* are more preferable.

"Linker" means an amino acid or nucleic acid sequence linking the two segments within a polypeptide, protein or nucleic acid in the invention. When linking for a polypeptide or protein of the invention, the length of the linker is no longer than 6 amino acids, preferably, no longer than four amino acids, more preferably, 3 amino acids. When linking for a nucleic acids of the invention, the length of the linker is no longer than 18 nucleotides, preferably no longer than 12 nucleotides, more preferably 9 nucleotides.

When referring to a polypeptide or protein, the term "variant" used herein includes variants of the polypeptide or protein with the same function but differ in sequence. These variants include, but not limited to, sequences obtained by deleting, inserting and/or substituting one or more (typically 1-30, preferably 1-20, more preferably 1-10, and most preferably 1-5) amino acid(s) in the sequence of the polypeptide or protein, and by adding one or more (usually less than 20, preferably less than 10, and more preferably within 5) amino acid(s) to its C-terminus and/or N-terminus. For example, in the art, substitution with amino acids of comparable or similar properties usually does not change the function of the polypeptide or protein. Amino acids with similar properties usually refer to a family of amino acids having similar side chains and have been clearly defined in the art. These families include amino acids with basic side chains (e.g., lysine, arginine, histidine), amino acids with acidic side chains (e.g., aspartate, glutamate), amino acids with uncharged polar side chain (e.g., glycine, asparagine, glutamine, serine, threonine, tyrosine, cysteine), amino acids with non-polar side chains (e.g., alanine, valine, leucine, isoleucine, proline, phenylalanine, methionine, tryptophan), amino acids with β-branched side chains (e.g., threonine, valine, isoleucine), and amino acids with aromatic side chains (e.g., tyrosine, phenylalanine, tryptophan, histidine). As another example, adding one or more amino acids to the C-terminus and/or N-terminus usually does not change the function of the polypeptide or protein either. As known to a person skilled in the art, genetic cloning process often requires design of suitable endonuclease sites, which will eventually introduce one or more irrelevant residues to the terminus of the polypeptide or protein to be expressed, but this does not affect the activity of the target polypeptide or protein. For another example, in order to construct a fusion protein, to promote the expression of a recombinant protein, to obtain a recombinant protein that can secrete itself into the extracellular environment of the host cells, or to facilitate the purification of a recombinant protein, it is often desirable to have the N-terminus, C-terminus, or other suitable regions of the protein added with some amino acids, for example, including, but not limited to, suitable connecting peptides, signal peptides, leader peptides, the terminal extensions, the glutathione S-transferase (GST), maltose E binding protein, Protein A, tags such as 6His or Flag, or factor Xa or thrombin or enterokinase protease cleavage sites. Variants of the polypeptide or protein may include: homologous sequences, conservative variants, allelic variants, natural mutants, induced mutants, polypeptide or protein encoded by a DNA which could hybridize with the DNA for said polypeptide or protein under high or low stringent conditions, as well as the polypeptide or protein derived from antiserum against said polypeptide or protein. These variants may also comprise polypeptide or protein whose sequence is at least about 70%, at least about 75%, at least about 80%, at least about 85%, at least about 90%, at least about 95%, at least about 98%, at least about 99%, or 100% sequence identity with said polypeptide or protein.

In the context of two or more polypeptides or nucleic acid sequences, the term "identical" or "percent identity" means, when compared and aligned for maximum correspondence over a comparing window or designated region using available methods such as comparing algorithms known in the art or by manual alignment and visual inspection, two or more sequences or sub-sequences are the same or have a specified percentage of amino acid residues or nucleotides that are the same (e.g., 60%, 65%, 70%, 75%, 80%, 85%, 90%, 91%, 92%, 93%, 94%, 95%, 96%, 97%, 98%, 99% or 100% are the same). For example, preferred algorithms that are suitable for determining the percent sequence identity or similarity are the BLAST and BLAST 2.0 algorithms, which can be found in Altschul (1977) Nucleic Acids Res. 25:3389 and Altschul (1990) J. Mol. Biol. 215:403, respectively.

The term "soluble fragment" used herein generally refers to fragments having at least about 10 consecutive amino acids of the full-length protein sequence, usually at least about 30 consecutive amino acids, preferably at least about 50 consecutive amino acids, more preferably at least about 80 consecutive amino acids, and optimally at least about 100 consecutive amino acids.

The terms "functional fragment", "derivative" and "analog" mean proteins retain substantially the same biological function or activity of the native YdiH protein in the invention. Functional fragments, derivatives or analogs of YdiH in the invention may be (i) proteins with one or more conservative or non-conservative amino acid substitution (preferably conservative), where the substituted amino acid residues may or may not be one encoded by the genetic code, or (ii) proteins containing substitutions of one or more amino acid residues having a substituent group, or (iii) proteins formed having the mature protein fused with another compound (such as compounds that extend half-life of the protein, for example, polyethylene glycol), or (iv) proteins formed by having said protein fused with additional amino acid sequence (such as leader sequence or secretory sequence, or sequence used for purification of the protein or proprotein sequence, or fusion protein formed with fragment of antigen IgG). In accordance with the teachings provided herein, these functional fragments, derivatives and analogs are well known to a person skilled in the art.

The differences between analogs and the native YdiH protein may be the difference in amino acid sequences, and may also be the difference in the forms of modifications that will not affect the sequence, or both. These proteins include natural or induced genetic variants. Induced variants can be obtained by a variety of techniques, such as generating random mutagenesis by irradiation or exposure to mutagens, and can also be obtained by directed mutagenesis or other known molecular biology techniques.

Analogs mentioned herein also include analogs with residue(s) different from natural L-amino acid (e.g., D-amino acids), as well as analogs with a non-naturally occurred or synthetic amino acid (such as β, γ-amino acids). It should be understood that the YdiH protein of the invention is not limited to the representative proteins, fragments, derivatives and analogs exemplified above. Forms of modification (usually without change of the primary structure): chemical derivatization of the protein in vivo or in vitro, such as acetylation or carboxylation. The modifications also include glycosylation, such as proteins generated by conducting glycosylation during protein synthesis and processing or further processing steps. This modification can be achieved by exposure of the protein to an enzyme that glycosylates (such as mammalian glycosylase or deglycosylase). The modifications also include sequences with phosphorylated amino acid residues (e.g. phosphotyrosine, phosphoserine, phosphothreonine), and further include protein modified to improve its anti-proteolytic properties, or to optimize the solubility.

The term "nucleic acid" used herein be in the form of DNA or RNA. Forms of DNA includes cDNA, genomic DNA or artificially synthesized DNA. The DNA may be single-stranded or double-stranded. The DNA may be coding strand or non-coding strand. The coding sequence that encodes the mature protein can be identical with the sequence shown in the coding region of SEQ ID NO: 9, 10, 11, 12 or 13, or its degenerate variants. "Degenerate variant" used in the invention refers to a nucleic acid sequence that encodes the fluorescent fusion protein of the invention, but is different from the coding region sequence shown in SEQ ID NO: 9, 10, 11, 12 or 13.

In the context of nucleic acid, the term "variants" used herein may be naturally occurring allelic variants or non-naturally occurring variants. These nucleotide variants include degenerate variants, substituted variants, deletion variants, and insertion variants. As known in the art, allelic variant is an alternate form of a nucleic acid, it may be caused by one or more nucleotide substitution, deletion or insertion, but does not substantially alter the function of the encoded protein. The nucleic acid of the invention may include nucleotide sequences with at least about 70%, at least about 75%, at least about 80%, at least about 85%, at least about 90%, at least about 95%, at least about 98%, at least about 99%, or 100% identity with said nucleic acid sequence.

As used herein, the term "hybridizing under stringent conditions" is used to describe conditions for hybridization and washing under which nucleotide sequences at least 60% homologous to each other typically remain hybridized to each other. Preferably, stringent conditions are the conditions that under which sequences at least 65%, more preferably at least 70%, and even more preferably at least 80% or higher homologous to each other typically remain hybridized to each other. The stringent condition is known to a person of ordinary skills in the art. In one preferred, non-limiting example, the stringent conditions are: (1) hybridization and elution under relatively low ionic strength and relatively high temperature, such as 0.2×SSC, 1% SDS, 0° C.; or (2) hybridization at the addition of denaturing agent, 50% (v/v) methyl amide, 0.1% fetal calf serum/0.1% Ficoll, 42° C., etc; or (3) hybridization occurred only between two sequences at least 90%, more preferably no less than 95% homologous to each other. Furthermore, the protein encoded by the nucleic acid sequences capable of hybridization has the same biological function and activity as the mature protein shown in SEQ ID NO: 4, 5, 6, 7 or 8.

The present invention also relates to a nucleic acid fragment hybridizes with the sequence described above. As used here, the length of "nucleic acid fragment" contains at least 15 nucleotides, preferably at least 30 nucleotides, more preferably at least 50 nucleotides, and most preferably at least 100 or more nucleotides. The nucleic acid fragment can be used for nucleic acid amplification techniques (e.g. PCR).

Generally, the full-length sequences or the fragments of the fluorescent sensor or fusion protein in the invention can be obtained by PCR amplification method, recombination method or artificially synthetic method. For PCR amplification, primers can be designed according to the relevant nucleotide sequence disclosed by the invention, and in particular, the sequence of the open reading frame, and commercially available cDNA library, or cDNA library prepared by person skilled in the art using routine methods could be used as template, thereby, obtaining the corresponding sequences by amplification. For longer sequences, two or more individual PCR amplifications are typically desired, which are followed by ligating the separately amplified fragment together in a proper order.

Once the corresponding sequence is obtained, a large quantities of the sequences can be achieved by recombination. Typically, the sequences is cloned into a vector, which is subsequently transferred into cell, and then the corresponding polypeptide or protein can be obtained from the proliferated host cells by routine isolation and purification methods.

Furthermore, artificial synthesis can also be used to synthesize the corresponding sequence, especially when the fragment is short. Typically, multiple smaller fragments are synthesized first, and later linked together to produce a fragment with much longer sequence.

So far, the DNA sequence that encoding the protein herein (or its fragment, derivative, analog or variant) can be obtained solely by chemical synthesis. Said DNA sequence can be introduced subsequently into various available DNA molecules (e.g. vectors) and cells that are already known in the art. Through mutant PCR or chemical synthesis methods, a mutation can be introduced into the sequence of the protein of the invention.

As used herein, the terms "expression vector" and "recombinant vector" may be used interchangeably, and refer to a prokaryotic or eukaryotic expression vector known in the art, such as a bacterial plasmid, bacteriophage, yeast plasmid, plant cell virus, mammalian cell virus such as adenovirus, retroviral or other vectors, which can replicate and stabilize in the host organism. One important feature of these recombinant vectors is that they typically comprise expression control sequences. As used herein, the term "expression control sequence" refers to an element that regulates transcription, translation and expression of a target gene, and may be operably linked with the target gene, said element may be an origin of replication, a promoter, a marker gene or translation control elements, including enhancers, operons, terminators, ribosome binding sites, etc., and the selection of expression control sequence depends on the host cell used. In present invention, suitable recombinant vector includes, but not limited to, bacterial plasmid. In the context of recombinant expression vector, "operably linked" means the target nucleotide sequence and the regulatory sequence are linked in a way that allows expression of the nucleotide sequence. Suitable methods for constructing expression vector which comprises the coding sequence of the fusion protein and appropriate transcriptional/translational control signals are well known to the person skilled in the art. These methods include in vitro recombinant DNA techniques, DNA synthesis techniques, in vivo recombination techniques, etc. Said DNA sequence may be effectively linked to a proper promoter in the expression vector to direct mRNA synthesis. Representative examples of promoters include *E. coli* lac or trp promoter; λ phage PL promoter; eukaryotic promoters include CMV immediate early promoter, HSV thymidine kinase promoter, early and late SV40 promoter, retrovirus LTR, and some other promoters known to control expression of genes in prokaryotic or eukaryotic cells or their viruses. Expression vector further comprises a ribosome binding site for the initiation of translation, and a transcription terminator.

A person of ordinary skills in the art will understand that design of the recombinant expression vector can vary depending on the host cell to be transformed, desired expression level of the protein and other factors. In addition, the recombinant expression vector preferably contains one or more selective marker genes to provide phenotypic traits, such as dihydrofolate reductase, neomycin resistance in eukaryotic cells, or tetracycline or ampicillin resistance in *E. coli*, for the selection of transformed host cells.

In one embodiment, the coding sequence of the fluorescent sensor or fusion protein in present invention is double digested with BamHI and HindIII and ligated into the pRSET$_b$ vector digested with BamHI and HindIII to obtain an *E. coli* recombinant expression vector. The expression vector of the present invention can be transferred into a host cell to produce a protein or peptide comprising the fusion protein. This transfer process may be carried out using routine transformation or transfection techniques well known to a person skilled in the art.

As used herein, the term "host cell", also known as recipient cells, refers to cells capable of receiving and accommodating recombinant DNA molecule(s), which is the place for recombinant gene amplification. An ideal recipient cell should satisfy two criteria: easily available and proliferating. The "host cell" in present invention may include prokaryotic cells and eukaryotic cells, specifically, include bacterial cells, yeast cells, insect cells and mammalian cells.

The expression vector in present invention can be used to express the fluorescent sensor or fusion proteins in prokaryotic or eukaryotic cells. Accordingly, the present invention relates to a host cell, preferably *E. coli*, having the expression vector of the invention incorporated therein. The host cell can be any prokaryotic or eukaryotic cell, representative examples include: bacterial cells including *E. coli, Streptomyces, Salmonella typhimurium*, fungal cells such as yeast, plant cells, insect cells as *Drosophila* S2 or Sf9, animal cells as CHO, COS, 293 cells or Bowes melanoma cells, etc., host cells described above are inclusive but not limiting. Said host cells are preferably those advantageous for expression of the gene product or the fermentative production, such cells are well known and routinely used in the art, for example, various *E. coli* cells and yeast cells. In one embodiment of the present invention, *E. coli* BL21 is selected to construct a host cell that expresses the fusion protein of present invention. The choice of appropriate carrier, promoter, enhancer and host cells is evident to a person of ordinary skills in the art.

As used herein, the term "transformation" and "transfection", "incorporating" and "transduction" refer to various techniques, already known in the art, to introduce exogenous nucleic acid (e.g., linear DNA or RNA (e.g., linearized vector or individual gene construct without vector)) or nucleic acid in the form of carrier (e.g., plasmids, cosmids, phage, phagemid, plasmid, transposon or other DNA) into a host cell, including calcium phosphate or calcium chloride coprecipitation, DEAE-mannan-mediated transfection, lipid transfection, natural competent cells, chemical-mediated transfer, or electroporation. When the host is a prokaryote such as *E. coli*, competent cells capable of absorbing DNA can be harvested after exponential growth phase, and treated with $CaCl_2$ method, the steps used therein are well known in the art. Another method uses $MgCl_2$. If necessary, the transformation can also be conducted by electroporation. When the host cell is a eukaryotic cell, DNA transfection methods can be used are as follows: calcium phosphate co-precipitation method, conventional mechanical methods such as microinjection, electroporation, liposome packaging, etc.

Transformed cell obtained thereby may be cultured using routine methods which are suitable for the expression in the host cells in order to express the fusion protein of the present invention. Depending on the host cells, the medium used for culture can be various conventional media. The culture is performed under conditions suitable for the growth of the host cells. When the host cells have grown to an appropriate cell density, the selected promoter is induced by an appropriate method (such as temperature shift or chemical induction), and the cells are further incubated for another period of time.

In the above method, the recombinant protein can be expressed within the cell, or on the cell membrane or secreted into extracellular environment. If desired, the recombinant protein can be isolated or purified using various separation methods based on its physical, chemical and other characteristics. These methods are well known to a person skilled in the art. Examples of such methods include, but not limited to: conventional refolding treatment, treatment with a protein precipitating agent (salting out), centrifugation, osmotic lysis of bacteria, ultra treatment, ultra centrifugation, molecular sieve chromatography (gel filtration), adsorption chromatography, ion exchange chromatography, high performance liquid chromatography (HPLC) and various other liquid chromatography techniques, and combinations thereof.

In one embodiment, the fluorescence sensor or a fusion protein of present invention is produced by fermentation of *E. coli* comprising the coding sequence of the fusion protein, followed by ammonium sulfate sedimentation, ion exchange chromatography, and purification using gel filtration chromatography to obtain the fluorescent sensor or a fusion protein of the invention in a pure form.

Uses of the fluorescent sensor or fusion protein of the present invention include, but not limited to, detection of NADH, detection of NADH in physiological state, detection of NADH in subcellular level, in situ detection of NADH, screening of drugs, diagnostics of diseases associated with NADH level.

Concentrations, contents, percentages, and other numerical values may be presented herein in a range format. It is to be understood that such range format is used merely for convenience and brevity, and it should be interpreted flexibly to include not only the numerical values explicitly recited as the upper and lower limits of the range, but also to include all the individual numerical values or sub-ranges encompassed within said range as if each numerical values or sub range is explicitly recited.

EXAMPLES

The invention is further illustrated by the specific examples described below. It should be understood that these examples are merely illustrative, and do not limit the scope of the present invention.

Unless otherwise indicated, experimental protocols in the following examples generally adopt customary conditions, such as those described in Sambrook et al., *Molecular Cloning: A Laboratory Guide* "(New York, USA: Cold Spring Harbor Laboratory Press, 1989); or the conditions according to the manufacturer's recommendations. Unless otherwise indicated herein, all percentages and parts are by weight.

I. Experimental Materials and Reagents

Reagents: Unless otherwise indicated, all reagents were purchased from Shanghai Sinopharm Chemical Reagent Co. Ltd. (Shanghai, China).

Tag enzymes, buffer, dNTP for PCR amplification; protease, buffer, T4 DNA ligase, T4 DNA ligase buffer, T4 polynucleotide kinase (PNK), T4 PNK buffer used in molecular biological experiments were all from Fermentas (Vilnius, Lithuania).

Example 1

Construction and Expression of pRSET$_b$-ydiH-YFP-ydiH (D2)

1. Amplification of Nucleic Acid Sequence of cpYFP

The coding sequence of yellow fluorescent protein (cpYFP) was amplified using pMD19-cpYFP (Nagai, T. et al., Proc Natl Acad Sci U.S.A. 2001, V.98(6), pp. 3197-3202) (obtained from Protein Chemistry Laboratory, East China University of Science and Technology (Shanghai, China)) as the template, and cpYFP F and cpYFP R as primers, where the primer sequences (primers were synthesized by Sangon Biotech (Shanghai) Co. Ltd., Shanghai, China) are as follows:

```
P1: SpeI
                                        (SEQ ID NO: 23)
GAAATCGAAACTAGTTACAACAGCCACAACGTCTATATC

P2: KpnI
                                        (SEQ ID NO: 24)
CCAAGCTTCGGGGTACCGTTGTACTCCAGCTTGTG
```

PCR Reaction System

| PCR system | |
|---|---|
| Template | 1 μl |
| Forward primer | 0.5 μl |
| Reverse primer | 0.5 μl |
| 10× Taq buffer | 5 μl |
| Taq enzyme | 1 μl |
| dNTP (10 mM) | 1 μl |
| ddH$_2$O | 41 μl |
| total | 50 μl |

PCR Reaction Conditions:

| | | | |
|---|---|---|---|
| | | 95° C. | 5 min |
| 30 cycles | { | 95° C. | 40 s |
| | | 55° C. | 40 s |
| | | 72° C. | 1 min |
| | | 72° C. | 10 min |

PCR amplification product was electrophoresed on a 1% agarose gel for 30 minutes to obtain cpYFP fragments of about 750 bp. cpYFP fragments were recovered and purified from the gel using Sangon DNA fragment recovery kit (Sangon Biotech (Shanghai) Co. Ltd., Shanghai, China) according to the manufacturer's instructions.

2. Extraction of Desired Gene Sequence from *Bacillus subtilis* 168 Cells a. Sample Processing (i) *Bacillus subtilis* 168 was obtained from China General Microbiological Culture Collection Center (Cat. No. 1.1656).

(ii) According to the conditions as described, 100 μl cultured *Bacillus subtilis* 168 was taken to measure the optical density of the broth at 600 nm, where $OD_{600}$=0.1 refers to a density of $1 \times 10^7$~$5 \times 10^7$ cells/ml, the actual number of cells was calculated thereby. Then 1 ml TRIzol reagent (Invitrogen, California, USA) would be added per $1 \times 10^7$ cells for processing.

(iii) A proper amount of broth was taken, centrifuged at 4° C., 5000 rpm for 10 minutes, and the supernatant was discarded.

(iv) Bacterial pellet was washed with 100 μl 1×TE buffer (10 mM Tris-HCl, 1 mM EDTA pH8.0, reagents were from Amresco corporation (Amresco, Ohio, USA)), and centrifuged at 5000 rpm for 10 minutes, and the supernatant was discarded.

(v) The bacterial pellet was resuspend in 100 μl 1×TE buffer (comprising 2 mg/ml lysozyme (from Majorbio Biotech Co. Ltd., Shanghai, China)) and incubated at 37° C. for 30 minutes.

b. Phase Separation (i) One milliliter of TRIzol reagent (Invitrogen) was added thereto and mixed by pipetting, and the mixture was allowed to stand at room temperature for 5 minutes.

(ii) Two hundred microliter of chloroform was added thereto and vortexed for 15 seconds, and the mixture was allowed to stand at room temperature for 2 to 3 minutes prior to centrifugation at 4° C., 12,000 g for 15 minutes.

(iii) The solution was segmented into layers upon centrifugation, comprising about 40% of upper aqueous phase containing RNA, and about 60% of lower organic phase containing DNA and protein. The upper aqueous phase was carefully pipetted out and removed.

c. Removal of Impurities

Fifty microliter of 10% SDS and 250 μl saturated aqueous sodium chloride solution were added into the organic phase, and vortexed to homogenous prior to centrifugation at 4° C., 12,000 g for 5 minutes, and the upper aqueous phase was discarded.

d. Ethanol Precipitation of DNA

Seven hundred and fifty microliter of precooled 95% ethanol was added into the organic phase and inverted to mix, and stand at −80° C. for 15 minutes to allow the DNA to precipitate.

e. DNA Washing (i) The upper organic phase was carefully discarded.

(ii) The precipitate was washed several times with 1 ml of 0.1 M sodium citrate/10% ethanol solution, centrifugation at 4° C., 12,000 g for 5 minutes was conducted after each wash.

(iii) A final wash was conducted with 75% ethanol and followed by centrifugation at 4° C., 12000 g for 5 minutes.

(iv) The ethanol was evaporated through air dry at room temperature.

f. Dissolving DNA

DNA pellet was dissolved into 50 μl of 8 mM NaOH solution, and stored at 4° C. or −20° C.

The gene for YdiH protein of *Bacillus subtilis* 168 (ydiH), in full length or fragment thereof (for amino acids 85-215), was amplified using genomic material extracted above as the template, and primers ydiH-1F and ydiH 1R, ydiH(D2) 2F and ydiH 2R, respectively, wherein amplification with ydiH-1F and ydiH 1R produced ydiH1, the full length YdiH protein gene (ydiH) having BaHI restriction site at 5' end and SpeI restriction site at 3' end; amplification with ydiH (D2) 2F and ydiH 2R produced ydiH(D2) 2, a fragment of YdiH Protein gene (ydiH) (for amino acids 85-215) having KpnI restriction site at 5' end and HindIII restriction site at 3' end. Sequences of the primers ydiH 1F, ydiH 1R, ydiH (D2) 2F and ydiH 2R are as follows:

```
ydiH 1F: BamHI
                                   (SEQ ID NO: 25)
CCGGATCCATGAATAAGGATCAATCAAAAATTC ydiH 1R: SpeI
                                   (SEQ ID NO: 26)
GCTGTTGTAACTAGTTTCGATTTCCTCTAAAACT ydiH(D2) 2F: KpnI
                                   (SEQ ID NO: 27)
CGGGGTACCATGACAGACGTCATCTTGATTGGTG ydiH 2R: HindIII
                                   (SEQ ID NO: 28)
CCCAAGCTTCTATTCGATTTCCTCTAAAAC
```

PCR Reaction System:

| PCR system | |
|---|---|
| Template | 1 μl |
| Forward primer | 0.5 μl |
| Reverse primer | 0.5 μl |
| 10× Taq buffer | 5 μl |
| Taq enzyme | 1 μl |
| dNTP (10 mM) | 1 μl |
| ddH$_2$O | 41 μl |
| total | 50 μl |

PCR Reaction Conditions:

| | | | |
|---|---|---|---|
| | | 95° C. | 5 min |
| 30 cycles | { | 95° C. | 40 s |
| | | 55° C. | 40 s |
| | | 72° C. | 1 min |
| | | 72° C. | 10 min |

PCR amplification product was purified on 1% agarose gel by electrophoresis for 30 minutes to obtain the ydiH 1 of about 700 bp and ydiH (D2) 2 fragment of about 450 bp. The amplified ydiH 1 and ydiH (D2) 2 fragments were recovered and purified from the gel using Sangon DNA fragment recovery and purification kit (Sangon Biotech (Shanghai) Co. Ltd., Shanghai, China) according to the manufacturer's instructions.

3. Ligation of the Target Gene Fragment to the Vector

Overlap extension PCR was conducted using ydiH 1 and cpYFP as templates, and ydiH 1F and cpYFP 1R as primers with the following PCR system:

| PCR system | |
|---|---|
| Template 1[(1)] | 1 μl |
| Template 2[(1)] | 1 μl |
| Forward primer[(2)] | 0.5 μl |
| Reverse primer[(2)] | 0.5 μl |
| 10× pfu buffer | 5 μl |
| pfu enzyme | 1 μl |
| dNTP (10 mM) | 1 μl |
| ddH$_2$O | 40 μl |
| total | 50 μl |

[(1)]Template fragments need to be purified.
[(2)]The forward and reverse primers were initially absent in the reaction system but added after 10 cycles.

PCR Reaction Conditions:

| PCR reaction conditions | | | |
|---|---|---|---|
| | | 95° C. | 5 min |
| | | 95° C. | 40 s |
| 10 cycles | { | 55° C. | 40 s |
| | | 72° C. | 1 min 15 s |
| | | 95° C. | 40 s |
| 20 cycles | { | 58° C. | 40 s |
| | | 72° C. | 2 min 10 s |
| | | 72° C. | 10 min |

PCR amplification product was subjected to electrophoresis on 1% agarose gel for 40 minutes for the ydiH-cpYFP fragment of about 1400 bp. The recovered and purified PCR fragment ydiH-YFP and vector plasmid pRSET$_b$ were double digested separately with the following digestion systems:

| Double enzyme digestion system | |
|---|---|
| Vector plasmid pRSET$_b$ | 10 μl |
| BamHI | 1 μl |
| HindIII | 2 μl |
| 10× BamHI buffer | 5 μl |
| ddH$_2$O | 32 μl |
| total | 50 μl |

| Double enzyme digestion system | |
|---|---|
| DNA fragment ydiH-YFP | 15 μl |
| BamHI | 1 μl |
| HindIII | 2 μl |
| 10× BamHI buffer | 5 μl |
| ddH$_2$O | 27 μl |
| Total | 50 μl |

Reaction conditions: 37° C., 5 hours.

After the reaction was concluded, 10 μl of 6× loading buffer was added to the 50 μl reaction system to stop the reaction. Then target fragments were isolated by agarose gel electrophoresis, recovered and purified using Sangon DNA fragment recovery kit (Sangon Biotech (Shanghai) Co. Ltd., Shanghai, China) according to the manufacturer's instructions.

The double digested fragment of ydiH-cpYFP and the double digested fragment of vector plasmid pRSET$_b$ recovered above were ligated using the following systems:

| Ligation system | |
| --- | --- |
| DNA fragment ydiH-YFP | 4 |
| Fragment pRSET$_b$ vector | 1 |
| T4 DNA ligase | 0.5 |
| 10x T4 DNA ligase buffer | 1 |
| ddH$_2$O | 3.5 |
| total | 10 |

Reaction conditions: 16° C., overnight. Ligated product pRSET$_b$-ydiH-YFP was formed thereby.

Finally, ydiH (D2) 2 described above and validated pRSET$_b$-ydiH-YFP were double digested as following:

| Double enzyme digestion system | |
| --- | --- |
| DNA fragment ydiH(D2) 2 | 15 μl |
| KpnI | 1 μl |
| HindIII | 3 μl |
| 10x KpnI buffer | 5 μl |
| ddH$_2$O | 26 μl |
| Total | 50 μl |

| Double enzyme digestion system | |
| --- | --- |
| Vector plasmid pRSET$_b$-ydiH-YFP | 10 μl |
| KpnI | 1 μl |
| HindIII | 2 μl |
| 10x KpnI buffer | 5 μl |
| ddH$_2$O | 32 μl |
| total | 50 μl |

Reaction conditions: 37° C. for 5 hours.

When the reaction was concluded, 10 μl of 6x loading buffer was added to the 50 μl reaction system to terminate the reaction. Target fragments were then isolated by agarose gel electrophoresis, recovered and purified using Sangon DNA fragment recovery kit (Sangon Biotech (Shanghai) Co. Ltd., Shanghai, China) according to the manufacturer's instructions.

As described above, the double digested product of ydiH (D2) 2 and pRSET$_b$-ydiH-YFP were recovered and ligated to form the final ligation product pRSET$_b$-ydiH-YFP-ydiH (D2).

Positive colonies identified by PCR identification were selected, and sequenced using universal primers at the Shanghai Branch of Beijing Liuhe BGI Technology Co., Ltd. The sequence data was analysed and compared using Vector NTI 8.0. The results showed that the plasmid was actually comprising inserted nucleotide sequence of ydiH-cpYFP-ydiH (D2) (sequence shown as SEQ ID NO: 9 in the sequence listing), which encodes the protein shown as SEQ ID NO: 4 in the sequence listing.

4. Transformation

The recombinant plasmid pRSET$_b$-ydiH-cpYFP-ydiH (D2) was transformed into competent E. coli BL21 (DE3) pLysS (purchased from Tiangen Biotech Co. Ltd., Beijing, China) to obtain recombinant E. coli BL-Frex, the detailed process is as follows:

(i) One microliter of plasmid or 10 μl of ligation product was added to 100 μl competent bacteria under sterile condition, then kept in ice bath for 45 minutes;

(ii) After ice bathing, the mixture was immediately heat shocked in a 42° C. water bath for 90 to 120 seconds;

(iii) Subjected to ice bath for another 5 minutes;

(iv) Recovered by adding 800 μl LB liquid medium and incubating at, 150 rpm on a shaker for 1 hour;

(v) Centrifuged at 4000 rpm for 5 minutes at room temperature, the supernatant was discarded;

(vi) The pellet was resuspended into a small amount of fresh LB, the entire suspension was then evenly spreaded on LB plates, which were inverted and incubated overnight at 37° C.

Positive colonies were selected using conventional Colony PCR, transferred to 5 ml LB liquid medium containing the appropriate selective pressure, and cultured overnight at 37° C., 220 rpm. The recombinant strain BL-Perex was cultured in LB medium at 37° C., and 0.1 mM IPTG was added when the OD for cell concentration reached 0.8. The expression was induced at 18° C. for 20 hours, and F-rex1 protein was isolated and purified from the bacterial lysate using Ni$^{2+}$ affinity chromatography column (General Electric Company, Uppsala, Sweden). The SDS-PAGE identified only one protein band at approximately 66.5 kD, which was the F-rex1 protein (FIG. 1). As shown in FIG. 1, band 1 is the F-rex protein purified by Ni$^{2+}$ affinity chromatography column, and band 2 is the marker.

Example 2

Construction and Expression of pRSET$_b$-ydiH (189)-YFP-ydiH(190)

1. Amplification the Nucleic Acid Sequence of cpYFP:

The coding sequence of yellow fluorescent protein (cpYFP) was amplified using pMD19-cpYFP as the template, and cpYFP F and cpYFP R as primers, where the primer sequences (primers were synthesized by Sangon Biotech (Shanghai) Co. Ltd., Shanghai, China) are as follows:

```
P1: PstI
                                    (SEQ ID NO: 29)
GAATCTGCAGGCTACAACAGCCACAACGTCTATATC

P2: KpnI
                                    (SEQ ID NO: 30)
CCAAGCTTCGGGGTACCGTTGTACTCCAGCTTGTG
```

PCR Reaction System

| PCR system | |
| --- | --- |
| Template | 1 μl |
| Forward primer | 0.5 μl |
| Reverse primer | 0.5 μl |
| 10x Pfu buffer | 5 μl |
| Pfu enzyme | 1 μl |
| dNTP (10 mM) | 1 μl |
| ddH$_2$O | 41 μl |
| total | 50 μl |

PCR Reaction Conditions:

| | 95° C. | 5 min |
|---|---|---|
| 30 cycles | 95° C. | 30 s |
| | 55° C. | 30 s |
| | 72° C. | 1 min 15 s |
| | 72° C. | 10 min |

PCR amplification product was electrophoresed on 1% agarose gel for 20 minutes to obtain cpYFP fragment of approximately 750 bp. cpYFP fragments were recovered and purified from the gel using Sangon DNA fragment recovery kit (Sangon Biotech (Shanghai) Co., Ltd., Shanghai, China) according to the manufacturer's instructions.

2. Amplification of Target Gene Sequence for YdiH Protein of *Thermus aquaticus*

The gene T-ydiH for YdiH protein of *Thermus aquaticus* was synthesized by Shanghai Generay Biotech Co. Ltd. (Shanghai, China) (synthesized according to the full-length gene sequence deposited in NCBI GenBank, NCBI Genbank AF061257.1).

Then the full length T-ydiH sequence for YdiH protein of *Thermus aquaticus* was amplified using the gene described above as the template, and ydiH IF and ydiH 2R as primers. The amplification using primers ydiH IF and ydiH 2R produced YdiH in full length for T-YdiH protein and having BamHI digestion site at 5' end and HindIII digestion site at 3' end, wherein the sequences of primer ydiH F and ydiH of 2R are as follows:

```
P3: BamHI
                                         (SEQ ID NO: 31)
CCGGATCCGATGAATAAGGATCAATCAAAAATTC

P4: HindIII
                                         (SEQ ID NO: 32)
CCCAAGCTTCTATTCGATTTCCTCTAAAAC
```

PCR Reaction System

| PCR system | |
|---|---|
| Template | 1 μl |
| Forward Primer | 0.5 μl |
| Reverse Primer | 0.5 μl |
| 10x Pfu buffer | 5 μl |
| Pfu enzyme | 1 μl |
| dNTP (10 mM) | 1 μl |
| ddH$_2$O | 41 μl |
| total | 50 μl |

PCR Reaction Conditions:

| | 95° C. | 5 min |
|---|---|---|
| | 95° C. | 40 s |
| 30 cycles | 55° C. | 40 s |
| | 72° C. | 1 min |
| | 72° C. | 10 min |

PCR amplification products was purified on 1% agarose gel by electrophoresis for 30 minutes to obtain the T-ydiH1 fragment of about 700 bp. The amplified T-ydiH fragment was recovered and purified using Sangon DNA fragment recovery purification kit (Sangon Biotech (Shanghai) Co. Ltd., Shanghai, China) according to the manufacturer's instructions.

3. Ligation of the Target Gene to the Vector

The recovered and purified PCR fragment T-ydiH and vector plasmid pRSET$_b$ were double digested separately with the following system:

| Double enzyme digestion system | |
|---|---|
| DNA fragment T-ydiH | 15 μl |
| BamHI | 1 μl |
| HindIII | 2 μl |
| 10x BamHI buffer | 5 μl |
| ddH$_2$O | 27 μl |
| total | 50 μl |

| Double enzyme digestion system | |
|---|---|
| Vector plasmid pRSET$_b$ | 10 μl |
| BamHI | 1 μl |
| HindIII | 2 μl |
| 10x BamHI buffer | 5 μl |
| ddH$_2$O | 32 μl |
| Total | 50 μl |

Reaction conditions: 37° C. for 5 hours.

After the reaction was concluded, 10 μl of 6x loading buffer was added to the 50 μl reaction system to stop the reaction. Then target fragments were isolated by agarose gel electrophoresis, recovered and purified using Sangon DNA fragment recovery kit (Sangon Biotech (Shanghai) Co. Ltd., Shanghai, China) according to the manufacturer's instructions.

The double digested fragment of T-ydiH and the double digested fragment of vector plasmid pRSET$_b$ as recovered above were ligated using the following system:

| Ligation system | |
|---|---|
| DNA fragment T-ydiH-YFP | 4 |
| Fragment pRSET$_b$ vector | 1 |
| T4 DNA ligase | 0.5 |
| 10x T4 DNA ligase buffer | 1 |
| ddH$_2$O | 3.5 |
| total | 10 |

Reaction conditions: 16° C. overnight. Ligated product pRSET$_b$-ydiH was formed thereby.

The full length pRSET$_b$-ydiH sequence was amplified using the validated PRSET$_b$-ydiH as a template, T-ydiH (L190) F and T-ydiH (F189) R as primers. The amplification using primers T-ydiH(L190) F and T-ydiH (F189) R produced a full length fragment ydiH-pRSET$_b$ of the pRSET$_b$-ydiH having PstI digestion site at 5' end and KpnI digestion site at 3' end, wherein the sequences of primers T-ydiH (L190) F and T-ydiH (F189) R are as follows:

```
P5: KpnI
                                         (SEQ ID NO: 33)
ATAGGTACCGGCCTGGCCGGCCTGACCCGGCTG

P6: PstI
                                         (SEQ ID NO: 34)
ATACTGCAGAGAAGTCCACGTTCTCCACGGCCACCTC
```

Finally, the yidH-pRSET$_b$ fragment produced thereby, and validated cpYFP fragment were double digested under following conditions:

| Double enzyme digestion system | |
|---|---|
| DNA fragment cpYFP | 15 μl |
| KpnI | 1.5 μl |
| PstI | 1.5 μl |
| 10x BamHI buffer | 5 μl |
| ddH$_2$O | 27 μl |
| total | 50 μl |

| Double enzyme digestion system | |
|---|---|
| DNA fragment yidH-pRSET$_b$ | 10 μl |
| KpnI | 1.5 μl |
| PstI | 1.5 μl |
| 10x BamHI buffer | 5 μl |
| ddH$_2$O | 32 μl |
| total | 50 μl |

Reaction conditions: 37° C., 5 hours.

After the reaction was concluded, 10 μl of 6× loading buffer was added to the 50 μl reaction system to terminate the reaction. Then target fragments were isolated by agarose gel electrophoresis, recovered and purified using Sangon DNA fragment recovery kits (Sangon Biotech (Shanghai) Co. Ltd., Shanghai, China) according to the manufacturer's instructions.

The double digested fragments of yidH-pRSET$_b$ and cpYFP as recovered above were ligated to form the final product pRSET$_b$-ydiH (189)-YFP-ydiH (190).

Positive colonies identified by Colony PCR were selected, sequenced using universal primers at the Shanghai Brance of Beijing Liuhe BGI Technology Co. Ltd. The determined sequence was compared and analysed using Vector NTI 8.0. The result showed that this plasmid was actually comprising inserted nucleotide sequence of ydiH (189)-YFP-ydiH (190) (sequence shown as SEQ ID NO: 13), and which encodes the protein shown as SEQ ID NO: 8 in the sequence listing.

4. Transformation

Recombinant plasmid pRSET$_b$-ydiH(189)-YFP-ydiH (190) was transformed into competent *E. coli* BL21 (DE3) pLysS (purchased from TIANGEN Biotech Co. Ltd., Beijing, China) to obtain the recombinant strain BL-Frex, the detailed process is as follows:

(i) One microliter of plasmid or 10 μl of ligation product was added to 100 μl of competent bacteria under sterile condition, then kept in ice bath for 45 minutes;

(ii) After ice bathing, the mixture was immediately heat shocked in a 42° C. water bath for 90 to 120 seconds;

(iii) Subjected to ice bath for another 5 minutes;

(iv) Recovered by adding 800 μl LB liquid medium, and incubating at 37° C., 220 rpm on a shaker for 1 hour;

(v) Centrifuged at 4000 rpm for 5 minutes at room temperature, and the supernatant was discarded;

(vi) The pellet was resuspended into a small amount of fresh LB, and the entire suspension was then evenly spreaded on LB plates, which were inverted and incubated overnight at 37° C.

Figure 2:
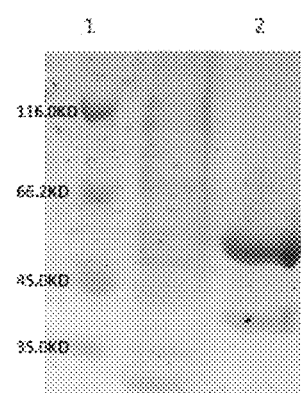
FIG. 2 shows SDS-PAGE characterizing F-rex2 separated and purified from *E. coli*.
Figure 12:
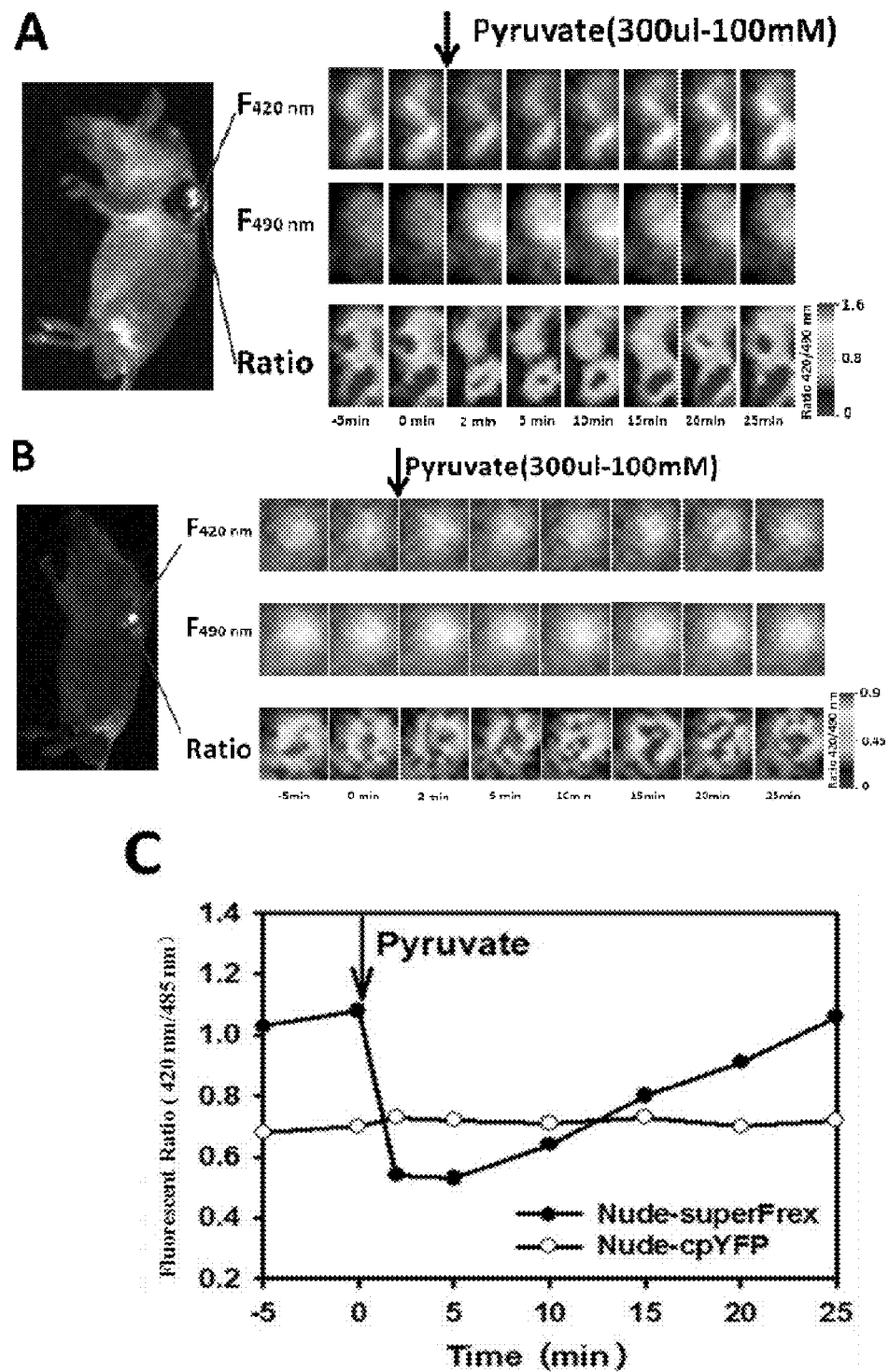
FIG. 12 shows a real-time detection of the metabolite levels of NADH/NAD⁺ ratio in tumors by sensor for NADH/NAD⁺ ratio fluorescent.

Positive colonies were selected using conventional Colony PCR, transferred to 5 ml LB liquid medium containing the appropriate selective pressure, and cultured overnight at 37° C., 220 rpm. The recombinant strain BL-Perex was cultured at 37° C., and 0.1 mM IPTG was added when the OD of cell concentration reached 0.8. The expression was induced at 18° C. for 20 hours, and F-rex2 protein was isolated and purified from the bacterial lysate using Ni$^{2+}$ affinity chromatography column (General Electric Company, Uppsala, Sweden). The SDS-PAGE identified only one protein band at approximately 50 kD, which was the F-rex2 protein (FIG. 2). As shown in FIG. 12, band 1 is the F-rex2 protein purified by Ni$^{2+}$ affinity chromatography column, while band 2 is the marker.

Example 3

Derivatives of YdiH-YFP-ydiH (D2) Sensors

Principle for Sensor Construction

Derivative sensors were engineered using intermediate plasmids for the construction of pRSET$_b$-ydiH-YFP-ydiH and other sensors as templates, and following the principle of site-directed mutagenesis.

Truncated mutant sequences are shown below:

| | | SEQ ID NO |
|---|---|---|
| Original sequence | 206 KHYSVLEEIE 215-TS-YFP-GT-ydiH | |
| Del T(2) | 206 KHYSVLEEIE 215-TS-YFP-G-ydiH | 104 |
| Del G | 206 KHYSVLEEIE 215-TS-YFP-T-ydiH | 103 |
| Del GT | 206 KHYSVLEEIE 215-TS-YFP-ydiH | 102 |
| Del S | 206 KHYSVLEEIE 215-T-YFP-GT-ydiH | 126 |
| Del T(1) | 206 KHYSVLEEIE 215-S-YFP-GT-ydiH | 101 |
| Del TS | 206 KHYSVLEEIE 215-YFP-GT-ydiH | 159 |
| C9 | 206 KHYSVLEEI 214-YFP-GT-ydiH | 100 |
| C8 | 206 KHYSVLEE 213-YFP-GT-ydiH | 99 |
| C2 | 206 KH 207-YFP-GT-ydiH | 93 |
| C1 | 206 K-YFP-GT-ydiH | 92 |

Establishment of the Mutant Library
1. Primer Design (Shanghai Sangon)

| SEQ ID No | Remark | Sequence(5'-3') |
|---|---|---|
| 35 | C9 Reverse | GATTTCCTCTAAAACTGAATAATGCTTC |
| 36 | C8 Reverse | TTCCTCTAAAACTGAATAATGCTTC |
| 37 | C6 Reverse | TAAAACTGAATAATGCTTCAAAAAATAAACCAG |
| 38 | C5 Reverse | AACTGAATAATGCTTCAAAAAATAAACCAG |
| 39 | C4 Reverse | TGAATAATGCTTCAAAAAATAAACCAG |
| 40 | C3 Reverse | ATAATGCTTCAAAAAATAAACCAGTG |
| 41 | C2 Reverse | ATGCTTCAAAAAATAAACCAGTGACTG |
| 42 | C1 Reverse | CTTCAAAAAATAAACCAGTGACTGAAGC |
| 43 | C9 Forward (general forward primer for C series) | TACAACAGCGACAACGTC |
| 44 | C7 Reverse | CTCTAAAACTGAATAATGCTTC |
| 45 | Del GT Forward | ATGACAGACGTCATCTTGATTG |
| 46 | Del GT Reverse | GTTGTACTCCAGCTTGTGCC |
| 47 | Del TS Forward | TACAACAGCGACAACGTCTATATCATG |
| 48 | Del TS Reverse | TTCGATTTCCTCTAAAACTGAATAATGC |

| SEQ ID No | Remark | Sequence(5'-3') |
|---|---|---|
| 49 | Del T(1) Forward | AGTTACAACAGCGACAACGTCTATATCATG |
| 50 | Del S-deletion Reverse | AGTTTCGATTTCCTCTAAAACTGAATAATGC |
| 51 | Del G-deletion Forward | ACCATGACAGACGTCATCTTGATTG |
| 52 | Del T(2)-deletion Reverse | ACCGTTGTACTCCAGCTTGTGCC |
| 53 | D118K Forward | TTTTAAGATAAATGAGAGTAAAATAGG |
| 54 | 118/120 mutation Reverse | GCCATAGAAATTTTTGTGTTATTG |
| 55 | D118R Forward | TTTTCGGATAAATGAGAGTAAAATAGG |
| 56 | N120K Forward | TTTTGATATAAAGGAGAGTAAAATAGG |
| 57 | N120R Forward | TTTTGATATACGGGAGAGTAAAATAGG |
| 58 | N120E Forward | TTTTGATATAGAAGAGAGTAAAATAGG |
| 59 | N120D Forward | TTTTGATATAGATGAGAGTAAAATAGG |
| 60 | D193N Forward | TAAATTTAGCAGTTGAGCTTCAG |
| 61 | 193/194 mutation Reverse | TATGATGAATTCGAATGTGTTC |
| 62 | D193K Forward | TAAAGTTAGCAGTTGAGCTTCAG |
| 63 | D193R Forward | TACGGTTAGCAGTTGAGCTTCAG |
| 64 | L194E Forward | TAGATGAAGCAGTTGAGCTTCAG |
| 65 | L194D Forward | TAGATGATGCAGTTGAGCTTCAG |
| 66 | L194K Forward | TAGATAAGGCAGTTGAGCTTCAG |
| 67 | L194R Forward | TAGATCGGGCAGTTGAGCTTCAG |

2. PCR Amplification

Truncated mutation and site-directed mutation were conducted using site-directed mutagenesis PCR.

Amplification system for PCR mutation (primer, enzyme, dNTP and others purchased from Fermentas):

| PCR sampling system | |
|---|---|
| Template | 0.1 μl |
| Forward Primer | 0.5 μl |
| Reverse Primer | 0.5 μl |
| 5× PrimeStar Buffer | 10 μl |
| PrimeStar polymerase | 0.5 μl |
| dNTP mix(10 mM) | 4 μl |
| ddH$_2$O | 33.5 μl |
| Total | 50 μl |

| PCR reaction conditions | | |
|---|---|---|
| | 98° C. | 5 min |
| 30 cycles { | 98° C. | 10 sec |
| | 55° C. | 5 sec |
| | 72° C. | 4.5 min |
| | 72° C. | 10 min |

3. Separation, Purification of DNA Fragments

DpnI Digestion

The PCR amplified fragment was first treated with DpnI enzyme (from Fermentas) for 3 hours at 37° C. to remove the potential template plasmid contamination. The reaction system was then denatured and deactivated at 80° C. for 20 minutes. The deactivated mixture could be directly used for subsequent molecular biological experiments.

Phosphorylation of DNA Fragment

At the presence of ATP, the DNA fragment was treated with T4 polynucleotide kinase (T4 PNK) (from Fermentas) at 37° C. for 1 h to phosphorylate the 5'-OH of DNA ribose ring, in order to allow the fragments to cyclize by self-ligation. Then the reaction system was denatured and deactivated at 75° C. for 10 minutes. The deactivated mixture could be directly used for subsequent molecular biological experiments.

Ligation

The phosphorylated DNA fragments (mutated DNA fragments: pRSET$_b$-ydiH-YFP or pRSET$_b$-YFP-ydiH) were cyclized by self ligation overnight at 16° C. with T4 DNA ligase enzyme (from Fermentas).

Double-Digestion of Mutant Plasmids

The extracted mutant plasmids pRSET$_b$-ydiH-YFP series and pRSET$_b$-YFP-ydiH series were double digested, respectively. The digestion systems are as follows:

| Double-digest system | |
|---|---|
| Mutant plasmid pRSET$_b$-ydiH-YFP series | 10 μl |
| BsrGI | 1 μl |
| HindIII | 2 μl |
| 10× Tango buffer | 5 μl |
| ddH$_2$O | 32 μl |
| Total | 50 μl |

| Double-digest system | |
|---|---|
| Mutant plasmid pRSET$_b$-YFP-ydiH series | 10 μl |
| BsrGI | 1 μl |
| HindIII | 2 μl |
| 10× Tangobuffer | 5 μl |
| ddH$_2$O | 32 μl |
| Total | 50 μl |

Reaction conditions: 37° C. for 5 h.

When the reaction was concluded, 10 μl of the 6× loading buffer was added to the 50 μl reaction system to terminate the reaction. The fragment was isolated by agarose gel electrophoresis, recovered and purified using adsorption column Detailed steps are described in "Shanghai Sangon Gel Purification Kits/DNA Recovery Kits".

For truncated mutations, digested fragment of pRSET$_b$-ydiH-YFP from proper mutant plasmid of pRSET$_b$-ydiH-YFP series was selected as desired, and then ligated with normal fragment of sequence YFP-ydiH without mutation. For site-directed mutagenesis, digested fragment of pRSET$_b$-ydiH-YFP from proper mutant plasmid of pRSET$_b$-ydiH-YFP series was selected as desired, and then ligated with digested fragment YFP-ydiH of pRSET$_b$-ydiH-YFP series containing site-directed mutation as well.

Ligation

Recovered and purified fragments pRSET$_b$-ydiH-YFP and YFP-ydiH were ligated using the following system:

| Ligation system | |
|---|---|
| Fragment YFP-ydiH | 4 |
| Fragment pRSET$_b$-ydiH-YFP | 1 |
| T4 DNA Ligase enzyme | 0.5 |
| 10x T4 DNA Ligase buffer | 1 |
| ddH$_2$O | 3.5 |
| Total | 10 |

Reaction conditions: 16° C., overnight.

The ligation products were labeled to form pRSET$_b$-ydiH-YFP-ydiH Truc v2.xx or pRSET$_b$-ydiH-YFP-ydiH.

Identification of Plasmid Mutations

Colonies identified as positive in Colony PCR were selected and sequenced using universal primers at the Shanghai Branch of Beijing Liuhe BGI Technology Co., Ltd. The determined sequences were then compared and analyzed by Vector NTI 8.0.

Construction of Sensor Series

Following sensors were produced according to the methods described above.

| Plasmid | NO. | SEQ ID NO |
|---|---|---|
| pRSET$_b$-ydiH-YFP-ydiH(D2)C1 | C1 | 92 |
| pRSET$_b$-ydiH-YFP-ydiH(D2)C2 | C2 | 93 |
| pRSET$_b$-ydiH-YFP-ydiH(D2)C3 | C3 | 94 |
| pRSET$_b$-ydiH-YFP-ydiH(D2)C4 | C4 | 95 |
| pRSET$_b$-ydiH-YFP-ydiH(D2)C5 | C5 | 96 |
| pRSET$_b$-ydiH-YFP-ydiH(D2)C6 | C6 | 97 |
| pRSET$_b$-ydiH-YFP-ydiH(D2)C7 | C7 | 98 |
| pRSET$_b$-ydiH-YFP-ydiH(D2)C8 | C8 | 99 |
| pRSET$_b$-ydiH-YFP-ydiH(D2)C9 | C9 | 100 |
| pRSET$_b$-ydiH-YFP-ydiH(D2)Del T | Del T(1) | 101 |
| pRSET$_b$-ydiH-YFP-ydiH(D2)Del GT | Del GT | 102 |
| pRSET$_b$-ydiH-YFP-ydiH(D2)Del G | Del G | 103 |
| pRSET$_b$-ydiH-YFP-ydiH(D2)Del T | Del T(2) | 104 |
| pRSET$_b$-ydiH-YFP-ydiH(D2)C3 D118R | C3 D118R | 105 |
| pRSET$_b$-ydiH-YFP-ydiH(D2)C3 N120K | C3 N120K | 106 |
| pRSET$_b$-ydiH-YFP-ydiH(D2)C3 N120R | C3 N120R | 107 |
| pRSET$_b$-ydiH-YFP-ydiH(D2)C3 N120E | C3 N120E | 108 |
| pRSET$_b$-ydiH-YFP-ydiH(D2)C3 N120D | C3 N120D | 109 |
| pRSET$_b$-ydiH-YFP-ydiH(D2)C3 D193N | C3 D193N | 110 |
| pRSET$_b$-ydiH-YFP-ydiH(D2)C3 D193K | C3 D193K | 111 |
| pRSET$_b$-ydiH-YFP-ydiH(D2)C3 L194K | C3 L194K | 112 |
| pRSET$_b$-ydiH-YFP-ydiH(D2)C3 L194R | C3 L194R | 113 |
| pRSET$_b$-ydiH-YFP-ydiH(D2)C3 L194E | C3 L194E | 114 |
| pRSET$_b$-ydiH-YFP-ydiH(D2)C3 L194D | C3 L194D | 115 |
| pRSET$_b$-ydiH-YFP-ydiH(D2)C8 D118R | C8 D118R | 116 |
| pRSET$_b$-ydiH-YFP-ydiH(D2)C8 N120K | C8 N120K | 117 |
| pRSET$_b$-ydiH-YFP-ydiH(D2)C8 N120R | C8 N120R | 118 |
| pRSET$_b$-ydiH-YFP-ydiH(D2)C8 N120E | C8 N120E | 119 |
| pRSET$_b$-ydiH-YFP-ydiH(D2)C8 N120D | C8 N120D | 120 |
| pRSET$_b$-ydiH-YFP-ydiH(D2)C8 D193N | C8 D193N | 121 |
| pRSET$_b$-ydiH-YFP-ydiH(D2)C8 D193K | C8 D193K | 122 |
| pRSET$_b$-ydiH-YFP-ydiH(D2)C8 L194K | C8 L194K | 123 |
| pRSET$_b$-ydiH-YFP-ydiH(D2)C8 L194R | C8 L194R | 124 |
| pRSET$_b$-ydiH-YFP-ydiH(D2)C8 L194E | C8 L194E | 125 |

Example 4

Derivative Sensors of ydiH(189)-YFP-ydiH(190)

Principle for Sensor Construction

Derivative sensors were engineered using intermediate plasmid for constructing sensors such as pRSET$_b$-ydiH(189)-YFP-ydiH(190) as templates and following the principle of site-directed mutagenesis.

Truncated mutant sequences are shown below:

| Name | Structure | SEQ ID NO |
|---|---|---|
| Original sequence | F189-SAG-YFP-GGC-L190 | 127 |
| 189/190-N1 | F189-AG-YFP-GGC-L190 | 128 |
| 189/190-N2 | F189-G-YFP-GGC-L190 | 129 |
| 189/190-N3 | F189-YFP-GGC-L190 | 130 |
| 189/190-C1 | F189-SAG-YFP-GG-L190 | 131 |
| 189/190-C2 | F189-SAG-YFP-G-L190 | 132 |
| 189/190-C3 | F189-SAG-YFP-L190 | 133 |
| 189/190-C1N1 | F189-AG-YFP-GG-L190 | 134 |
| 189/190-C1N2 | F189-G-YFP-GG-L190 | 135 |
| 189/190-C1N3 | F189-YFP-GG-L190 | 136 |
| 189/190-C2N1 | F189-AG-YFP-G-L190 | 137 |
| 189/190-C2N2 | F189-G-YFP-G-L190 | 138 |
| 189/190-C2N3 | F189-YFP-G-L190 | 139 |
| 189/190-C3N1 | F189-AG-YFP-L190 | 140 |
| 189/190-C3N2 | F189-G-YFP-L190 | 141 |
| 189/190-C3N3 | F189-YFP-L190 | 142 |

Establishment of Mutant Library

1. Primer Design (Shanghai Sangon)

| SEQ ID No | Remark | | Sequence(5'-3') |
|---|---|---|---|
| 68 | 189/190-N1 | (F) | GCAGGCTACAACAGCGACAACGTC |
| 69 | 189/190-N1 | (R) | GAAGTCCACGTTCTCCACGGCCAC |
| 70 | 189/190-N2 | (F) | GGCTACAACAGCGACAACGTCTATATCATG |
| 71 | 189/190-N3 | (F) | TACAACAGCGACAACGTCTATATCATGGC |
| 72 | 189/190-C1 | (F) | CTGGCCGGCCTGACCCGGCTGAG |
| 73 | 189/190-C1 | (R) | GGTACCGTTGTACTCCAGCTTGTGCCCCAGG |
| 74 | 189/190-C2 | (R) | ACCGTTGTACTCCAGCTTGTGCCCCAGGATG |
| 75 | 189/190-C3 | (R) | GTTGTACTCCAGCTTGTGCCCCAGGATGTTGC |
| 76 | Trex(D2) | (F) | ATGAACCGGAAGTGGGCCTG |
| 77 | Trex(D2) | (R) | CGGATCCTTATCGTCATCGTCGTAC |
| 78 | D112SV113H | (F) | CATGACCCCGAGAAGGTGGGC |
| 79 | D112SV113H | (R) | CGAGAAGAAGCCCCGCAGCTC |

2. PCR Amplification

Truncated mutation and site-directed mutation were conducted using site-directed mutagenesis PCR.

Amplification system for PCR mutation (Primer, enzyme, dNTP and others purchased from Fermentas):

| PCR reaction conditions | | |
|---|---|---|
| | 98° C. | 5 min |
| | 98° C. | 10 sec |
| 30 cycles | 55° C. | 5 sec |
| | 72° C. | 4.5 min |
| | 72° C. | 10 min |

| PCR amplification system | |
|---|---|
| Template | 0.1 µl |
| Forward Primer | 0.5 µl |
| Reverse Primer | 0.5 µl |
| 5x PrimeStar Buffer | 10 µl |
| PrimeStar polymerase | 0.5 µl |
| dNTP mix(10 mM) | 4 µl |
| ddH$_2$O | 33.5 µl |
| Total | 50 µl |

3. Separation, Purification of DNA Fragments

DpnI Digestion

The PCR amplified fragment was first treated with DpnI enzyme (from Fermentas) for 3 hours at 37° C. to remove the potential template plasmid contamination. The reaction system was then denatured and deactivated at 80° C. for 20 minutes. The deactivated mixture could be directly used for subsequent molecular biological experiments.

Phosphorylation of DNA Fragment

At the presence of ATP, the DNA fragment was treated with T4 polynucleotide kinase (T4 PNK) (from Fermentas) at 37° C. for 1 h to phosphorylate the 5'-OH of DNA ribose ring, in order to allow the fragment to cyclize by self-ligation. Then the reaction system was denatured and deactivated at 75° C. for 10 minutes. The deactivated mixture could be directly used for subsequent molecular biological experiments.

Ligation

The phosphorylated DNA fragments (mutated DNA fragments: pRSET$_b$-ydiH-YFP or pRSET$_b$-YFP-ydiH) were cyclized by self ligation overnight at 16° C. with T4 DNA ligase enzyme (from Fermentas).

Identification of Plasmid Mutations

Colonies identified as positive in Colony PCR were selected and sequenced using universal primers at the Shanghai Branch of Beijing Liuhe BGI Technology Co., Ltd. The determined sequence was then compared and analyzed by Vector NTI 8.0.

Construction of Sensor Series

Following sensors were produced according to the methods described above, and numbered respectively.

| Plasmid | NO. | SEQ ID NO |
|---|---|---|
| pRSET$_b$-ydiH(189)-YFP-ydiH(190) | F-rex2-1.0 | 127 |
| pRSET$_b$-ydiH(189)-YFP-ydiH(190)-N1 | F-rex2-2.0 | 128 |
| pRSET$_b$-ydiH(189)-YFP-ydiH(190)-N2 | F-rex2-2.1 | 129 |
| pRSET$_b$-ydiH(189)-YFP-ydiH(190)-N3 | F-rex2-2.2 | 130 |
| pRSET$_b$-ydiH(189)-YFP-ydiH(190)-C1 | F-rex2-2.3 | 131 |
| pRSET$_b$-ydiH(189)-YFP-ydiH(190)-C2 | F-rex2-2.4 | 132 |
| pRSET$_b$-ydiH(189)-YFP-ydiH(190)-C3 | F-rex2-2.5 | 133 |
| pRSET$_b$-ydiH(189)-YFP-ydiH(190)-C1N1 | F-rex2-2.6 | 134 |
| pRSET$_b$-ydiH(189)-YFP-ydiH(190)-C1N2 | F-rex2-2.7 | 135 |
| pRSET$_b$-ydiH(189)-YFP-ydiH(190)-C1N3 | F-rex2-2.8 | 136 |
| pRSET$_b$-ydiH(189)-YFP-ydiH(190)-C2N1 | F-rex2-2.9 | 137 |
| pRSET$_b$-ydiH(189)-YFP-ydiH(190)-C2N2 | F-rex2-2.10 | 138 |
| pRSET$_b$-ydiH(189)-YFP-ydiH(190)-C2N3 | F-rex2-2.11 | 139 |
| pRSET$_b$-ydiH(189)-YFP-ydiH(190)-C3N1 | F-rex2-2.12 | 140 |
| pRSET$_b$-ydiH(189)-YFP-ydiH(190)-C3N2 | F-rex2-2.13 | 141 |
| pRSET$_b$-ydiH(189)-YFP-ydiH(190)-C3N3 | F-rex2-2.14 | 142 |
| pRSET$_b$-Trex(D2)-ydiH(189)-YFP-ydiH(190) | F-rex2-2.15 | 143 |
| pRSET$_b$-Trex(D2)-ydiH(189)-YFP-ydiH(190)-N1 | F-rex2-2.16 | 144 |
| pRSET$_b$-Trex(D2)-ydiH(189)-YFP-ydiH(190)-N2 | F-rex2-2.17 | 145 |
| pRSET$_b$-Trex(D2)-ydiH(189)-YFP-ydiH(190)-N3 | F-rex2-2.18 | 146 |
| pRSET$_b$-Trex(D2)-ydiH(189)-YFP-ydiH(190)-C1 | F-rex2-2.19 | 147 |
| pRSET$_b$-Trex(D2)-ydiH(189)-YFP-ydiH(190)-C2 | F-rex2-2.20 | 148 |
| pRSET$_b$-Trex(D2)-ydiH(189)-YFP-ydiH(190)-C3 | F-rex2-2.21 | 149 |
| pRSET$_b$-Trex(D2)-ydiH(189)-YFP-ydiH(190)-C1N1 | F-rex2-2.22 | 150 |
| pRSET$_b$-Trex(D2)-ydiH(189)-YFP-ydiH(190)-C1N2 | F-rex2-2.23 | 151 |
| pRSET$_b$-Trex(D2)-ydiH(189)-YFP-ydiH(190)-C1N3 | F-rex2-2.24 | 152 |
| pRSET$_b$-Trex(D2)-ydiH(189)-YFP-ydiH(190)-C2N1 | F-rex2-2.25 | 153 |
| pRSET$_b$-Trex(D2)-ydiH(189)-YFP-ydiH(190)-C2N2 | F-rex2-2.26 | 154 |
| pRSET$_b$-Trex(D2)-ydiH(189)-YFP-ydiH(190)-C2N3 | F-rex2-2.27 | 155 |
| pRSET$_b$-Trex(D2)-ydiH(189)-YFP-ydiH(190)-C3N1 | F-rex2-2.28 | 156 |
| pRSET$_b$-Trex(D2)-ydiH(189)-YFP-ydiH(190)-C3N2 | F-rex2-2.29 | 157 |
| pRSET$_b$-Trex(D2)-ydiH(189)-YFP-ydiH(190)-C3N3 | F-rex2-2.30 | 158 |

Example 5

Spectral Characteristics of Fluorescent Sensors for NADH

The fluorescent sensors that prepared above were dissolved in assay buffer (100 mM KPi, pH7.4) to formulate fluorescent sensor solutions to a final concentration of 10 µM. Then their absorption spectra were measured using a Multi-functional Fluorescence Microplate Reader (Synergy2, Biotek) (FIG. 3A).

Their excitation and emission spectra were determined using a fluorescence spectrophotometer (Cary Eclipse Fluorescence spectrophotometer, Varian) (FIG. 3B).

Figure 4:
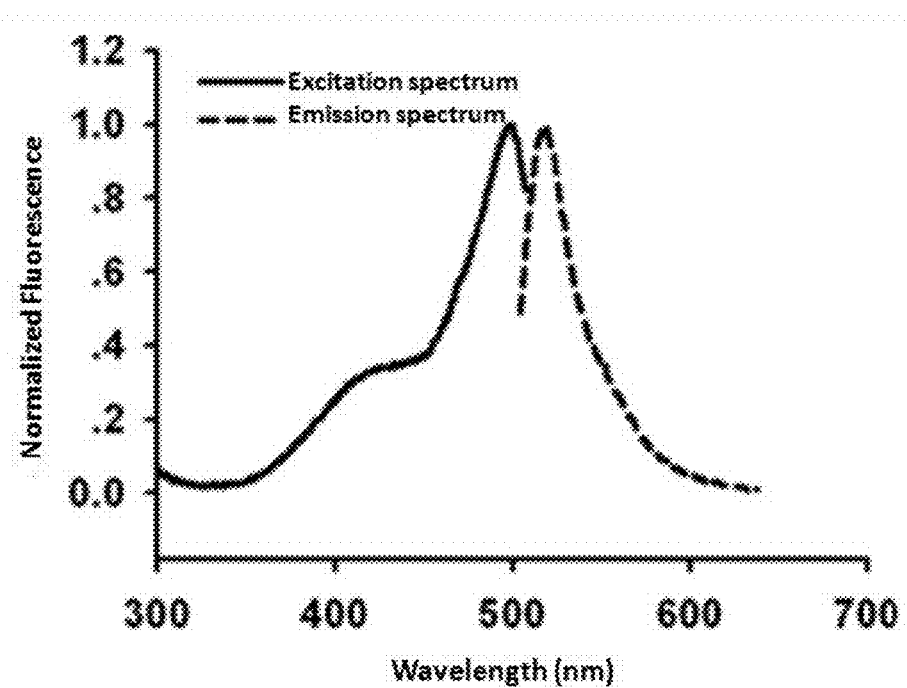
FIG. 4 shows basic spectral characteristics of the nicotinamide adenine dinucleotide fluorescent sensor F-rex2.

Experimental results indicated that, F-rex1 had two excitation peaks at 400 nm and 490 nm, respectively, and the latter exhibited an intensity five times of that of the former. However, F-rex1 had only one emission peak at 521 nm. Meanwhile, F-rex2 protein has two excitation peaks at 410 nm and 500 nm, respectively, and the latter exhibited an intensity about half of that of the former. However, F-rex2 had only one emission peak at 518 nm (FIG. 4).

Example 6

Characteristics of Fluorescent Sensors for NADH in Responses to Pyridine Nucleotide Analogs Under Physiological Conditions The fluorescent sensors prepared above were dissolved in assay buffer (100 mM KPi, pH7.4) to formulate protein solutions to a final concentration of 1 µM. Pyridine nucleotide analogs NAD$^+$, NADH, ATP, ADP, NADP$^+$ and NADPH (Merck Biosciences GmbH, Darmstadt, Germany) were prepared in assay buffer (100 mM KPi, pH7.4) for stock solutions at a final concentration of 8 mM, which were diluted to 80 µM before use.

Two hundred microliter of the 1 µM solution of fluorescent sensors was taken, and first titrated 5x with 4 µl of the 80 µM NAD$^+$ or NADH or ATP or ADP or NADP$^+$ or NADPH, then further titrated 5x with 4 µl of the 8 mM NAD$^+$ or NADH or ATP or ADP or NADP$^+$ or NADPH. After each titration, the solution was vortexed 5 seconds to allow the reaction to complete, then the fluorescent intensity of 528 nm emission upon 485 nm excitation was measured using a Multi-functional Fluorescence Microplate Reader (Synergy2, Biotek).

Figure 5:
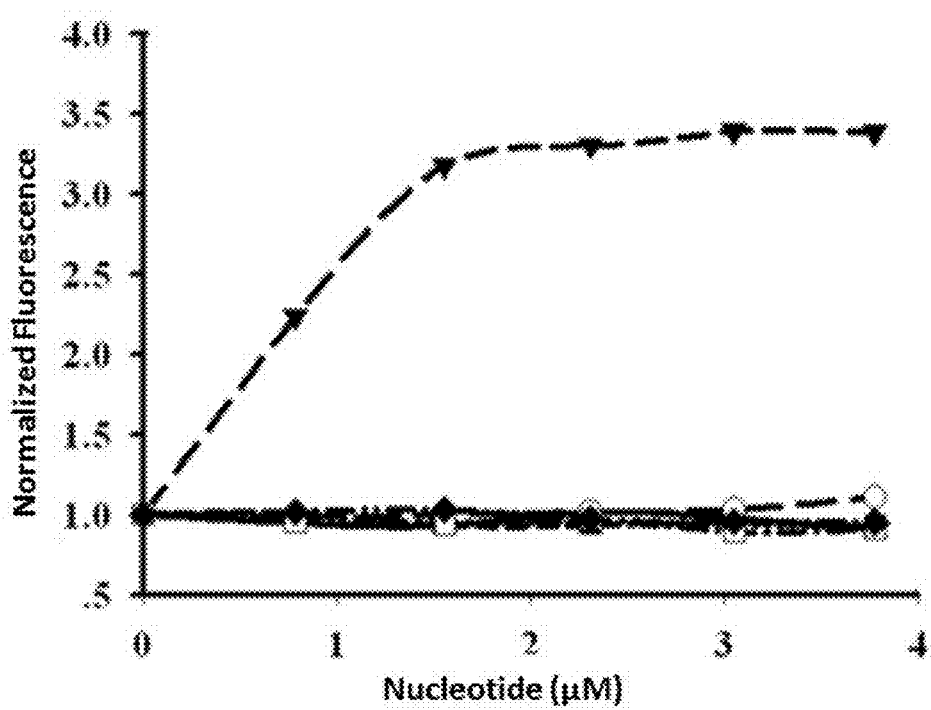
FIG. 5 shows response of fluorescent sensor F-rex1 for reduced nicotinamide adenine dinucleotide to pyridine nucleotide analogs under simulated physiological conditions in vitro.
Figure 6:
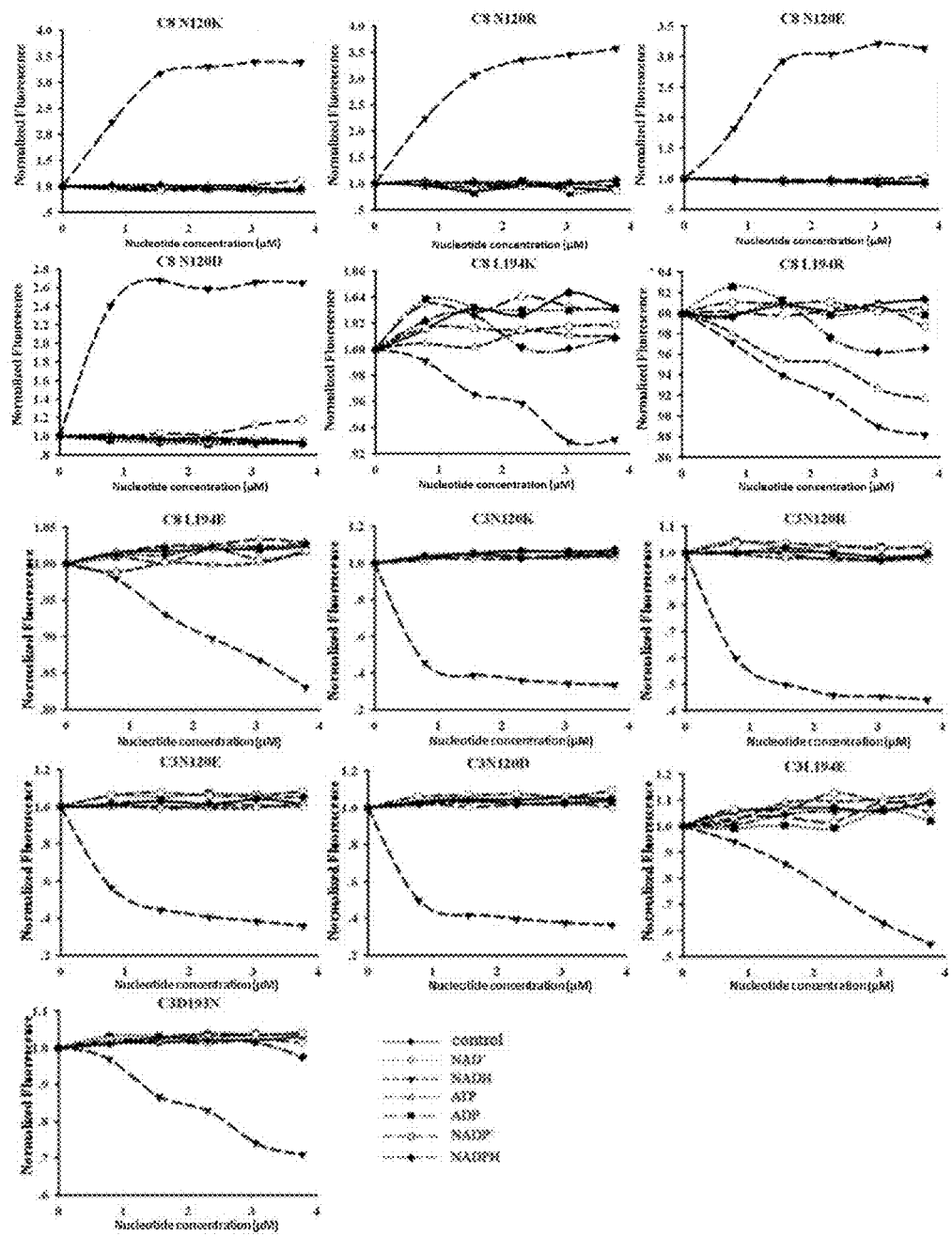
FIG. 6 shows response of the derivatized fluorescent sensor for reduced nicotinamide adenine dinucleotide to pyridine nucleotide analogs under simulated physiological conditions in vitro.

Measurements demonstrated that, NADH fluorescent sensors exhibited robust response to NADH at the physiological concentration (<100 μM NADH), but no notable response to other pyridine nucleotide was observed (FIGS. 5 and 6).

Example 7

Localization and Expression of Fluorescent Sensor for NADH in Different Subcellular Organelles The NADH fluorescence sensor gene (Frex) was obtained using pRSET$_b$-ydiH-cpYFP-ydiH(D2) as template, and double-digesting it with BamHI and HindIII. The digested fragment was recovered and ligated to the following vectors: pcDNA3.1-Hygro-Cyto, pcDNA3.1-Hygro-Mito, pcDNA3.1-Hygro-Nuc, pcDNA3.1-Hygro-Mem, pcDNA3.1-Hygro-Golgi, pcDNA3.1-Hygro-ER and pcDNA3.1-Hygro-Peroxi respectively (engineered in Protein Chemistry Laboratory of East China University of Science and Technology, Shanghai, China).

Preparation: unless otherwise indicated, all primers used herein were synthesized by Shanghai Sangon (Sangon Biotech (Sangon Co. Ltd., Shanghai, China). First, vector pcDNA3.1-Hygro-Cyto was constructed based on pcDNA3.1-Hygro (+) (Invitrogen, California, U.S.A.). Two primers: Cyto Forward Primer and Cyto Reverse Primer, were designed.

```
Cyto Forward Primer:
                                      (SEQ ID No 80)
CTAGCATGGCGGATCCACTAGTAAGCTTAAGC Cyto Reverse Primer:
                                      (SEQ ID No 81)
TCGAGCTTAAGCTTACTAGTGGATCCGCCATG
```

This primer pair contains restriction sites and the start codon ATG, and the structure was "NheI-ATG-GC-BamHI-HindIII-XhoI". Following steps for dual primer annealing with the obtained primers was carried out.
1. The primer powder was dissolved to 100 μM in specific buffer (10 mM Tris, pH7.5-8.0; 50 mM NaCl, 1 mM EDTA).
2. Equimolar amounts of the primer pair to be annealed were mixed to a total volume of no greater than 500 μl.
3. The mixture was heated to 95° C. and then slowly cooled to room temperature (below 30° C.), then stored at −20° C. before use.

For organelle targeting signal Mito (SEQ ID No 82) and Golgi (SEQ ID No 83), the signal was introduced into vector pcDNA3.1-Hygro(+) through double-digestion utilizing synthesized targeting signal containing NheI restriction site allocated at 5' end and BamHI restriction site allocated at 3' end.

| Double-digestion system | |
| --- | --- |
| DNA fragment | 10 μl |
| NheI | 1 μl |
| BamHI | 1 μl |
| 10x Tangobuffer | 5 μl |
| ddH$_2$O | 33 μl |
| Total | 50 μl |

| Double-digestion system | |
| --- | --- |
| Vector:pcDNA3.1-Hygro(+) | 10 μl |
| NheI | 1 μl |
| BamHI | 1 μl |
| 10x Tangobuffer | 5 μl |
| ddH$_2$O | 33 μl |
| Total | 50 μl |

Similarly, for organelle targeting signal Nuc, Mem, ER and Peroxi, a pair of restriction sites were allocated to their both ends, respectively. Synthesized primers were utilized in dual primer annealing for the formation of double-stranded DNA, double-stranded DNA fragment with sticky ends obtained directly thereby was subsequently ligated with double-digested vector pcDNA3.1-Hygro(+).

```
Nuc Forward Primer:
                                      (SEQ ID No 84)
AGCTTGATCCAAAAAAGAAGAGAAAGGTAGATCCAAAAAAGAAGAGA

AAGGTAGATCCAAAAAAGAAGAGAAAGGTAGC

Nuc Reverse Primer:
                                      (SEQ ID No 85)
TCGAGCTACCTTTCTCTTCTTTTTTGGATCTACCTTTCTCTTCTTTTT

GGATCTACCTTTCTCTTCTTTTTTGGATCA

Mem Forward Primer:
                                      (SEQ ID No 86)
CTAGCATGGCGCTGTGCTGTATGAGAAGAACCAAACAGGTTGAAAAG

AATGATGAGGACCAAAAGATCGCG

Mem Reverse Primer:
                                      (SEQ ID No 87)
GATCCGCGATCTTTTGGTCCTCATCATTCTTTTCAACCTGTTTGGTTCT

TCTCATACAGCACAGCGCCATG

ER Forward Primer:
                                      (SEQ ID No 88)
CTAGCATGGCGCTGCTATCCGTGCCGTTGCTGCTCGGCCTCCTCGG

CCTGGCCGTCGCCGCG

ER Reverse Primer:
                                      (SEQ ID No 89)
GATCCGCGGCGACGGCCAGGCCGAGGAGGCCGAGCAGCAACGGCAC

GGATAGCAGCGCCATG

Peroxi Forward Primer:
                                      (SEQ ID No 90)
AGCTTTCCAAGCTGTAAC Peroxi Reverse Primer:
                                      (SEQ ID No 91)
TCGAGTTACAGCTTGGAA
```

Recombinant plasmids pcDNA3.1-Hygro-Cyto-Frex, pcDNA3.1-Hygro-mito-Frex, pcDNA3.1-Hygro-Frex-Nuc, pcDNA3.1-Hygro-mem-Frex, pcDNA3.1-Hygro-golgi-Frex, pcDNA3.1-Hygro-Frex-ER and pcDNA3.1-Hygro-Frex-peroxi were constructed, and then sequenced. The results demonstrated that the nucleotide sequences of Frex fragment were the same as SEQ ID NO: 9. HEK293 cells, HEK293FT cells and Cos7 cells were transfected with these recombinant plasmids, respectively. The transfected cells were observed under a laser scanning confocal microscope (Nikon, Japan) with two excitation wavelengths at 405 nm and 488 nm, while the emission wavelength was 500-550 nm.

Figure 7:
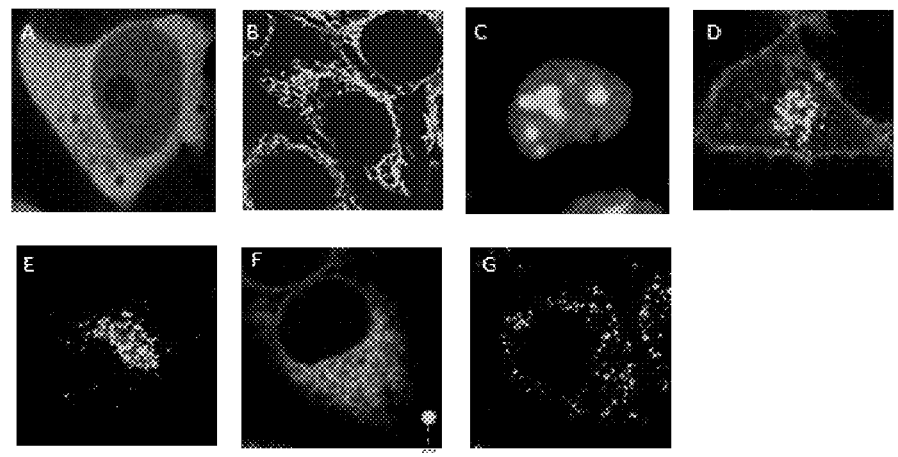
FIG. 7 shows changes of NADH in HEK293FT cells after the treatment of 3-NP and AOA.

Experimental results indicated that, in HEK293FT cells, Frex-Cyto was efficiently and accurately located in the cytoplasm (FIG. 7A); Frex-Mito was efficiently and accurately located in the mitochondria (FIG. 7B); Frex-Nuc was efficiently and accurately located in the nucleus (FIG. 7C); Frex-Mem was efficiently and accurately located in the membrane (FIG. 7D); Frex-Golgi was efficiently and accurately located in the Glogi (FIG. 7E); Frex-ER was efficiently and accurately located in the endoplasmic reticulum (FIG. 7F); Frex-Pero was efficiently and accurately located in the peroxisomes (FIG. 7G).

Example 8

Utilizing the Sensor Series to Indicate Changes of Intracellular Reduced Nicotinamide Adenine Dinucleotide (1) Fluorescent sensors for reduced nicotinamide adenine dinucleotide used in real-time measurements of increases of NADH levels in different subcellular compartments as the result of trans-membrane entrance of NADH into the cell.

Figures 1, 8:
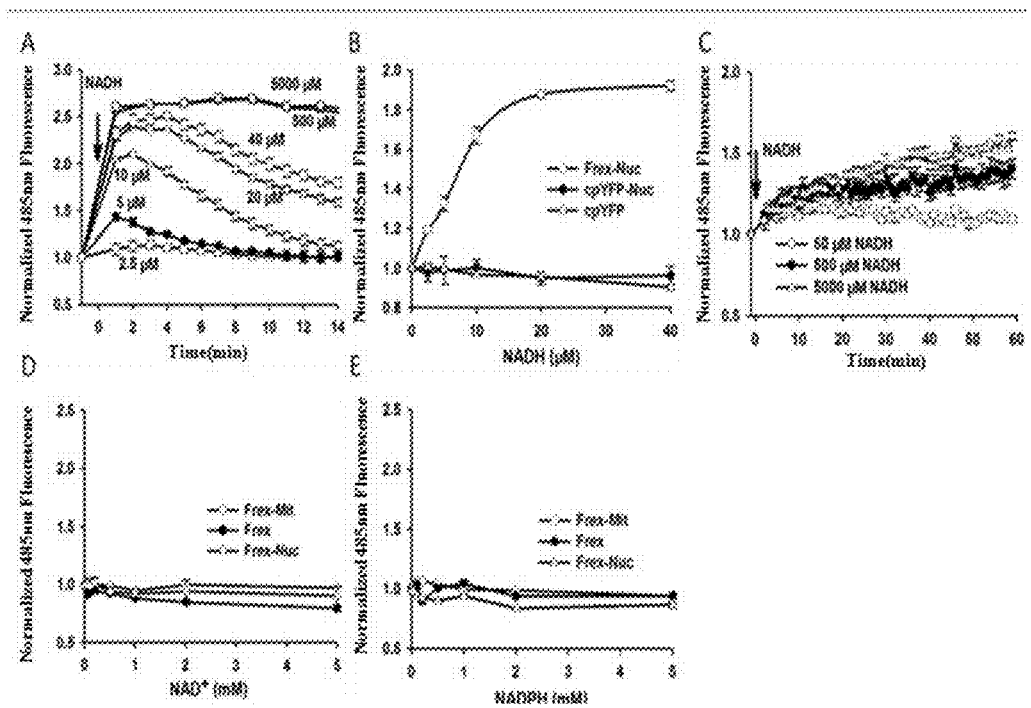
Figures 2, 8:
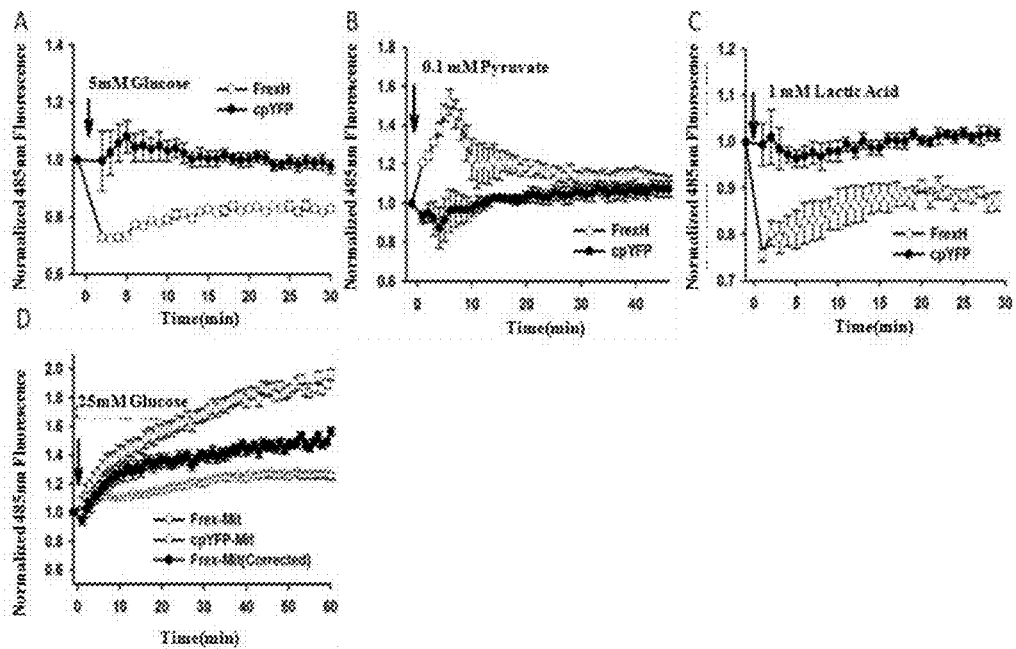
Figures 3, 8:
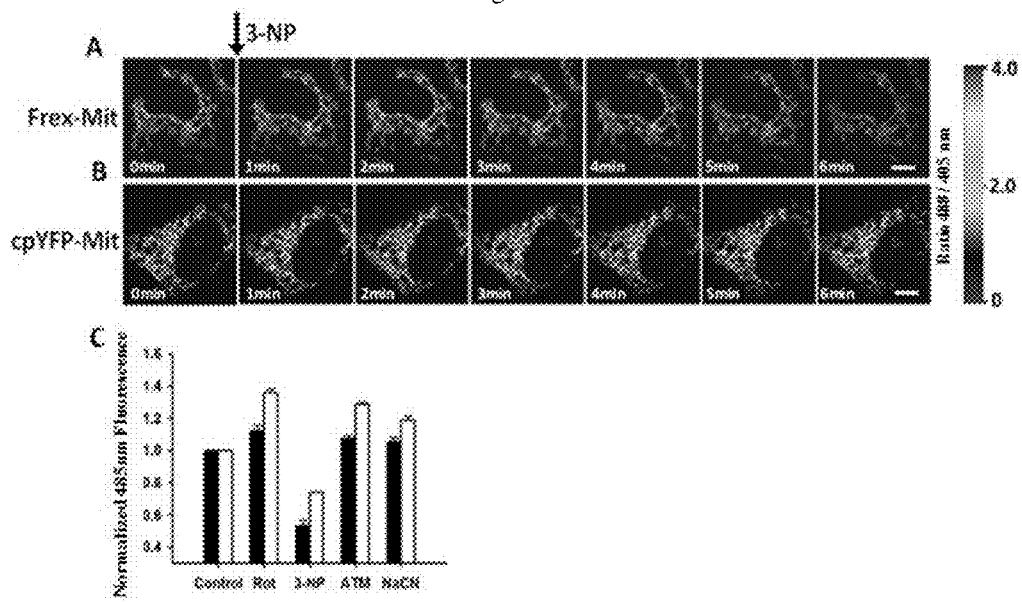

As described in Example 7, the fluorescence sensors for reduced nicotinamide adenine dinucleotide were expressed in different subcellular organelles of 293FT cells. Results showed that this series of sensors are capable of detecting, in real time, the changes in intracellular NADH levels upon the addition of external NADH in cell culture medium (FIG. 8-1A). Following the addition of external NADH into cell culture medium, transfected cells were observed under a laser scanning confocal microscope (Nikon, Japan). The results indicated that, the emission fluorescence at 528 nm upon 485 nm excitation of the sensor was 2.5 times stronger than that of the control group, proving NADH could enter cells across the membrane and lead to the immediate increase of intracellular NADH levels; FIG. 8-1D and FIG. 8-1E showed that the fluorescence sensor for reduced nicotinamide adenine dinucleotide was not interfered by NADH analogs such as $NAD^+$, NADPH, etc. As to the control group in comparison, the cpYFP presented alone was not affected by extra NADH either. Therefore, effects of pH and the variation in cpYFP per se by environmental changes could be excluded. This series of sensors were further utilized to detect influences of extra NADH on other organelles, and observed that extra NADH could also increase the NADH levels in nucleus and mitochondria, the results for nucleus study are shown in FIG. 8-1B, and those for mitochondria study are shown in FIG. 8-1C. In conclusion, our results indicated that fluorescent sensors for nicotinamide adenine dinucleotide could serve as a good gauge for the increase of NADH levels in mammalian cells upon the transmembrane entrance of NADH.

(2) Fluorescent sensor for nicotinamide adenine dinucleotide used in real-time measurements of NADH levels in different subcellular compartments regulated by glucose, pyruvate and lactate.

Glycolysis is an important pathway of producing NADH and it plays a vital role in regulating intracellular NADH levels. The nicotinamide adenine dinucleotide fluorescent sensors were used to test how several important metabolites in this pathway, glucose, pyruvate and lactate, would influence the NADH levels in different subcellular compartments. FIG. 8-2A shows results within cytoplasm and FIG. 8-2D shows results within mitochondria. These results indicated that, as one source of cellular energy, glucose could lead to the increase the cytoplasmic and mitochondrial levels of NADH. As products of glycolysis pathway, pyruvate and lactate are presented in the cytoplasm with a dynamic balance between them. At increased intracellular levels of pyruvate, lactate dehydrogenase consumes NADH and produces lactate and $NAD^+$, and in turn, leads to the decrease of NADH levels in cytoplasm. At increased intracellular levels of lactate, lactate dehydrogenase consumes $NAD^+$ and produces pyruvate and NADH, and in turn, leads to the increase of NADH levels in cytoplasm. FIG. 8-2B shows that pyruvate could cause a rapid decline of NADH levels in cytoplasm, but it resumed to normal levels over time. FIG. 8-2C shows that lactate could cause a rapid increase of NADH levels in cytoplasm, but also resumed to normal levels over time. In conclusion, these results demonstrated that the fluorescence sensors for nicotinamide adenine dinucleotide could monitor, in real-time, the regulated dynamic balance of NADH levels in cytoplasm.

(3) Fluorescent sensors for reduced nicotinamide adenine dinucleotide used in real-time detection of NADH levels in mitochondria regulated by oxidative phosphorylation pathway.

NADH that produced via glycolysis pathway and tricarboxylic acid cycle pathway will be oxidized by the oxidative phosphorylation pathway of mitochondrial respiratory chain, and then generate ATP to provide energy for various life activities. Fluorescent sensors for nicotinamide adenine dinucleotide were used to measure changes of NADH levels in mitochondria when various complexes in the respiratory chain were inhibited. FIG. 8-3A shows a 6-minute dynamic profile of the NADH sensor, which was expressed in mitochondria, upon 3-NP treatment. FIG. 8-3B shows a 6-minute dynamic profile of the control protein cpYFP, which was expressed in mitochondria, upon 3-NP treatment. Time interval between the figures was 1 min. The cells were observed before and after treatment under a laser scanning confocal microscope (Nikon, Japan). Results showed that, complex II inhibitor 3-NP caused a greatly decline of NADH levels in mitochondrial because of inhibited TCA cycle, whereas in the control group, cpYFP showed no obvious change. FIG. 8-3C shows the measurement of the effect of other complex inhibitors on NADH levels in mitochondria using fluorescent sensor for nicotinamide adenine dinucleotide. Results showed that, upon treated with complex I inhibitor rotenone, complex III inhibitor antimycin A, and complex IV inhibitor NaCN, respectively, for 30 min, the fluorescence (ex 485, em 528) of the sensor was increased, indicating that these inhibitors prevented the oxidation of NADH by inhibiting oxidative phosphorylation pathway, thus, led to the increase of NADH levels in mitochondria (FIG. 8-3C).

Example 9

Figures 1, 9:
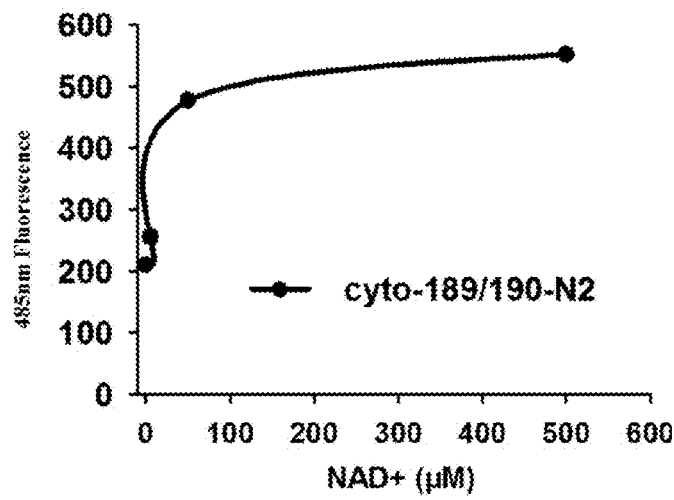
Figures 2, 9:
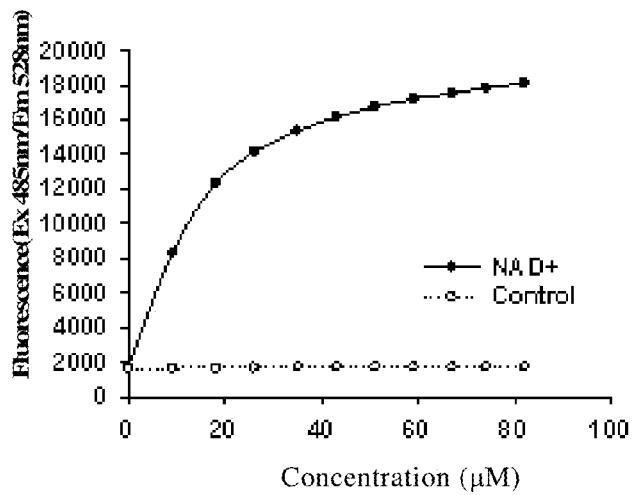
Figures 3, 9:
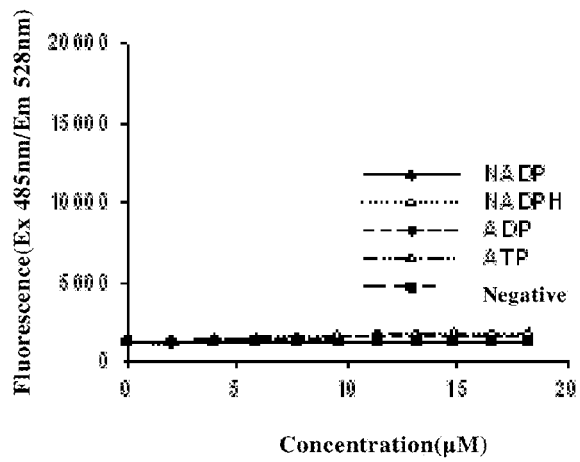

Measurement of Changes in Intracellular $NAD^+$ Level by Fluorescent Sensors for Oxidized Nicotinamide Adenine Dinucleotide Fluorescent sensor for oxidized nicotinamideadenine dinucleotide has a structure with cpYFP inserted into Trex between two amino acids, F189 and L190. The sequence of said sensor is SEQ ID NO: 129. Said sensor was prepared as described in Example 4. By expressing said sensors in cytoplasm of 293FT cells, we found that real-time monitor of the effects on intracellular NAD levels of adding $NAD^+$ into cell culture medium could be well achieved using this series of sensors (FIG. 9-1). As shown in FIG. 9-1, upon the addition of external $NAD^+$ into cell culture medium, the fluorescence of 528 nm emission upon 485 nm excitation was rapidly enhanced by about 2.8 times, proving that fluorescence sensor for oxidized nicotinamide adenine dinucleotide is a good gauge for the increase of $NAD^+$ levels in mammalian cells upon the transmembrane entrance of $NAD^+$. In protein detection with single channel 485 nm excitation and 528 nm emission, Frex-2 sensors responded to $NAD^+$ by about 1000% (FIG. 9-2), while they exhibited no response to NADP, NADPH, ADP and ATP (FIG. 9-3).

Example 10

Figures 1, 10:
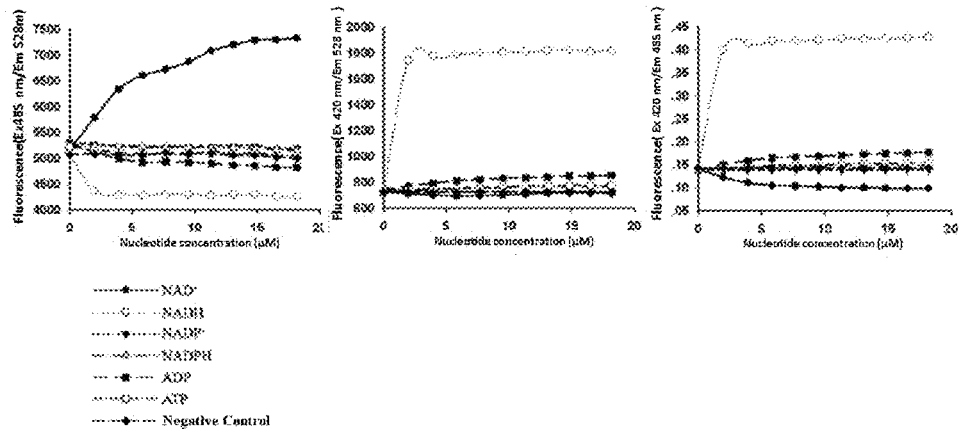
Figures 2, 10:
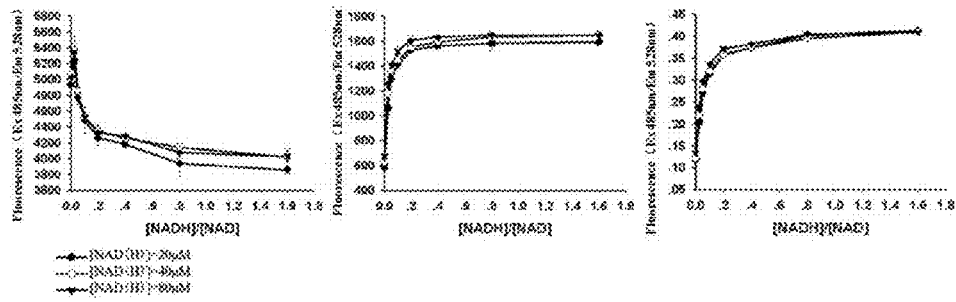
Figures 3, 10:
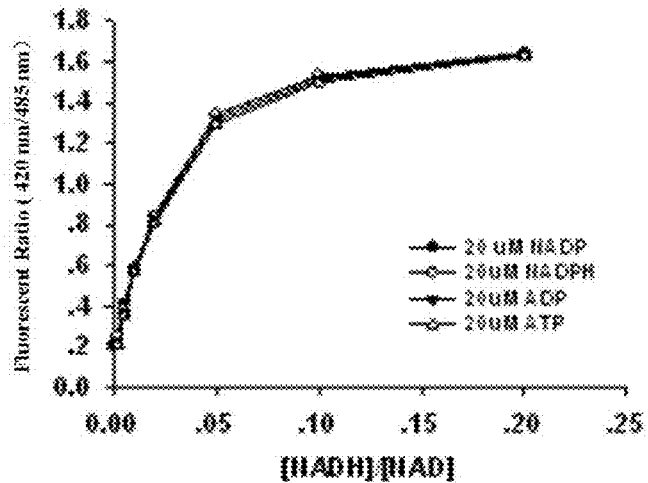

Measurement of Changes in NADH/NAD+ Ratio by Fluorescent Sensors for Reduced/Oxidized Nicotinamide Adenine Dinucleotide Ratio Fluorescent sensor for reduced/oxidized nicotinamide adenine dinucleotide ratio has a structure with cpYFP inserted into Trex between two amino acids, F189 and L190. The sequence of said sensor is SEQ ID NO: 148. Said sensor was prepared as described in Example 4. Said sensor exhibited response only to NADH and NAD+, but no response to NADH analogs. Upon 485 nm excitation, binding with NADH and NAD+ could both lead increased fluorescence emission at 528 nm. However, upon 420 nm excitation, said sensor could only respond to NADH binding. Since 420 nm and 485 nm excitation could both produce emission fluorescence at 528 nm, different excitation wavelengths could be used to measure the ratio of fluorescence intensity emitted at 528 nm (420 nm/485 nm), it has been found that NADH binding increases the response in said fluorescence ratio, while NAD+ binding decreases the response in said fluorescence ratio (FIG. 10-1). This pattern is more evident when the total concentration of NADH and NAD+ remained unchanged, but would not change with the total concentration per se (FIG. 10-2).

Figure 3:
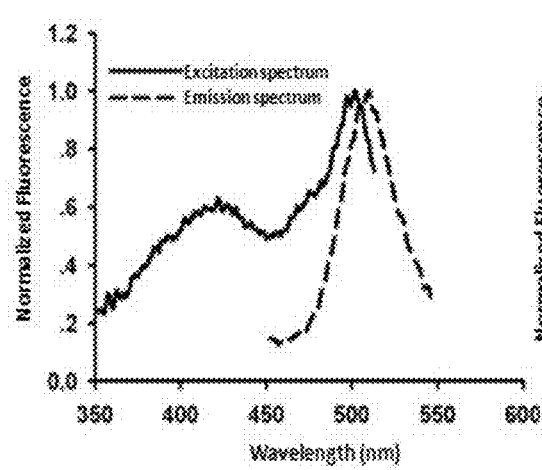
FIG. 3 shows basic spectral characteristics of the nicotinamide adenine dinucleotide fluorescent sensor F-rex1.
Figure 3:
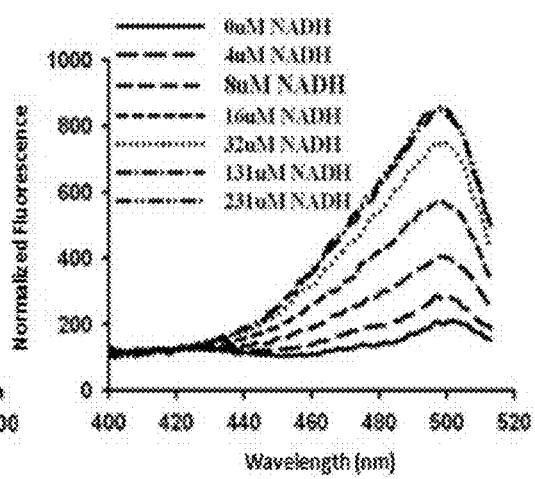

At the presence of 20 uM NADP, NADPH, ADP and ATP, titration of [NADH]/[NAD+] at indicated ratio was conducted, we could find the responsive value and variation pattern were not affected, indicating that NADP, NADPH, ADP and ATP have no effect on the sensor (FIG. 10-3).

Therefore, said sensor could be used not only as a sensor for reduced/oxidized nicotinamide adenine dinucleotide ratio but also a sensor for reduced nicotinamide adenine dinucleotide alone.

Example 11

High-Throughput Drug Screening Based on Fluorescence Sensor for Reduced/Oxidized Nicotinamide Adenine Dinucleotide Ratio It is generally believed that there is a dynamic balance between the concentration of pyruvate and lactate in cytoplasm and the concentration of free NADH and NAD+ in cytoplasm. In healthy tissues, pyruvate produced by glycolysis mainly enters mitochondria to participate TCA cycle and eventually generates a large amount of energy through oxidative phosphorylation. But in malignant tissues, pyruvate is mainly reduced to lactate by lactate dehydrogenase, accompanied by oxidizing NADH to NAD+. We developed a new method of high-throughput drug screening based the metabolic variation using superFrex, a fluorescent sensor for reduced/oxidized nicotinamide adenine dinucleotide ratio.

Figure 11:
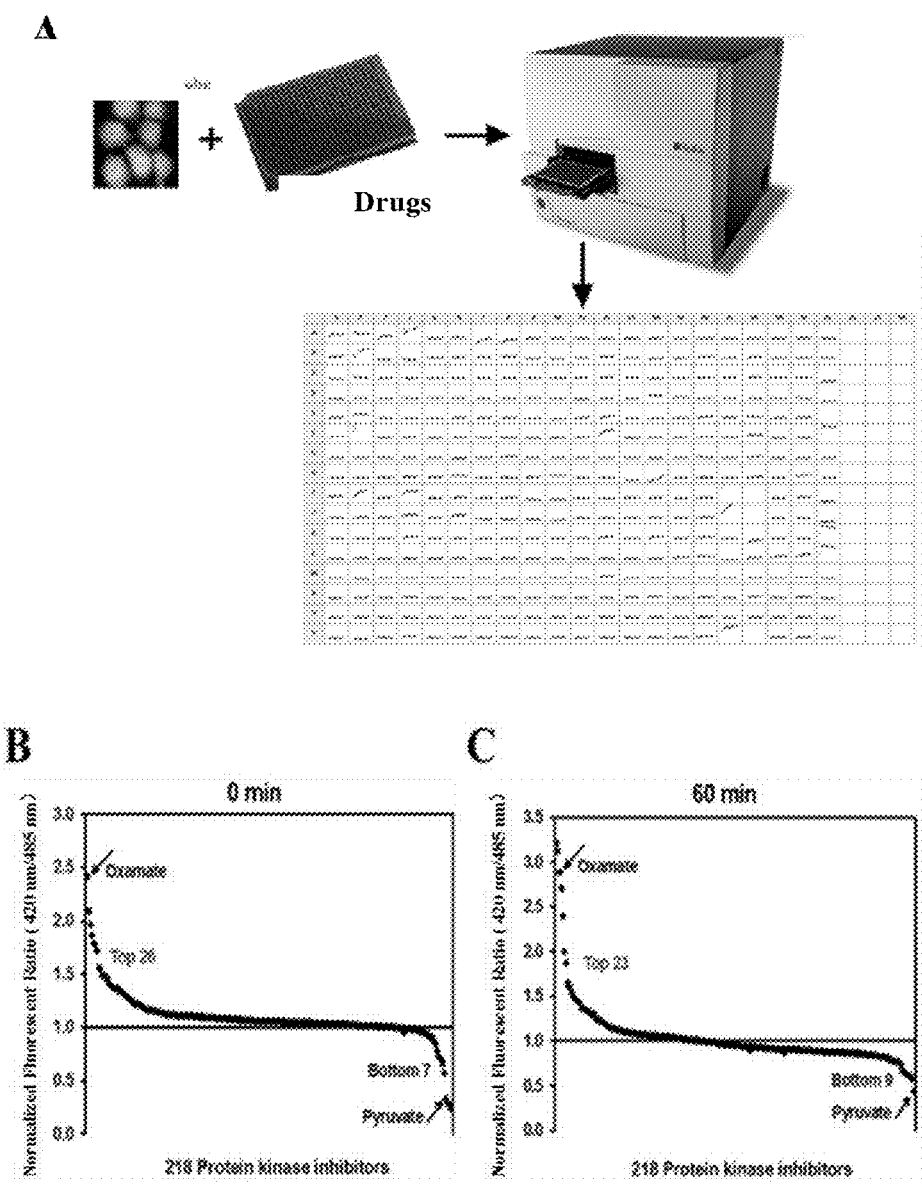
FIG. 11 shows a high-throughput drug screening scheme based on the sensor for NADH/NAD⁺ ratio fluorescence.

Stable cell lines expressing superFrex were mixed with different agents, then loaded into a black 384-well plate, and the fluorescence of superFrex was measured with a Multifunctional Microplate Reader (FIG. 11-A). For instance, from Merck's Protein kinase inhibitor compound library, we discovered 23-26 compounds increasing the ratio of intracellular lactate/pyruvate, and 7-9 compounds reducing the ratio of intracellular lactate/pyruvate (FIG. 11-B, 11-C). By further analyzing these compounds for the effect on the proliferation of normal cells and tumor cells, several lead compounds were eventually identified. These lead compounds could, at a certain dose range, effectively kill tumor cells but exhibited no toxicity to normal cells, therefore, has the potential to be developed as anticancer drugs.

Example 12

Measurement of NADH Metabolism in Tumor Cells Using Fluorescent Sensor for Reduced/Oxidized Nicotinamide Adenine Dinucleotide Ratio H1299 tumor cells were transfected with pcDNA3.1-cyt-superFrex, and then screened under Hygromycin B for 2 weeks. Single clones of H1299 stable cell lines that exhibiting robuse expression of superFrex were obtained by flow cytometry sorting (H1299-superFrex). Male nude mice of 5-6 weeks old were subcutaneously injected with 200 μl of H1299-superFrex cell suspension ($1.0 \times 10^7$ cells) into their right armpits and housed for 3-4 weeks at SPF Animal facility, tumors in the nude mice grew to 0.6-1.0 cm. The nude mice were anaesthetized and then injected with 300 μl of sodium pyruvate (100 mM) via the tail vein. Effects of the agent on tumor metabolism were observed immediately with Kodak multifunctional vivo imaging system (Carestream, USA). Experimental results showed that, pyruvate resulted a quick decrease in the fluorescence of 420 nm channel of superFrex in tumor tissues, and a quick increase in the fluorescence of 490 nm channel of superFrex, leading to a decrease in ratio 420/490 nm (FIG. 12-A). As the experimental control, tumor cells expressing cpYFP exhibited no difference caused thereby (FIG. 12-B), indicating pyruvate caused the decrease of NADH/NAD+ ratios in tumor cells. Over time, pyruvate was gradually consumed metabolically, and the ratio of NADH/NAD+ in tumor cells resumed the initial level (FIG. 12-C). In summary, superFrex, the fluorescent sensor for reduced/oxidized nicotinamide adenine dinucleotide ratio, works well in real-time monitoring of the NADH metabolism in tumor tissues.

Other Embodiments

A number of embodiments are described herein. However, it should be understood that, in view of this specification, variations and modifications will be apparent to those skilled in the art, without departing from the spirit and scope of the invention. Therefore, these alternative embodiments are also included within the scope of the appended claims.

What is claimed is:

1. A genetically encoded fluorescent sensor for NADH, said fluorescent sensor being a fusion protein comprising (a) a polypeptide sensitive to environmental NADH, and (b) a segment that exhibits the environmental NADH by change in its spectral characteristics,
wherein the polypeptide sensitive to NADH is:
(1) a polypeptide derived from ydiH, a bacterial transcription factor Rex protein, wherein the polypeptide is encoded by a sequence selected from SEQ ID NO: 1 or 3;
(2) a homologous or non-homologous sequence that is 95% identical to the sequence of (1); or
(3) a homologous or non-homologous sequence that is 90% identical to the sequence of (1);
a NADH binding fragment or NADH binding domain thereof; and
wherein the segment that exhibits the environmental NADH by change in the spectral characteristic is a fluorescent protein sequence or a derivative thereof and is inserted between residue 189 and residue 190 of the polypeptide encoded by SEQ ID NO: 1 or between full length of the polypeptide encoded by SEQ ID NO: 3 and residues 85-215 of the polypeptide encoded by SEQ ID NO: 3.

2. The fluorescent sensor for NADH according to claim 1, wherein the fluorescent sensor comprises:
   (1) an amino acid sequence selected from the group consisting of SEQ ID NO: 4, 5, 6, 7, and 8;
   (2) a homologous or non-homologous sequence that is 95% identical to the sequence of (1); or
   (3) a homologous or non-homologous sequence that is 90% identical to the sequence of (1).

3. The fluorescent sensor according to claim 1, wherein the fluorescent sensor further comprises specific subcellular localization signal, wherein the localization signal allows localization of a target protein into a specified subcellular organelle.

4. A kit for detection of NADH, drug screening or disease diagnosis, comprising the fluorescent sensor according to claim 1.

* * * * *

SEQUENCE LISTING

<160> NUMBER OF SEQ ID NOS: 159

<210> SEQ ID NO 1
<211> LENGTH: 636
<212> TYPE: DNA

<213> ORGANISM: Thermus aquaticus

<400> SEQUENCE: 1

| | | | | | | |
|---|---|---|---|---|---|---|
| atgaaggtcc | ccgaagcggc | catcagccgc | ctgatcacct | acctccgcat | cttggaggag | 60 |
| ctggaggccc | aggggggttca | ccggacgagc | tccgagcagc | ttggggagct | cgcccaggtc | 120 |
| acggccttcc | aggtgcggaa | ggacctttcc | tacttcggct | cctacgggac | gcgcggggtg | 180 |
| gggtacaccg | tccccgtcct | gaagcggag | ctccgccaca | tcctgggct | caaccgcaag | 240 |
| tggggcctgt | gcatcgtggg | catgggccgg | ctcgggagcg | ccctggccga | ctacccgggg | 300 |
| ttcggggaga | gctttgagct | taggggcttc | tttgacgtgg | accggagaa | ggtgggccgc | 360 |
| ccggtgcggg | gcggggtcat | tgagcacgtg | gacctcctgc | ccagcgggt | tcccggccgc | 420 |
| attgagatcg | ccctcctcac | cgtgccccgg | gaagcggccc | agaaggcggc | ggacctgttg | 480 |
| gtggcggcgg | ggatcaaggg | gatcctgaac | ttcccccgg | tggtcctcga | ggtgcccaag | 540 |
| gaggtggcgg | tggagaacgt | ggacttcttg | gcggggctca | cgcggctttc | tttcgctatc | 600 |
| ctgaaccca | agtggcggga | agagatgatg | gggtga | | | 636 |

<210> SEQ ID NO 2
<211> LENGTH: 777
<212> TYPE: DNA
<213> ORGANISM: Streptomyces coelicolor A3(2)

<400> SEQUENCE: 2

| | | | | | | |
|---|---|---|---|---|---|---|
| atggcaactg | gccgagcaca | ccgaccggcg | acccgcagcc | gagggattcc | cgaggccacc | 60 |
| gtcgccaggc | ttccgctgta | cctccgcgca | ctgaccgcgc | tgtccgagcg | ctcggtgccc | 120 |
| acggtctcct | ccgaggagct | ggcggccgcc | gcggggtca | actccgcgaa | gctgcgcaag | 180 |
| gacttctcct | acctcggctc | ctacgggacc | cgcggtgtcg | gctacgacgt | cgagtatctc | 240 |
| gtctaccaga | tctcgcgcga | actcggcctc | acccaggact | ggccggttgt | gatcgtcggt | 300 |
| atcggcaacc | tcggtgccgc | gctcgccaac | tacggtggtt | cgcctcccg | cgggttccgc | 360 |
| gtcgccgcgc | tcatcgacgc | cgatccggga | atggccggaa | agcccgtcgc | cggcatcccg | 420 |
| gtgcagcaca | ccgacgagct | ggagaagatc | atccaggacg | acggtgtctc | gatcggtgtg | 480 |
| atcgcgaccc | ccgccggcgc | cgcccagcag | gtctgcgacc | gcctcgtggc | cgccggtgtc | 540 |
| acctccatcc | tgaacttcgc | gccgaccgtg | ctgaacgtcc | cgagggcgt | cgacgtgcgc | 600 |
| aaggtcgacc | tctccatcga | gctgcagatc | ctcgccttcc | acgagcagcg | caaggcgggc | 660 |
| gaggaggccg | cggccgacgg | cgccgcaccg | ccgtcgccg | ccgcaagca | gcagcgctcc | 720 |
| accggctccg | ccgaccaggg | acccgacggg | gacgtacccg | ccgtgatgcc | ggcatga | 777 |

<210> SEQ ID NO 3
<211> LENGTH: 648
<212> TYPE: DNA
<213> ORGANISM: Bacillus subtilis strain 168

<400> SEQUENCE: 3

| | | | | | | |
|---|---|---|---|---|---|---|
| atgaataagg | atcaatcaaa | aattccgcag | gcgacggcga | aacggctgcc | gctttactat | 60 |
| cgcttttaa | agaatctgca | tgcgtcagga | aaacagcgtg | tatcatccgc | tgaactcagt | 120 |
| gatgccgtaa | aggttgattc | tgccacgatt | cggagggatt | tttcctattt | tggagctctt | 180 |
| ggcaaaaaag | gatacggata | taatgtggat | tatttgctgt | cttttttccg | gaaaacgctt | 240 |
| gatcaggatg | agatgacaga | cgtcatcttg | attggtgtcg | ggaacttggg | aacggcattt | 300 |
| cttcactata | atttcacaaa | aaacaataac | acaaaaattt | ctatggcttt | tgatataaat | 360 |

-continued

```
gagagtaaaa taggaactga ggtaggcggc gtgcccgtct ataaccttga tgaccttgaa    420
caacacgtaa aagatgaatc agttgccatt cttacagtgc cagcagttgc cgctcaatcc    480
attacagaca gattggtcgc attaggaatc aagggaatcc ttaattttac gccggcccgt    540
ttgaatgtgc cggaacacat tcgaattcat catatagatt tagcagttga gcttcagtca    600
ctggtttatt ttttgaagca ttattcagtt ttagaggaaa tcgaatag                 648
```

```
<210> SEQ ID NO 4
<211> LENGTH: 629
<212> TYPE: PRT
<213> ORGANISM: artificial sequence
<220> FEATURE:
<223> OTHER INFORMATION: synthetic fluorescent sensor

<400> SEQUENCE: 4
```

| | | | | | | | | | | | | | | |
|---|---|---|---|---|---|---|---|---|---|---|---|---|---|---|
| Met | Arg | Gly | Ser | His | His | His | His | His | Gly | Met | Ala | Ser | Met | Thr |
| 1 | | | | 5 | | | | | 10 | | | | | 15 |
| Gly | Gly | Gln | Gln | Met | Gly | Arg | Asp | Leu | Tyr | Asp | Asp | Asp | Lys | Asp |
| | | | 20 | | | | | 25 | | | | | 30 | |
| Pro | Met | Asn | Lys | Asp | Gln | Ser | Lys | Ile | Pro | Gln | Ala | Thr | Ala | Lys | Arg |
| | | | 35 | | | | | 40 | | | | | 45 | | |
| Leu | Pro | Leu | Tyr | Tyr | Arg | Phe | Leu | Lys | Asn | Leu | His | Ala | Ser | Gly | Lys |
| | 50 | | | | | 55 | | | | | 60 | | | | |
| Gln | Arg | Val | Ser | Ser | Ala | Glu | Leu | Ser | Asp | Ala | Val | Lys | Val | Asp | Ser |
| 65 | | | | | 70 | | | | | 75 | | | | | 80 |
| Ala | Thr | Ile | Arg | Arg | Asp | Phe | Ser | Tyr | Phe | Gly | Ala | Leu | Gly | Lys | Lys |
| | | | | 85 | | | | | 90 | | | | | 95 | |
| Gly | Tyr | Gly | Tyr | Asn | Val | Asp | Tyr | Leu | Leu | Ser | Phe | Phe | Arg | Lys | Thr |
| | | | 100 | | | | | 105 | | | | | 110 | | |
| Leu | Asp | Gln | Asp | Glu | Met | Thr | Asp | Val | Ile | Leu | Ile | Gly | Val | Gly | Asn |
| | | 115 | | | | | 120 | | | | | 125 | | | |
| Leu | Gly | Thr | Ala | Phe | Leu | His | Tyr | Asn | Phe | Thr | Lys | Asn | Asn | Asn | Thr |
| | 130 | | | | | 135 | | | | | 140 | | | | |
| Lys | Ile | Ser | Met | Ala | Phe | Asp | Ile | Asn | Glu | Ser | Lys | Ile | Gly | Thr | Glu |
| 145 | | | | | 150 | | | | | 155 | | | | | 160 |
| Val | Gly | Gly | Val | Pro | Val | Tyr | Asn | Leu | Asp | Asp | Leu | Glu | Gln | His | Val |
| | | | | 165 | | | | | 170 | | | | | 175 | |
| Lys | Asp | Glu | Ser | Val | Ala | Ile | Leu | Thr | Val | Pro | Ala | Val | Ala | Ala | Gln |
| | | | 180 | | | | | 185 | | | | | 190 | | |
| Ser | Ile | Thr | Asp | Arg | Leu | Val | Ala | Leu | Gly | Ile | Lys | Gly | Ile | Leu | Asn |
| | | 195 | | | | | 200 | | | | | 205 | | | |
| Phe | Thr | Pro | Ala | Arg | Leu | Asn | Val | Pro | Glu | His | Ile | Arg | Ile | His | His |
| | 210 | | | | | 215 | | | | | 220 | | | | |
| Ile | Asp | Leu | Ala | Val | Glu | Leu | Gln | Ser | Leu | Val | Tyr | Phe | Leu | Lys | His |
| 225 | | | | | 230 | | | | | 235 | | | | | 240 |
| Tyr | Ser | Val | Leu | Glu | Glu | Ile | Glu | Thr | Ser | Tyr | Asn | Ser | Asp | Asn | Val |
| | | | | 245 | | | | | 250 | | | | | 255 | |
| Tyr | Ile | Met | Ala | Asp | Lys | Gln | Lys | Asn | Gly | Ile | Lys | Ala | Asn | Phe | Lys |
| | | | 260 | | | | | 265 | | | | | 270 | | |
| Ile | Arg | His | Asn | Val | Glu | Asp | Gly | Ser | Val | Gln | Leu | Ala | Asp | His | Tyr |
| | | 275 | | | | | 280 | | | | | 285 | | | |
| Gln | Gln | Asn | Thr | Pro | Ile | Gly | Asp | Gly | Pro | Val | Leu | Leu | Pro | Asp | Asn |
| | 290 | | | | | 295 | | | | | 300 | | | | |
| His | Tyr | Leu | Ser | Phe | Gln | Ser | Val | Leu | Ser | Lys | Asp | Pro | Asn | Glu | Lys |

-continued

```
            305                 310                 315                 320
        Arg Asp His Met Val Leu Leu Glu Phe Val Thr Ala Ala Gly Ile Thr
                        325                 330                 335
        Leu Gly Met Asp Glu Leu Tyr Asn Val Asp Gly Ser Gly Gly Thr
                        340                 345                 350
        Gly Ser Lys Gly Glu Glu Leu Phe Thr Gly Val Val Pro Ile Leu Val
                        355                 360                 365
        Glu Leu Asp Gly Asp Val Asn Gly His Lys Phe Ser Val Ser Gly Glu
                    370                 375                 380
        Gly Glu Gly Asp Ala Thr Tyr Gly Lys Leu Thr Leu Lys Leu Ile Cys
        385                 390                 395                 400
        Thr Thr Gly Lys Leu Pro Val Pro Trp Pro Thr Leu Val Thr Thr Leu
                        405                 410                 415
        Gly Tyr Gly Leu Lys Cys Phe Ala Arg Tyr Pro Asp His Met Lys Gln
                        420                 425                 430
        His Asp Phe Phe Lys Ser Ala Met Pro Glu Gly Tyr Val Gln Glu Arg
                    435                 440                 445
        Thr Ile Phe Phe Lys Asp Asp Gly Asn Tyr Lys Thr Arg Ala Glu Val
                    450                 455                 460
        Lys Phe Glu Gly Asp Thr Leu Val Asn Arg Ile Glu Leu Lys Gly Ile
        465                 470                 475                 480
        Gly Phe Lys Glu Asp Gly Asn Ile Leu Gly His Lys Leu Glu Tyr Asn
                        485                 490                 495
        Gly Thr Met Thr Asp Val Ile Leu Ile Gly Val Gly Asn Leu Gly Thr
                        500                 505                 510
        Ala Phe Leu His Tyr Asn Phe Thr Lys Asn Asn Thr Lys Ile Ser
                        515                 520                 525
        Met Ala Phe Asp Ile Asn Glu Ser Lys Ile Gly Thr Glu Val Gly Gly
                    530                 535                 540
        Val Pro Val Tyr Asn Leu Asp Asp Leu Glu Gln His Val Lys Asp Glu
        545                 550                 555                 560
        Ser Val Ala Ile Leu Thr Val Pro Ala Val Ala Gln Ser Ile Thr
                        565                 570                 575
        Asp Arg Leu Val Ala Leu Gly Ile Lys Gly Ile Leu Asn Phe Thr Pro
                        580                 585                 590
        Ala Arg Leu Asn Val Pro Glu His Ile Arg Ile His His Ile Asp Leu
                    595                 600                 605
        Ala Val Glu Leu Gln Ser Leu Val Tyr Phe Leu Lys His Tyr Ser Val
                    610                 615                 620
        Leu Glu Glu Ile Glu
        625

<210> SEQ ID NO 5
<211> LENGTH: 897
<212> TYPE: PRT
<213> ORGANISM: artificial sequence
<220> FEATURE:
<223> OTHER INFORMATION: amino acid sequence of synthetic fluorescent
      sensor Frex

<400> SEQUENCE: 5

Met Asn Lys Asp Gln Ser Lys Ile Pro Gln Ala Thr Ala Lys Arg Leu
1               5                   10                  15
Pro Leu Tyr Tyr Arg Phe Leu Lys Asn Leu His Ala Ser Gly Lys Gln
            20                  25                  30
```

-continued

```
Arg Val Ser Ser Ala Glu Leu Ser Asp Ala Val Lys Val Asp Ser Ala
         35                  40                  45

Thr Ile Arg Arg Asp Phe Ser Tyr Phe Gly Ala Leu Gly Lys Lys Gly
 50                  55                  60

Tyr Gly Tyr Asn Val Asp Tyr Leu Leu Ser Phe Phe Arg Lys Thr Leu
 65                  70                  75                  80

Asp Gln Asp Glu Met Thr Asp Val Ile Leu Ile Gly Val Gly Asn Leu
                 85                  90                  95

Gly Thr Ala Phe Leu His Tyr Asn Phe Thr Lys Asn Asn Asn Thr Lys
            100                 105                 110

Ile Ser Met Ala Phe Asp Ile Asn Glu Ser Lys Ile Gly Thr Glu Val
        115                 120                 125

Gly Gly Val Pro Val Tyr Asn Leu Asp Asp Leu Glu Gln His Val Lys
130                 135                 140

Asp Glu Ser Val Ala Ile Leu Thr Val Pro Ala Val Ala Ala Gln Ser
145                 150                 155                 160

Ile Thr Asp Arg Leu Val Ala Leu Gly Ile Lys Gly Ile Leu Asn Phe
                165                 170                 175

Thr Pro Ala Arg Leu Asn Val Pro Glu His Ile Arg Ile His His Ile
            180                 185                 190

Asp Leu Ala Val Glu Leu Gln Ser Leu Val Tyr Phe Leu Lys His Tyr
        195                 200                 205

Ser Val Leu Glu Glu Ile Glu Thr Ser Tyr Asn Ser Asp Asn Val Tyr
210                 215                 220

Ile Met Ala Asp Lys Gln Lys Asn Gly Ile Lys Ala Asn Phe Lys Ile
225                 230                 235                 240

Arg His Asn Val Glu Asp Gly Ser Val Gln Leu Ala Asp His Tyr Gln
                245                 250                 255

Gln Asn Thr Pro Ile Gly Asp Gly Pro Val Leu Leu Pro Asp Asn His
            260                 265                 270

Tyr Leu Ser Phe Gln Ser Val Leu Ser Lys Asp Pro Asn Glu Lys Arg
        275                 280                 285

Asp His Met Val Leu Leu Glu Phe Val Thr Ala Ala Gly Ile Thr Leu
290                 295                 300

Gly Met Asp Glu Leu Tyr Asn Val Asp Gly Gly Ser Gly Gly Thr Gly
305                 310                 315                 320

Ser Lys Gly Glu Glu Leu Phe Thr Gly Val Val Pro Ile Leu Val Glu
                325                 330                 335

Leu Asp Gly Asp Val Asn Gly His Lys Phe Ser Val Ser Gly Glu Gly
            340                 345                 350

Glu Gly Asp Ala Thr Tyr Gly Lys Leu Thr Leu Lys Leu Ile Cys Thr
        355                 360                 365

Thr Gly Lys Leu Pro Val Pro Trp Pro Thr Leu Val Thr Thr Leu Gly
370                 375                 380

Tyr Gly Leu Lys Cys Phe Ala Arg Tyr Pro Asp His Met Lys Gln His
385                 390                 395                 400

Asp Phe Phe Lys Ser Ala Met Pro Glu Gly Tyr Val Gln Glu Arg Thr
                405                 410                 415

Ile Phe Phe Lys Asp Asp Gly Asn Tyr Lys Thr Arg Ala Glu Val Lys
            420                 425                 430

Phe Glu Gly Asp Thr Leu Val Asn Arg Ile Glu Leu Lys Gly Ile Gly
        435                 440                 445

Phe Lys Glu Asp Gly Asn Ile Leu Gly His Lys Leu Glu Tyr Asn Gly
```

-continued

```
                450             455             460
Thr Met Asn Lys Asp Gln Ser Lys Ile Pro Gln Ala Thr Ala Lys Arg
465                 470                 475                 480

Leu Pro Leu Tyr Tyr Arg Phe Leu Lys Asn Leu His Ala Ser Gly Lys
                485                 490                 495

Gln Arg Val Ser Ser Ala Glu Leu Ser Asp Ala Val Lys Val Asp Ser
                500                 505                 510

Ala Thr Ile Arg Arg Asp Phe Ser Tyr Phe Gly Ala Leu Gly Lys Lys
                515                 520                 525

Gly Tyr Gly Tyr Asn Val Asp Tyr Leu Leu Ser Phe Phe Arg Lys Thr
                530                 535                 540

Leu Asp Gln Asp Glu Met Thr Asp Val Ile Leu Ile Gly Val Gly Asn
545                 550                 555                 560

Leu Gly Thr Ala Phe Leu His Tyr Asn Phe Thr Lys Asn Asn Asn Thr
                565                 570                 575

Lys Ile Ser Met Ala Phe Asp Ile Asn Glu Ser Lys Ile Gly Thr Glu
                580                 585                 590

Val Gly Gly Val Pro Val Tyr Asn Leu Asp Asp Leu Glu Gln His Val
                595                 600                 605

Lys Asp Glu Ser Val Ala Ile Leu Thr Val Pro Ala Val Ala Ala Gln
610                 615                 620

Ser Ile Thr Asp Arg Leu Val Ala Leu Gly Ile Lys Gly Ile Leu Asn
625                 630                 635                 640

Phe Thr Pro Ala Arg Leu Asn Val Pro Glu His Ile Arg Ile His His
                645                 650                 655

Ile Asp Leu Ala Val Glu Leu Gln Ser Leu Val Tyr Phe Leu Lys His
                660                 665                 670

Tyr Ser Val Leu Glu Glu Ile Glu Lys Leu Met Asn Lys Asp Gln Ser
                675                 680                 685

Lys Ile Pro Gln Ala Thr Ala Lys Arg Leu Pro Leu Tyr Tyr Arg Phe
                690                 695                 700

Leu Lys Asn Leu His Ala Ser Gly Lys Gln Arg Val Ser Ser Ala Glu
705                 710                 715                 720

Leu Ser Asp Ala Val Lys Val Asp Ser Ala Thr Ile Arg Arg Asp Phe
                725                 730                 735

Ser Tyr Phe Gly Ala Leu Gly Lys Lys Gly Tyr Gly Tyr Asn Val Asp
                740                 745                 750

Tyr Leu Leu Ser Phe Phe Arg Lys Thr Leu Asp Gln Asp Glu Met Thr
                755                 760                 765

Asp Val Ile Leu Ile Gly Val Gly Asn Leu Gly Thr Ala Phe Leu His
                770                 775                 780

Tyr Asn Phe Thr Lys Asn Asn Asn Thr Lys Ile Ser Met Ala Phe Asp
785                 790                 795                 800

Ile Asn Glu Ser Lys Ile Gly Thr Glu Val Gly Gly Val Pro Val Tyr
                805                 810                 815

Asn Leu Asp Asp Leu Glu Gln His Val Lys Asp Glu Ser Val Ala Ile
                820                 825                 830

Leu Thr Val Pro Ala Val Ala Ala Gln Ser Ile Thr Asp Arg Leu Val
                835                 840                 845

Ala Leu Gly Ile Lys Gly Ile Leu Asn Phe Thr Pro Ala Arg Leu Asn
850                 855                 860

Val Pro Glu His Ile Arg Ile His His Ile Asp Leu Ala Val Glu Leu
865                 870                 875                 880
```

```
Gln Ser Leu Val Tyr Phe Leu Lys His Tyr Ser Val Leu Glu Glu Ile
            885                 890                 895

Glu

<210> SEQ ID NO 6
<211> LENGTH: 697
<212> TYPE: PRT
<213> ORGANISM: artificial sequence
<220> FEATURE:
<223> OTHER INFORMATION: amino acid sequence of synthetic fluorescent
      sensor Frex

<400> SEQUENCE: 6

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Phe Gly Tyr Gly Leu Met Cys Phe Ala Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Tyr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys Thr
225                 230                 235                 240

Ser Met Asn Lys Asp Gln Ser Lys Ile Pro Gln Ala Thr Ala Lys Arg
                245                 250                 255

Leu Pro Leu Tyr Tyr Arg Phe Leu Lys Asn Leu His Ala Ser Gly Lys
            260                 265                 270

Gln Arg Val Ser Ser Ala Glu Leu Ser Asp Ala Val Lys Val Asp Ser
        275                 280                 285

Ala Thr Ile Arg Arg Asp Phe Ser Tyr Phe Gly Ala Leu Gly Lys Lys
    290                 295                 300

Gly Tyr Gly Tyr Asn Val Asp Tyr Leu Leu Ser Phe Phe Arg Lys Thr
305                 310                 315                 320

Leu Asp Gln Asp Glu Met Thr Asp Val Ile Leu Ile Gly Val Gly Asn
                325                 330                 335
```

```
Leu Gly Thr Ala Phe Leu His Tyr Asn Phe Thr Lys Asn Asn Asn Thr
                340                 345                 350

Lys Ile Ser Met Ala Phe Asp Ile Asn Glu Ser Lys Ile Gly Thr Glu
            355                 360                 365

Val Gly Val Pro Val Tyr Asn Leu Asp Asp Leu Glu Gln His Val
370                 375                 380

Lys Asp Glu Ser Val Ala Ile Leu Thr Val Pro Ala Val Ala Ala Gln
385                 390                 395                 400

Ser Ile Thr Asp Arg Leu Val Ala Leu Gly Ile Lys Gly Ile Leu Asn
                405                 410                 415

Phe Thr Pro Ala Arg Leu Asn Val Pro Glu His Ile Arg Ile His His
                420                 425                 430

Ile Asp Leu Ala Val Glu Leu Gln Ser Leu Val Tyr Phe Leu Lys His
                435                 440                 445

Tyr Ser Val Leu Glu Glu Ile Glu Gly Thr Met Val Ser Lys Gly Glu
        450                 455                 460

Glu Leu Phe Thr Gly Val Val Pro Ile Leu Val Glu Leu Asp Gly Asp
465                 470                 475                 480

Val Asn Gly His Lys Phe Ser Val Ser Gly Glu Gly Glu Gly Asp Ala
                485                 490                 495

Thr Tyr Gly Lys Leu Thr Leu Lys Phe Ile Cys Thr Thr Gly Lys Leu
            500                 505                 510

Pro Val Pro Trp Pro Thr Leu Val Thr Thr Leu Thr Trp Gly Val Gln
                515                 520                 525

Cys Phe Ser Arg Tyr Pro Asp His Met Lys Gln His Asp Phe Phe Lys
530                 535                 540

Ser Ala Met Pro Glu Gly Tyr Val Gln Glu Arg Thr Ile Phe Phe Lys
545                 550                 555                 560

Asp Asp Gly Asn Tyr Lys Thr Arg Ala Glu Val Lys Phe Glu Gly Asp
                565                 570                 575

Thr Leu Val Asn Arg Ile Glu Leu Lys Gly Ile Asp Phe Lys Glu Asp
                580                 585                 590

Gly Asn Ile Leu Gly His Lys Leu Glu Tyr Asn Tyr Ile Ser His Asn
            595                 600                 605

Val Tyr Ile Thr Ala Asp Lys Gln Lys Asn Gly Ile Lys Ala Asn Phe
        610                 615                 620

Lys Ile Arg His Asn Ile Glu Asp Gly Ser Val Gln Leu Ala Asp His
625                 630                 635                 640

Tyr Gln Gln Asn Thr Pro Ile Gly Asp Gly Pro Val Leu Leu Pro Asp
                645                 650                 655

Asn His Tyr Leu Ser Thr Gln Ser Ala Leu Ser Lys Asp Pro Asn Glu
                660                 665                 670

Lys Arg Asp His Met Val Leu Leu Glu Phe Val Thr Ala Ala Gly Ile
            675                 680                 685

Thr Leu Gly Met Asp Glu Leu Tyr Lys
        690                 695

<210> SEQ ID NO 7
<211> LENGTH: 463
<212> TYPE: PRT
<213> ORGANISM: artificial sequence
<220> FEATURE:
<223> OTHER INFORMATION: amino acid sequence of synthetic fluorescent
      sensor Frex
```

```
<400> SEQUENCE: 7

Met Lys Val Pro Glu Ala Ala Ile Ser Arg Leu Ile Thr Tyr Leu Arg
1               5                   10                  15

Ile Leu Glu Glu Leu Glu Ala Gln Gly Val His Arg Thr Ser Ser Glu
            20                  25                  30

Gln Leu Gly Glu Leu Ala Gln Val Thr Ala Phe Gln Val Arg Lys Asp
        35                  40                  45

Leu Ser Tyr Phe Gly Ser Tyr Gly Thr Arg Gly Val Gly Tyr Thr Val
    50                  55                  60

Pro Val Leu Lys Arg Glu Leu Arg His Ile Leu Gly Leu Asn Arg Lys
65                  70                  75                  80

Trp Gly Leu Cys Ile Val Gly Met Gly Arg Leu Gly Ser Ala Leu Ala
                85                  90                  95

Asp Tyr Pro Gly Phe Gly Glu Ser Phe Glu Leu Arg Gly Phe Phe Asp
            100                 105                 110

Val Asp Pro Glu Lys Val Gly Arg Pro Val Arg Gly Val Ile Glu
        115                 120                 125

His Val Asp Leu Leu Pro Gln Arg Val Pro Gly Arg Ile Glu Ile Ala
130                 135                 140

Leu Leu Thr Val Pro Arg Glu Ala Ala Gln Lys Ala Ala Asp Leu Leu
145                 150                 155                 160

Val Ala Ala Gly Ile Lys Gly Ile Leu Asn Phe Ala Pro Val Val Leu
                165                 170                 175

Glu Val Pro Lys Glu Val Ala Val Glu Asn Val Asp Phe Ser Ala Gly
            180                 185                 190

Tyr Asn Ser Asp Asn Val Tyr Ile Met Ala Asp Lys Gln Lys Asn Gly
        195                 200                 205

Ile Lys Ala Asn Phe Lys Ile Arg His Asn Val Glu Asp Gly Ser Val
    210                 215                 220

Gln Leu Ala Asp His Tyr Gln Gln Asn Thr Pro Ile Gly Asp Gly Pro
225                 230                 235                 240

Val Leu Leu Pro Asp Asn His Tyr Leu Ser Phe Gln Ser Val Leu Ser
                245                 250                 255

Lys Asp Pro Asn Glu Lys Arg Asp His Met Val Leu Leu Glu Phe Val
            260                 265                 270

Thr Ala Ala Gly Ile Thr Leu Gly Met Asp Glu Leu Tyr Asn Val Asp
        275                 280                 285

Gly Gly Ser Gly Gly Thr Gly Ser Lys Gly Glu Glu Leu Phe Thr Gly
    290                 295                 300

Val Val Pro Ile Leu Val Glu Leu Asp Gly Asp Val Asn Gly His Lys
305                 310                 315                 320

Phe Ser Val Ser Gly Glu Gly Glu Gly Asp Ala Thr Tyr Gly Lys Leu
                325                 330                 335

Thr Leu Lys Leu Ile Cys Thr Thr Gly Lys Leu Pro Val Pro Trp Pro
            340                 345                 350

Thr Leu Val Thr Thr Leu Gly Tyr Gly Leu Lys Cys Phe Ala Arg Tyr
        355                 360                 365

Pro Asp His Met Lys Gln His Asp Phe Phe Lys Ser Ala Met Pro Glu
    370                 375                 380

Gly Tyr Val Gln Glu Arg Thr Ile Phe Phe Lys Asp Asp Gly Asn Tyr
385                 390                 395                 400

Lys Thr Arg Ala Glu Val Lys Phe Glu Gly Asp Thr Leu Val Asn Arg
                405                 410                 415
```

```
Ile Glu Leu Lys Gly Ile Gly Phe Lys Glu Asp Gly Asn Ile Leu Gly
                420                 425                 430

His Lys Leu Glu Tyr Asn Gly Thr Gly Leu Ala Gly Leu Thr Arg Leu
                435                 440                 445

Ser Phe Ala Ile Leu Asn Pro Lys Trp Arg Glu Glu Met Met Gly
                450                 455                 460

<210> SEQ ID NO 8
<211> LENGTH: 680
<212> TYPE: PRT
<213> ORGANISM: artificial sequence
<220> FEATURE:
<223> OTHER INFORMATION: amino acid sequence of synthetic fluorescent
      sensor Frex

<400> SEQUENCE: 8

Met Lys Val Pro Glu Ala Ala Ile Ser Arg Leu Ile Thr Tyr Leu Arg
1               5                   10                  15

Ile Leu Glu Glu Leu Glu Ala Gln Gly Val His Arg Thr Ser Ser Glu
                20                  25                  30

Gln Leu Gly Glu Leu Ala Gln Val Thr Ala Phe Gln Val Arg Lys Asp
            35                  40                  45

Leu Ser Tyr Phe Gly Ser Tyr Gly Thr Arg Gly Val Gly Tyr Thr Val
    50                  55                  60

Pro Val Leu Lys Arg Glu Leu Arg His Ile Leu Gly Leu Asn Arg Lys
65                  70                  75                  80

Trp Gly Leu Cys Ile Val Gly Met Gly Arg Leu Gly Ser Ala Leu Ala
                85                  90                  95

Asp Tyr Pro Gly Phe Gly Glu Ser Phe Glu Leu Arg Gly Phe Phe Asp
                100                 105                 110

Val Asp Pro Glu Lys Val Gly Arg Pro Val Arg Gly Val Ile Glu
            115                 120                 125

His Val Asp Leu Leu Pro Gln Arg Val Pro Gly Arg Ile Glu Ile Ala
        130                 135                 140

Leu Leu Thr Val Pro Arg Glu Ala Ala Gln Lys Ala Ala Asp Leu Leu
145                 150                 155                 160

Val Ala Ala Gly Ile Lys Gly Ile Leu Asn Phe Ala Pro Val Val Leu
                165                 170                 175

Glu Val Pro Lys Glu Val Ala Val Glu Asn Val Asp Phe Ser Ala Gly
                180                 185                 190

Tyr Asn Ser Asp Asn Val Tyr Ile Met Ala Asp Lys Gln Lys Asn Gly
            195                 200                 205

Ile Lys Ala Asn Phe Lys Ile Arg His Asn Val Glu Asp Gly Ser Val
    210                 215                 220

Gln Leu Ala Asp His Tyr Gln Gln Asn Thr Pro Ile Gly Asp Gly Pro
225                 230                 235                 240

Val Leu Leu Pro Asp Asn His Tyr Leu Ser Phe Gln Ser Val Leu Ser
                245                 250                 255

Lys Asp Pro Asn Glu Lys Arg Asp His Met Val Leu Leu Glu Phe Val
                260                 265                 270

Thr Ala Ala Gly Ile Thr Leu Gly Met Asp Glu Leu Tyr Asn Val Asp
            275                 280                 285

Gly Gly Ser Gly Gly Thr Gly Ser Lys Gly Glu Glu Leu Phe Thr Gly
    290                 295                 300

Val Val Pro Ile Leu Val Glu Leu Asp Gly Asp Val Asn Gly His Lys
```

```
                305                 310                 315                 320
        Phe Ser Val Ser Gly Glu Gly Glu Gly Asp Ala Thr Tyr Gly Lys Leu
                        325                 330                 335
        Thr Leu Lys Leu Ile Cys Thr Thr Gly Lys Leu Pro Val Pro Trp Pro
                        340                 345                 350
        Thr Leu Val Thr Thr Leu Gly Tyr Gly Leu Lys Cys Phe Ala Arg Tyr
                        355                 360                 365
        Pro Asp His Met Lys Gln His Asp Phe Phe Lys Ser Ala Met Pro Glu
                        370                 375                 380
        Gly Tyr Val Gln Glu Arg Thr Ile Phe Phe Lys Asp Asp Gly Asn Tyr
        385                 390                 395                 400
        Lys Thr Arg Ala Glu Val Lys Phe Glu Gly Asp Thr Leu Val Asn Arg
                        405                 410                 415
        Ile Glu Leu Lys Gly Ile Gly Phe Lys Glu Asp Gly Asn Ile Leu Gly
                        420                 425                 430
        His Lys Leu Glu Tyr Asn Gly Thr Gly Leu Ala Gly Leu Thr Arg Leu
                        435                 440                 445
        Ser Phe Ala Ile Leu Asn Pro Lys Trp Arg Glu Glu Met Met Gly Lys
        450                 455                 460
        Leu Met Asn Lys Asp Gln Ser Lys Ile Pro Gln Ala Thr Ala Lys Arg
        465                 470                 475                 480
        Leu Pro Leu Tyr Tyr Arg Phe Leu Lys Asn Leu His Ala Ser Gly Lys
                        485                 490                 495
        Gln Arg Val Ser Ser Ala Glu Leu Ser Asp Ala Val Lys Val Asp Ser
                        500                 505                 510
        Ala Thr Ile Arg Arg Asp Phe Ser Tyr Phe Gly Ala Leu Gly Lys Lys
                        515                 520                 525
        Gly Tyr Gly Tyr Asn Val Asp Tyr Leu Leu Ser Phe Phe Arg Lys Thr
                        530                 535                 540
        Leu Asp Gln Asp Glu Met Thr Asp Val Ile Leu Ile Gly Val Gly Asn
        545                 550                 555                 560
        Leu Gly Thr Ala Phe Leu His Tyr Asn Phe Thr Lys Asn Asn Asn Thr
                        565                 570                 575
        Lys Ile Ser Met Ala Phe Asp Ile Asn Glu Ser Lys Ile Gly Thr Glu
                        580                 585                 590
        Val Gly Gly Val Pro Val Tyr Asn Leu Asp Asp Leu Glu Gln His Val
                        595                 600                 605
        Lys Asp Glu Ser Val Ala Ile Leu Thr Val Pro Ala Val Ala Ala Gln
        610                 615                 620
        Ser Ile Thr Asp Arg Leu Val Ala Leu Gly Ile Lys Gly Ile Leu Asn
        625                 630                 635                 640
        Phe Thr Pro Ala Arg Leu Asn Val Pro Glu His Ile Arg Ile His His
                        645                 650                 655
        Ile Asp Leu Ala Val Glu Leu Gln Ser Leu Val Tyr Phe Leu Lys His
                        660                 665                 670
        Tyr Ser Val Leu Glu Glu Ile Glu
                        675                 680

<210> SEQ ID NO 9
<211> LENGTH: 1890
<212> TYPE: DNA
<213> ORGANISM: artificial sequence
<220> FEATURE:
<223> OTHER INFORMATION: Synthetic polynucleotide
```

<400> SEQUENCE: 9

```
atgcggggtt ctcatcatca tcatcatcat ggtatggcta gcatgactgg tggacagcaa      60
atgggtcggg atctgtacga cgatgacgat aaggatccga tgaataagga tcaatcaaaa     120
attccgcagg cgacggcgaa acggctgccg ctttactatc gcttttaaa gaatctgcat      180
gcgtcaggaa acagcgtgt atcatccgct gaactcagtg atgccgtaaa ggttgattct     240
gccacgattc ggagggattt ttcctatttt ggagctcttg gcaaaaaagg atacggatat     300
aatgtggatt atttgctgtc ttttttccgg aaaacgcttg atcaggatga gatgacagac     360
gtcatcttga ttggtgtcgg aacttgggga acggcatttc ttcactataa tttcacaaaa     420
aacaataaca caaaaatttc tatggctttt gatataaatg agagtaaaat aggaactgag     480
gtaggcggcg tgcccgtcta taaccttgat gaccttgaac aacacgtaaa agatgaatca     540
gttgccattc ttacagtgcc agcagttgcc gctcaatcca ttacagacag attggtcgca     600
ttaggaatca agggaatcct taattttacg ccggcccgtt tgaatgtgcc ggaacacatt     660
cgaattcatc atatagattt gcagttgag cttcagtcac tggtttattt tttgaagcat     720
tattcagttt tagaggaaat cgaaactagt tacaacagcg acaacgtcta tatcatggcc     780
gacaagcaga gaacggcat caaggccaac ttcaagatcc gccacaacgt cgaggacggc     840
agcgtgcagc tcgccgacca ctaccagcag aacaccccca tcggcgacgg ccccgtgctg     900
ctgccccgaca ccactaccct gagcttccag tccgtcctga gcaaagaccc caacgagaag     960
cgcgatcaca tggtcctgct ggagttcgtg accgccgccg ggatcactct cggcatggac    1020
gagctgtaca cgtggatgg cggtagcggt ggcaccggca gcaagggcga ggagctgttc    1080
accggggtgg tgcccatcct ggtcgagctg gacggcgacg taaacggcca caagttcagc    1140
gtgtccggcg agggcgaggg cgatgccacc tacggcaagc tgaccctgaa gctgatctgc    1200
accaccggca agctgcccgt gccctggccc accctcgtga ccaccctcgg ctacggcctg    1260
aagtgcttcg cccgctaccc cgaccacatg aagcagcacg acttcttcaa gtccgccatg    1320
cccgaaggct acgtccagga gcgcaccatc ttcttcaagg acgacggcaa ctacaagacc    1380
cgcgccgagg tgaagttcga gggcgacacc ctggtgaacc gcatcgagct gaagggcatc    1440
ggcttcaagg aggacggcaa catcctgggg cacaagctgg agtacaacgg taccatgaca    1500
gacgtcatct tgattggtgt cgggaacttg ggaacggcat tcttcactaa tttcaca       1560
aaaaacaata acacaaaaat ttctatggct tttgatataa atgagagtaa aataggaact    1620
gaggtaggcg gcgtgcccgt ctataacctt gatgaccttg aacaacacgt aaaagatgaa    1680
tcagttgcca ttcttacagt gccagcagtt gccgctcaat ccattacaga cagattggtc    1740
gcattaggaa tcaagggaat ccttaatttt acgccggccc gtttgaatgt gccggaacac    1800
attcgaattc atcatataga tttagcagtt gagcttcagt cactggttta ttttttgaag    1860
cattattcag ttttagagga aatcgaatag                                    1890
```

<210> SEQ ID NO 10
<211> LENGTH: 2694
<212> TYPE: DNA
<213> ORGANISM: artificial sequence
<220> FEATURE:
<223> OTHER INFORMATION: Synthetic nucleotide sequence encoding for Frex

<400> SEQUENCE: 10

```
atgaataagg atcaatcaaa aattccgcag gcgacggcga acggctgccg gctttactat      60
cgcttttaa agaatctgca tgcgtcagga aacagcgtg tatcatccgc tgaactcagt      120
```

```
gatgccgtaa aggttgattc tgccacgatt cggagggatt tttcctatttt tggagctctt    180 ggcaaaaaag gatacggata taatgtggat tatttgctgt cttttttccg gaaaacgctt    240
gatcaggatg agatgacaga cgtcatcttg attggtgtcg ggaacttggg aacggcattt    300
cttcactata atttcacaaa aacaataac acaaaaattt ctatggcttt tgatataaat     360
gagagtaaaa taggaactga ggtaggcggc gtgcccgtct ataaccttga tgaccttgaa    420
caacacgtaa aagatgaatc agttgccatt cttacagtgc cagcagttgc cgctcaatcc    480
attacagaca gattggtcgc attaggaatc aagggaatcc ttaattttac gccggcccgt    540
ttgaatgtgc cggaacacat tcgaattcat catatagatt tagcagttga gcttcagtca    600
ctggtttatt ttttgaagca ttattcagtt ttagaggaaa tcgaaactag ttacaacagc    660
gacaacgtct atatcatggc cgacaagcag aagaacggca tcaaggccaa cttcaagatc    720
cgccacaacg tcgaggacgg cagcgtgcag ctcgccgacc actaccagca gaacaccccc    780
atcggcgacg gccccgtgct gctgcccgac aaccactacc tgagcttcca gtccgtcctg    840
agcaaagacc ccaacgagaa gcgcgatcac atggtcctgc tggagttcgt gaccgccgcc    900
gggatcactc tcggcatgga cgagctgtac aacgtggatg cggtagcgg tggcaccggc     960 agcaagggcg aggagctgtt caccggggtg gtgcccatcc tggtcgagct ggacggcgac    1020
gtaaacggcc acaagttcag cgtgtccggc gagggcgagg gcgatgccac ctacggcaag    1080
ctgaccctga agctgatctg caccaccggc aagctgcccg tgccctggcc caccctcgtg    1140
accaccctcg gctacggcct gaagtgcttc gcccgctacc ccgaccacat gaagcagcac    1200
gacttcttca gtccgccat gcccgaaggc tacgtccagg agcgcaccat cttcttcaag     1260
gacgacggca actacaagac ccgcgccgag gtgaagttcg agggcgacac cctggtgaac    1320
cgcatcgagc tgaagggcat cggcttcaag gaggacggca acatcctggg gcacaagctg    1380
gagtacaacg gtaccatgaa taaggatcaa tcaaaaattc gcaggcgac ggcgaaacgg     1440 ctgccgcttt actatcgctt tttaaagaat ctgcatgcgt caggaaaaca gcgtgtatca    1500
tccgctgaac tcagtgatgc cgtaaaggtt gattctgcca cgattcggag ggatttttcc    1560
tattttggag ctcttggcaa aaaaggatac ggatataatg tggattattt gctgtctttt    1620
ttccggaaaa cgcttgatca ggatgagatg acagacgtca tcttgattgg tgtcgggaac    1680
ttgggaacgg catttcttca ctataatttc acaaaaaaca ataacacaaa aatttctatg    1740
gcttttgata taaatgagag taaaatagga actgaggtag gcggcgtgcc cgtctataac    1800
cttgatgacc ttgaacaaca cgtaaaagat gaatcagttg ccattcttac agtgccagca    1860
gttgccgctc aatccattac agacagattg gtcgcattag gaatcaaggg aatccttaat    1920
tttacgccgg cccgtttgaa tgtgccggaa cacattcgaa ttcatcatat agatttagca    1980
gttgagcttc agtcactggt ttatttttg aagcattatt cagttttaga ggaaatcgaa     2040
aagcttatga ataaggatca atcaaaaatt ccgcaggcga cggcgaaacg gctgccgctt    2100
tactatcgct ttttaaagaa tctgcatgcg tcaggaaaac agcgtgtatc atccgctgaa    2160
ctcagtgatg ccgtaaaggt tgattctgcc acgattcgga gggatttttc tattttgga    2220 gctcttggca aaaaaggata cggatataat gtggattatt tgctgtcttt tttccggaaa    2280
acgcttgatc aggatgagat gacagacgtc atcttgattg gtgtcgggaa cttgggaacg    2340
gcatttcttc actataattt cacaaaaaac aataacacaa aatttctat ggcttttgat     2400 ataaatgaga gtaaaatagg aactgaggta ggcggcgtgc ccgtctataa ccttgatgac    2460
```

-continued

| | |
|---|---|
| cttgaacaac acgtaaaaga tgaatcagtt gccattctta cagtgccagc agttgccgct | 2520 |
| caatccatta cagacagatt ggtcgcatta ggaatcaagg gaatccttaa ttttacgccg | 2580 |
| gcccgtttga atgtgccgga acacattcga attcatcata tagatttagc agttgagctt | 2640 |
| cagtcactgg tttatttttt gaagcattat tcagttttag aggaaatcga atag | 2694 |

<210> SEQ ID NO 11
<211> LENGTH: 2094
<212> TYPE: DNA
<213> ORGANISM: artificial sequence
<220> FEATURE:
<223> OTHER INFORMATION: Synthetic nucleotide sequence encoding for Frex

<400> SEQUENCE: 11

| | |
|---|---|
| atggtgagca agggcgagga gctgttcacc ggggtggtgc ccatcctggt cgagctggac | 60 |
| ggcgacgtaa acggccacaa gttcagcgtg tccggcgagg gcgagggcga tgccacctac | 120 |
| ggcaagctga ccctgaagtt catctgcacc accggcaagc tgcccgtgcc ctggcccacc | 180 |
| ctcgtgacca ccttcggcta cggcctgatg tgcttcgccc gctaccccga ccacatgaag | 240 |
| cagcacgact tcttcaagtc cgccatgccc gaaggctacg tccaggagcg caccatcttc | 300 |
| ttcaaggaca cggcaactaa agacccgc gccgaggtga agttcgaggg cgacaccctg | 360 |
| gtgaaccgca tcgagctgaa gggcatcgac ttcaaggagg acggcaacat cctggggcac | 420 |
| aagctggagt acaactacaa cagccacaac gtctatatca tggccgacaa gcagaagaac | 480 |
| ggcatcaagg tgaacttcaa gatccgccac aacatcgagg acggcagcgt gcagctcgcc | 540 |
| gaccactacc agcagaacac ccccatcggc gacggccccg tgctgctgcc cgacaaccac | 600 |
| tacctgagct accagtccgc cctgagcaaa gaccccaacg agaagcgcga tcacatggtc | 660 |
| ctgctggagt tcgtgaccgc cgccgggatc actctcggca tggacgagct gtacaagact | 720 |
| agtatgaata aggatcaatc aaaaattccg caggcgacgg cgaaacggct gccgctttac | 780 |
| tatcgctttt taagaatct gcatgcgtca ggaaaacagc gtgtatcatc cgctgaactc | 840 |
| agtgatgccg taaggttga ttctgccacg attcggaggg atttttccta ttttggagct | 900 |
| cttggcaaaa aaggatacgg atataatgtg gattatttgc tgtcttttt ccggaaaacg | 960 |
| cttgatcagg atgagatgac agacgtcatc ttgattggtg tcgggaactt gggaacggca | 1020 |
| tttcttcact ataatttcac aaaaaacaat aacacaaaaa tttctatggc ttttgatata | 1080 |
| aatgagagta aaataggaac tgaggtaggc ggcgtgcccg tctataacct tgatgacctt | 1140 |
| gaacaacacg taaagatga atcagttgcc attcttacag tgccagcagt tgccgctcaa | 1200 |
| tccattacag acagattggt cgcattagga atcaagggaa tccttaatt tacgccggcc | 1260 |
| cgtttgaatg tgccggaaca cattcgaatt catcatatag atttagcagt tgagcttcag | 1320 |
| tcactggttt attttttgaa gcattattca gttttagagg aaatcgaagg taccatggtg | 1380 |
| agcaagggcg aggagctgtt caccggggtg gtgcccatcc tggtcgagct ggacggcgac | 1440 |
| gtaaacggcc acaagttcag cgtgtccggc gagggcgagg gcgatgccac ctacggcaag | 1500 |
| ctgaccctga gttcatctg caccaccggc aagctgcccg tgcctggcc caccctcgtg | 1560 |
| accaccctga cctggggcgt gcagtgcttc agccgctacc ccgaccacat gaagcagcac | 1620 |
| gacttcttca gtccgccat gcccgaaggc tacgtccagg agcgcaccat cttcttcaag | 1680 |
| gacgacggca actacaagac ccgcgccgag gtgaagttcg agggcgacac cctggtgaac | 1740 |
| cgcatcgagc tgaagggcat cgacttcaag gaggacggca acatcctggg gcacaagctg | 1800 |
| gagtacaact acatcagcca caacgtctat atcaccgccg acaagcagaa gaacggcatc | 1860 |

```
aaggccaact tcaagatccg ccacaacatc gaggacggca gcgtgcagct cgccgaccac    1920
taccagcaga acacccccat cggcgacggc cccgtgctgc tgcccgacaa ccactacctg    1980
agcacccagt ccgccctgag caaagacccc aacgagaagc gcgatcacat ggtcctgctg    2040
gagttcgtga ccgccgccgg gatcactctc ggcatggacg agctgtacaa gtaa          2094

<210> SEQ ID NO 12
<211> LENGTH: 1392
<212> TYPE: DNA
<213> ORGANISM: artificial sequence
<220> FEATURE:
<223> OTHER INFORMATION: Synthetic nucleotide sequence encoding for Frex

<400> SEQUENCE: 12
atgaaggtgc ccgaggccgc catcagccgg ctgatcacct acctgcggat tctggaggag      60
ctggaggccc agggcgtgca ccggaccagc agcgagcagc tgggcgagct ggcccaggtg     120
accgccttcc aggtgcggaa ggacctgagc tacttcggca gctacggcac ccggggcgtg     180
ggctacaccg tgcccgtgct gaagcgggag ctgcggcaca tcctgggcct gaaccggaag     240
tggggcctgt gcatcgtggg catgggccgg ctgggcagcg ccctggccga ctaccccggc     300
ttcggcgaga gcttcgagct gcggggcttc ttcgacgtcg accccgagaa ggtgggccgg     360
cccgtgcggg gcgccgtgat cgagcacgta gatctgctgc ccagcgggt gcccggccgg     420 atcgagatcg ccctgctgac cgtgccccgg gaggccgccc agaaggccgc cgacctgctg     480
gtggccgccg gcatcaaggg catcctgaac ttcgcaccgg tggtgctgga ggtgcccaag     540
gaggtggccg tggagaacgt ggacttctct gcaggctaca acagcgacaa cgtctatatc     600
atggccgaca gcagaagaa cggcatcaag gccaacttca agatccgcca caacgtcgag     660
gacggcagcg tgcagctcgc cgaccactac cagcagaaca cccccatcgg cgacggcccc     720
gtgctgctgc ccgacaacca ctacctgagc ttccagtccg tcctgagcaa agaccccaac     780
gagaagcgcg atcacatggt cctgctggag ttcgtgaccg ccgccggat cactctcggc     840 atggacgagc tgtacaacgt ggatggcggt agcggtggca ccggcagcaa gggcgaggag     900
ctgttcaccg gggtggtgcc catcctggtc gagctggacg gcgacgtaaa cggccacaag     960
ttcagcgtgt ccggcgaggg cgagggcgat gccacctacg gcaagctgac cctgaagctg    1020
atctgcacca ccggcaagct gcccgtgccc tggcccaccc tcgtgaccac cctcggctac    1080
ggcctgaagt gcttcgcccg ctaccccgac cacatgaagc agcacgactt cttcaagtcc    1140
gccatgcccg aaggctacgt ccaggagcgc accatcttct tcaaggacga cggcaactac    1200
aagacccgcg ccgaggtgaa gttcgagggc gacaccctgg tgaaccgcat cgagctgaag    1260
ggcatcggct tcaaggagga cggcaacatc ctggggcaca gctggagta caacggtacc    1320 ggcctggccg gcctgacccg gctgagcttc gccatcctga ccccaagtg gcgggaggag    1380 atgatgggct aa                                                       1392

<210> SEQ ID NO 13
<211> LENGTH: 2043
<212> TYPE: DNA
<213> ORGANISM: artificial sequence
<220> FEATURE:
<223> OTHER INFORMATION: Synthetic nucleotide sequence encoding for Frex

<400> SEQUENCE: 13
atgaaggtgc ccgaggccgc catcagccgg ctgatcacct acctgcggat tctggaggag      60
```

```
ctggaggccc agggcgtgca ccggaccagc agcgagcagc tgggcgagct ggcccaggtg      120
accgccttcc aggtgcggaa ggacctgagc tacttcggca gctacggcac ccggggcgtg      180
ggctacaccg tgcccgtgct gaagcgggag ctgcggcaca tcctgggcct gaaccggaag      240
tggggcctgt gcatcgtggg catgggccgg ctggcagcg ccctggccga ctaccccggc       300
ttcggcgaga gcttcgagct gcggggcttc ttcgacgtcg accccgagaa ggtgggccgg      360
cccgtgcggg gcggcgtgat cgagcacgta gatctgctgc cccagcgggt gcccggccgg      420
atcgagatcg ccctgctgac cgtgccccgg gaggccgccc agaaggccgc cgacctgctg      480
gtggccgccg gcatcaaggg catcctgaac ttcgcaccgg tggtgctgga ggtgcccaag      540
gaggtggccg tggagaacgt ggacttctct gcaggctaca cagcgacaa cgtctatatc       600
atggccgaca gcagaagaa cggcatcaag gccaacttca agatccgcca caacgtcgag       660
gacggcagcg tgcagctcgc cgaccactac cagcagaaca cccccatcgg cgacggcccc      720
gtgctgctgc ccgacaacca ctacctgagc ttccagtccg tcctgagcaa agaccccaac      780
gagaagcgcg atcacatggt cctgctggag ttcgtgaccg ccgccgggat cactctcggc      840
atggacgagc tgtacaacgt ggatggcggt agcggtggca ccggcagcaa gggcgaggag      900
ctgttcaccg gggtggtgcc catcctggtc gagctggacg gcgacgtaaa cggccacaag      960
ttcagcgtgt ccggcgaggg cgagggcgat gccacctacg gcaagctgac cctgaagctg     1020
atctgcacca ccggcaagct gcccgtgccc tggcccaccc tcgtgaccac cctcggctac     1080
ggcctgaagt gcttcgcccg ctaccccgac cacatgaagc agcacgactt cttcaagtcc     1140
gccatgcccg aaggctacgt ccaggagcgc accatcttct tcaaggacga cggcaactac     1200
aagacccgcg ccgaggtgaa gttcgagggc gacaccctgg tgaaccgcat cgagctgaag     1260
ggcatcggct tcaaggagga cggcaacatc ctggggcaca agctggagta caacggtacc     1320
ggcctggccg gcctgaccg gctgagcttc gccatcctga ccccaagtg cgggaggag        1380
atgatgggca gcttatgaa taaggatcaa tcaaaaattc gcaggcgac ggcgaaacgg       1440
ctgccgcttt actatcgctt tttaaagaat ctgcatgcgt caggaaaaca gcgtgtatca     1500
tccgctgaac tcagtgatgc cgtaaaggtt gattctgcca cgattcggag ggatttttcc     1560
tatttggag ctcttggcaa aaaggatac ggatataatg tggattattt gctgtctttt        1620
ttccggaaaa cgcttgatca ggatgagatg acagacgtca tcttgattgg tgtcgggaac     1680
ttgggaacgg catttcttca ctataatttc acaaaaaaca ataacacaaa aatttctatg     1740
gcttttgata taaatgagag taaaatagga actgaggtag gcgcgtgcc cgtctataac      1800
cttgatgacc ttgaacaaca cgtaaaagat gaatcagttg ccattcttac agtgccagca     1860
gttgccgctc aatccattac agacagattg gtcgcattag gaatcaaggg aatccttaat     1920
tttacgccgg cccgtttgaa tgtgccggaa cacattcgaa ttcatcatat agatttagca     1980
gttgagcttc agtcactggt ttatttttg aagcattatt cagttttaga ggaaatcgaa      2040
taa                                                                  2043
```

<210> SEQ ID NO 14
<211> LENGTH: 84
<212> TYPE: PRT
<213> ORGANISM: Bacillus subtilis strain 168

<400> SEQUENCE: 14

```
Met Asn Lys Asp Gln Ser Lys Ile Pro Gln Ala Thr Ala Lys Arg Leu
1               5                   10                  15
```

Pro Leu Tyr Tyr Arg Phe Leu Lys Asn Leu His Ala Ser Gly Lys Gln
            20                  25                  30

Arg Val Ser Ser Ala Glu Leu Ser Asp Ala Val Lys Val Asp Ser Ala
        35                  40                  45

Thr Ile Arg Arg Asp Phe Ser Tyr Phe Gly Ala Leu Gly Lys Lys Gly
50                      55                  60

Tyr Gly Tyr Asn Val Asp Tyr Leu Leu Ser Phe Phe Arg Lys Thr Leu
65                  70                  75                  80

Asp Gln Asp Glu

<210> SEQ ID NO 15
<211> LENGTH: 79
<212> TYPE: PRT
<213> ORGANISM: Thermus aquaticus

<400> SEQUENCE: 15

Met Lys Val Pro Glu Ala Ala Ile Ser Arg Leu Ile Thr Tyr Leu Arg
1               5                   10                  15

Ile Leu Glu Glu Leu Glu Ala Gln Gly Val His Arg Thr Ser Ser Glu
            20                  25                  30

Gln Leu Gly Glu Leu Ala Gln Val Thr Ala Phe Gln Val Arg Lys Asp
        35                  40                  45

Leu Ser Tyr Phe Gly Ser Tyr Gly Thr Arg Gly Val Gly Tyr Thr Val
    50                  55                  60

Pro Val Leu Lys Arg Glu Leu Arg His Ile Leu Gly Leu Asn Arg
65                  70                  75

<210> SEQ ID NO 16
<211> LENGTH: 110
<212> TYPE: PRT
<213> ORGANISM: Bacillus subtilis strain 168

<400> SEQUENCE: 16

Met Thr Asp Val Ile Leu Ile Gly Val Gly Asn Leu Gly Thr Ala Phe
1               5                   10                  15

Leu His Tyr Asn Phe Thr Lys Asn Asn Asn Thr Lys Ile Ser Met Ala
            20                  25                  30

Phe Asp Ile Asn Glu Ser Lys Ile Gly Thr Glu Val Gly Gly Val Pro
        35                  40                  45

Val Tyr Asn Leu Asp Asp Leu Glu Gln His Val Lys Asp Glu Ser Val
    50                  55                  60

Ala Ile Leu Thr Val Pro Ala Val Ala Ala Gln Ser Ile Thr Asp Arg
65                  70                  75                  80

Leu Val Ala Leu Gly Ile Lys Gly Ile Leu Asn Phe Thr Pro Ala Arg
                85                  90                  95

Leu Asn Val Pro Glu His Ile Arg Ile His His Ile Asp Leu
            100                 105                 110

<210> SEQ ID NO 17
<211> LENGTH: 110
<212> TYPE: PRT
<213> ORGANISM: Thermus aquaticus

<400> SEQUENCE: 17

Lys Trp Gly Leu Cys Ile Val Gly Met Gly Arg Leu Gly Ser Ala Leu
1               5                   10                  15

Ala Asp Tyr Pro Gly Phe Gly Glu Ser Phe Glu Leu Arg Gly Phe Phe
            20                  25                  30

```
Asp Val Asp Pro Glu Lys Val Gly Arg Pro Val Arg Gly Gly Val Ile
            35                  40                  45

Glu His Val Asp Leu Leu Pro Gln Arg Val Pro Gly Arg Ile Glu Ile
 50                  55                  60

Ala Leu Leu Thr Val Pro Arg Glu Ala Ala Gln Lys Ala Ala Asp Leu
 65                  70                  75                  80

Leu Val Ala Ala Gly Ile Lys Gly Ile Leu Asn Phe Ala Pro Val Val
                 85                  90                  95

Leu Glu Val Pro Lys Glu Val Ala Val Glu Asn Val Asp Phe
                100                 105                 110

<210> SEQ ID NO 18
<211> LENGTH: 96
<212> TYPE: PRT
<213> ORGANISM: Bacillus subtilis strain 168

<400> SEQUENCE: 18

Asn Glu Ser Lys Ile Gly Thr Glu Val Gly Gly Val Pro Val Tyr Asn
 1               5                  10                  15

Leu Asp Asp Leu Glu Gln His Val Lys Asp Glu Ser Val Ala Ile Leu
                20                  25                  30

Thr Val Pro Ala Val Ala Ala Gln Ser Ile Thr Asp Arg Leu Val Ala
            35                  40                  45

Leu Gly Ile Lys Gly Ile Leu Asn Phe Thr Pro Ala Arg Leu Asn Val
 50                  55                  60

Pro Glu His Ile Arg Ile His Ile Asp Leu Ala Val Glu Leu Gln
 65                  70                  75                  80

Ser Leu Val Tyr Phe Leu Lys His Tyr Ser Val Leu Glu Glu Ile Glu
                 85                  90                  95

<210> SEQ ID NO 19
<211> LENGTH: 98
<212> TYPE: PRT
<213> ORGANISM: Thermus aquaticus

<400> SEQUENCE: 19

Asp Pro Glu Lys Val Gly Arg Pro Val Arg Gly Gly Val Ile Glu His
 1               5                  10                  15

Val Asp Leu Leu Pro Gln Arg Val Pro Gly Arg Ile Glu Ile Ala Leu
                20                  25                  30

Leu Thr Val Pro Arg Glu Ala Ala Gln Lys Ala Ala Asp Leu Leu Val
            35                  40                  45

Ala Ala Gly Ile Lys Gly Ile Leu Asn Phe Ala Pro Val Val Leu Glu
 50                  55                  60

Val Pro Lys Glu Val Ala Val Glu Asn Val Asp Phe Leu Ala Gly Leu
 65                  70                  75                  80

Thr Arg Leu Ser Phe Ala Ile Leu Asn Pro Lys Trp Arg Glu Met
                 85                  90                  95

Met Gly

<210> SEQ ID NO 20
<211> LENGTH: 238
<212> TYPE: PRT
<213> ORGANISM: Aequorea victoria

<400> SEQUENCE: 20

Met Ser Lys Gly Glu Glu Leu Phe Thr Gly Val Val Pro Ile Leu Val
```

```
                1               5                   10                  15
        Glu Leu Asp Gly Asp Val Asn Gly His Lys Phe Ser Val Ser Gly Glu
                        20                  25                  30

Gly Glu Gly Asp Ala Thr Tyr Gly Lys Leu Thr Leu Lys Phe Ile Cys
                        35                  40                  45

Thr Thr Gly Lys Leu Pro Val Pro Trp Pro Thr Leu Val Thr Thr Phe
                50                      55                  60

Ser Tyr Gly Val Gln Cys Phe Ser Arg Tyr Pro Asp His Met Lys Gln
        65                      70                  75                      80

His Asp Phe Phe Lys Ser Ala Met Pro Glu Gly Tyr Val Gln Glu Arg
                        85                  90                  95

Thr Ile Phe Phe Lys Asp Asp Gly Asn Tyr Lys Thr Arg Ala Glu Val
                        100                 105                 110

Lys Phe Glu Gly Asp Thr Leu Val Asn Arg Ile Glu Leu Lys Gly Ile
                        115                 120                 125

Asp Phe Lys Glu Asp Gly Asn Ile Leu Gly His Lys Leu Glu Tyr Asn
        130                     135                 140

Tyr Asn Ser His Asn Val Tyr Ile Met Ala Asp Lys Gln Lys Asn Gly
        145                     150                 155                     160

Ile Lys Val Asn Phe Lys Ile Arg His Asn Ile Glu Asp Gly Ser Val
                        165                 170                 175

Gln Leu Ala Asp His Tyr Gln Gln Asn Thr Pro Ile Gly Asp Gly Pro
                        180                 185                 190

Val Leu Leu Pro Asp Asn His Tyr Leu Ser Thr Gln Ser Ala Leu Ser
                        195                 200                 205

Lys Asp Pro Asn Glu Lys Arg Asp His Met Val Leu Leu Glu Phe Val
        210                     215                 220

Thr Ala Ala Gly Ile Thr His Gly Met Asp Glu Leu Tyr Lys
        225                     230                 235

<210> SEQ ID NO 21
<211> LENGTH: 239
<212> TYPE: PRT
<213> ORGANISM: Aequorea victoria

<400> SEQUENCE: 21

Met Val Ser Lys Gly Glu Glu Leu Phe Thr Gly Val Val Pro Ile Leu
        1               5                   10                  15

Val Glu Leu Asp Gly Asp Val Asn Gly His Lys Phe Ser Val Ser Gly
                        20                  25                  30

Glu Gly Glu Gly Asp Ala Thr Tyr Gly Lys Leu Thr Leu Lys Phe Ile
                        35                  40                  45

Cys Thr Thr Gly Lys Leu Pro Val Pro Trp Pro Thr Leu Val Thr Thr
                50                      55                  60

Phe Gly Tyr Gly Leu Gln Cys Phe Ala Arg Tyr Pro Asp His Met Lys
        65                      70                  75                      80

Gln His Asp Phe Phe Lys Ser Ala Met Pro Glu Gly Tyr Val Gln Glu
                        85                  90                  95

Arg Thr Ile Phe Phe Lys Asp Asp Gly Asn Tyr Lys Thr Arg Ala Glu
                        100                 105                 110

Val Lys Phe Glu Gly Asp Thr Leu Val Asn Arg Ile Glu Leu Lys Gly
                        115                 120                 125

Ile Asp Phe Lys Glu Asp Gly Asn Ile Leu Gly His Lys Leu Glu Tyr
                        130                 135                 140
```

```
Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Tyr Gln Ser Ala Leu
        195                 200                 205

Ser Lys Asp Pro Asn Glu Lys Arg Asp His Met Val Leu Leu Glu Phe
210                 215                 220

Val Thr Ala Ala Gly Ile Thr Leu Gly Met Asp Glu Leu Tyr Lys
225                 230                 235
```

<210> SEQ ID NO 22
<211> LENGTH: 246
<212> TYPE: PRT
<213> ORGANISM: Aequorea victoria

<400> SEQUENCE: 22

```
Tyr Asn Ser Asp Asn Val Tyr Ile Met Ala Asp Lys Gln Lys Asn Gly
1               5                   10                  15

Ile Lys Ala Asn Phe Lys Ile Arg His Asn Val Glu Asp Gly Ser Val
                20                  25                  30

Gln Leu Ala Asp His Tyr Gln Gln Asn Thr Pro Ile Gly Asp Gly Pro
            35                  40                  45

Val Leu Leu Pro Asp Asn His Tyr Leu Ser Phe Gln Ser Val Leu Ser
        50                  55                  60

Lys Asp Pro Asn Glu Lys Arg Asp His Met Val Leu Leu Glu Phe Val
65                  70                  75                  80

Thr Ala Ala Gly Ile Thr Leu Gly Met Asp Glu Leu Tyr Asn Val Asp
                85                  90                  95

Gly Gly Ser Gly Gly Thr Gly Ser Lys Gly Glu Glu Leu Phe Thr Gly
                100                 105                 110

Val Val Pro Ile Leu Val Glu Leu Asp Gly Asp Val Asn Gly His Lys
            115                 120                 125

Phe Ser Val Ser Gly Glu Gly Glu Gly Asp Ala Thr Tyr Gly Lys Leu
130                 135                 140

Thr Leu Lys Leu Ile Cys Thr Thr Gly Lys Leu Pro Val Pro Trp Pro
145                 150                 155                 160

Thr Leu Val Thr Thr Leu Gly Tyr Gly Leu Lys Cys Phe Ala Arg Tyr
                165                 170                 175

Pro Asp His Met Lys Gln His Asp Phe Phe Lys Ser Ala Met Pro Glu
            180                 185                 190

Gly Tyr Val Gln Glu Arg Thr Ile Phe Phe Lys Asp Asp Gly Asn Tyr
        195                 200                 205

Lys Thr Arg Ala Glu Val Lys Phe Glu Gly Asp Thr Leu Val Asn Arg
210                 215                 220

Ile Glu Leu Lys Gly Ile Gly Phe Lys Glu Asp Gly Asn Ile Leu Gly
225                 230                 235                 240

His Lys Leu Glu Tyr Asn
                245
```

<210> SEQ ID NO 23
<211> LENGTH: 39
<212> TYPE: DNA
<213> ORGANISM: artificial sequence
<220> FEATURE:
<223> OTHER INFORMATION: primer P1

<400> SEQUENCE: 23
gaaatcgaaa ctagttacaa cagccacaac gtctatatc                           39

<210> SEQ ID NO 24
<211> LENGTH: 35
<212> TYPE: DNA
<213> ORGANISM: artificial sequence
<220> FEATURE:
<223> OTHER INFORMATION: primer P2

<400> SEQUENCE: 24
ccaagcttcg gggtaccgtt gtactccagc ttgtg                               35

<210> SEQ ID NO 25
<211> LENGTH: 33
<212> TYPE: DNA
<213> ORGANISM: artificial sequence
<220> FEATURE:
<223> OTHER INFORMATION: primer ydiH 1F

<400> SEQUENCE: 25
ccggatccat gaataaggat caatcaaaaa ttc                                 33

<210> SEQ ID NO 26
<211> LENGTH: 34
<212> TYPE: DNA
<213> ORGANISM: artificial sequence
<220> FEATURE:
<223> OTHER INFORMATION: primer ydiH 1R

<400> SEQUENCE: 26
gctgttgtaa ctagtttcga tttcctctaa aact                                34

<210> SEQ ID NO 27
<211> LENGTH: 34
<212> TYPE: DNA
<213> ORGANISM: artificial sequence
<220> FEATURE:
<223> OTHER INFORMATION: primer ydiH(D2) 2F

<400> SEQUENCE: 27
cggggtacca tgacagacgt catcttgatt ggtg                                34

<210> SEQ ID NO 28
<211> LENGTH: 30
<212> TYPE: DNA
<213> ORGANISM: artificial sequence
<220> FEATURE:
<223> OTHER INFORMATION: primer ydiH 2R

<400> SEQUENCE: 28
cccaagcttc tattcgattt cctctaaaac                                     30

<210> SEQ ID NO 29
<211> LENGTH: 36
<212> TYPE: DNA
<213> ORGANISM: artificial sequence
<220> FEATURE:
<223> OTHER INFORMATION: primer P1

<400> SEQUENCE: 29
gaatctgcag gctacaacag ccacaacgtc tatatc                              36

```
<210> SEQ ID NO 30
<211> LENGTH: 35
<212> TYPE: DNA
<213> ORGANISM: artificial sequence
<220> FEATURE:
<223> OTHER INFORMATION: primer P2

<400> SEQUENCE: 30
ccaagcttcg gggtaccgtt gtactccagc ttgtg                                35

<210> SEQ ID NO 31
<211> LENGTH: 34
<212> TYPE: DNA
<213> ORGANISM: artificial sequence
<220> FEATURE:
<223> OTHER INFORMATION: primer P3

<400> SEQUENCE: 31
ccggatccga tgaataagga tcaatcaaaa attc                                 34

<210> SEQ ID NO 32
<211> LENGTH: 30
<212> TYPE: DNA
<213> ORGANISM: artificial sequence
<220> FEATURE:
<223> OTHER INFORMATION: primer P4

<400> SEQUENCE: 32
cccaagcttc tattcgattt cctctaaaac                                      30

<210> SEQ ID NO 33
<211> LENGTH: 33
<212> TYPE: DNA
<213> ORGANISM: artificial sequence
<220> FEATURE:
<223> OTHER INFORMATION: primer P5

<400> SEQUENCE: 33
ataggtaccg gcctggccgg cctgacccgg ctg                                  33

<210> SEQ ID NO 34
<211> LENGTH: 37
<212> TYPE: DNA
<213> ORGANISM: artificial sequence
<220> FEATURE:
<223> OTHER INFORMATION: primer P6

<400> SEQUENCE: 34
atactgcaga gaagtccacg ttctccacgg ccacctc                              37

<210> SEQ ID NO 35
<211> LENGTH: 28
<212> TYPE: DNA
<213> ORGANISM: artificial sequence
<220> FEATURE:
<223> OTHER INFORMATION: C9 reverse primer

<400> SEQUENCE: 35
gatttcctct aaaactgaat aatgcttc                                        28

<210> SEQ ID NO 36
<211> LENGTH: 25
<212> TYPE: DNA
<213> ORGANISM: artificial sequence
<220> FEATURE:
<223> OTHER INFORMATION: C8 reverse primer
```

```
<400> SEQUENCE: 36
ttcctctaaa actgaataat gcttc                                          25

<210> SEQ ID NO 37
<211> LENGTH: 33
<212> TYPE: DNA
<213> ORGANISM: artificial sequence
<220> FEATURE:
<223> OTHER INFORMATION: C6 reverse primer

<400> SEQUENCE: 37
taaaactgaa taatgcttca aaaataaac cag                                  33

<210> SEQ ID NO 38
<211> LENGTH: 30
<212> TYPE: DNA
<213> ORGANISM: artificial sequence
<220> FEATURE:
<223> OTHER INFORMATION: C5 reverse primer

<400> SEQUENCE: 38
aactgaataa tgcttcaaaa aataaaccag                                     30

<210> SEQ ID NO 39
<211> LENGTH: 27
<212> TYPE: DNA
<213> ORGANISM: artificial sequence
<220> FEATURE:
<223> OTHER INFORMATION: C4 reverse primer

<400> SEQUENCE: 39
tgaataatgc ttcaaaaaat aaaccag                                        27

<210> SEQ ID NO 40
<211> LENGTH: 26
<212> TYPE: DNA
<213> ORGANISM: artificial sequence
<220> FEATURE:
<223> OTHER INFORMATION: C3 reverse primer

<400> SEQUENCE: 40
ataatgcttc aaaaaataaa ccagtg                                         26

<210> SEQ ID NO 41
<211> LENGTH: 27
<212> TYPE: DNA
<213> ORGANISM: artificial sequence
<220> FEATURE:
<223> OTHER INFORMATION: C2 reverse primer

<400> SEQUENCE: 41
atgcttcaaa aaataaacca gtgactg                                        27

<210> SEQ ID NO 42
<211> LENGTH: 28
<212> TYPE: DNA
<213> ORGANISM: artificial sequence
<220> FEATURE:
<223> OTHER INFORMATION: C1 reverse primer

<400> SEQUENCE: 42
cttcaaaaaa taaaccagtg actgaagc                                       28

<210> SEQ ID NO 43
```

-continued

<211> LENGTH: 18
<212> TYPE: DNA
<213> ORGANISM: artificial sequence
<220> FEATURE:
<223> OTHER INFORMATION: C9 forward primer

<400> SEQUENCE: 43
tacaacagcg acaacgtc                                                 18

<210> SEQ ID NO 44
<211> LENGTH: 22
<212> TYPE: DNA
<213> ORGANISM: artificial sequence
<220> FEATURE:
<223> OTHER INFORMATION: C7 reverse primer

<400> SEQUENCE: 44
ctctaaaact gaataatgct tc                                            22

<210> SEQ ID NO 45
<211> LENGTH: 22
<212> TYPE: DNA
<213> ORGANISM: artificial sequence
<220> FEATURE:
<223> OTHER INFORMATION: Del GT forward primer

<400> SEQUENCE: 45
atgacagacg tcatcttgat tg                                            22

<210> SEQ ID NO 46
<211> LENGTH: 20
<212> TYPE: DNA
<213> ORGANISM: artificial sequence
<220> FEATURE:
<223> OTHER INFORMATION: Del GT reverse primer

<400> SEQUENCE: 46
gttgtactcc agcttgtgcc                                               20

<210> SEQ ID NO 47
<211> LENGTH: 27
<212> TYPE: DNA
<213> ORGANISM: artificial sequence
<220> FEATURE:
<223> OTHER INFORMATION: Del TS forward primer

<400> SEQUENCE: 47
tacaacagcg acaacgtcta tatcatg                                       27

<210> SEQ ID NO 48
<211> LENGTH: 28
<212> TYPE: DNA
<213> ORGANISM: artificial sequence
<220> FEATURE:
<223> OTHER INFORMATION: Del TS reverse primer

<400> SEQUENCE: 48
ttcgatttcc tctaaaactg aataatgc                                      28

<210> SEQ ID NO 49
<211> LENGTH: 30
<212> TYPE: DNA
<213> ORGANISM: artificial sequence
<220> FEATURE:
<223> OTHER INFORMATION: Del T(1)forward primer

<400> SEQUENCE: 49
agttacaaca gcgacaacgt ctatatcatg    30

<210> SEQ ID NO 50
<211> LENGTH: 31
<212> TYPE: DNA
<213> ORGANISM: artificial sequence
<220> FEATURE:
<223> OTHER INFORMATION: Del S reverse primer

<400> SEQUENCE: 50
agtttcgatt tcctctaaaa ctgaataatg c    31

<210> SEQ ID NO 51
<211> LENGTH: 25
<212> TYPE: DNA
<213> ORGANISM: artificial sequence
<220> FEATURE:
<223> OTHER INFORMATION: Del G forward primer

<400> SEQUENCE: 51
accatgacag acgtcatctt gattg    25

<210> SEQ ID NO 52
<211> LENGTH: 23
<212> TYPE: DNA
<213> ORGANISM: artificial sequence
<220> FEATURE:
<223> OTHER INFORMATION: Del T(2) reverse primer

<400> SEQUENCE: 52
accgttgtac tccagcttgt gcc    23

<210> SEQ ID NO 53
<211> LENGTH: 27
<212> TYPE: DNA
<213> ORGANISM: artificial sequence
<220> FEATURE:
<223> OTHER INFORMATION: D118K forward primer

<400> SEQUENCE: 53
ttttaagata aatgagagta aaatagg    27

<210> SEQ ID NO 54
<211> LENGTH: 24
<212> TYPE: DNA
<213> ORGANISM: artificial sequence
<220> FEATURE:
<223> OTHER INFORMATION: 118/120 mutation reverse primer

<400> SEQUENCE: 54
gccatagaaa ttttgtgtt attg    24

<210> SEQ ID NO 55
<211> LENGTH: 27
<212> TYPE: DNA
<213> ORGANISM: artificial sequence
<220> FEATURE:
<223> OTHER INFORMATION: D118R forward primer

<400> SEQUENCE: 55
ttttcggata aatgagagta aaatagg    27

<210> SEQ ID NO 56
<211> LENGTH: 27
<212> TYPE: DNA

```
<213> ORGANISM: artificial sequence
<220> FEATURE:
<223> OTHER INFORMATION: N120K forward primer

<400> SEQUENCE: 56
ttttgatata aaggagagta aaatagg                                              27

<210> SEQ ID NO 57
<211> LENGTH: 27
<212> TYPE: DNA
<213> ORGANISM: artificial sequence
<220> FEATURE:
<223> OTHER INFORMATION: N120R forward primer

<400> SEQUENCE: 57
ttttgatata cgggagagta aaatagg                                              27

<210> SEQ ID NO 58
<211> LENGTH: 27
<212> TYPE: DNA
<213> ORGANISM: artificial sequence
<220> FEATURE:
<223> OTHER INFORMATION: N120E forward primer

<400> SEQUENCE: 58
ttttgatata gaagagagta aaatagg                                              27

<210> SEQ ID NO 59
<211> LENGTH: 27
<212> TYPE: DNA
<213> ORGANISM: artificial sequence
<220> FEATURE:
<223> OTHER INFORMATION: N120D forward primer

<400> SEQUENCE: 59
ttttgatata gatgagagta aaatagg                                              27

<210> SEQ ID NO 60
<211> LENGTH: 23
<212> TYPE: DNA
<213> ORGANISM: artificial sequence
<220> FEATURE:
<223> OTHER INFORMATION: D193N forward primer

<400> SEQUENCE: 60
taaatttagc agttgagctt cag                                                  23

<210> SEQ ID NO 61
<211> LENGTH: 22
<212> TYPE: DNA
<213> ORGANISM: artificial sequence
<220> FEATURE:
<223> OTHER INFORMATION: 193/194 mutation reverse primer

<400> SEQUENCE: 61
tatgatgaat tcgaatgtgt tc                                                   22

<210> SEQ ID NO 62
<211> LENGTH: 23
<212> TYPE: DNA
<213> ORGANISM: artificial sequence
<220> FEATURE:
<223> OTHER INFORMATION: D193K forward primer

<400> SEQUENCE: 62
taaagttagc agttgagctt cag                                                  23
```

<210> SEQ ID NO 63
<211> LENGTH: 23
<212> TYPE: DNA
<213> ORGANISM: artificial sequence
<220> FEATURE:
<223> OTHER INFORMATION: D193R forward primer

<400> SEQUENCE: 63
tacggttagc agttgagctt cag                                    23

<210> SEQ ID NO 64
<211> LENGTH: 23
<212> TYPE: DNA
<213> ORGANISM: artificial sequence
<220> FEATURE:
<223> OTHER INFORMATION: L194E forward primer

<400> SEQUENCE: 64
tagatgaagc agttgagctt cag                                    23

<210> SEQ ID NO 65
<211> LENGTH: 23
<212> TYPE: DNA
<213> ORGANISM: artificial sequence
<220> FEATURE:
<223> OTHER INFORMATION: L194D forward primer

<400> SEQUENCE: 65
tagatgatgc agttgagctt cag                                    23

<210> SEQ ID NO 66
<211> LENGTH: 23
<212> TYPE: DNA
<213> ORGANISM: artificial sequence
<220> FEATURE:
<223> OTHER INFORMATION: L194K forward primer

<400> SEQUENCE: 66
tagataaggc agttgagctt cag                                    23

<210> SEQ ID NO 67
<211> LENGTH: 23
<212> TYPE: DNA
<213> ORGANISM: artificial sequence
<220> FEATURE:
<223> OTHER INFORMATION: L194R forward primer

<400> SEQUENCE: 67
tagatcgggc agttgagctt cag                                    23

<210> SEQ ID NO 68
<211> LENGTH: 24
<212> TYPE: DNA
<213> ORGANISM: artificial sequence
<220> FEATURE:
<223> OTHER INFORMATION: 189/190-N1 forward primer

<400> SEQUENCE: 68
gcaggctaca acagcgacaa cgtc                                   24

<210> SEQ ID NO 69
<211> LENGTH: 24
<212> TYPE: DNA
<213> ORGANISM: artificial sequence
<220> FEATURE:

```
<223> OTHER INFORMATION: 189/190-N1 reverse primer

<400> SEQUENCE: 69
gaagtccacg ttctccacgg ccac                                              24

<210> SEQ ID NO 70
<211> LENGTH: 30
<212> TYPE: DNA
<213> ORGANISM: artificial sequence
<220> FEATURE:
<223> OTHER INFORMATION: 189/190-N2 forward primer

<400> SEQUENCE: 70
ggctacaaca gcgacaacgt ctatatcatg                                        30

<210> SEQ ID NO 71
<211> LENGTH: 29
<212> TYPE: DNA
<213> ORGANISM: artificial sequence
<220> FEATURE:
<223> OTHER INFORMATION: 189/190-N3 forward primer

<400> SEQUENCE: 71
tacaacagcg acaacgtcta tatcatggc                                         29

<210> SEQ ID NO 72
<211> LENGTH: 23
<212> TYPE: DNA
<213> ORGANISM: artificial sequence
<220> FEATURE:
<223> OTHER INFORMATION: 189/190-C1 forward primer

<400> SEQUENCE: 72
ctggccggcc tgacccggct gag                                               23

<210> SEQ ID NO 73
<211> LENGTH: 31
<212> TYPE: DNA
<213> ORGANISM: artificial sequence
<220> FEATURE:
<223> OTHER INFORMATION: 189/190-C1 reverse primer

<400> SEQUENCE: 73
ggtaccgttg tactccagct tgtgccccag g                                      31

<210> SEQ ID NO 74
<211> LENGTH: 31
<212> TYPE: DNA
<213> ORGANISM: artificial sequence
<220> FEATURE:
<223> OTHER INFORMATION: 189/190-C2 reverse primer

<400> SEQUENCE: 74
accgttgtac tccagcttgt gccccaggat g                                      31

<210> SEQ ID NO 75
<211> LENGTH: 32
<212> TYPE: DNA
<213> ORGANISM: artificial sequence
<220> FEATURE:
<223> OTHER INFORMATION: 189/190-C3 reverse primer

<400> SEQUENCE: 75
gttgtactcc agcttgtgcc ccaggatgtt gc                                     32
```

```
<210> SEQ ID NO 76
<211> LENGTH: 21
<212> TYPE: DNA
<213> ORGANISM: artificial sequence
<220> FEATURE:
<223> OTHER INFORMATION: Trex(D2)forward primer

<400> SEQUENCE: 76
atgaaccgga agtggggcct g                                              21

<210> SEQ ID NO 77
<211> LENGTH: 25
<212> TYPE: DNA
<213> ORGANISM: artificial sequence
<220> FEATURE:
<223> OTHER INFORMATION: Trex(D2) reverse primer

<400> SEQUENCE: 77
cggatcctta tcgtcatcgt cgtac                                          25

<210> SEQ ID NO 78
<211> LENGTH: 21
<212> TYPE: DNA
<213> ORGANISM: artificial sequence
<220> FEATURE:
<223> OTHER INFORMATION: D112SV113H forward primer

<400> SEQUENCE: 78
catgaccccg agaaggtggg c                                              21

<210> SEQ ID NO 79
<211> LENGTH: 21
<212> TYPE: DNA
<213> ORGANISM: artificial sequence
<220> FEATURE:
<223> OTHER INFORMATION: D112SV113H reverse primer

<400> SEQUENCE: 79
cgagaagaag ccccgcagct c                                              21

<210> SEQ ID NO 80
<211> LENGTH: 32
<212> TYPE: DNA
<213> ORGANISM: artificial sequence
<220> FEATURE:
<223> OTHER INFORMATION: Cyto primer F

<400> SEQUENCE: 80
ctagcatggc ggatccacta gtaagcttaa gc                                  32

<210> SEQ ID NO 81
<211> LENGTH: 32
<212> TYPE: DNA
<213> ORGANISM: artificial sequence
<220> FEATURE:
<223> OTHER INFORMATION: Cyto primer R

<400> SEQUENCE: 81
tcgagcttaa gcttactagt ggatccgcca tg                                  32

<210> SEQ ID NO 82
<211> LENGTH: 128
<212> TYPE: DNA
<213> ORGANISM: artificial sequence
<220> FEATURE:
<223> OTHER INFORMATION: Localization signal Mito
```

```
<400> SEQUENCE: 82
ctggctagca tgaggaagat gctcgcggcc gtctcccgcg tgctgtctgg cgcttctcag        60
aagccggcaa gcagagtgct ggtagcatcc cgtaattttg caaatgatgc tacatttaag       120
gatccact                                                                128

<210> SEQ ID NO 83
<211> LENGTH: 272
<212> TYPE: DNA
<213> ORGANISM: artificial sequence
<220> FEATURE:
<223> OTHER INFORMATION: Localization signal Golgi

<400> SEQUENCE: 83
gctggctagc atggcgaggc ttcgggagcc gctcctgagc ggcagcgccg cgatgccagg        60
cgcgtcccta cagcgggcct gccgcctgct cgtggccgtc tgcgctctgc accttggcgt       120
caccctcgtt tactacctgg ctggccgcga cctgagccgc ctgccccaac tggtcggagt       180
ctccacaccg ctgcagggcg gctcgaacag tgccgccgcc atcgggcagt cctccgggga       240
gctccggacc ggaggggccg cggatccact ag                                     272

<210> SEQ ID NO 84
<211> LENGTH: 79
<212> TYPE: DNA
<213> ORGANISM: artificial sequence
<220> FEATURE:
<223> OTHER INFORMATION: Nuc primer F

<400> SEQUENCE: 84
agcttgatcc aaaaagaag agaaaggtag atccaaaaaa gaagagaaag gtagatccaa         60
aaaagaagag aaaggtagc                                                     79

<210> SEQ ID NO 85
<211> LENGTH: 79
<212> TYPE: DNA
<213> ORGANISM: artificial sequence
<220> FEATURE:
<223> OTHER INFORMATION: Nuc primer R

<400> SEQUENCE: 85
tcgagctacc tttctcttct tttttggatc taccttctc ttcttttttg gatctacctt         60
tctcttcttt tttggatca                                                     79

<210> SEQ ID NO 86
<211> LENGTH: 71
<212> TYPE: DNA
<213> ORGANISM: artificial sequence
<220> FEATURE:
<223> OTHER INFORMATION: Mem primer F

<400> SEQUENCE: 86
ctagcatggc gctgtgctgt atgagaagaa ccaaacaggt tgaaaagaat gatgaggacc        60
aaaagatcgc g                                                             71

<210> SEQ ID NO 87
<211> LENGTH: 71
<212> TYPE: DNA
<213> ORGANISM: artificial sequence
<220> FEATURE:
<223> OTHER INFORMATION: Mem primer R

<400> SEQUENCE: 87
```

```
gatccgcgat cttttggtcc tcatcattct tttcaacctg tttggttctt ctcatacagc    60
acagcgccat g                                                        71
```

<210> SEQ ID NO 88
<211> LENGTH: 62
<212> TYPE: DNA
<213> ORGANISM: artificial sequence
<220> FEATURE:
<223> OTHER INFORMATION: ER primer F

<400> SEQUENCE: 88

```
ctagcatggc gctgctatcc gtgccgttgc tgctcggcct cctcggcctg gccgtcgccg    60
cg                                                                  62
```

<210> SEQ ID NO 89
<211> LENGTH: 62
<212> TYPE: DNA
<213> ORGANISM: artificial sequence
<220> FEATURE:
<223> OTHER INFORMATION: ER primer R

<400> SEQUENCE: 89

```
gatccgcggc gacggccagg ccgaggaggc cgagcagcaa cggcacggat agcagcgcca    60
tg                                                                  62
```

<210> SEQ ID NO 90
<211> LENGTH: 18
<212> TYPE: DNA
<213> ORGANISM: artificial sequence
<220> FEATURE:
<223> OTHER INFORMATION: Peroxi primer F

<400> SEQUENCE: 90

```
agctttccaa gctgtaac                                                 18
```

<210> SEQ ID NO 91
<211> LENGTH: 18
<212> TYPE: DNA
<213> ORGANISM: artificial sequence
<220> FEATURE:
<223> OTHER INFORMATION: Peroxi primer R

<400> SEQUENCE: 91

```
tcgagttaca gcttggaa                                                 18
```

<210> SEQ ID NO 92
<211> LENGTH: 620
<212> TYPE: PRT
<213> ORGANISM: artificial sequence
<220> FEATURE:
<223> OTHER INFORMATION: Synthetic fluorescent sensor, mutant

<400> SEQUENCE: 92

```
Met Arg Gly Ser His His His His His His Gly Met Ala Ser Met Thr
 1               5                  10                  15

Gly Gly Gln Gln Met Gly Arg Asp Leu Tyr Asp Asp Asp Lys Asp
            20                  25                  30

Pro Met Asn Lys Asp Gln Ser Lys Ile Pro Gln Ala Thr Ala Lys Arg
        35                  40                  45

Leu Pro Leu Tyr Tyr Arg Phe Leu Lys Asn Leu His Ala Ser Gly Lys
    50                  55                  60
```

-continued

```
Gln Arg Val Ser Ser Ala Glu Leu Ser Asp Ala Val Lys Val Asp Ser
 65                  70                  75                  80
Ala Thr Ile Arg Arg Asp Phe Ser Tyr Phe Gly Ala Leu Gly Lys Lys
                 85                  90                  95
Gly Tyr Gly Tyr Asn Val Asp Tyr Leu Leu Ser Phe Phe Arg Lys Thr
            100                 105                 110
Leu Asp Gln Asp Glu Met Thr Asp Val Ile Leu Ile Gly Val Gly Asn
        115                 120                 125
Leu Gly Thr Ala Phe Leu His Tyr Asn Phe Thr Lys Asn Asn Asn Thr
130                 135                 140
Lys Ile Ser Met Ala Phe Asp Ile Asn Glu Ser Lys Ile Gly Thr Glu
145                 150                 155                 160
Val Gly Gly Val Pro Val Tyr Asn Leu Asp Asp Leu Glu Gln His Val
                165                 170                 175
Lys Asp Glu Ser Val Ala Ile Leu Thr Val Pro Ala Val Ala Ala Gln
            180                 185                 190
Ser Ile Thr Asp Arg Leu Val Ala Leu Gly Ile Lys Gly Ile Leu Asn
        195                 200                 205
Phe Thr Pro Ala Arg Leu Asn Val Pro Glu His Ile Arg Ile His His
210                 215                 220
Ile Asp Leu Ala Val Glu Leu Gln Ser Leu Val Tyr Phe Leu Lys Tyr
225                 230                 235                 240
Asn Ser Asp Asn Val Tyr Ile Met Ala Asp Lys Gln Lys Asn Gly Ile
                245                 250                 255
Lys Ala Asn Phe Lys Ile Arg His Asn Val Glu Asp Gly Ser Val Gln
            260                 265                 270
Leu Ala Asp His Tyr Gln Gln Asn Thr Pro Ile Gly Asp Gly Pro Val
        275                 280                 285
Leu Leu Pro Asp Asn His Tyr Leu Ser Phe Gln Ser Val Leu Ser Lys
290                 295                 300
Asp Pro Asn Glu Lys Arg Asp His Met Val Leu Leu Glu Phe Val Thr
305                 310                 315                 320
Ala Ala Gly Ile Thr Leu Gly Met Asp Glu Leu Tyr Asn Val Asp Gly
                325                 330                 335
Gly Ser Gly Gly Thr Gly Ser Lys Gly Glu Glu Leu Phe Thr Gly Val
            340                 345                 350
Val Pro Ile Leu Val Glu Leu Asp Gly Asp Val Asn Gly His Lys Phe
        355                 360                 365
Ser Val Ser Gly Glu Gly Glu Gly Asp Ala Thr Tyr Gly Lys Leu Thr
370                 375                 380
Leu Lys Leu Ile Cys Thr Thr Gly Lys Leu Pro Val Pro Trp Pro Thr
385                 390                 395                 400
Leu Val Thr Thr Leu Gly Tyr Gly Leu Lys Cys Phe Ala Arg Tyr Pro
                405                 410                 415
Asp His Met Lys Gln His Asp Phe Phe Lys Ser Ala Met Pro Glu Gly
            420                 425                 430
Tyr Val Gln Glu Arg Thr Ile Phe Phe Lys Asp Asp Gly Asn Tyr Lys
        435                 440                 445
Thr Arg Ala Glu Val Lys Phe Glu Gly Asp Thr Leu Val Asn Arg Ile
450                 455                 460
Glu Leu Lys Gly Ile Gly Phe Lys Glu Asp Gly Asn Ile Leu Gly His
465                 470                 475                 480
Lys Leu Glu Tyr Asn Gly Thr Met Thr Asp Val Ile Leu Ile Gly Val
```

```
                    485             490             495
Gly Asn Leu Gly Thr Ala Phe Leu His Tyr Asn Phe Thr Lys Asn Asn
                500             505             510

Asn Thr Lys Ile Ser Met Ala Phe Asp Ile Asn Glu Ser Lys Ile Gly
                515             520             525

Thr Glu Val Gly Gly Val Pro Val Tyr Asn Leu Asp Asp Leu Glu Gln
                530             535             540

His Val Lys Asp Glu Ser Val Ala Ile Leu Thr Val Pro Ala Val Ala
545             550             555             560

Ala Gln Ser Ile Thr Asp Arg Leu Val Ala Leu Gly Ile Lys Gly Ile
                565             570             575

Leu Asn Phe Thr Pro Ala Arg Leu Asn Val Pro Glu His Ile Arg Ile
                580             585             590

His His Ile Asp Leu Ala Val Glu Leu Gln Ser Leu Val Tyr Phe Leu
                595             600             605

Lys His Tyr Ser Val Leu Glu Glu Ile Glu Lys Leu
                610             615             620

<210> SEQ ID NO 93
<211> LENGTH: 621
<212> TYPE: PRT
<213> ORGANISM: artificial sequence
<220> FEATURE:
<223> OTHER INFORMATION: Synthetic fluorescent sensor, mutant

<400> SEQUENCE: 93

Met Arg Gly Ser His His His His His Gly Met Ala Ser Met Thr
1               5               10              15

Gly Gly Gln Gln Met Gly Arg Asp Leu Tyr Asp Asp Asp Lys Asp
                20              25              30

Pro Met Asn Lys Asp Gln Ser Lys Ile Pro Gln Ala Thr Ala Lys Arg
                35              40              45

Leu Pro Leu Tyr Tyr Arg Phe Leu Lys Asn Leu His Ala Ser Gly Lys
    50              55              60

Gln Arg Val Ser Ser Ala Glu Leu Ser Asp Ala Val Lys Val Asp Ser
65              70              75              80

Ala Thr Ile Arg Arg Asp Phe Ser Tyr Phe Gly Ala Leu Gly Lys Lys
                85              90              95

Gly Tyr Gly Tyr Asn Val Asp Tyr Leu Leu Ser Phe Phe Arg Lys Thr
                100             105             110

Leu Asp Gln Asp Glu Met Thr Asp Val Ile Leu Ile Gly Val Gly Asn
                115             120             125

Leu Gly Thr Ala Phe Leu His Tyr Asn Phe Thr Lys Asn Asn Asn Thr
    130             135             140

Lys Ile Ser Met Ala Phe Asp Ile Asn Glu Ser Lys Ile Gly Thr Glu
145             150             155             160

Val Gly Gly Val Pro Val Tyr Asn Leu Asp Asp Leu Glu Gln His Val
                165             170             175

Lys Asp Glu Ser Val Ala Ile Leu Thr Val Pro Ala Val Ala Ala Gln
                180             185             190

Ser Ile Thr Asp Arg Leu Val Ala Leu Gly Ile Lys Gly Ile Leu Asn
                195             200             205

Phe Thr Pro Ala Arg Leu Asn Val Pro Glu His Ile Arg Ile His His
    210             215             220

Ile Asp Leu Ala Val Glu Leu Gln Ser Leu Val Tyr Phe Leu Lys His
```

```
            225                 230                 235                 240
Tyr Asn Ser Asp Asn Val Tyr Ile Met Ala Asp Lys Gln Lys Asn Gly
                    245                 250                 255
Ile Lys Ala Asn Phe Lys Ile Arg His Asn Val Glu Asp Gly Ser Val
                    260                 265                 270
Gln Leu Ala Asp His Tyr Gln Gln Asn Thr Pro Ile Gly Asp Gly Pro
                    275                 280                 285
Val Leu Leu Pro Asp Asn His Tyr Leu Ser Phe Gln Ser Val Leu Ser
                    290                 295                 300
Lys Asp Pro Asn Glu Lys Arg Asp His Met Val Leu Leu Glu Phe Val
305                 310                 315                 320
Thr Ala Ala Gly Ile Thr Leu Gly Met Asp Glu Leu Tyr Asn Val Asp
                    325                 330                 335
Gly Gly Ser Gly Gly Thr Gly Ser Lys Gly Glu Glu Leu Phe Thr Gly
                    340                 345                 350
Val Val Pro Ile Leu Val Glu Leu Asp Gly Asp Val Asn Gly His Lys
                    355                 360                 365
Phe Ser Val Ser Gly Glu Gly Glu Gly Asp Ala Thr Tyr Gly Lys Leu
                    370                 375                 380
Thr Leu Lys Leu Ile Cys Thr Thr Gly Lys Leu Pro Val Pro Trp Pro
385                 390                 395                 400
Thr Leu Val Thr Thr Leu Gly Tyr Gly Leu Lys Cys Phe Ala Arg Tyr
                    405                 410                 415
Pro Asp His Met Lys Gln His Asp Phe Phe Lys Ser Ala Met Pro Glu
                    420                 425                 430
Gly Tyr Val Gln Glu Arg Thr Ile Phe Phe Lys Asp Asp Gly Asn Tyr
                    435                 440                 445
Lys Thr Arg Ala Glu Val Lys Phe Glu Gly Asp Thr Leu Val Asn Arg
                    450                 455                 460
Ile Glu Leu Lys Gly Ile Gly Phe Lys Glu Asp Gly Asn Ile Leu Gly
465                 470                 475                 480
His Lys Leu Glu Tyr Asn Gly Thr Met Thr Asp Val Ile Leu Ile Gly
                    485                 490                 495
Val Gly Asn Leu Gly Thr Ala Phe Leu His Tyr Asn Phe Thr Lys Asn
                    500                 505                 510
Asn Asn Thr Lys Ile Ser Met Ala Phe Asp Ile Asn Glu Ser Lys Ile
                    515                 520                 525
Gly Thr Glu Val Gly Gly Val Pro Val Tyr Asn Leu Asp Asp Leu Glu
                    530                 535                 540
Gln His Val Lys Asp Glu Ser Val Ala Ile Leu Thr Val Pro Ala Val
545                 550                 555                 560
Ala Ala Gln Ser Ile Thr Asp Arg Leu Val Ala Leu Gly Ile Lys Gly
                    565                 570                 575
Ile Leu Asn Phe Thr Pro Ala Arg Leu Asn Val Pro Glu His Ile Arg
                    580                 585                 590
Ile His His Ile Asp Leu Ala Val Glu Leu Gln Ser Leu Val Tyr Phe
                    595                 600                 605
Leu Lys His Tyr Ser Val Leu Glu Glu Ile Glu Lys Leu
                    610                 615                 620

<210> SEQ ID NO 94
<211> LENGTH: 622
<212> TYPE: PRT
<213> ORGANISM: artificial sequence
```

<220> FEATURE:
<223> OTHER INFORMATION: Synthetic fluorescent sensor, mutant

<400> SEQUENCE: 94

```
Met Arg Gly Ser His His His His His Gly Met Ala Ser Met Thr
1               5                   10                  15

Gly Gly Gln Gln Met Gly Arg Asp Leu Tyr Asp Asp Asp Lys Asp
            20                  25                  30

Pro Met Asn Lys Asp Gln Ser Lys Ile Pro Gln Ala Thr Ala Lys Arg
        35                  40                  45

Leu Pro Leu Tyr Tyr Arg Phe Leu Lys Asn Leu His Ala Ser Gly Lys
    50                  55                  60

Gln Arg Val Ser Ser Ala Glu Leu Ser Asp Ala Val Lys Val Asp Ser
65                  70                  75                  80

Ala Thr Ile Arg Arg Asp Phe Ser Tyr Phe Gly Ala Leu Gly Lys Lys
                85                  90                  95

Gly Tyr Gly Tyr Asn Val Asp Tyr Leu Leu Ser Phe Phe Arg Lys Thr
            100                 105                 110

Leu Asp Gln Asp Glu Met Thr Asp Val Ile Leu Ile Gly Val Gly Asn
        115                 120                 125

Leu Gly Thr Ala Phe Leu His Tyr Asn Phe Thr Lys Asn Asn Asn Thr
130                 135                 140

Lys Ile Ser Met Ala Phe Asp Ile Asn Glu Ser Lys Ile Gly Thr Glu
145                 150                 155                 160

Val Gly Gly Val Pro Val Tyr Asn Leu Asp Asp Leu Glu Gln His Val
                165                 170                 175

Lys Asp Glu Ser Val Ala Ile Leu Thr Val Pro Ala Val Ala Ala Gln
            180                 185                 190

Ser Ile Thr Asp Arg Leu Val Ala Leu Gly Ile Lys Gly Ile Leu Asn
        195                 200                 205

Phe Thr Pro Ala Arg Leu Asn Val Pro Glu His Ile Arg Ile His His
210                 215                 220

Ile Asp Leu Ala Val Glu Leu Gln Ser Leu Val Tyr Phe Leu Lys His
225                 230                 235                 240

Tyr Tyr Asn Ser Asp Asn Val Tyr Ile Met Ala Asp Lys Gln Lys Asn
                245                 250                 255

Gly Ile Lys Ala Asn Phe Lys Ile Arg His Asn Val Glu Asp Gly Ser
            260                 265                 270

Val Gln Leu Ala Asp His Tyr Gln Gln Asn Thr Pro Ile Gly Asp Gly
        275                 280                 285

Pro Val Leu Leu Pro Asp Asn His Tyr Leu Ser Phe Gln Ser Val Leu
290                 295                 300

Ser Lys Asp Pro Asn Glu Lys Arg Asp His Met Val Leu Leu Glu Phe
305                 310                 315                 320

Val Thr Ala Ala Gly Ile Thr Leu Gly Met Asp Glu Leu Tyr Asn Val
                325                 330                 335

Asp Gly Gly Ser Gly Gly Thr Gly Ser Lys Gly Glu Glu Leu Phe Thr
            340                 345                 350

Gly Val Val Pro Ile Leu Val Glu Leu Asp Gly Asp Val Asn Gly His
        355                 360                 365

Lys Phe Ser Val Ser Gly Glu Gly Glu Gly Asp Ala Thr Tyr Gly Lys
370                 375                 380

Leu Thr Leu Lys Leu Ile Cys Thr Thr Gly Lys Leu Pro Val Pro Trp
385                 390                 395                 400
```

```
Pro Thr Leu Val Thr Thr Leu Gly Tyr Gly Leu Lys Cys Phe Ala Arg
            405                 410                 415

Tyr Pro Asp His Met Lys Gln His Asp Phe Phe Lys Ser Ala Met Pro
            420                 425                 430

Glu Gly Tyr Val Gln Glu Arg Thr Ile Phe Phe Lys Asp Asp Gly Asn
            435                 440                 445

Tyr Lys Thr Arg Ala Glu Val Lys Phe Glu Gly Asp Thr Leu Val Asn
            450                 455                 460

Arg Ile Glu Leu Lys Gly Ile Gly Phe Lys Glu Asp Gly Asn Ile Leu
465                 470                 475                 480

Gly His Lys Leu Glu Tyr Asn Gly Thr Met Thr Asp Val Ile Leu Ile
            485                 490                 495

Gly Val Gly Asn Leu Gly Thr Ala Phe Leu His Tyr Asn Phe Thr Lys
            500                 505                 510

Asn Asn Asn Thr Lys Ile Ser Met Ala Phe Asp Ile Asn Glu Ser Lys
            515                 520                 525

Ile Gly Thr Glu Val Gly Val Pro Val Tyr Asn Leu Asp Asp Leu
            530                 535                 540

Glu Gln His Val Lys Asp Glu Ser Val Ala Ile Leu Thr Val Pro Ala
545                 550                 555                 560

Val Ala Ala Gln Ser Ile Thr Asp Arg Leu Val Ala Leu Gly Ile Lys
            565                 570                 575

Gly Ile Leu Asn Phe Thr Pro Ala Arg Leu Asn Val Pro Glu His Ile
            580                 585                 590

Arg Ile His His Ile Asp Leu Ala Val Glu Leu Gln Ser Leu Val Tyr
            595                 600                 605

Phe Leu Lys His Tyr Ser Val Leu Glu Glu Ile Glu Lys Leu
            610                 615                 620

<210> SEQ ID NO 95
<211> LENGTH: 623
<212> TYPE: PRT
<213> ORGANISM: artificial sequence
<220> FEATURE:
<223> OTHER INFORMATION: Synthetic fluorescent sensor, mutant

<400> SEQUENCE: 95

Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

Pro Met Asn Lys Asp Gln Ser Lys Ile Pro Gln Ala Thr Ala Lys Arg
            35                  40                  45

Leu Pro Leu Tyr Tyr Arg Phe Leu Lys Asn Leu His Ala Ser Gly Lys
        50                  55                  60

Gln Arg Val Ser Ser Ala Glu Leu Ser Asp Ala Val Lys Val Asp Ser
65                  70                  75                  80

Ala Thr Ile Arg Arg Asp Phe Ser Tyr Phe Gly Ala Leu Gly Lys Lys
            85                  90                  95

Gly Tyr Gly Tyr Asn Val Asp Tyr Leu Leu Ser Phe Phe Arg Lys Thr
            100                 105                 110

Leu Asp Gln Asp Glu Met Thr Asp Val Ile Leu Ile Gly Val Gly Asn
            115                 120                 125

Leu Gly Thr Ala Phe Leu His Tyr Asn Phe Thr Lys Asn Asn Asn Thr
            130                 135                 140
```

```
Lys Ile Ser Met Ala Phe Asp Ile Asn Glu Ser Lys Ile Gly Thr Glu
145                 150                 155                 160

Val Gly Gly Val Pro Val Tyr Asn Leu Asp Asp Leu Glu Gln His Val
            165                 170                 175

Lys Asp Glu Ser Val Ala Ile Leu Thr Val Pro Ala Val Ala Ala Gln
        180                 185                 190

Ser Ile Thr Asp Arg Leu Val Ala Leu Gly Ile Lys Gly Ile Leu Asn
    195                 200                 205

Phe Thr Pro Ala Arg Leu Asn Val Pro Glu His Ile Arg Ile His His
210                 215                 220

Ile Asp Leu Ala Val Glu Leu Gln Ser Leu Val Tyr Phe Leu Lys His
225                 230                 235                 240

Tyr Ser Tyr Asn Ser Asp Asn Val Tyr Ile Met Ala Asp Lys Gln Lys
            245                 250                 255

Asn Gly Ile Lys Ala Asn Phe Lys Ile Arg His Asn Val Glu Asp Gly
        260                 265                 270

Ser Val Gln Leu Ala Asp His Tyr Gln Gln Asn Thr Pro Ile Gly Asp
    275                 280                 285

Gly Pro Val Leu Leu Pro Asp Asn His Tyr Leu Ser Phe Gln Ser Val
290                 295                 300

Leu Ser Lys Asp Pro Asn Glu Lys Arg Asp His Met Val Leu Leu Glu
305                 310                 315                 320

Phe Val Thr Ala Ala Gly Ile Thr Leu Gly Met Asp Glu Leu Tyr Asn
            325                 330                 335

Val Asp Gly Gly Ser Gly Gly Thr Gly Ser Lys Gly Glu Glu Leu Phe
        340                 345                 350

Thr Gly Val Val Pro Ile Leu Val Glu Leu Asp Gly Asp Val Asn Gly
    355                 360                 365

His Lys Phe Ser Val Ser Gly Glu Gly Glu Gly Asp Ala Thr Tyr Gly
370                 375                 380

Lys Leu Thr Leu Lys Leu Ile Cys Thr Thr Gly Lys Leu Pro Val Pro
385                 390                 395                 400

Trp Pro Thr Leu Val Thr Thr Leu Gly Tyr Gly Leu Lys Cys Phe Ala
            405                 410                 415

Arg Tyr Pro Asp His Met Lys Gln His Asp Phe Phe Lys Ser Ala Met
        420                 425                 430

Pro Glu Gly Tyr Val Gln Glu Arg Thr Ile Phe Phe Lys Asp Asp Gly
    435                 440                 445

Asn Tyr Lys Thr Arg Ala Glu Val Lys Phe Glu Gly Asp Thr Leu Val
450                 455                 460

Asn Arg Ile Glu Leu Lys Gly Ile Gly Phe Lys Glu Asp Gly Asn Ile
465                 470                 475                 480

Leu Gly His Lys Leu Glu Tyr Asn Gly Thr Met Thr Asp Val Ile Leu
            485                 490                 495

Ile Gly Val Gly Asn Leu Gly Thr Ala Phe Leu His Tyr Asn Phe Thr
        500                 505                 510

Lys Asn Asn Asn Thr Lys Ile Ser Met Ala Phe Asp Ile Asn Glu Ser
    515                 520                 525

Lys Ile Gly Thr Glu Val Gly Val Pro Val Tyr Asn Leu Asp Asp
530                 535                 540

Leu Glu Gln His Val Lys Asp Glu Ser Val Ala Ile Leu Thr Val Pro
545                 550                 555                 560
```

```
Ala Val Ala Ala Gln Ser Ile Thr Asp Arg Leu Val Ala Leu Gly Ile
                565                 570                 575

Lys Gly Ile Leu Asn Phe Thr Pro Ala Arg Leu Asn Val Pro Glu His
            580                 585                 590

Ile Arg Ile His His Ile Asp Leu Ala Val Glu Leu Gln Ser Leu Val
                595                 600                 605

Tyr Phe Leu Lys His Tyr Ser Val Leu Glu Glu Ile Glu Lys Leu
            610                 615                 620

<210> SEQ ID NO 96
<211> LENGTH: 624
<212> TYPE: PRT
<213> ORGANISM: artificial sequence
<220> FEATURE:
<223> OTHER INFORMATION: Synthetic fluorescent sensor, mutant

<400> SEQUENCE: 96

Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

Pro Met Asn Lys Asp Gln Ser Lys Ile Pro Gln Ala Thr Ala Lys Arg
            35                  40                  45

Leu Pro Leu Tyr Tyr Arg Phe Leu Lys Asn Leu His Ala Ser Gly Lys
50                  55                  60

Gln Arg Val Ser Ser Ala Glu Leu Ser Asp Ala Val Lys Val Asp Ser
65                  70                  75                  80

Ala Thr Ile Arg Arg Asp Phe Ser Tyr Phe Gly Ala Leu Gly Lys Lys
                85                  90                  95

Gly Tyr Gly Tyr Asn Val Asp Tyr Leu Leu Ser Phe Phe Arg Lys Thr
            100                 105                 110

Leu Asp Gln Asp Glu Met Thr Asp Val Ile Leu Ile Gly Val Gly Asn
        115                 120                 125

Leu Gly Thr Ala Phe Leu His Tyr Asn Phe Thr Lys Asn Asn Asn Thr
130                 135                 140

Lys Ile Ser Met Ala Phe Asp Ile Asn Glu Ser Lys Ile Gly Thr Glu
145                 150                 155                 160

Val Gly Gly Val Pro Val Tyr Asn Leu Asp Asp Leu Glu Gln His Val
                165                 170                 175

Lys Asp Glu Ser Val Ala Ile Leu Thr Val Pro Ala Val Ala Ala Gln
            180                 185                 190

Ser Ile Thr Asp Arg Leu Val Ala Leu Gly Ile Lys Gly Ile Leu Asn
        195                 200                 205

Phe Thr Pro Ala Arg Leu Asn Val Pro Glu His Ile Arg Ile His His
210                 215                 220

Ile Asp Leu Ala Val Glu Leu Gln Ser Leu Val Tyr Phe Leu Lys His
225                 230                 235                 240

Tyr Ser Val Tyr Asn Ser Asp Asn Val Tyr Ile Met Ala Asp Lys Gln
                245                 250                 255

Lys Asn Gly Ile Lys Ala Asn Phe Lys Ile Arg His Asn Val Glu Asp
            260                 265                 270

Gly Ser Val Gln Leu Ala Asp His Tyr Gln Gln Asn Thr Pro Ile Gly
        275                 280                 285

Asp Gly Pro Val Leu Leu Pro Asp Asn His Tyr Leu Ser Phe Gln Ser
290                 295                 300
```

Val Leu Ser Lys Asp Pro Asn Glu Lys Arg Asp His Met Val Leu Leu
305                 310                 315                 320

Glu Phe Val Thr Ala Ala Gly Ile Thr Leu Gly Met Asp Glu Leu Tyr
            325                 330                 335

Asn Val Asp Gly Gly Ser Gly Gly Thr Gly Ser Lys Gly Glu Glu Leu
            340                 345                 350

Phe Thr Gly Val Val Pro Ile Leu Val Glu Leu Asp Gly Asp Val Asn
            355                 360                 365

Gly His Lys Phe Ser Val Ser Gly Glu Gly Glu Gly Asp Ala Thr Tyr
            370                 375                 380

Gly Lys Leu Thr Leu Lys Leu Ile Cys Thr Thr Gly Lys Leu Pro Val
385                 390                 395                 400

Pro Trp Pro Thr Leu Val Thr Thr Leu Gly Tyr Gly Leu Lys Cys Phe
            405                 410                 415

Ala Arg Tyr Pro Asp His Met Lys Gln His Asp Phe Phe Lys Ser Ala
            420                 425                 430

Met Pro Glu Gly Tyr Val Gln Glu Arg Thr Ile Phe Phe Lys Asp Asp
            435                 440                 445

Gly Asn Tyr Lys Thr Arg Ala Glu Val Lys Phe Glu Gly Asp Thr Leu
450                 455                 460

Val Asn Arg Ile Glu Leu Lys Gly Ile Gly Phe Lys Glu Asp Gly Asn
465                 470                 475                 480

Ile Leu Gly His Lys Leu Glu Tyr Asn Gly Thr Met Thr Asp Val Ile
            485                 490                 495

Leu Ile Gly Val Gly Asn Leu Gly Thr Ala Phe Leu His Tyr Asn Phe
            500                 505                 510

Thr Lys Asn Asn Asn Thr Lys Ile Ser Met Ala Phe Asp Ile Asn Glu
            515                 520                 525

Ser Lys Ile Gly Thr Glu Val Gly Gly Val Pro Val Tyr Asn Leu Asp
530                 535                 540

Asp Leu Glu Gln His Val Lys Asp Glu Ser Val Ala Ile Leu Thr Val
545                 550                 555                 560

Pro Ala Val Ala Ala Gln Ser Ile Thr Asp Arg Leu Val Ala Leu Gly
            565                 570                 575

Ile Lys Gly Ile Leu Asn Phe Thr Pro Ala Arg Leu Asn Val Pro Glu
            580                 585                 590

His Ile Arg Ile His His Ile Asp Leu Ala Val Glu Leu Gln Ser Leu
            595                 600                 605

Val Tyr Phe Leu Lys His Tyr Ser Val Leu Glu Ile Glu Lys Leu
610                 615                 620

<210> SEQ ID NO 97
<211> LENGTH: 625
<212> TYPE: PRT
<213> ORGANISM: artificial sequence
<220> FEATURE:
<223> OTHER INFORMATION: Synthetic fluorescent sensor, mutant

<400> SEQUENCE: 97

Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

Pro Met Asn Lys Asp Gln Ser Lys Ile Pro Gln Ala Thr Ala Lys Arg
            35                  40                  45

-continued

```
Leu Pro Leu Tyr Tyr Arg Phe Leu Lys Asn Leu His Ala Ser Gly Lys
 50                  55                  60

Gln Arg Val Ser Ser Ala Glu Leu Ser Asp Ala Val Lys Val Asp Ser
 65                  70                  75                  80

Ala Thr Ile Arg Arg Asp Phe Ser Tyr Phe Gly Ala Leu Gly Lys Lys
                 85                  90                  95

Gly Tyr Gly Tyr Asn Val Asp Tyr Leu Leu Ser Phe Arg Lys Thr
            100                 105                 110

Leu Asp Gln Asp Glu Met Thr Asp Val Ile Leu Ile Gly Val Gly Asn
        115                 120                 125

Leu Gly Thr Ala Phe Leu His Tyr Asn Phe Thr Lys Asn Asn Asn Thr
130                 135                 140

Lys Ile Ser Met Ala Phe Asp Ile Asn Glu Ser Lys Ile Gly Thr Glu
145                 150                 155                 160

Val Gly Gly Val Pro Val Tyr Asn Leu Asp Asp Leu Glu Gln His Val
                165                 170                 175

Lys Asp Glu Ser Val Ala Ile Leu Thr Val Pro Ala Val Ala Ala Gln
            180                 185                 190

Ser Ile Thr Asp Arg Leu Val Ala Leu Gly Ile Lys Gly Ile Leu Asn
        195                 200                 205

Phe Thr Pro Ala Arg Leu Asn Val Pro Glu His Ile Arg Ile His His
210                 215                 220

Ile Asp Leu Ala Val Glu Leu Gln Ser Leu Val Tyr Phe Leu Lys His
225                 230                 235                 240

Tyr Ser Val Leu Tyr Asn Ser Asp Asn Val Tyr Ile Met Ala Asp Lys
                245                 250                 255

Gln Lys Asn Gly Ile Lys Ala Asn Phe Lys Ile Arg His Asn Val Glu
            260                 265                 270

Asp Gly Ser Val Gln Leu Ala Asp His Tyr Gln Gln Asn Thr Pro Ile
        275                 280                 285

Gly Asp Gly Pro Val Leu Leu Pro Asp Asn His Tyr Leu Ser Phe Gln
290                 295                 300

Ser Val Leu Ser Lys Asp Pro Asn Glu Lys Arg Asp His Met Val Leu
305                 310                 315                 320

Leu Glu Phe Val Thr Ala Ala Gly Ile Thr Leu Gly Met Asp Glu Leu
                325                 330                 335

Tyr Asn Val Asp Gly Gly Ser Gly Gly Thr Gly Ser Lys Gly Glu Glu
            340                 345                 350

Leu Phe Thr Gly Val Val Pro Ile Leu Val Glu Leu Asp Gly Asp Val
        355                 360                 365

Asn Gly His Lys Phe Ser Val Ser Gly Glu Gly Glu Gly Asp Ala Thr
370                 375                 380

Tyr Gly Lys Leu Thr Leu Lys Leu Ile Cys Thr Thr Gly Lys Leu Pro
385                 390                 395                 400

Val Pro Trp Pro Thr Leu Val Thr Thr Leu Gly Tyr Gly Leu Lys Cys
                405                 410                 415

Phe Ala Arg Tyr Pro Asp His Met Lys Gln His Asp Phe Phe Lys Ser
            420                 425                 430

Ala Met Pro Glu Gly Tyr Val Gln Glu Arg Thr Ile Phe Phe Lys Asp
        435                 440                 445

Asp Gly Asn Tyr Lys Thr Arg Ala Glu Val Lys Phe Glu Gly Asp Thr
450                 455                 460

Leu Val Asn Arg Ile Glu Leu Lys Gly Ile Gly Phe Lys Glu Asp Gly
```

```
                465                 470                 475                 480
Asn Ile Leu Gly His Lys Leu Glu Tyr Asn Gly Thr Met Thr Asp Val
                        485                 490                 495

Ile Leu Ile Gly Val Gly Asn Leu Gly Thr Ala Phe Leu His Tyr Asn
                500                 505                 510

Phe Thr Lys Asn Asn Asn Thr Lys Ile Ser Met Ala Phe Asp Ile Asn
                515                 520                 525

Glu Ser Lys Ile Gly Thr Glu Val Gly Val Pro Val Tyr Asn Leu
            530                 535                 540

Asp Leu Glu Gln His Val Lys Asp Glu Ser Val Ala Ile Leu Thr
545                 550                 555                 560

Val Pro Ala Val Ala Ala Gln Ser Ile Thr Asp Arg Leu Val Ala Leu
                565                 570                 575

Gly Ile Lys Gly Ile Leu Asn Phe Thr Pro Ala Arg Leu Asn Val Pro
                580                 585                 590

Glu His Ile Arg Ile His His Ile Asp Leu Ala Val Glu Leu Gln Ser
            595                 600                 605

Leu Val Tyr Phe Leu Lys His Tyr Ser Val Leu Glu Ile Glu Lys
    610                 615                 620

Leu
625

<210> SEQ ID NO 98
<211> LENGTH: 626
<212> TYPE: PRT
<213> ORGANISM: artificial sequence
<220> FEATURE:
<223> OTHER INFORMATION: Synthetic fluorescent sensor, mutant

<400> SEQUENCE: 98

Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

Pro Met Asn Lys Asp Gln Ser Lys Ile Pro Gln Ala Thr Ala Lys Arg
            35                  40                  45

Leu Pro Leu Tyr Tyr Arg Phe Leu Lys Asn Leu His Ala Ser Gly Lys
    50                  55                  60

Gln Arg Val Ser Ser Ala Glu Leu Ser Asp Ala Val Lys Val Asp Ser
65                  70                  75                  80

Ala Thr Ile Arg Arg Asp Phe Ser Tyr Phe Gly Ala Leu Gly Lys Lys
                85                  90                  95

Gly Tyr Gly Tyr Asn Val Asp Tyr Leu Leu Ser Phe Phe Arg Lys Thr
            100                 105                 110

Leu Asp Gln Asp Glu Met Thr Asp Val Ile Leu Ile Gly Val Gly Asn
        115                 120                 125

Leu Gly Thr Ala Phe Leu His Tyr Asn Phe Thr Lys Asn Asn Asn Thr
    130                 135                 140

Lys Ile Ser Met Ala Phe Asp Ile Asn Glu Ser Lys Ile Gly Thr Glu
145                 150                 155                 160

Val Gly Gly Val Pro Val Tyr Asn Leu Asp Asp Leu Glu Gln His Val
                165                 170                 175

Lys Asp Glu Ser Val Ala Ile Leu Thr Val Pro Ala Val Ala Ala Gln
            180                 185                 190

Ser Ile Thr Asp Arg Leu Val Ala Leu Gly Ile Lys Gly Ile Leu Asn
```

```
                195                 200                 205
Phe Thr Pro Ala Arg Leu Asn Val Pro Glu His Ile Arg Ile His His
210                 215                 220

Ile Asp Leu Ala Val Glu Leu Gln Ser Leu Val Tyr Phe Leu Lys His
225                 230                 235                 240

Tyr Ser Val Leu Glu Tyr Asn Ser Asp Asn Val Tyr Ile Met Ala Asp
                245                 250                 255

Lys Gln Lys Asn Gly Ile Lys Ala Asn Phe Lys Ile Arg His Asn Val
            260                 265                 270

Glu Asp Gly Ser Val Gln Leu Ala Asp His Tyr Gln Gln Asn Thr Pro
        275                 280                 285

Ile Gly Asp Gly Pro Val Leu Leu Pro Asp Asn His Tyr Leu Ser Phe
290                 295                 300

Gln Ser Val Leu Ser Lys Asp Pro Asn Glu Lys Arg Asp His Met Val
305                 310                 315                 320

Leu Leu Glu Phe Val Thr Ala Ala Gly Ile Thr Leu Gly Met Asp Glu
                325                 330                 335

Leu Tyr Asn Val Asp Gly Gly Ser Gly Gly Thr Gly Ser Lys Gly Glu
            340                 345                 350

Glu Leu Phe Thr Gly Val Val Pro Ile Leu Val Glu Leu Asp Gly Asp
        355                 360                 365

Val Asn Gly His Lys Phe Ser Val Ser Gly Glu Gly Glu Gly Asp Ala
370                 375                 380

Thr Tyr Gly Lys Leu Thr Leu Lys Leu Ile Cys Thr Thr Gly Lys Leu
385                 390                 395                 400

Pro Val Pro Trp Pro Thr Leu Val Thr Thr Leu Gly Tyr Gly Leu Lys
                405                 410                 415

Cys Phe Ala Arg Tyr Pro Asp His Met Lys Gln His Asp Phe Phe Lys
            420                 425                 430

Ser Ala Met Pro Glu Gly Tyr Val Gln Glu Arg Thr Ile Phe Phe Lys
        435                 440                 445

Asp Asp Gly Asn Tyr Lys Thr Arg Ala Glu Val Lys Phe Glu Gly Asp
450                 455                 460

Thr Leu Val Asn Arg Ile Glu Leu Lys Gly Ile Gly Phe Lys Glu Asp
465                 470                 475                 480

Gly Asn Ile Leu Gly His Lys Leu Glu Tyr Asn Gly Thr Met Thr Asp
                485                 490                 495

Val Ile Leu Ile Gly Val Gly Asn Leu Gly Thr Ala Phe Leu His Tyr
            500                 505                 510

Asn Phe Thr Lys Asn Asn Thr Lys Ile Ser Met Ala Phe Asp Ile
        515                 520                 525

Asn Glu Ser Lys Ile Gly Thr Glu Val Gly Gly Val Pro Val Tyr Asn
530                 535                 540

Leu Asp Asp Leu Glu Gln His Val Lys Asp Glu Ser Val Ala Ile Leu
545                 550                 555                 560

Thr Val Pro Ala Val Ala Ala Gln Ser Ile Thr Asp Arg Leu Val Ala
                565                 570                 575

Leu Gly Ile Lys Gly Ile Leu Asn Phe Thr Pro Ala Arg Leu Asn Val
            580                 585                 590

Pro Glu His Ile Arg Ile His His Ile Asp Leu Ala Val Glu Leu Gln
        595                 600                 605

Ser Leu Val Tyr Phe Leu Lys His Tyr Ser Val Leu Glu Glu Ile Glu
610                 615                 620
```

Lys Leu
625

<210> SEQ ID NO 99
<211> LENGTH: 627
<212> TYPE: PRT
<213> ORGANISM: artificial sequence
<220> FEATURE:
<223> OTHER INFORMATION: Synthetic fluorescent sensor, mutant

<400> SEQUENCE: 99

Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

Pro Met Asn Lys Asp Gln Ser Lys Ile Pro Gln Ala Thr Ala Lys Arg
        35                  40                  45

Leu Pro Leu Tyr Tyr Arg Phe Leu Lys Asn Leu His Ala Ser Gly Lys
    50                  55                  60

Gln Arg Val Ser Ser Ala Glu Leu Ser Asp Ala Val Lys Val Asp Ser
65                  70                  75                  80

Ala Thr Ile Arg Arg Asp Phe Ser Tyr Phe Gly Ala Leu Gly Lys Lys
                85                  90                  95

Gly Tyr Gly Tyr Asn Val Asp Tyr Leu Leu Ser Phe Phe Arg Lys Thr
            100                 105                 110

Leu Asp Gln Asp Glu Met Thr Asp Val Ile Leu Ile Gly Val Gly Asn
        115                 120                 125

Leu Gly Thr Ala Phe Leu His Tyr Asn Phe Thr Lys Asn Asn Asn Thr
    130                 135                 140

Lys Ile Ser Met Ala Phe Asp Ile Asn Glu Ser Lys Ile Gly Thr Glu
145                 150                 155                 160

Val Gly Gly Val Pro Val Tyr Asn Leu Asp Asp Leu Glu Gln His Val
                165                 170                 175

Lys Asp Glu Ser Val Ala Ile Leu Thr Val Pro Ala Val Ala Ala Gln
            180                 185                 190

Ser Ile Thr Asp Arg Leu Val Ala Leu Gly Ile Lys Gly Ile Leu Asn
        195                 200                 205

Phe Thr Pro Ala Arg Leu Asn Val Pro Glu His Ile Arg Ile His His
    210                 215                 220

Ile Asp Leu Ala Val Glu Leu Gln Ser Leu Val Tyr Phe Leu Lys His
225                 230                 235                 240

Tyr Ser Val Leu Glu Glu Tyr Asn Ser Asp Asn Val Tyr Ile Met Ala
                245                 250                 255

Asp Lys Gln Lys Asn Gly Ile Lys Ala Asn Phe Lys Ile Arg His Asn
            260                 265                 270

Val Glu Asp Gly Ser Val Gln Leu Ala Asp His Tyr Gln Gln Asn Thr
        275                 280                 285

Pro Ile Gly Asp Gly Pro Val Leu Leu Pro Asp Asn His Tyr Leu Ser
    290                 295                 300

Phe Gln Ser Val Leu Ser Lys Asp Pro Asn Glu Lys Arg Asp His Met
305                 310                 315                 320

Val Leu Leu Glu Phe Val Thr Ala Ala Gly Ile Thr Leu Gly Met Asp
                325                 330                 335

Glu Leu Tyr Asn Val Asp Gly Gly Ser Gly Gly Thr Gly Ser Lys Gly
            340                 345                 350

```
Glu Glu Leu Phe Thr Gly Val Val Pro Ile Leu Val Glu Leu Asp Gly
            355                 360                 365
Asp Val Asn Gly His Lys Phe Ser Val Ser Gly Glu Gly Glu Gly Asp
        370                 375                 380
Ala Thr Tyr Gly Lys Leu Thr Leu Lys Leu Ile Cys Thr Thr Gly Lys
385                 390                 395                 400
Leu Pro Val Pro Trp Pro Thr Leu Val Thr Thr Leu Gly Tyr Gly Leu
                405                 410                 415
Lys Cys Phe Ala Arg Tyr Pro Asp His Met Lys Gln His Asp Phe Phe
            420                 425                 430
Lys Ser Ala Met Pro Glu Gly Tyr Val Gln Glu Arg Thr Ile Phe Phe
        435                 440                 445
Lys Asp Asp Gly Asn Tyr Lys Thr Arg Ala Glu Val Lys Phe Glu Gly
    450                 455                 460
Asp Thr Leu Val Asn Arg Ile Glu Leu Lys Gly Ile Gly Phe Lys Glu
465                 470                 475                 480
Asp Gly Asn Ile Leu Gly His Lys Leu Glu Tyr Asn Gly Thr Met Thr
                485                 490                 495
Asp Val Ile Leu Ile Gly Val Gly Asn Leu Gly Thr Ala Phe Leu His
            500                 505                 510
Tyr Asn Phe Thr Lys Asn Asn Asn Thr Lys Ile Ser Met Ala Phe Asp
        515                 520                 525
Ile Asn Glu Ser Lys Ile Gly Thr Glu Val Gly Val Pro Val Tyr
    530                 535                 540
Asn Leu Asp Asp Leu Glu Gln His Val Lys Asp Glu Ser Val Ala Ile
545                 550                 555                 560
Leu Thr Val Pro Ala Val Ala Ala Gln Ser Ile Thr Asp Arg Leu Val
                565                 570                 575
Ala Leu Gly Ile Lys Gly Ile Leu Asn Phe Thr Pro Ala Arg Leu Asn
            580                 585                 590
Val Pro Glu His Ile Arg Ile His His Ile Asp Leu Ala Val Glu Leu
        595                 600                 605
Gln Ser Leu Val Tyr Phe Leu Lys His Tyr Ser Val Leu Glu Glu Ile
    610                 615                 620
Glu Lys Leu
625

<210> SEQ ID NO 100
<211> LENGTH: 628
<212> TYPE: PRT
<213> ORGANISM: artificial sequence
<220> FEATURE:
<223> OTHER INFORMATION: Synthetic fluorescent sensor, mutant

<400> SEQUENCE: 100

Met Arg Gly Ser His His His His His His Gly Met Ala Ser Met Thr
1               5                   10                  15
Gly Gly Gln Gln Met Gly Arg Asp Leu Tyr Asp Asp Asp Lys Asp
            20                  25                  30
Pro Met Asn Lys Asp Gln Ser Lys Ile Pro Gln Ala Thr Ala Lys Arg
        35                  40                  45
Leu Pro Leu Tyr Tyr Arg Phe Leu Lys Asn Leu His Ala Ser Gly Lys
    50                  55                  60
Gln Arg Val Ser Ser Ala Glu Leu Ser Asp Ala Val Lys Val Asp Ser
65                  70                  75                  80
```

-continued

```
Ala Thr Ile Arg Arg Asp Phe Ser Tyr Phe Gly Ala Leu Gly Lys Lys
                85                  90                  95
Gly Tyr Gly Tyr Asn Val Asp Tyr Leu Leu Ser Phe Phe Arg Lys Thr
                100                 105                 110
Leu Asp Gln Asp Glu Met Thr Asp Val Ile Leu Ile Gly Val Gly Asn
                115                 120                 125
Leu Gly Thr Ala Phe Leu His Tyr Asn Phe Thr Lys Asn Asn Asn Thr
        130                 135                 140
Lys Ile Ser Met Ala Phe Asp Ile Asn Glu Ser Lys Ile Gly Thr Glu
145                 150                 155                 160
Val Gly Gly Val Pro Val Tyr Asn Leu Asp Asp Leu Glu Gln His Val
                165                 170                 175
Lys Asp Glu Ser Val Ala Ile Leu Thr Val Pro Ala Val Ala Ala Gln
                180                 185                 190
Ser Ile Thr Asp Arg Leu Val Ala Leu Gly Ile Lys Gly Ile Leu Asn
            195                 200                 205
Phe Thr Pro Ala Arg Leu Asn Val Pro Glu His Ile Arg Ile His His
        210                 215                 220
Ile Asp Leu Ala Val Glu Leu Gln Ser Leu Val Tyr Phe Leu Lys His
225                 230                 235                 240
Tyr Ser Val Leu Glu Glu Ile Tyr Asn Ser Asp Asn Val Tyr Ile Met
                245                 250                 255
Ala Asp Lys Gln Lys Asn Gly Ile Lys Ala Asn Phe Lys Ile Arg His
                260                 265                 270
Asn Val Glu Asp Gly Ser Val Gln Leu Ala Asp His Tyr Gln Gln Asn
            275                 280                 285
Thr Pro Ile Gly Asp Gly Pro Val Leu Leu Pro Asp Asn His Tyr Leu
        290                 295                 300
Ser Phe Gln Ser Val Leu Ser Lys Asp Pro Asn Glu Lys Arg Asp His
305                 310                 315                 320
Met Val Leu Leu Glu Phe Val Thr Ala Ala Gly Ile Thr Leu Gly Met
                325                 330                 335
Asp Glu Leu Tyr Asn Val Asp Gly Gly Ser Gly Gly Thr Gly Ser Lys
                340                 345                 350
Gly Glu Glu Leu Phe Thr Gly Val Val Pro Ile Leu Val Glu Leu Asp
            355                 360                 365
Gly Asp Val Asn Gly His Lys Phe Ser Val Ser Gly Glu Gly Glu Gly
        370                 375                 380
Asp Ala Thr Tyr Gly Lys Leu Thr Leu Lys Leu Ile Cys Thr Thr Gly
385                 390                 395                 400
Lys Leu Pro Val Pro Trp Pro Thr Leu Val Thr Thr Leu Gly Tyr Gly
                405                 410                 415
Leu Lys Cys Phe Ala Arg Tyr Pro Asp His Met Lys Gln His Asp Phe
                420                 425                 430
Phe Lys Ser Ala Met Pro Glu Gly Tyr Val Gln Glu Arg Thr Ile Phe
            435                 440                 445
Phe Lys Asp Asp Gly Asn Tyr Lys Thr Arg Ala Glu Val Lys Phe Glu
        450                 455                 460
Gly Asp Thr Leu Val Asn Arg Ile Glu Leu Lys Gly Ile Gly Phe Lys
465                 470                 475                 480
Glu Asp Gly Asn Ile Leu Gly His Lys Leu Glu Tyr Asn Gly Thr Met
                485                 490                 495
```

```
Thr Asp Val Ile Leu Ile Gly Val Gly Asn Leu Gly Thr Ala Phe Leu
            500                 505                 510

His Tyr Asn Phe Thr Lys Asn Asn Thr Lys Ile Ser Met Ala Phe
        515                 520                 525

Asp Ile Asn Glu Ser Lys Ile Gly Thr Glu Val Gly Val Pro Val
    530                 535                 540

Tyr Asn Leu Asp Asp Leu Glu Gln His Val Lys Asp Glu Ser Val Ala
545                 550                 555                 560

Ile Leu Thr Val Pro Ala Val Ala Ala Gln Ser Ile Thr Asp Arg Leu
                565                 570                 575

Val Ala Leu Gly Ile Lys Gly Ile Leu Asn Phe Thr Pro Ala Arg Leu
            580                 585                 590

Asn Val Pro Glu His Ile Arg Ile His His Ile Asp Leu Ala Val Glu
        595                 600                 605

Leu Gln Ser Leu Val Tyr Phe Leu Lys His Tyr Ser Val Leu Glu Glu
    610                 615                 620

Ile Glu Lys Leu
625

<210> SEQ ID NO 101
<211> LENGTH: 630
<212> TYPE: PRT
<213> ORGANISM: artificial sequence
<220> FEATURE:
<223> OTHER INFORMATION: Synthetic fluorescent sensor, mutant

<400> SEQUENCE: 101

Met Arg Gly Ser His His His His His His Gly Met Ala Ser Met Thr
1               5                   10                  15

Gly Gly Gln Gln Met Gly Arg Asp Leu Tyr Asp Asp Asp Asp Lys Asp
            20                  25                  30

Pro Met Asn Lys Asp Gln Ser Lys Ile Pro Gln Ala Thr Ala Lys Arg
        35                  40                  45

Leu Pro Leu Tyr Tyr Arg Phe Leu Lys Asn Leu His Ala Ser Gly Lys
    50                  55                  60

Gln Arg Val Ser Ser Ala Glu Leu Ser Asp Ala Val Lys Val Asp Ser
65                  70                  75                  80

Ala Thr Ile Arg Arg Asp Phe Ser Tyr Phe Gly Ala Leu Gly Lys Lys
                85                  90                  95

Gly Tyr Gly Tyr Asn Val Asp Tyr Leu Leu Ser Phe Arg Lys Thr
            100                 105                 110

Leu Asp Gln Asp Glu Met Thr Asp Val Ile Leu Ile Gly Val Gly Asn
        115                 120                 125

Leu Gly Thr Ala Phe Leu His Tyr Asn Phe Thr Lys Asn Asn Thr
    130                 135                 140

Lys Ile Ser Met Ala Phe Asp Ile Asn Glu Ser Lys Ile Gly Thr Glu
145                 150                 155                 160

Val Gly Gly Val Pro Val Tyr Asn Leu Asp Asp Leu Glu Gln His Val
                165                 170                 175

Lys Asp Glu Ser Val Ala Ile Leu Thr Val Pro Ala Val Ala Ala Gln
            180                 185                 190

Ser Ile Thr Asp Arg Leu Val Ala Leu Gly Ile Lys Gly Ile Leu Asn
        195                 200                 205

Phe Thr Pro Ala Arg Leu Asn Val Pro Glu His Ile Arg Ile His His
    210                 215                 220
```

```
Ile Asp Leu Ala Val Glu Leu Gln Ser Leu Val Tyr Phe Leu Lys His
225                 230                 235                 240

Tyr Ser Val Leu Glu Glu Ile Glu Ser Tyr Asn Ser Asp Asn Val Tyr
            245                 250                 255

Ile Met Ala Asp Lys Gln Lys Asn Gly Ile Lys Ala Asn Phe Lys Ile
        260                 265                 270

Arg His Asn Val Glu Asp Gly Ser Val Gln Leu Ala Asp His Tyr Gln
    275                 280                 285

Gln Asn Thr Pro Ile Gly Asp Gly Pro Val Leu Leu Pro Asp Asn His
290                 295                 300

Tyr Leu Ser Phe Gln Ser Val Leu Ser Lys Asp Pro Asn Glu Lys Arg
305                 310                 315                 320

Asp His Met Val Leu Leu Glu Phe Val Thr Ala Ala Gly Ile Thr Leu
                325                 330                 335

Gly Met Asp Glu Leu Tyr Asn Val Asp Gly Ser Gly Gly Thr Gly
                340                 345                 350

Ser Lys Gly Glu Glu Leu Phe Thr Gly Val Val Pro Ile Leu Val Glu
        355                 360                 365

Leu Asp Gly Asp Val Asn Gly His Lys Phe Ser Val Ser Gly Glu Gly
370                 375                 380

Glu Gly Asp Ala Thr Tyr Gly Lys Leu Thr Leu Lys Leu Ile Cys Thr
385                 390                 395                 400

Thr Gly Lys Leu Pro Val Pro Trp Pro Thr Leu Val Thr Thr Leu Gly
                405                 410                 415

Tyr Gly Leu Lys Cys Phe Ala Arg Tyr Pro Asp His Met Lys Gln His
            420                 425                 430

Asp Phe Phe Lys Ser Ala Met Pro Glu Gly Tyr Val Gln Glu Arg Thr
        435                 440                 445

Ile Phe Phe Lys Asp Asp Gly Asn Tyr Lys Thr Arg Ala Glu Val Lys
    450                 455                 460

Phe Glu Gly Asp Thr Leu Val Asn Arg Ile Glu Leu Lys Gly Ile Gly
465                 470                 475                 480

Phe Lys Glu Asp Gly Asn Ile Leu Gly His Lys Leu Glu Tyr Asn Gly
                485                 490                 495

Thr Met Thr Asp Val Ile Leu Ile Gly Val Gly Asn Leu Gly Thr Ala
            500                 505                 510

Phe Leu His Tyr Asn Phe Thr Lys Asn Asn Thr Lys Ile Ser Met
        515                 520                 525

Ala Phe Asp Ile Asn Glu Ser Lys Ile Gly Thr Glu Val Gly Gly Val
530                 535                 540

Pro Val Tyr Asn Leu Asp Asp Leu Glu Gln His Val Lys Asp Glu Ser
545                 550                 555                 560

Val Ala Ile Leu Thr Val Pro Ala Val Ala Ala Gln Ser Ile Thr Asp
                565                 570                 575

Arg Leu Val Ala Leu Gly Ile Lys Gly Ile Leu Asn Phe Thr Pro Ala
            580                 585                 590

Arg Leu Asn Val Pro Glu His Ile Arg Ile His His Ile Asp Leu Ala
        595                 600                 605

Val Glu Leu Gln Ser Leu Val Tyr Phe Leu Lys His Tyr Ser Val Leu
    610                 615                 620

Glu Glu Ile Glu Lys Leu
625                 630
```

```
<210> SEQ ID NO 102
<211> LENGTH: 629
<212> TYPE: PRT
<213> ORGANISM: artificial sequence
<220> FEATURE:
<223> OTHER INFORMATION: Synthetic fluorescent sensor, mutant

<400> SEQUENCE: 102

Met Arg Gly Ser His His His His His Gly Met Ala Ser Met Thr
1               5                   10                  15

Gly Gly Gln Gln Met Gly Arg Asp Leu Tyr Asp Asp Asp Lys Asp
                20                  25                  30

Pro Met Asn Lys Asp Gln Ser Lys Ile Pro Gln Ala Thr Ala Lys Arg
        35                  40                  45

Leu Pro Leu Tyr Tyr Arg Phe Leu Lys Asn Leu His Ala Ser Gly Lys
    50                  55                  60

Gln Arg Val Ser Ser Ala Glu Leu Ser Asp Ala Val Lys Val Asp Ser
65                  70                  75                  80

Ala Thr Ile Arg Arg Asp Phe Ser Tyr Phe Gly Ala Leu Gly Lys Lys
                85                  90                  95

Gly Tyr Gly Tyr Asn Val Asp Tyr Leu Leu Ser Phe Phe Arg Lys Thr
            100                 105                 110

Leu Asp Gln Asp Glu Met Thr Asp Val Ile Leu Ile Gly Val Gly Asn
        115                 120                 125

Leu Gly Thr Ala Phe Leu His Tyr Asn Phe Thr Lys Asn Asn Asn Thr
    130                 135                 140

Lys Ile Ser Met Ala Phe Asp Ile Asn Glu Ser Lys Ile Gly Thr Glu
145                 150                 155                 160

Val Gly Gly Val Pro Val Tyr Asn Leu Asp Asp Leu Glu Gln His Val
                165                 170                 175

Lys Asp Glu Ser Val Ala Ile Leu Thr Val Pro Ala Val Ala Ala Gln
            180                 185                 190

Ser Ile Thr Asp Arg Leu Val Ala Leu Gly Ile Lys Gly Ile Leu Asn
        195                 200                 205

Phe Thr Pro Ala Arg Leu Asn Val Pro Glu His Ile Arg Ile His His
    210                 215                 220

Ile Asp Leu Ala Val Glu Leu Gln Ser Leu Val Tyr Phe Leu Lys His
225                 230                 235                 240

Tyr Ser Val Leu Glu Glu Ile Glu Thr Ser Tyr Asn Ser Asp Asn Val
                245                 250                 255

Tyr Ile Met Ala Asp Lys Gln Lys Asn Gly Ile Lys Ala Asn Phe Lys
            260                 265                 270

Ile Arg His Asn Val Glu Asp Gly Ser Val Gln Leu Ala Asp His Tyr
        275                 280                 285

Gln Gln Asn Thr Pro Ile Gly Asp Gly Pro Val Leu Leu Pro Asp Asn
    290                 295                 300

His Tyr Leu Ser Phe Gln Ser Val Leu Ser Lys Asp Pro Asn Glu Lys
305                 310                 315                 320

Arg Asp His Met Val Leu Leu Glu Phe Val Thr Ala Ala Gly Ile Thr
                325                 330                 335

Leu Gly Met Asp Glu Leu Tyr Asn Val Asp Gly Gly Ser Gly Gly Thr
            340                 345                 350

Gly Ser Lys Gly Glu Glu Leu Phe Thr Gly Val Val Pro Ile Leu Val
        355                 360                 365

Glu Leu Asp Gly Asp Val Asn Gly His Lys Phe Ser Val Ser Gly Glu
```

```
                370                 375                 380
Gly Glu Gly Asp Ala Thr Tyr Gly Lys Leu Thr Leu Lys Leu Ile Cys
385                 390                 395                 400

Thr Thr Gly Lys Leu Pro Val Pro Trp Pro Thr Leu Val Thr Thr Leu
                405                 410                 415

Gly Tyr Gly Leu Lys Cys Phe Ala Arg Tyr Pro Asp His Met Lys Gln
                420                 425                 430

His Asp Phe Phe Lys Ser Ala Met Pro Glu Gly Tyr Val Gln Glu Arg
                435                 440                 445

Thr Ile Phe Phe Lys Asp Asp Gly Asn Tyr Lys Thr Arg Ala Glu Val
                450                 455                 460

Lys Phe Glu Gly Asp Thr Leu Val Asn Arg Ile Glu Leu Lys Gly Ile
465                 470                 475                 480

Gly Phe Lys Glu Asp Gly Asn Ile Leu Gly His Lys Leu Glu Tyr Asn
                485                 490                 495

Met Thr Asp Val Ile Leu Ile Gly Val Gly Asn Leu Gly Thr Ala Phe
                500                 505                 510

Leu His Tyr Asn Phe Thr Lys Asn Asn Thr Lys Ile Ser Met Ala
                515                 520                 525

Phe Asp Ile Asn Glu Ser Lys Ile Gly Thr Glu Val Gly Gly Val Pro
530                 535                 540

Val Tyr Asn Leu Asp Asp Leu Glu Gln His Val Lys Asp Glu Ser Val
545                 550                 555                 560

Ala Ile Leu Thr Val Pro Ala Val Ala Ala Gln Ser Ile Thr Asp Arg
                565                 570                 575

Leu Val Ala Leu Gly Ile Lys Gly Ile Leu Asn Phe Thr Pro Ala Arg
                580                 585                 590

Leu Asn Val Pro Glu His Ile Arg Ile His His Ile Asp Leu Ala Val
                595                 600                 605

Glu Leu Gln Ser Leu Val Tyr Phe Leu Lys His Tyr Ser Val Leu Glu
                610                 615                 620

Glu Ile Glu Lys Leu
625

<210> SEQ ID NO 103
<211> LENGTH: 630
<212> TYPE: PRT
<213> ORGANISM: artificial sequence
<220> FEATURE:
<223> OTHER INFORMATION: Synthetic fluorescent sensor, mutant

<400> SEQUENCE: 103

Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
                20                  25                  30

Pro Met Asn Lys Asp Gln Ser Lys Ile Pro Gln Ala Thr Ala Lys Arg
                35                  40                  45

Leu Pro Leu Tyr Tyr Arg Phe Leu Lys Asn Leu His Ala Ser Gly Lys
                50                  55                  60

Gln Arg Val Ser Ser Ala Glu Leu Ser Asp Ala Val Lys Val Asp Ser
65                  70                  75                  80

Ala Thr Ile Arg Arg Asp Phe Ser Tyr Phe Gly Ala Leu Gly Lys Lys
                85                  90                  95

Gly Tyr Gly Tyr Asn Val Asp Tyr Leu Leu Ser Phe Phe Arg Lys Thr
```

```
                100                 105                 110
Leu Asp Gln Asp Glu Met Thr Asp Val Ile Leu Ile Gly Val Gly Asn
            115                 120                 125
Leu Gly Thr Ala Phe Leu His Tyr Asn Phe Thr Lys Asn Asn Asn Thr
        130                 135                 140
Lys Ile Ser Met Ala Phe Asp Ile Asn Glu Ser Lys Ile Gly Thr Glu
145                 150                 155                 160
Val Gly Gly Val Pro Val Tyr Asn Leu Asp Asp Leu Glu Gln His Val
                165                 170                 175
Lys Asp Glu Ser Val Ala Ile Leu Thr Val Pro Ala Val Ala Ala Gln
            180                 185                 190
Ser Ile Thr Asp Arg Leu Val Ala Leu Gly Ile Lys Gly Ile Leu Asn
        195                 200                 205
Phe Thr Pro Ala Arg Leu Asn Val Pro Glu His Ile Arg Ile His His
    210                 215                 220
Ile Asp Leu Ala Val Glu Leu Gln Ser Leu Val Tyr Phe Leu Lys His
225                 230                 235                 240
Tyr Ser Val Leu Glu Glu Ile Glu Thr Ser Tyr Asn Ser Asp Asn Val
                245                 250                 255
Tyr Ile Met Ala Asp Lys Gln Lys Asn Gly Ile Lys Ala Asn Phe Lys
            260                 265                 270
Ile Arg His Asn Val Glu Asp Gly Ser Val Gln Leu Ala Asp His Tyr
        275                 280                 285
Gln Gln Asn Thr Pro Ile Gly Asp Gly Pro Val Leu Leu Pro Asp Asn
    290                 295                 300
His Tyr Leu Ser Phe Gln Ser Val Leu Ser Lys Asp Pro Asn Glu Lys
305                 310                 315                 320
Arg Asp His Met Val Leu Leu Glu Phe Val Thr Ala Ala Gly Ile Thr
                325                 330                 335
Leu Gly Met Asp Glu Leu Tyr Asn Val Asp Gly Gly Ser Gly Gly Thr
            340                 345                 350
Gly Ser Lys Gly Glu Glu Leu Phe Thr Gly Val Val Pro Ile Leu Val
        355                 360                 365
Glu Leu Asp Gly Asp Val Asn Gly His Lys Phe Ser Val Ser Gly Glu
    370                 375                 380
Gly Glu Gly Asp Ala Thr Tyr Gly Lys Leu Thr Leu Lys Leu Ile Cys
385                 390                 395                 400
Thr Thr Gly Lys Leu Pro Val Pro Trp Pro Thr Leu Val Thr Thr Leu
                405                 410                 415
Gly Tyr Gly Leu Lys Cys Phe Ala Arg Tyr Pro Asp His Met Lys Gln
            420                 425                 430
His Asp Phe Phe Lys Ser Ala Met Pro Glu Gly Tyr Val Gln Glu Arg
        435                 440                 445
Thr Ile Phe Phe Lys Asp Asp Gly Asn Tyr Lys Thr Arg Ala Glu Val
    450                 455                 460
Lys Phe Glu Gly Asp Thr Leu Val Asn Arg Ile Glu Leu Lys Gly Ile
465                 470                 475                 480
Gly Phe Lys Glu Asp Gly Asn Ile Leu Gly His Lys Leu Glu Tyr Asn
                485                 490                 495
Thr Met Thr Asp Val Ile Leu Ile Gly Val Gly Asn Leu Gly Thr Ala
            500                 505                 510
Phe Leu His Tyr Asn Phe Thr Lys Asn Asn Asn Thr Lys Ile Ser Met
        515                 520                 525
```

```
Ala Phe Asp Ile Asn Glu Ser Lys Ile Gly Thr Glu Val Gly Gly Val
        530                 535                 540

Pro Val Tyr Asn Leu Asp Asp Leu Glu Gln His Val Lys Asp Glu Ser
545                 550                 555                 560

Val Ala Ile Leu Thr Val Pro Ala Val Ala Ala Gln Ser Ile Thr Asp
                565                 570                 575

Arg Leu Val Ala Leu Gly Ile Lys Gly Ile Leu Asn Phe Thr Pro Ala
            580                 585                 590

Arg Leu Asn Val Pro Glu His Ile Arg Ile His His Ile Asp Leu Ala
        595                 600                 605

Val Glu Leu Gln Ser Leu Val Tyr Phe Leu Lys His Tyr Ser Val Leu
    610                 615                 620

Glu Glu Ile Glu Lys Leu
625                 630

<210> SEQ ID NO 104
<211> LENGTH: 630
<212> TYPE: PRT
<213> ORGANISM: artificial sequence
<220> FEATURE:
<223> OTHER INFORMATION: Synthetic fluorescent sensor, mutant

<400> SEQUENCE: 104

Met Arg Gly Ser His His His His His Gly Met Ala Ser Met Thr
1               5                   10                  15

Gly Gly Gln Gln Met Gly Arg Asp Leu Tyr Asp Asp Asp Lys Asp
                20                  25                  30

Pro Met Asn Lys Asp Gln Ser Lys Ile Pro Gln Ala Thr Ala Lys Arg
        35                  40                  45

Leu Pro Leu Tyr Tyr Arg Phe Leu Lys Asn Leu His Ala Ser Gly Lys
    50                  55                  60

Gln Arg Val Ser Ser Ala Glu Leu Ser Asp Ala Val Lys Val Asp Ser
65                  70                  75                  80

Ala Thr Ile Arg Arg Asp Phe Ser Tyr Phe Gly Ala Leu Gly Lys Lys
                85                  90                  95

Gly Tyr Gly Tyr Asn Val Asp Tyr Leu Leu Ser Phe Phe Arg Lys Thr
                100                 105                 110

Leu Asp Gln Asp Glu Met Thr Asp Val Ile Leu Ile Gly Val Gly Asn
            115                 120                 125

Leu Gly Thr Ala Phe Leu His Tyr Asn Phe Thr Lys Asn Asn Asn Thr
    130                 135                 140

Lys Ile Ser Met Ala Phe Asp Ile Asn Glu Ser Lys Ile Gly Thr Glu
145                 150                 155                 160

Val Gly Gly Val Pro Val Tyr Asn Leu Asp Asp Leu Glu Gln His Val
                165                 170                 175

Lys Asp Glu Ser Val Ala Ile Leu Thr Val Pro Ala Val Ala Ala Gln
            180                 185                 190

Ser Ile Thr Asp Arg Leu Val Ala Leu Gly Ile Lys Gly Ile Leu Asn
    195                 200                 205

Phe Thr Pro Ala Arg Leu Asn Val Pro Glu His Ile Arg Ile His His
    210                 215                 220

Ile Asp Leu Ala Val Glu Leu Gln Ser Leu Val Tyr Phe Leu Lys His
225                 230                 235                 240

Tyr Ser Val Leu Glu Glu Ile Glu Thr Ser Tyr Asn Ser Asp Asn Val
                245                 250                 255
```

Tyr Ile Met Ala Asp Lys Gln Lys Asn Gly Ile Lys Ala Asn Phe Lys
        260                 265                 270

Ile Arg His Asn Val Glu Asp Gly Ser Val Gln Leu Ala Asp His Tyr
            275                 280                 285

Gln Gln Asn Thr Pro Ile Gly Asp Gly Pro Val Leu Leu Pro Asp Asn
290                 295                 300

His Tyr Leu Ser Phe Gln Ser Val Leu Ser Lys Asp Pro Asn Glu Lys
305                 310                 315                 320

Arg Asp His Met Val Leu Leu Glu Phe Val Thr Ala Ala Gly Ile Thr
                325                 330                 335

Leu Gly Met Asp Glu Leu Tyr Asn Val Asp Gly Gly Ser Gly Gly Thr
                340                 345                 350

Gly Ser Lys Gly Glu Glu Leu Phe Thr Gly Val Val Pro Ile Leu Val
            355                 360                 365

Glu Leu Asp Gly Asp Val Asn Gly His Lys Phe Ser Val Ser Gly Glu
    370                 375                 380

Gly Glu Gly Asp Ala Thr Tyr Gly Lys Leu Thr Leu Lys Leu Ile Cys
385                 390                 395                 400

Thr Thr Gly Lys Leu Pro Val Pro Trp Pro Thr Leu Val Thr Thr Leu
                405                 410                 415

Gly Tyr Gly Leu Lys Cys Phe Ala Arg Tyr Pro Asp His Met Lys Gln
            420                 425                 430

His Asp Phe Phe Lys Ser Ala Met Pro Glu Gly Tyr Val Gln Glu Arg
        435                 440                 445

Thr Ile Phe Phe Lys Asp Asp Gly Asn Tyr Lys Thr Arg Ala Glu Val
    450                 455                 460

Lys Phe Glu Gly Asp Thr Leu Val Asn Arg Ile Glu Leu Lys Gly Ile
465                 470                 475                 480

Gly Phe Lys Glu Asp Gly Asn Ile Leu Gly His Lys Leu Glu Tyr Asn
                485                 490                 495

Gly Met Thr Asp Val Ile Leu Ile Gly Val Gly Asn Leu Gly Thr Ala
            500                 505                 510

Phe Leu His Tyr Asn Phe Thr Lys Asn Asn Thr Lys Ile Ser Met
        515                 520                 525

Ala Phe Asp Ile Asn Glu Ser Lys Ile Gly Thr Glu Val Gly Val
530                 535                 540

Pro Val Tyr Asn Leu Asp Asp Leu Glu Gln His Val Lys Asp Glu Ser
545                 550                 555                 560

Val Ala Ile Leu Thr Val Pro Ala Val Ala Ala Gln Ser Ile Thr Asp
                565                 570                 575

Arg Leu Val Ala Leu Gly Ile Lys Gly Ile Leu Asn Phe Thr Pro Ala
            580                 585                 590

Arg Leu Asn Val Pro Glu His Ile Arg Ile His His Ile Asp Leu Ala
        595                 600                 605

Val Glu Leu Gln Ser Leu Val Tyr Phe Leu Lys His Tyr Ser Val Leu
    610                 615                 620

Glu Glu Ile Glu Lys Leu
625                 630

<210> SEQ ID NO 105
<211> LENGTH: 622
<212> TYPE: PRT
<213> ORGANISM: artificial sequence
<220> FEATURE:

<223> OTHER INFORMATION: Synthetic fluorescent sensor, mutant

<400> SEQUENCE: 105

```
Met Arg Gly Ser His His His His His Gly Met Ala Ser Met Thr
1               5                   10                  15

Gly Gly Gln Gln Met Gly Arg Asp Leu Tyr Asp Asp Asp Lys Asp
            20                  25                  30

Pro Met Asn Lys Asp Gln Ser Lys Ile Pro Gln Ala Thr Ala Lys Arg
        35                  40                  45

Leu Pro Leu Tyr Tyr Arg Phe Leu Lys Asn Leu His Ala Ser Gly Lys
    50                  55                  60

Gln Arg Val Ser Ser Ala Glu Leu Ser Asp Ala Val Lys Val Asp Ser
65                  70                  75                  80

Ala Thr Ile Arg Arg Asp Phe Ser Tyr Phe Gly Ala Leu Gly Lys Lys
                85                  90                  95

Gly Tyr Gly Tyr Asn Val Asp Tyr Leu Leu Ser Phe Arg Lys Thr
            100                 105                 110

Leu Asp Gln Asp Glu Met Thr Asp Val Ile Leu Ile Gly Val Gly Asn
            115                 120                 125

Leu Gly Thr Ala Phe Leu His Tyr Asn Phe Thr Lys Asn Asn Asn Thr
130                 135                 140

Lys Ile Ser Met Ala Phe Arg Ile Asn Glu Ser Lys Ile Gly Thr Glu
145                 150                 155                 160

Val Gly Gly Val Pro Val Tyr Asn Leu Asp Asp Leu Glu Gln His Val
                165                 170                 175

Lys Asp Glu Ser Val Ala Ile Leu Thr Val Pro Ala Val Ala Ala Gln
            180                 185                 190

Ser Ile Thr Asp Arg Leu Val Ala Leu Gly Ile Lys Gly Ile Leu Asn
        195                 200                 205

Phe Thr Pro Ala Arg Leu Asn Val Pro Glu His Ile Arg Ile His His
    210                 215                 220

Ile Asp Leu Ala Val Glu Leu Gln Ser Leu Val Tyr Phe Leu Lys His
225                 230                 235                 240

Tyr Tyr Asn Ser Asp Asn Val Tyr Ile Met Ala Asp Lys Gln Lys Asn
                245                 250                 255

Gly Ile Lys Ala Asn Phe Lys Ile Arg His Asn Val Glu Asp Gly Ser
            260                 265                 270

Val Gln Leu Ala Asp His Tyr Gln Gln Asn Thr Pro Ile Gly Asp Gly
        275                 280                 285

Pro Val Leu Leu Pro Asp Asn His Tyr Leu Ser Phe Gln Ser Val Leu
    290                 295                 300

Ser Lys Asp Pro Asn Glu Lys Arg Asp His Met Val Leu Leu Glu Phe
305                 310                 315                 320

Val Thr Ala Ala Gly Ile Thr Leu Gly Met Asp Glu Leu Tyr Asn Val
                325                 330                 335

Asp Gly Gly Ser Gly Gly Thr Gly Ser Lys Gly Glu Glu Leu Phe Thr
            340                 345                 350

Gly Val Val Pro Ile Leu Val Glu Leu Asp Gly Asp Val Asn Gly His
        355                 360                 365

Lys Phe Ser Val Ser Gly Glu Gly Glu Gly Asp Ala Thr Tyr Gly Lys
    370                 375                 380

Leu Thr Leu Lys Leu Ile Cys Thr Thr Gly Lys Leu Pro Val Pro Trp
385                 390                 395                 400
```

```
Pro Thr Leu Val Thr Thr Leu Gly Tyr Gly Leu Lys Cys Phe Ala Arg
                405                 410                 415

Tyr Pro Asp His Met Lys Gln His Asp Phe Phe Lys Ser Ala Met Pro
            420                 425                 430

Glu Gly Tyr Val Gln Glu Arg Thr Ile Phe Phe Lys Asp Asp Gly Asn
        435                 440                 445

Tyr Lys Thr Arg Ala Glu Val Lys Phe Glu Gly Asp Thr Leu Val Asn
    450                 455                 460

Arg Ile Glu Leu Lys Gly Ile Gly Phe Lys Glu Asp Gly Asn Ile Leu
465                 470                 475                 480

Gly His Lys Leu Glu Tyr Asn Gly Thr Met Thr Asp Val Ile Leu Ile
                485                 490                 495

Gly Val Gly Asn Leu Gly Thr Ala Phe Leu His Tyr Asn Phe Thr Lys
            500                 505                 510

Asn Asn Asn Thr Lys Ile Ser Met Ala Phe Arg Ile Asn Glu Ser Lys
        515                 520                 525

Ile Gly Thr Glu Val Gly Val Pro Val Tyr Asn Leu Asp Asp Leu
    530                 535                 540

Glu Gln His Val Lys Asp Glu Ser Val Ala Ile Leu Thr Val Pro Ala
545                 550                 555                 560

Val Ala Ala Gln Ser Ile Thr Asp Arg Leu Val Ala Leu Gly Ile Lys
                565                 570                 575

Gly Ile Leu Asn Phe Thr Pro Ala Arg Leu Asn Val Pro Glu His Ile
            580                 585                 590

Arg Ile His His Ile Asp Leu Ala Val Glu Leu Gln Ser Leu Val Tyr
        595                 600                 605

Phe Leu Lys His Tyr Ser Val Leu Glu Glu Ile Glu Lys Leu
    610                 615                 620

<210> SEQ ID NO 106
<211> LENGTH: 622
<212> TYPE: PRT
<213> ORGANISM: artificial sequence
<220> FEATURE:
<223> OTHER INFORMATION: Synthetic fluorescent sensor, mutant

<400> SEQUENCE: 106

Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

Pro Met Asn Lys Asp Gln Ser Lys Ile Pro Gln Ala Thr Ala Lys Arg
        35                  40                  45

Leu Pro Leu Tyr Tyr Arg Phe Leu Lys Asn Leu His Ala Ser Gly Lys
    50                  55                  60

Gln Arg Val Ser Ser Ala Glu Leu Ser Asp Ala Val Lys Val Asp Ser
65                  70                  75                  80

Ala Thr Ile Arg Arg Asp Phe Ser Tyr Phe Gly Ala Leu Gly Lys Lys
                85                  90                  95

Gly Tyr Gly Tyr Asn Val Asp Tyr Leu Leu Ser Phe Phe Arg Lys Thr
            100                 105                 110

Leu Asp Gln Asp Glu Met Thr Asp Val Ile Leu Ile Gly Val Gly Asn
        115                 120                 125

Leu Gly Thr Ala Phe Leu His Tyr Asn Phe Thr Lys Asn Asn Asn Thr
    130                 135                 140
```

-continued

Lys Ile Ser Met Ala Phe Asp Ile Lys Glu Ser Lys Ile Gly Thr Glu
145                 150                 155                 160

Val Gly Gly Val Pro Val Tyr Asn Leu Asp Asp Leu Glu Gln His Val
                165                 170                 175

Lys Asp Glu Ser Val Ala Ile Leu Thr Val Pro Ala Val Ala Ala Gln
            180                 185                 190

Ser Ile Thr Asp Arg Leu Val Ala Leu Gly Ile Lys Gly Ile Leu Asn
        195                 200                 205

Phe Thr Pro Ala Arg Leu Asn Val Pro Glu His Ile Arg Ile His His
    210                 215                 220

Ile Asp Leu Ala Val Glu Leu Gln Ser Leu Val Tyr Phe Leu Lys His
225                 230                 235                 240

Tyr Tyr Asn Ser Asp Asn Val Tyr Ile Met Ala Asp Lys Gln Lys Asn
                245                 250                 255

Gly Ile Lys Ala Asn Phe Lys Ile Arg His Asn Val Glu Asp Gly Ser
            260                 265                 270

Val Gln Leu Ala Asp His Tyr Gln Gln Asn Thr Pro Ile Gly Asp Gly
        275                 280                 285

Pro Val Leu Leu Pro Asp Asn His Tyr Leu Ser Phe Gln Ser Val Leu
    290                 295                 300

Ser Lys Asp Pro Asn Glu Lys Arg Asp His Met Val Leu Leu Glu Phe
305                 310                 315                 320

Val Thr Ala Ala Gly Ile Thr Leu Gly Met Asp Glu Leu Tyr Asn Val
                325                 330                 335

Asp Gly Gly Ser Gly Gly Thr Gly Ser Lys Gly Glu Glu Leu Phe Thr
            340                 345                 350

Gly Val Val Pro Ile Leu Val Glu Leu Asp Gly Asp Val Asn Gly His
        355                 360                 365

Lys Phe Ser Val Ser Gly Glu Gly Glu Gly Asp Ala Thr Tyr Gly Lys
    370                 375                 380

Leu Thr Leu Lys Leu Ile Cys Thr Thr Gly Lys Leu Pro Val Pro Trp
385                 390                 395                 400

Pro Thr Leu Val Thr Thr Leu Gly Tyr Gly Leu Lys Cys Phe Ala Arg
                405                 410                 415

Tyr Pro Asp His Met Lys Gln His Asp Phe Phe Lys Ser Ala Met Pro
            420                 425                 430

Glu Gly Tyr Val Gln Glu Arg Thr Ile Phe Phe Lys Asp Asp Gly Asn
        435                 440                 445

Tyr Lys Thr Arg Ala Glu Val Lys Phe Glu Gly Asp Thr Leu Val Asn
    450                 455                 460

Arg Ile Glu Leu Lys Gly Ile Gly Phe Lys Glu Asp Gly Asn Ile Leu
465                 470                 475                 480

Gly His Lys Leu Glu Tyr Asn Gly Thr Met Thr Asp Val Ile Leu Ile
                485                 490                 495

Gly Val Gly Asn Leu Gly Thr Ala Phe Leu His Tyr Asn Phe Thr Lys
            500                 505                 510

Asn Asn Asn Thr Lys Ile Ser Met Ala Phe Asp Ile Lys Glu Ser Lys
        515                 520                 525

Ile Gly Thr Glu Val Gly Gly Val Pro Val Tyr Asn Leu Asp Asp Leu
    530                 535                 540

Glu Gln His Val Lys Asp Glu Ser Val Ala Ile Leu Thr Val Pro Ala
545                 550                 555                 560

Val Ala Ala Gln Ser Ile Thr Asp Arg Leu Val Ala Leu Gly Ile Lys 565                 570                 575
Gly Ile Leu Asn Phe Thr Pro Ala Arg Leu Asn Val Pro Glu His Ile
                580                 585                 590

Arg Ile His His Ile Asp Leu Ala Val Glu Leu Gln Ser Leu Val Tyr
            595                 600                 605

Phe Leu Lys His Tyr Ser Val Leu Glu Glu Ile Glu Lys Leu
        610                 615                 620

<210> SEQ ID NO 107
<211> LENGTH: 622
<212> TYPE: PRT
<213> ORGANISM: artificial sequence
<220> FEATURE:
<223> OTHER INFORMATION: Synthetic fluorescent sensor, mutant

<400> SEQUENCE: 107

Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

Pro Met Asn Lys Asp Gln Ser Lys Ile Pro Gln Ala Thr Ala Lys Arg
            35                  40                  45

Leu Pro Leu Tyr Tyr Arg Phe Leu Lys Asn Leu His Ala Ser Gly Lys
50              55                  60

Gln Arg Val Ser Ser Ala Glu Leu Ser Asp Ala Val Lys Val Asp Ser
65              70                  75                  80

Ala Thr Ile Arg Arg Asp Phe Ser Tyr Phe Gly Ala Leu Gly Lys Lys
                85                  90                  95

Gly Tyr Gly Tyr Asn Val Asp Tyr Leu Leu Ser Phe Phe Arg Lys Thr
            100                 105                 110

Leu Asp Gln Asp Glu Met Thr Asp Val Ile Leu Ile Gly Val Gly Asn
        115                 120                 125

Leu Gly Thr Ala Phe Leu His Tyr Asn Phe Thr Lys Asn Asn Asn Thr
    130                 135                 140

Lys Ile Ser Met Ala Phe Asp Ile Arg Glu Ser Lys Ile Gly Thr Glu
145                 150                 155                 160

Val Gly Gly Val Pro Val Tyr Asn Leu Asp Asp Leu Glu Gln His Val
                165                 170                 175

Lys Asp Glu Ser Val Ala Ile Leu Thr Val Pro Ala Val Ala Ala Gln
            180                 185                 190

Ser Ile Thr Asp Arg Leu Val Ala Leu Gly Ile Lys Gly Ile Leu Asn
        195                 200                 205

Phe Thr Pro Ala Arg Leu Asn Val Pro Glu His Ile Arg Ile His His
    210                 215                 220

Ile Asp Leu Ala Val Glu Leu Gln Ser Leu Val Tyr Phe Leu Lys His
225                 230                 235                 240

Tyr Tyr Asn Ser Asp Asn Val Tyr Ile Met Ala Asp Lys Gln Lys Asn
                245                 250                 255

Gly Ile Lys Ala Asn Phe Lys Ile Arg His Asn Val Glu Asp Gly Ser
            260                 265                 270

Val Gln Leu Ala Asp His Tyr Gln Gln Asn Thr Pro Ile Gly Asp Gly
        275                 280                 285

Pro Val Leu Leu Pro Asp Asn His Tyr Leu Ser Phe Gln Ser Val Leu
    290                 295                 300

Ser Lys Asp Pro Asn Glu Lys Arg Asp His Met Val Leu Leu Glu Phe

```
            305                 310                 315                 320
        Val Thr Ala Ala Gly Ile Thr Leu Gly Met Asp Glu Leu Tyr Asn Val
                        325                 330                 335

Asp Gly Gly Ser Gly Gly Thr Gly Ser Lys Gly Glu Glu Leu Phe Thr
                        340                 345                 350

Gly Val Val Pro Ile Leu Val Glu Leu Asp Gly Asp Val Asn Gly His
                        355                 360                 365

Lys Phe Ser Val Ser Gly Glu Gly Glu Gly Asp Ala Thr Tyr Gly Lys
                        370                 375                 380

Leu Thr Leu Lys Leu Ile Cys Thr Thr Gly Lys Leu Pro Val Pro Trp
        385                 390                 395                 400

Pro Thr Leu Val Thr Thr Leu Gly Tyr Gly Leu Lys Cys Phe Ala Arg
                        405                 410                 415

Tyr Pro Asp His Met Lys Gln His Asp Phe Phe Lys Ser Ala Met Pro
                        420                 425                 430

Glu Gly Tyr Val Gln Glu Arg Thr Ile Phe Phe Lys Asp Asp Gly Asn
                        435                 440                 445

Tyr Lys Thr Arg Ala Glu Val Lys Phe Glu Gly Asp Thr Leu Val Asn
                        450                 455                 460

Arg Ile Glu Leu Lys Gly Ile Gly Phe Lys Glu Asp Gly Asn Ile Leu
        465                 470                 475                 480

Gly His Lys Leu Glu Tyr Asn Gly Thr Met Thr Asp Val Ile Leu Ile
                        485                 490                 495

Gly Val Gly Asn Leu Gly Thr Ala Phe Leu His Tyr Asn Phe Thr Lys
                        500                 505                 510

Asn Asn Asn Thr Lys Ile Ser Met Ala Phe Asp Ile Arg Glu Ser Lys
                        515                 520                 525

Ile Gly Thr Glu Val Gly Val Pro Val Tyr Asn Leu Asp Asp Leu
                        530                 535                 540

Glu Gln His Val Lys Asp Glu Ser Val Ala Ile Leu Thr Val Pro Ala
        545                 550                 555                 560

Val Ala Ala Gln Ser Ile Thr Asp Arg Leu Val Ala Leu Gly Ile Lys
                        565                 570                 575

Gly Ile Leu Asn Phe Thr Pro Ala Arg Leu Asn Val Pro Glu His Ile
                        580                 585                 590

Arg Ile His His Ile Asp Leu Ala Val Glu Leu Gln Ser Leu Val Tyr
                        595                 600                 605

Phe Leu Lys His Tyr Ser Val Leu Glu Glu Ile Glu Lys Leu
        610                 615                 620

<210> SEQ ID NO 108
<211> LENGTH: 622
<212> TYPE: PRT
<213> ORGANISM: artificial sequence
<220> FEATURE:
<223> OTHER INFORMATION: Synthetic fluorescent sensor, mutant

<400> SEQUENCE: 108

Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
                20                  25                  30

Pro Met Asn Lys Asp Gln Ser Lys Ile Pro Gln Ala Thr Ala Lys Arg
                35                  40                  45

Leu Pro Leu Tyr Tyr Arg Phe Leu Lys Asn Leu His Ala Ser Gly Lys
```

```
            50                  55                  60
Gln Arg Val Ser Ser Ala Glu Leu Ser Asp Ala Val Lys Val Asp Ser
 65                  70                  75                  80

Ala Thr Ile Arg Arg Asp Phe Ser Tyr Phe Gly Ala Leu Gly Lys Lys
                     85                  90                  95

Gly Tyr Gly Tyr Asn Val Asp Tyr Leu Leu Ser Phe Phe Arg Lys Thr
                100                 105                 110

Leu Asp Gln Asp Glu Met Thr Asp Val Ile Leu Ile Gly Val Gly Asn
                115                 120                 125

Leu Gly Thr Ala Phe Leu His Tyr Asn Phe Thr Lys Asn Asn Asn Thr
                130                 135                 140

Lys Ile Ser Met Ala Phe Asp Ile Glu Glu Ser Lys Ile Gly Thr Glu
145                 150                 155                 160

Val Gly Gly Val Pro Val Tyr Asn Leu Asp Asp Leu Glu Gln His Val
                165                 170                 175

Lys Asp Glu Ser Val Ala Ile Leu Thr Val Pro Ala Val Ala Ala Gln
                180                 185                 190

Ser Ile Thr Asp Arg Leu Val Ala Leu Gly Ile Lys Gly Ile Leu Asn
                195                 200                 205

Phe Thr Pro Ala Arg Leu Asn Val Pro Glu His Ile Arg Ile His His
                210                 215                 220

Ile Asp Leu Ala Val Glu Leu Gln Ser Leu Val Tyr Phe Leu Lys His
225                 230                 235                 240

Tyr Tyr Asn Ser Asp Asn Val Tyr Ile Met Ala Asp Lys Gln Lys Asn
                245                 250                 255

Gly Ile Lys Ala Asn Phe Lys Ile Arg His Asn Val Glu Asp Gly Ser
                260                 265                 270

Val Gln Leu Ala Asp His Tyr Gln Gln Asn Thr Pro Ile Gly Asp Gly
                275                 280                 285

Pro Val Leu Leu Pro Asp Asn His Tyr Leu Ser Phe Gln Ser Val Leu
                290                 295                 300

Ser Lys Asp Pro Asn Glu Lys Arg Asp His Met Val Leu Leu Glu Phe
305                 310                 315                 320

Val Thr Ala Ala Gly Ile Thr Leu Gly Met Asp Glu Leu Tyr Asn Val
                325                 330                 335

Asp Gly Gly Ser Gly Gly Thr Gly Ser Lys Gly Glu Glu Leu Phe Thr
                340                 345                 350

Gly Val Val Pro Ile Leu Val Glu Leu Asp Gly Asp Val Asn Gly His
                355                 360                 365

Lys Phe Ser Val Ser Gly Glu Gly Glu Gly Asp Ala Thr Tyr Gly Lys
                370                 375                 380

Leu Thr Leu Lys Leu Ile Cys Thr Thr Gly Lys Leu Pro Val Pro Trp
385                 390                 395                 400

Pro Thr Leu Val Thr Thr Leu Gly Tyr Gly Leu Lys Cys Phe Ala Arg
                405                 410                 415

Tyr Pro Asp His Met Lys Gln His Asp Phe Phe Lys Ser Ala Met Pro
                420                 425                 430

Glu Gly Tyr Val Gln Glu Arg Thr Ile Phe Phe Lys Asp Asp Gly Asn
                435                 440                 445

Tyr Lys Thr Arg Ala Glu Val Lys Phe Glu Gly Asp Thr Leu Val Asn
                450                 455                 460

Arg Ile Glu Leu Lys Gly Ile Gly Phe Lys Glu Asp Gly Asn Ile Leu
465                 470                 475                 480
```

```
Gly His Lys Leu Glu Tyr Asn Gly Thr Met Thr Asp Val Ile Leu Ile
                485                 490                 495
Gly Val Gly Asn Leu Gly Thr Ala Phe Leu His Tyr Asn Phe Thr Lys
            500                 505                 510
Asn Asn Asn Thr Lys Ile Ser Met Ala Phe Asp Ile Glu Glu Ser Lys
            515                 520                 525
Ile Gly Thr Glu Val Gly Gly Val Pro Val Tyr Asn Leu Asp Asp Leu
            530                 535                 540
Glu Gln His Val Lys Asp Glu Ser Val Ala Ile Leu Thr Val Pro Ala
545                 550                 555                 560
Val Ala Ala Gln Ser Ile Thr Asp Arg Leu Val Ala Leu Gly Ile Lys
                565                 570                 575
Gly Ile Leu Asn Phe Thr Pro Ala Arg Leu Asn Val Pro Glu His Ile
                580                 585                 590
Arg Ile His His Ile Asp Leu Ala Val Glu Leu Gln Ser Leu Val Tyr
                595                 600                 605
Phe Leu Lys His Tyr Ser Val Leu Glu Glu Ile Glu Lys Leu
                610                 615                 620

<210> SEQ ID NO 109
<211> LENGTH: 622
<212> TYPE: PRT
<213> ORGANISM: artificial sequence
<220> FEATURE:
<223> OTHER INFORMATION: Synthetic fluorescent sensor, mutant

<400> SEQUENCE: 109

Met Arg Gly Ser His His His His His His Gly Met Ala Ser Met Thr
1               5                   10                  15
Gly Gly Gln Gln Met Gly Arg Asp Leu Tyr Asp Asp Asp Lys Asp
            20                  25                  30
Pro Met Asn Lys Asp Gln Ser Lys Ile Pro Gln Ala Thr Ala Lys Arg
            35                  40                  45
Leu Pro Leu Tyr Tyr Arg Phe Leu Lys Asn Leu His Ala Ser Gly Lys
        50                  55                  60
Gln Arg Val Ser Ser Ala Glu Leu Ser Asp Ala Val Lys Val Asp Ser
65                  70                  75                  80
Ala Thr Ile Arg Arg Asp Phe Ser Tyr Phe Gly Ala Leu Gly Lys Lys
                85                  90                  95
Gly Tyr Gly Tyr Asn Val Asp Tyr Leu Leu Ser Phe Phe Arg Lys Thr
            100                 105                 110
Leu Asp Gln Asp Glu Met Thr Asp Val Ile Leu Ile Gly Val Gly Asn
            115                 120                 125
Leu Gly Thr Ala Phe Leu His Tyr Asn Phe Thr Lys Asn Asn Asn Thr
        130                 135                 140
Lys Ile Ser Met Ala Phe Asp Ile Asp Glu Ser Lys Ile Gly Thr Glu
145                 150                 155                 160
Val Gly Gly Val Pro Val Tyr Asn Leu Asp Asp Leu Glu Gln His Val
                165                 170                 175
Lys Asp Glu Ser Val Ala Ile Leu Thr Val Pro Ala Val Ala Ala Gln
            180                 185                 190
Ser Ile Thr Asp Arg Leu Val Ala Leu Gly Ile Lys Gly Ile Leu Asn
            195                 200                 205
Phe Thr Pro Ala Arg Leu Asn Val Pro Glu His Ile Arg Ile His His
        210                 215                 220
```

-continued

Ile Asp Leu Ala Val Glu Leu Gln Ser Leu Val Tyr Phe Leu Lys His
225                 230                 235                 240

Tyr Tyr Asn Ser Asp Asn Val Tyr Ile Met Ala Asp Lys Gln Lys Asn
            245                 250                 255

Gly Ile Lys Ala Asn Phe Lys Ile Arg His Asn Val Glu Asp Gly Ser
        260                 265                 270

Val Gln Leu Ala Asp His Tyr Gln Gln Asn Thr Pro Ile Gly Asp Gly
    275                 280                 285

Pro Val Leu Leu Pro Asp Asn His Tyr Leu Ser Phe Gln Ser Val Leu
290                 295                 300

Ser Lys Asp Pro Asn Glu Lys Arg Asp His Met Val Leu Leu Glu Phe
305                 310                 315                 320

Val Thr Ala Ala Gly Ile Thr Leu Gly Met Asp Glu Leu Tyr Asn Val
                325                 330                 335

Asp Gly Gly Ser Gly Gly Thr Gly Ser Lys Gly Glu Glu Leu Phe Thr
            340                 345                 350

Gly Val Val Pro Ile Leu Val Glu Leu Asp Gly Asp Val Asn Gly His
        355                 360                 365

Lys Phe Ser Val Ser Gly Glu Gly Glu Gly Asp Ala Thr Tyr Gly Lys
    370                 375                 380

Leu Thr Leu Lys Leu Ile Cys Thr Thr Gly Lys Leu Pro Val Pro Trp
385                 390                 395                 400

Pro Thr Leu Val Thr Thr Leu Gly Tyr Gly Leu Lys Cys Phe Ala Arg
                405                 410                 415

Tyr Pro Asp His Met Lys Gln His Asp Phe Phe Lys Ser Ala Met Pro
            420                 425                 430

Glu Gly Tyr Val Gln Glu Arg Thr Ile Phe Phe Lys Asp Asp Gly Asn
        435                 440                 445

Tyr Lys Thr Arg Ala Glu Val Lys Phe Glu Gly Asp Thr Leu Val Asn
    450                 455                 460

Arg Ile Glu Leu Lys Gly Ile Gly Phe Lys Glu Asp Gly Asn Ile Leu
465                 470                 475                 480

Gly His Lys Leu Glu Tyr Asn Gly Thr Met Thr Asp Val Ile Leu Ile
                485                 490                 495

Gly Val Gly Asn Leu Gly Thr Ala Phe Leu His Tyr Asn Phe Thr Lys
            500                 505                 510

Asn Asn Asn Thr Lys Ile Ser Met Ala Phe Asp Ile Asp Glu Ser Lys
    515                 520                 525

Ile Gly Thr Glu Val Gly Gly Val Pro Val Tyr Asn Leu Asp Asp Leu
530                 535                 540

Glu Gln His Val Lys Asp Glu Ser Val Ala Ile Leu Thr Val Pro Ala
545                 550                 555                 560

Val Ala Ala Gln Ser Ile Thr Asp Arg Leu Val Ala Leu Gly Ile Lys
                565                 570                 575

Gly Ile Leu Asn Phe Thr Pro Ala Arg Leu Asn Val Pro Glu His Ile
            580                 585                 590

Arg Ile His His Ile Asp Leu Ala Val Glu Leu Gln Ser Leu Val Tyr
    595                 600                 605

Phe Leu Lys His Tyr Ser Val Leu Glu Glu Ile Glu Lys Leu
610                 615                 620

<210> SEQ ID NO 110
<211> LENGTH: 622

```
<212> TYPE: PRT
<213> ORGANISM: artificial sequence
<220> FEATURE:
<223> OTHER INFORMATION: Synthetic fluorescent sensor, mutant

<400> SEQUENCE: 110
```

| | | | | | | | | | | | | | | |
|---|---|---|---|---|---|---|---|---|---|---|---|---|---|---|
| Met | Arg | Gly | Ser | His | His | His | His | His | Gly | Met | Ala | Ser | Met | Thr |
| 1 | | | | 5 | | | | | 10 | | | | | 15 |
| Gly | Gly | Gln | Gln | Met | Gly | Arg | Asp | Leu | Tyr | Asp | Asp | Asp | Lys | Asp |
| | | | 20 | | | | | 25 | | | | | 30 | |
| Pro | Met | Asn | Lys | Asp | Gln | Ser | Lys | Ile | Pro | Gln | Ala | Thr | Ala | Lys | Arg |
| | | 35 | | | | | 40 | | | | | 45 | | |
| Leu | Pro | Leu | Tyr | Tyr | Arg | Phe | Leu | Lys | Asn | Leu | His | Ala | Ser | Gly | Lys |
| | 50 | | | | | 55 | | | | | 60 | | | | |
| Gln | Arg | Val | Ser | Ser | Ala | Glu | Leu | Ser | Asp | Ala | Val | Lys | Val | Asp | Ser |
| 65 | | | | | 70 | | | | | 75 | | | | | 80 |
| Ala | Thr | Ile | Arg | Arg | Asp | Phe | Ser | Tyr | Phe | Gly | Ala | Leu | Gly | Lys | Lys |
| | | | | 85 | | | | | 90 | | | | | 95 | |
| Gly | Tyr | Gly | Tyr | Asn | Val | Asp | Tyr | Leu | Leu | Ser | Phe | Phe | Arg | Lys | Thr |
| | | | 100 | | | | | 105 | | | | | 110 | | |
| Leu | Asp | Gln | Asp | Glu | Met | Thr | Asp | Val | Ile | Leu | Ile | Gly | Val | Gly | Asn |
| | | | | 115 | | | | | 120 | | | | | 125 | |
| Leu | Gly | Thr | Ala | Phe | Leu | His | Tyr | Asn | Phe | Thr | Lys | Asn | Asn | Asn | Thr |
| | 130 | | | | | 135 | | | | | 140 | | | | |
| Lys | Ile | Ser | Met | Ala | Phe | Asp | Ile | Asn | Glu | Ser | Lys | Ile | Gly | Thr | Glu |
| 145 | | | | | 150 | | | | | 155 | | | | | 160 |
| Val | Gly | Gly | Val | Pro | Val | Tyr | Asn | Leu | Asp | Asp | Leu | Glu | Gln | His | Val |
| | | | | 165 | | | | | 170 | | | | | 175 | |
| Lys | Asp | Glu | Ser | Val | Ala | Ile | Leu | Thr | Val | Pro | Ala | Val | Ala | Ala | Gln |
| | | | 180 | | | | | 185 | | | | | 190 | | |
| Ser | Ile | Thr | Asp | Arg | Leu | Val | Ala | Leu | Gly | Ile | Lys | Gly | Ile | Leu | Asn |
| | | | | 195 | | | | | 200 | | | | | 205 | |
| Phe | Thr | Pro | Ala | Arg | Leu | Asn | Val | Pro | Glu | His | Ile | Arg | Ile | His | His |
| | 210 | | | | | 215 | | | | | 220 | | | | |
| Ile | Asn | Leu | Ala | Val | Glu | Leu | Gln | Ser | Leu | Val | Tyr | Phe | Leu | Lys | His |
| 225 | | | | | 230 | | | | | 235 | | | | | 240 |
| Tyr | Tyr | Asn | Ser | Asp | Asn | Val | Tyr | Ile | Met | Ala | Asp | Lys | Gln | Lys | Asn |
| | | | | 245 | | | | | 250 | | | | | 255 | |
| Gly | Ile | Lys | Ala | Asn | Phe | Lys | Ile | Arg | His | Asn | Val | Glu | Asp | Gly | Ser |
| | | | 260 | | | | | 265 | | | | | 270 | | |
| Val | Gln | Leu | Ala | Asp | His | Tyr | Gln | Gln | Asn | Thr | Pro | Ile | Gly | Asp | Gly |
| | | | | 275 | | | | | 280 | | | | | 285 | |
| Pro | Val | Leu | Leu | Pro | Asp | Asn | His | Tyr | Leu | Ser | Phe | Gln | Ser | Val | Leu |
| | 290 | | | | | 295 | | | | | 300 | | | | |
| Ser | Lys | Asp | Pro | Asn | Glu | Lys | Arg | Asp | His | Met | Val | Leu | Leu | Glu | Phe |
| 305 | | | | | 310 | | | | | 315 | | | | | 320 |
| Val | Thr | Ala | Ala | Gly | Ile | Thr | Leu | Gly | Met | Asp | Glu | Leu | Tyr | Asn | Val |
| | | | | 325 | | | | | 330 | | | | | 335 | |
| Asp | Gly | Gly | Ser | Gly | Gly | Thr | Gly | Ser | Lys | Gly | Glu | Glu | Leu | Phe | Thr |
| | | | 340 | | | | | 345 | | | | | 350 | | |
| Gly | Val | Val | Pro | Ile | Leu | Val | Glu | Leu | Asp | Gly | Asp | Val | Asn | Gly | His |
| | | | | 355 | | | | | 360 | | | | | 365 | |
| Lys | Phe | Ser | Val | Ser | Gly | Glu | Gly | Glu | Gly | Asp | Ala | Thr | Tyr | Gly | Lys |
| | 370 | | | | | 375 | | | | | 380 | | | | |

```
Leu Thr Leu Lys Leu Ile Cys Thr Thr Gly Lys Leu Pro Val Pro Trp
385                 390                 395                 400

Pro Thr Leu Val Thr Thr Leu Gly Tyr Gly Leu Lys Cys Phe Ala Arg
            405                 410                 415

Tyr Pro Asp His Met Lys Gln His Asp Phe Phe Lys Ser Ala Met Pro
            420                 425                 430

Glu Gly Tyr Val Gln Glu Arg Thr Ile Phe Phe Lys Asp Asp Gly Asn
            435                 440                 445

Tyr Lys Thr Arg Ala Glu Val Lys Phe Glu Gly Asp Thr Leu Val Asn
450                 455                 460

Arg Ile Glu Leu Lys Gly Ile Gly Phe Lys Glu Asp Gly Asn Ile Leu
465                 470                 475                 480

Gly His Lys Leu Glu Tyr Asn Gly Thr Met Thr Asp Val Ile Leu Ile
            485                 490                 495

Gly Val Gly Asn Leu Gly Thr Ala Phe Leu His Tyr Asn Phe Thr Lys
            500                 505                 510

Asn Asn Asn Thr Lys Ile Ser Met Ala Phe Asp Ile Asn Glu Ser Lys
            515                 520                 525

Ile Gly Thr Glu Val Gly Gly Val Pro Val Tyr Asn Leu Asp Asp Leu
530                 535                 540

Glu Gln His Val Lys Asp Glu Ser Val Ala Ile Leu Thr Val Pro Ala
545                 550                 555                 560

Val Ala Ala Gln Ser Ile Thr Asp Arg Leu Val Ala Leu Gly Ile Lys
                565                 570                 575

Gly Ile Leu Asn Phe Thr Pro Ala Arg Leu Asn Val Pro Glu His Ile
            580                 585                 590

Arg Ile His His Ile Asn Leu Ala Val Glu Leu Gln Ser Leu Val Tyr
            595                 600                 605

Phe Leu Lys His Tyr Ser Val Leu Glu Glu Ile Glu Lys Leu
            610                 615                 620

<210> SEQ ID NO 111
<211> LENGTH: 622
<212> TYPE: PRT
<213> ORGANISM: artificial sequence
<220> FEATURE:
<223> OTHER INFORMATION: Synthetic fluorescent sensor, mutant

<400> SEQUENCE: 111

Met Arg Gly Ser His His His His His Gly Met Ala Ser Met Thr
1               5                   10                  15

Gly Gly Gln Gln Met Gly Arg Asp Leu Tyr Asp Asp Asp Lys Asp
            20                  25                  30

Pro Met Asn Lys Asp Gln Ser Lys Ile Pro Gln Ala Thr Ala Lys Arg
            35                  40                  45

Leu Pro Leu Tyr Tyr Arg Phe Leu Lys Asn Leu His Ala Ser Gly Lys
50                  55                  60

Gln Arg Val Ser Ser Ala Glu Leu Ser Asp Ala Val Lys Val Asp Ser
65                  70                  75                  80

Ala Thr Ile Arg Arg Asp Phe Ser Tyr Phe Gly Ala Leu Gly Lys Lys
                85                  90                  95

Gly Tyr Gly Tyr Asn Val Asp Tyr Leu Leu Ser Phe Arg Lys Thr
            100                 105                 110

Leu Asp Gln Asp Glu Met Thr Asp Val Ile Leu Ile Gly Val Gly Asn
            115                 120                 125
```

```
Leu Gly Thr Ala Phe Leu His Tyr Asn Phe Thr Lys Asn Asn Asn Thr
130                 135                 140

Lys Ile Ser Met Ala Phe Asp Ile Asn Glu Ser Lys Ile Gly Thr Glu
145                 150                 155                 160

Val Gly Gly Val Pro Val Tyr Asn Leu Asp Asp Leu Glu Gln His Val
                165                 170                 175

Lys Asp Glu Ser Val Ala Ile Leu Thr Val Pro Ala Val Ala Ala Gln
            180                 185                 190

Ser Ile Thr Asp Arg Leu Val Ala Leu Gly Ile Lys Gly Ile Leu Asn
        195                 200                 205

Phe Thr Pro Ala Arg Leu Asn Val Pro Glu His Ile Arg Ile His His
210                 215                 220

Ile Lys Leu Ala Val Glu Leu Gln Ser Leu Val Tyr Phe Leu Lys His
225                 230                 235                 240

Tyr Tyr Asn Ser Asp Asn Val Tyr Ile Met Ala Asp Lys Gln Lys Asn
                245                 250                 255

Gly Ile Lys Ala Asn Phe Lys Ile Arg His Asn Val Glu Asp Gly Ser
            260                 265                 270

Val Gln Leu Ala Asp His Tyr Gln Gln Asn Thr Pro Ile Gly Asp Gly
        275                 280                 285

Pro Val Leu Leu Pro Asp Asn His Tyr Leu Ser Phe Gln Ser Val Leu
290                 295                 300

Ser Lys Asp Pro Asn Glu Lys Arg Asp His Met Val Leu Leu Glu Phe
305                 310                 315                 320

Val Thr Ala Ala Gly Ile Thr Leu Gly Met Asp Glu Leu Tyr Asn Val
                325                 330                 335

Asp Gly Gly Ser Gly Gly Thr Gly Ser Lys Gly Glu Glu Leu Phe Thr
            340                 345                 350

Gly Val Val Pro Ile Leu Val Glu Leu Asp Gly Asp Val Asn Gly His
        355                 360                 365

Lys Phe Ser Val Ser Gly Glu Gly Glu Gly Asp Ala Thr Tyr Gly Lys
370                 375                 380

Leu Thr Leu Lys Leu Ile Cys Thr Thr Gly Lys Leu Pro Val Pro Trp
385                 390                 395                 400

Pro Thr Leu Val Thr Thr Leu Gly Tyr Gly Leu Lys Cys Phe Ala Arg
                405                 410                 415

Tyr Pro Asp His Met Lys Gln His Asp Phe Phe Lys Ser Ala Met Pro
            420                 425                 430

Glu Gly Tyr Val Gln Glu Arg Thr Ile Phe Phe Lys Asp Asp Gly Asn
        435                 440                 445

Tyr Lys Thr Arg Ala Glu Val Lys Phe Glu Gly Asp Thr Leu Val Asn
450                 455                 460

Arg Ile Glu Leu Lys Gly Ile Gly Phe Lys Glu Asp Gly Asn Ile Leu
465                 470                 475                 480

Gly His Lys Leu Glu Tyr Asn Gly Thr Met Thr Asp Val Ile Leu Ile
                485                 490                 495

Gly Val Gly Asn Leu Gly Thr Ala Phe Leu His Tyr Asn Phe Thr Lys
            500                 505                 510

Asn Asn Asn Thr Lys Ile Ser Met Ala Phe Asp Ile Asn Glu Ser Lys
        515                 520                 525

Ile Gly Thr Glu Val Gly Gly Val Pro Val Tyr Asn Leu Asp Asp Leu
530                 535                 540

Glu Gln His Val Lys Asp Glu Ser Val Ala Ile Leu Thr Val Pro Ala
```

```
545                 550                 555                 560
Val Ala Ala Gln Ser Ile Thr Asp Arg Leu Val Ala Leu Gly Ile Lys
                565                 570                 575

Gly Ile Leu Asn Phe Thr Pro Ala Arg Leu Asn Val Pro Glu His Ile
                580                 585                 590

Arg Ile His His Ile Lys Leu Ala Val Glu Leu Gln Ser Leu Val Tyr
                595                 600                 605

Phe Leu Lys His Tyr Ser Val Leu Glu Glu Ile Glu Lys Leu
                610                 615                 620

<210> SEQ ID NO 112
<211> LENGTH: 622
<212> TYPE: PRT
<213> ORGANISM: artificial sequence
<220> FEATURE:
<223> OTHER INFORMATION: Synthetic fluorescent sensor, mutant

<400> SEQUENCE: 112

Met Arg Gly Ser His His His His His His Gly Met Ala Ser Met Thr
1               5                   10                  15

Gly Gly Gln Gln Met Gly Arg Asp Leu Tyr Asp Asp Asp Asp Lys Asp
                20                  25                  30

Pro Met Asn Lys Asp Gln Ser Lys Ile Pro Gln Ala Thr Ala Lys Arg
            35                  40                  45

Leu Pro Leu Tyr Tyr Arg Phe Leu Lys Asn Leu His Ala Ser Gly Lys
    50                  55                  60

Gln Arg Val Ser Ser Ala Glu Leu Ser Asp Ala Val Lys Val Asp Ser
65                  70                  75                  80

Ala Thr Ile Arg Arg Asp Phe Ser Tyr Phe Gly Ala Leu Gly Lys Lys
                85                  90                  95

Gly Tyr Gly Tyr Asn Val Asp Tyr Leu Leu Ser Phe Phe Arg Lys Thr
                100                 105                 110

Leu Asp Gln Asp Glu Met Thr Asp Val Ile Leu Ile Gly Val Gly Asn
                115                 120                 125

Leu Gly Thr Ala Phe Leu His Tyr Asn Phe Thr Lys Asn Asn Asn Thr
    130                 135                 140

Lys Ile Ser Met Ala Phe Asp Ile Asn Glu Ser Lys Ile Gly Thr Glu
145                 150                 155                 160

Val Gly Gly Val Pro Val Tyr Asn Leu Asp Asp Leu Glu Gln His Val
                165                 170                 175

Lys Asp Glu Ser Val Ala Ile Leu Thr Val Pro Ala Val Ala Ala Gln
                180                 185                 190

Ser Ile Thr Asp Arg Leu Val Ala Leu Gly Ile Lys Gly Ile Leu Asn
                195                 200                 205

Phe Thr Pro Ala Arg Leu Asn Val Pro Glu His Ile Arg Ile His His
    210                 215                 220

Ile Asp Lys Ala Val Glu Leu Gln Ser Leu Val Tyr Phe Leu Lys His
225                 230                 235                 240

Tyr Tyr Asn Ser Asp Asn Val Tyr Ile Met Ala Asp Lys Gln Lys Asn
                245                 250                 255

Gly Ile Lys Ala Asn Phe Lys Ile Arg His Asn Val Glu Asp Gly Ser
                260                 265                 270

Val Gln Leu Ala Asp His Tyr Gln Gln Asn Thr Pro Ile Gly Asp Gly
                275                 280                 285

Pro Val Leu Leu Pro Asp Asn His Tyr Leu Ser Phe Gln Ser Val Leu
```

```
            290                 295                 300
Ser Lys Asp Pro Asn Glu Lys Arg Asp His Met Val Leu Leu Glu Phe
305                 310                 315                 320

Val Thr Ala Ala Gly Ile Thr Leu Gly Met Asp Glu Leu Tyr Asn Val
                325                 330                 335

Asp Gly Gly Ser Gly Gly Thr Gly Ser Lys Gly Glu Glu Leu Phe Thr
                340                 345                 350

Gly Val Val Pro Ile Leu Val Glu Leu Asp Gly Asp Val Asn Gly His
                355                 360                 365

Lys Phe Ser Val Ser Gly Glu Gly Glu Gly Asp Ala Thr Tyr Gly Lys
    370                 375                 380

Leu Thr Leu Lys Leu Ile Cys Thr Thr Gly Lys Leu Pro Val Pro Trp
385                 390                 395                 400

Pro Thr Leu Val Thr Thr Leu Gly Tyr Gly Leu Lys Cys Phe Ala Arg
                405                 410                 415

Tyr Pro Asp His Met Lys Gln His Asp Phe Phe Lys Ser Ala Met Pro
                420                 425                 430

Glu Gly Tyr Val Gln Glu Arg Thr Ile Phe Phe Lys Asp Asp Gly Asn
                435                 440                 445

Tyr Lys Thr Arg Ala Glu Val Lys Phe Glu Gly Asp Thr Leu Val Asn
    450                 455                 460

Arg Ile Glu Leu Lys Gly Ile Gly Phe Lys Glu Asp Gly Asn Ile Leu
465                 470                 475                 480

Gly His Lys Leu Glu Tyr Asn Gly Thr Met Thr Asp Val Ile Leu Ile
                485                 490                 495

Gly Val Gly Asn Leu Gly Thr Ala Phe Leu His Tyr Asn Phe Thr Lys
                500                 505                 510

Asn Asn Asn Thr Lys Ile Ser Met Ala Phe Asp Ile Asn Glu Ser Lys
                515                 520                 525

Ile Gly Thr Glu Val Gly Gly Val Pro Val Tyr Asn Leu Asp Asp Leu
                530                 535                 540

Glu Gln His Val Lys Asp Glu Ser Val Ala Ile Leu Thr Val Pro Ala
545                 550                 555                 560

Val Ala Ala Gln Ser Ile Thr Asp Arg Leu Val Ala Leu Gly Ile Lys
                565                 570                 575

Gly Ile Leu Asn Phe Thr Pro Ala Arg Leu Asn Val Pro Glu His Ile
                580                 585                 590

Arg Ile His His Ile Asp Lys Ala Val Glu Leu Gln Ser Leu Val Tyr
                595                 600                 605

Phe Leu Lys His Tyr Ser Val Leu Glu Glu Ile Glu Lys Leu
    610                 615                 620

<210> SEQ ID NO 113
<211> LENGTH: 622
<212> TYPE: PRT
<213> ORGANISM: artificial sequence
<220> FEATURE:
<223> OTHER INFORMATION: Synthetic fluorescent sensor, mutant

<400> SEQUENCE: 113

Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
                20                  25                  30

Pro Met Asn Lys Asp Gln Ser Lys Ile Pro Gln Ala Thr Ala Lys Arg
```

```
            35                  40                  45
Leu Pro Leu Tyr Tyr Arg Phe Leu Lys Asn Leu His Ala Ser Gly Lys
 50                  55                  60

Gln Arg Val Ser Ser Ala Glu Leu Ser Asp Ala Val Lys Val Asp Ser
 65                  70                  75                  80

Ala Thr Ile Arg Arg Asp Phe Ser Tyr Phe Gly Ala Leu Gly Lys Lys
                 85                  90                  95

Gly Tyr Gly Tyr Asn Val Asp Tyr Leu Leu Ser Phe Phe Arg Lys Thr
                100                 105                 110

Leu Asp Gln Asp Glu Met Thr Asp Val Ile Leu Ile Gly Val Gly Asn
                115                 120                 125

Leu Gly Thr Ala Phe Leu His Tyr Asn Phe Thr Lys Asn Asn Asn Thr
130                 135                 140

Lys Ile Ser Met Ala Phe Asp Ile Asn Glu Ser Lys Ile Gly Thr Glu
145                 150                 155                 160

Val Gly Gly Val Pro Val Tyr Asn Leu Asp Asp Leu Glu Gln His Val
                165                 170                 175

Lys Asp Glu Ser Val Ala Ile Leu Thr Val Pro Ala Val Ala Ala Gln
                180                 185                 190

Ser Ile Thr Asp Arg Leu Val Ala Leu Gly Ile Lys Gly Ile Leu Asn
                195                 200                 205

Phe Thr Pro Ala Arg Leu Asn Val Pro Glu His Ile Arg Ile His His
210                 215                 220

Ile Asp Arg Ala Val Glu Leu Gln Ser Leu Val Tyr Phe Leu Lys His
225                 230                 235                 240

Tyr Tyr Asn Ser Asp Asn Val Tyr Ile Met Ala Asp Lys Gln Lys Asn
                245                 250                 255

Gly Ile Lys Ala Asn Phe Lys Ile Arg His Asn Val Glu Asp Gly Ser
                260                 265                 270

Val Gln Leu Ala Asp His Tyr Gln Gln Asn Thr Pro Ile Gly Asp Gly
                275                 280                 285

Pro Val Leu Leu Pro Asp Asn His Tyr Leu Ser Phe Gln Ser Val Leu
                290                 295                 300

Ser Lys Asp Pro Asn Glu Lys Arg Asp His Met Val Leu Leu Glu Phe
305                 310                 315                 320

Val Thr Ala Ala Gly Ile Thr Leu Gly Met Asp Glu Leu Tyr Asn Val
                325                 330                 335

Asp Gly Gly Ser Gly Gly Thr Gly Ser Lys Gly Glu Glu Leu Phe Thr
                340                 345                 350

Gly Val Val Pro Ile Leu Val Glu Leu Asp Gly Asp Val Asn Gly His
                355                 360                 365

Lys Phe Ser Val Ser Gly Glu Gly Gly Asp Ala Thr Tyr Gly Lys
                370                 375                 380

Leu Thr Leu Lys Leu Ile Cys Thr Thr Gly Lys Leu Pro Val Pro Trp
385                 390                 395                 400

Pro Thr Leu Val Thr Thr Leu Gly Tyr Gly Leu Lys Cys Phe Ala Arg
                405                 410                 415

Tyr Pro Asp His Met Lys Gln His Asp Phe Phe Lys Ser Ala Met Pro
                420                 425                 430

Glu Gly Tyr Val Gln Glu Arg Thr Ile Phe Phe Lys Asp Asp Gly Asn
                435                 440                 445

Tyr Lys Thr Arg Ala Glu Val Lys Phe Glu Gly Asp Thr Leu Val Asn
450                 455                 460
```

Arg Ile Glu Leu Lys Gly Ile Gly Phe Lys Glu Asp Gly Asn Ile Leu
465                 470                 475                 480

Gly His Lys Leu Glu Tyr Asn Gly Thr Met Thr Asp Val Ile Leu Ile
            485                 490                 495

Gly Val Gly Asn Leu Gly Thr Ala Phe Leu His Tyr Asn Phe Thr Lys
            500                 505                 510

Asn Asn Asn Thr Lys Ile Ser Met Ala Phe Asp Ile Asn Glu Ser Lys
            515                 520                 525

Ile Gly Thr Glu Val Gly Val Pro Val Tyr Asn Leu Asp Asp Leu
530                 535                 540

Glu Gln His Val Lys Asp Glu Ser Val Ala Ile Leu Thr Val Pro Ala
545                 550                 555                 560

Val Ala Ala Gln Ser Ile Thr Asp Arg Leu Val Ala Leu Gly Ile Lys
            565                 570                 575

Gly Ile Leu Asn Phe Thr Pro Ala Arg Leu Asn Val Pro Glu His Ile
            580                 585                 590

Arg Ile His His Ile Asp Arg Ala Val Glu Leu Gln Ser Leu Val Tyr
            595                 600                 605

Phe Leu Lys His Tyr Ser Val Leu Glu Glu Ile Glu Lys Leu
        610                 615                 620

<210> SEQ ID NO 114
<211> LENGTH: 622
<212> TYPE: PRT
<213> ORGANISM: artificial sequence
<220> FEATURE:
<223> OTHER INFORMATION: Synthetic fluorescent sensor, mutant

<400> SEQUENCE: 114

Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

Pro Met Asn Lys Asp Gln Ser Lys Ile Pro Gln Ala Thr Ala Lys Arg
            35                  40                  45

Leu Pro Leu Tyr Tyr Arg Phe Leu Lys Asn Leu His Ala Ser Gly Lys
50                  55                  60

Gln Arg Val Ser Ser Ala Glu Leu Ser Asp Ala Val Lys Val Asp Ser
65                  70                  75                  80

Ala Thr Ile Arg Arg Asp Phe Ser Tyr Phe Gly Ala Leu Gly Lys Lys
            85                  90                  95

Gly Tyr Gly Tyr Asn Val Asp Tyr Leu Leu Ser Phe Arg Lys Thr
            100                 105                 110

Leu Asp Gln Asp Glu Met Thr Asp Val Ile Leu Ile Gly Val Gly Asn
            115                 120                 125

Leu Gly Thr Ala Phe Leu His Tyr Asn Phe Thr Lys Asn Asn Asn Thr
            130                 135                 140

Lys Ile Ser Met Ala Phe Asp Ile Asn Glu Ser Lys Ile Gly Thr Glu
145                 150                 155                 160

Val Gly Val Pro Val Tyr Asn Leu Asp Asp Leu Glu Gln His Val
            165                 170                 175

Lys Asp Glu Ser Val Ala Ile Leu Thr Val Pro Ala Val Ala Ala Gln
            180                 185                 190

Ser Ile Thr Asp Arg Leu Val Ala Leu Gly Ile Lys Gly Ile Leu Asn
            195                 200                 205

```
Phe Thr Pro Ala Arg Leu Asn Val Pro Glu His Ile Arg Ile His His
    210                 215                 220

Ile Asp Glu Ala Val Glu Leu Gln Ser Leu Val Tyr Phe Leu Lys His
225                 230                 235                 240

Tyr Tyr Asn Ser Asp Asn Val Tyr Ile Met Ala Asp Lys Gln Lys Asn
                245                 250                 255

Gly Ile Lys Ala Asn Phe Lys Ile Arg His Asn Val Glu Asp Gly Ser
                260                 265                 270

Val Gln Leu Ala Asp His Tyr Gln Gln Asn Thr Pro Ile Gly Asp Gly
    275                 280                 285

Pro Val Leu Leu Pro Asp Asn His Tyr Leu Ser Phe Gln Ser Val Leu
    290                 295                 300

Ser Lys Asp Pro Asn Glu Lys Arg Asp His Met Val Leu Leu Glu Phe
305                 310                 315                 320

Val Thr Ala Ala Gly Ile Thr Leu Gly Met Asp Glu Leu Tyr Asn Val
                325                 330                 335

Asp Gly Gly Ser Gly Gly Thr Gly Ser Lys Gly Glu Glu Leu Phe Thr
                340                 345                 350

Gly Val Val Pro Ile Leu Val Glu Leu Asp Gly Asp Val Asn Gly His
                355                 360                 365

Lys Phe Ser Val Ser Gly Glu Gly Glu Gly Asp Ala Thr Tyr Gly Lys
370                 375                 380

Leu Thr Leu Lys Leu Ile Cys Thr Thr Gly Lys Leu Pro Val Pro Trp
385                 390                 395                 400

Pro Thr Leu Val Thr Thr Leu Gly Tyr Gly Leu Lys Cys Phe Ala Arg
                405                 410                 415

Tyr Pro Asp His Met Lys Gln His Asp Phe Phe Lys Ser Ala Met Pro
                420                 425                 430

Glu Gly Tyr Val Gln Glu Arg Thr Ile Phe Phe Lys Asp Asp Gly Asn
                435                 440                 445

Tyr Lys Thr Arg Ala Glu Val Lys Phe Glu Gly Asp Thr Leu Val Asn
    450                 455                 460

Arg Ile Glu Leu Lys Gly Ile Gly Phe Lys Glu Asp Gly Asn Ile Leu
465                 470                 475                 480

Gly His Lys Leu Glu Tyr Asn Gly Thr Met Thr Asp Val Ile Leu Ile
                485                 490                 495

Gly Val Gly Asn Leu Gly Thr Ala Phe Leu His Tyr Asn Phe Thr Lys
                500                 505                 510

Asn Asn Asn Thr Lys Ile Ser Met Ala Phe Asp Ile Asn Glu Ser Lys
    515                 520                 525

Ile Gly Thr Glu Val Gly Gly Val Pro Val Tyr Asn Leu Asp Asp Leu
530                 535                 540

Glu Gln His Val Lys Asp Glu Ser Val Ala Ile Leu Thr Val Pro Ala
545                 550                 555                 560

Val Ala Ala Gln Ser Ile Thr Asp Arg Leu Val Ala Leu Gly Ile Lys
                565                 570                 575

Gly Ile Leu Asn Phe Thr Pro Ala Arg Leu Asn Val Pro Glu His Ile
                580                 585                 590

Arg Ile His His Ile Asp Glu Ala Val Glu Leu Gln Ser Leu Val Tyr
    595                 600                 605

Phe Leu Lys His Tyr Ser Val Leu Glu Glu Ile Glu Lys Leu
610                 615                 620
```

<210> SEQ ID NO 115
<211> LENGTH: 622
<212> TYPE: PRT
<213> ORGANISM: artificial sequence
<220> FEATURE:
<223> OTHER INFORMATION: Synthetic fluorescent sensor, mutant

<400> SEQUENCE: 115

| | | | | | | | | | | | | | | |
|---|---|---|---|---|---|---|---|---|---|---|---|---|---|---|
| Met | Arg | Gly | Ser | His | His | His | His | His | Gly | Met | Ala | Ser | Met | Thr |
| 1 | | | | 5 | | | | | 10 | | | | | 15 |
| Gly | Gly | Gln | Gln | Met | Gly | Arg | Asp | Leu | Tyr | Asp | Asp | Asp | Lys | Asp |
| | | | 20 | | | | | 25 | | | | | 30 | |
| Pro | Met | Asn | Lys | Asp | Gln | Ser | Lys | Ile | Pro | Gln | Ala | Thr | Ala | Lys | Arg |
| | | 35 | | | | | 40 | | | | | 45 | | |
| Leu | Pro | Leu | Tyr | Tyr | Arg | Phe | Leu | Lys | Asn | Leu | His | Ala | Ser | Gly | Lys |
| | 50 | | | | | 55 | | | | | 60 | | | | |
| Gln | Arg | Val | Ser | Ser | Ala | Glu | Leu | Ser | Asp | Ala | Val | Lys | Val | Asp | Ser |
| 65 | | | | | 70 | | | | | 75 | | | | | 80 |
| Ala | Thr | Ile | Arg | Arg | Asp | Phe | Ser | Tyr | Phe | Gly | Ala | Leu | Gly | Lys | Lys |
| | | | | 85 | | | | | 90 | | | | | 95 | |
| Gly | Tyr | Gly | Tyr | Asn | Val | Asp | Tyr | Leu | Leu | Ser | Phe | Phe | Arg | Lys | Thr |
| | | | 100 | | | | | 105 | | | | | 110 | | |
| Leu | Asp | Gln | Asp | Glu | Met | Thr | Asp | Val | Ile | Leu | Ile | Gly | Val | Gly | Asn |
| | | | | 115 | | | | | 120 | | | | | 125 | |
| Leu | Gly | Thr | Ala | Phe | Leu | His | Tyr | Asn | Phe | Thr | Lys | Asn | Asn | Asn | Thr |
| | 130 | | | | | 135 | | | | | 140 | | | | |
| Lys | Ile | Ser | Met | Ala | Phe | Asp | Ile | Asn | Glu | Ser | Lys | Ile | Gly | Thr | Glu |
| 145 | | | | | 150 | | | | | 155 | | | | | 160 |
| Val | Gly | Gly | Val | Pro | Val | Tyr | Asn | Leu | Asp | Asp | Leu | Glu | Gln | His | Val |
| | | | | 165 | | | | | 170 | | | | | 175 | |
| Lys | Asp | Glu | Ser | Val | Ala | Ile | Leu | Thr | Val | Pro | Ala | Val | Ala | Ala | Gln |
| | | | 180 | | | | | 185 | | | | | 190 | | |
| Ser | Ile | Thr | Asp | Arg | Leu | Val | Ala | Leu | Gly | Ile | Lys | Gly | Ile | Leu | Asn |
| | | 195 | | | | | 200 | | | | | 205 | | | |
| Phe | Thr | Pro | Ala | Arg | Leu | Asn | Val | Pro | Glu | His | Ile | Arg | Ile | His | His |
| | 210 | | | | | 215 | | | | | 220 | | | | |
| Ile | Asp | Asp | Ala | Val | Glu | Leu | Gln | Ser | Leu | Val | Tyr | Phe | Leu | Lys | His |
| 225 | | | | | 230 | | | | | 235 | | | | | 240 |
| Tyr | Tyr | Asn | Ser | Asp | Asn | Val | Tyr | Ile | Met | Ala | Asp | Lys | Gln | Lys | Asn |
| | | | | 245 | | | | | 250 | | | | | 255 | |
| Gly | Ile | Lys | Ala | Asn | Phe | Lys | Ile | Arg | His | Asn | Val | Glu | Asp | Gly | Ser |
| | | | 260 | | | | | 265 | | | | | 270 | | |
| Val | Gln | Leu | Ala | Asp | His | Tyr | Gln | Gln | Asn | Thr | Pro | Ile | Gly | Asp | Gly |
| | | 275 | | | | | 280 | | | | | 285 | | | |
| Pro | Val | Leu | Leu | Pro | Asp | Asn | His | Tyr | Leu | Ser | Phe | Gln | Ser | Val | Leu |
| | 290 | | | | | 295 | | | | | 300 | | | | |
| Ser | Lys | Asp | Pro | Asn | Glu | Lys | Arg | Asp | His | Met | Val | Leu | Leu | Glu | Phe |
| 305 | | | | | 310 | | | | | 315 | | | | | 320 |
| Val | Thr | Ala | Ala | Gly | Ile | Thr | Leu | Gly | Met | Asp | Glu | Leu | Tyr | Asn | Val |
| | | | | 325 | | | | | 330 | | | | | 335 | |
| Asp | Gly | Gly | Ser | Gly | Gly | Thr | Gly | Ser | Lys | Gly | Glu | Glu | Leu | Phe | Thr |
| | | | 340 | | | | | 345 | | | | | 350 | | |
| Gly | Val | Val | Pro | Ile | Leu | Val | Glu | Leu | Asp | Gly | Asp | Val | Asn | Gly | His |
| | | 355 | | | | | 360 | | | | | 365 | | | |

```
Lys Phe Ser Val Ser Gly Glu Gly Glu Gly Asp Ala Thr Tyr Gly Lys
    370                 375                 380

Leu Thr Leu Lys Leu Ile Cys Thr Thr Gly Lys Leu Pro Val Pro Trp
385                 390                 395                 400

Pro Thr Leu Val Thr Thr Leu Gly Tyr Gly Leu Lys Cys Phe Ala Arg
                405                 410                 415

Tyr Pro Asp His Met Lys Gln His Asp Phe Phe Lys Ser Ala Met Pro
                420                 425                 430

Glu Gly Tyr Val Gln Glu Arg Thr Ile Phe Phe Lys Asp Asp Gly Asn
            435                 440                 445

Tyr Lys Thr Arg Ala Glu Val Lys Phe Glu Gly Asp Thr Leu Val Asn
450                 455                 460

Arg Ile Glu Leu Lys Gly Ile Gly Phe Lys Glu Asp Gly Asn Ile Leu
465                 470                 475                 480

Gly His Lys Leu Glu Tyr Asn Gly Thr Met Thr Asp Val Ile Leu Ile
                485                 490                 495

Gly Val Gly Asn Leu Gly Thr Ala Phe Leu His Tyr Asn Phe Thr Lys
                500                 505                 510

Asn Asn Asn Thr Lys Ile Ser Met Ala Phe Asp Ile Asn Glu Ser Lys
            515                 520                 525

Ile Gly Thr Glu Val Gly Gly Val Pro Val Tyr Asn Leu Asp Asp Leu
530                 535                 540

Glu Gln His Val Lys Asp Glu Ser Val Ala Ile Leu Thr Val Pro Ala
545                 550                 555                 560

Val Ala Ala Gln Ser Ile Thr Asp Arg Leu Val Ala Leu Gly Ile Lys
                565                 570                 575

Gly Ile Leu Asn Phe Thr Pro Ala Arg Leu Asn Val Pro Glu His Ile
                580                 585                 590

Arg Ile His His Ile Asp Asp Ala Val Glu Leu Gln Ser Leu Val Tyr
            595                 600                 605

Phe Leu Lys His Tyr Ser Val Leu Glu Glu Ile Glu Lys Leu
610                 615                 620

<210> SEQ ID NO 116
<211> LENGTH: 627
<212> TYPE: PRT
<213> ORGANISM: artificial sequence
<220> FEATURE:
<223> OTHER INFORMATION: Synthetic fluorescent sensor, mutant

<400> SEQUENCE: 116

Met Arg Gly Ser His His His His Gly Met Ala Ser Met Thr
1               5                   10                  15

Gly Gly Gln Gln Met Gly Arg Asp Leu Tyr Asp Asp Asp Lys Asp
            20                  25                  30

Pro Met Asn Lys Asp Gln Ser Lys Ile Pro Gln Ala Thr Ala Lys Arg
            35                  40                  45

Leu Pro Leu Tyr Tyr Arg Phe Leu Lys Asn Leu His Ala Ser Gly Lys
        50                  55                  60

Gln Arg Val Ser Ser Ala Glu Leu Ser Asp Ala Val Lys Val Asp Ser
65                  70                  75                  80

Ala Thr Ile Arg Arg Asp Phe Ser Tyr Phe Gly Ala Leu Gly Lys Lys
                85                  90                  95

Gly Tyr Gly Tyr Asn Val Asp Tyr Leu Leu Ser Phe Phe Arg Lys Thr
            100                 105                 110
```

-continued

```
Leu Asp Gln Asp Glu Met Thr Asp Val Ile Leu Ile Gly Val Gly Asn
            115                 120                 125

Leu Gly Thr Ala Phe Leu His Tyr Asn Phe Thr Lys Asn Asn Asn Thr
130                 135                 140

Lys Ile Ser Met Ala Phe Arg Ile Asn Glu Ser Lys Ile Gly Thr Glu
145                 150                 155                 160

Val Gly Gly Val Pro Val Tyr Asn Leu Asp Asp Leu Glu Gln His Val
                165                 170                 175

Lys Asp Glu Ser Val Ala Ile Leu Thr Val Pro Ala Val Ala Ala Gln
            180                 185                 190

Ser Ile Thr Asp Arg Leu Val Ala Leu Gly Ile Lys Gly Ile Leu Asn
            195                 200                 205

Phe Thr Pro Ala Arg Leu Asn Val Pro Glu His Ile Arg Ile His His
210                 215                 220

Ile Asp Leu Ala Val Glu Leu Gln Ser Leu Val Tyr Phe Leu Lys His
225                 230                 235                 240

Tyr Ser Val Leu Glu Glu Tyr Asn Ser Asp Asn Val Tyr Ile Met Ala
                245                 250                 255

Asp Lys Gln Lys Asn Gly Ile Lys Ala Asn Phe Lys Ile Arg His Asn
            260                 265                 270

Val Glu Asp Gly Ser Val Gln Leu Ala Asp His Tyr Gln Gln Asn Thr
            275                 280                 285

Pro Ile Gly Asp Gly Pro Val Leu Leu Pro Asp Asn His Tyr Leu Ser
            290                 295                 300

Phe Gln Ser Val Leu Ser Lys Asp Pro Asn Glu Lys Arg Asp His Met
305                 310                 315                 320

Val Leu Leu Glu Phe Val Thr Ala Ala Gly Ile Thr Leu Gly Met Asp
                325                 330                 335

Glu Leu Tyr Asn Val Asp Gly Gly Ser Gly Gly Thr Gly Ser Lys Gly
            340                 345                 350

Glu Glu Leu Phe Thr Gly Val Val Pro Ile Leu Val Glu Leu Asp Gly
            355                 360                 365

Asp Val Asn Gly His Lys Phe Ser Val Ser Gly Glu Gly Glu Gly Asp
370                 375                 380

Ala Thr Tyr Gly Lys Leu Thr Leu Lys Leu Ile Cys Thr Thr Gly Lys
385                 390                 395                 400

Leu Pro Val Pro Trp Pro Thr Leu Val Thr Thr Leu Gly Tyr Gly Leu
                405                 410                 415

Lys Cys Phe Ala Arg Tyr Pro Asp His Met Lys Gln His Asp Phe Phe
            420                 425                 430

Lys Ser Ala Met Pro Glu Gly Tyr Val Gln Glu Arg Thr Ile Phe Phe
            435                 440                 445

Lys Asp Asp Gly Asn Tyr Lys Thr Arg Ala Glu Val Lys Phe Glu Gly
450                 455                 460

Asp Thr Leu Val Asn Arg Ile Glu Leu Lys Gly Ile Gly Phe Lys Glu
465                 470                 475                 480

Asp Gly Asn Ile Leu Gly His Lys Leu Glu Tyr Asn Gly Thr Met Thr
                485                 490                 495

Asp Val Ile Leu Ile Gly Val Gly Asn Leu Gly Thr Ala Phe Leu His
            500                 505                 510

Tyr Asn Phe Thr Lys Asn Asn Asn Thr Lys Ile Ser Met Ala Phe Arg
            515                 520                 525

Ile Asn Glu Ser Lys Ile Gly Thr Glu Val Gly Gly Val Pro Val Tyr
```

```
                  530               535              540
Asn Leu Asp Asp Leu Glu Gln His Val Lys Asp Glu Ser Val Ala Ile
545                 550               555               560

Leu Thr Val Pro Ala Val Ala Ala Gln Ser Ile Thr Asp Arg Leu Val
                565               570               575

Ala Leu Gly Ile Lys Gly Ile Leu Asn Phe Thr Pro Ala Arg Leu Asn
                580               585               590

Val Pro Glu His Ile Arg Ile His His Ile Asp Leu Ala Val Glu Leu
                595               600               605

Gln Ser Leu Val Tyr Phe Leu Lys His Tyr Ser Val Leu Glu Glu Ile
                610               615               620

Glu Lys Leu
625

<210> SEQ ID NO 117
<211> LENGTH: 627
<212> TYPE: PRT
<213> ORGANISM: artificial sequence
<220> FEATURE:
<223> OTHER INFORMATION: Synthetic fluorescent sensor, mutant

<400> SEQUENCE: 117

Met Arg Gly Ser His His His His His His Gly Met Ala Ser Met Thr
1               5                   10                  15

Gly Gly Gln Gln Met Gly Arg Asp Leu Tyr Asp Asp Asp Asp Lys Asp
                20                  25                  30

Pro Met Asn Lys Asp Gln Ser Lys Ile Pro Gln Ala Thr Ala Lys Arg
            35                  40                  45

Leu Pro Leu Tyr Tyr Arg Phe Leu Lys Asn Leu His Ala Ser Gly Lys
50                  55                  60

Gln Arg Val Ser Ser Ala Glu Leu Ser Asp Ala Val Lys Val Asp Ser
65                  70                  75                  80

Ala Thr Ile Arg Arg Asp Phe Ser Tyr Phe Gly Ala Leu Gly Lys Lys
                85                  90                  95

Gly Tyr Gly Tyr Asn Val Asp Tyr Leu Leu Ser Phe Phe Arg Lys Thr
                100                 105                 110

Leu Asp Gln Asp Glu Met Thr Asp Val Ile Leu Ile Gly Val Gly Asn
            115                 120                 125

Leu Gly Thr Ala Phe Leu His Tyr Asn Phe Thr Lys Asn Asn Asn Thr
130                 135                 140

Lys Ile Ser Met Ala Phe Asp Ile Lys Glu Ser Lys Ile Gly Thr Glu
145                 150                 155                 160

Val Gly Gly Val Pro Val Tyr Asn Leu Asp Asp Leu Glu Gln His Val
                165                 170                 175

Lys Asp Glu Ser Val Ala Ile Leu Thr Val Pro Ala Val Ala Ala Gln
            180                 185                 190

Ser Ile Thr Asp Arg Leu Val Ala Leu Gly Ile Lys Gly Ile Leu Asn
            195                 200                 205

Phe Thr Pro Ala Arg Leu Asn Val Pro Glu His Ile Arg Ile His His
        210                 215                 220

Ile Asp Leu Ala Val Glu Leu Gln Ser Leu Val Tyr Phe Leu Lys His
225                 230                 235                 240

Tyr Ser Val Leu Glu Glu Tyr Asn Ser Asp Asn Val Tyr Ile Met Ala
                245                 250                 255

Asp Lys Gln Lys Asn Gly Ile Lys Ala Asn Phe Lys Ile Arg His Asn
```

```
                260                 265                 270
Val Glu Asp Gly Ser Val Gln Leu Ala Asp His Tyr Gln Gln Asn Thr
            275                 280                 285

Pro Ile Gly Asp Gly Pro Val Leu Leu Pro Asp Asn His Tyr Leu Ser
        290                 295                 300

Phe Gln Ser Val Leu Ser Lys Asp Pro Asn Glu Lys Arg Asp His Met
305                 310                 315                 320

Val Leu Leu Glu Phe Val Thr Ala Ala Gly Ile Thr Leu Gly Met Asp
                325                 330                 335

Glu Leu Tyr Asn Val Asp Gly Ser Gly Gly Thr Gly Ser Lys Gly
            340                 345                 350

Glu Glu Leu Phe Thr Gly Val Val Pro Ile Leu Val Glu Leu Asp Gly
                355                 360                 365

Asp Val Asn Gly His Lys Phe Ser Val Ser Gly Glu Gly Glu Gly Asp
            370                 375                 380

Ala Thr Tyr Gly Lys Leu Thr Leu Lys Leu Ile Cys Thr Thr Gly Lys
385                 390                 395                 400

Leu Pro Val Pro Trp Pro Thr Leu Val Thr Thr Leu Gly Tyr Gly Leu
                405                 410                 415

Lys Cys Phe Ala Arg Tyr Pro Asp His Met Lys Gln His Asp Phe Phe
            420                 425                 430

Lys Ser Ala Met Pro Glu Gly Tyr Val Gln Glu Arg Thr Ile Phe Phe
            435                 440                 445

Lys Asp Asp Gly Asn Tyr Lys Thr Arg Ala Glu Val Lys Phe Glu Gly
        450                 455                 460

Asp Thr Leu Val Asn Arg Ile Glu Leu Lys Gly Ile Gly Phe Lys Glu
465                 470                 475                 480

Asp Gly Asn Ile Leu Gly His Lys Leu Glu Tyr Asn Gly Thr Met Thr
                485                 490                 495

Asp Val Ile Leu Ile Gly Val Gly Asn Leu Gly Thr Ala Phe Leu His
                500                 505                 510

Tyr Asn Phe Thr Lys Asn Asn Asn Thr Lys Ile Ser Met Ala Phe Asp
            515                 520                 525

Ile Lys Glu Ser Lys Ile Gly Thr Glu Val Gly Gly Val Pro Val Tyr
        530                 535                 540

Asn Leu Asp Asp Leu Glu Gln His Val Lys Asp Glu Ser Val Ala Ile
545                 550                 555                 560

Leu Thr Val Pro Ala Val Ala Ala Gln Ser Ile Thr Asp Arg Leu Val
                565                 570                 575

Ala Leu Gly Ile Lys Gly Ile Leu Asn Phe Thr Pro Ala Arg Leu Asn
            580                 585                 590

Val Pro Glu His Ile Arg Ile His His Ile Asp Leu Ala Val Glu Leu
            595                 600                 605

Gln Ser Leu Val Tyr Phe Leu Lys His Tyr Ser Val Leu Glu Glu Ile
            610                 615                 620

Glu Lys Leu
625

<210> SEQ ID NO 118
<211> LENGTH: 627
<212> TYPE: PRT
<213> ORGANISM: artificial sequence
<220> FEATURE:
<223> OTHER INFORMATION: Synthetic fluorescent sensor, mutant
```

<400> SEQUENCE: 118

```
Met Arg Gly Ser His His His His His His Gly Met Ala Ser Met Thr
1               5                   10                  15
Gly Gly Gln Gln Met Gly Arg Asp Leu Tyr Asp Asp Asp Lys Asp
            20                  25                  30
Pro Met Asn Lys Asp Gln Ser Lys Ile Pro Gln Ala Thr Ala Lys Arg
        35                  40                  45
Leu Pro Leu Tyr Tyr Arg Phe Leu Lys Asn Leu His Ala Ser Gly Lys
    50                  55                  60
Gln Arg Val Ser Ser Ala Glu Leu Ser Asp Ala Val Lys Val Asp Ser
65                  70                  75                  80
Ala Thr Ile Arg Arg Asp Phe Ser Tyr Phe Gly Ala Leu Gly Lys Lys
                85                  90                  95
Gly Tyr Gly Tyr Asn Val Asp Tyr Leu Leu Ser Phe Phe Arg Lys Thr
            100                 105                 110
Leu Asp Gln Asp Glu Met Thr Asp Val Ile Leu Ile Gly Val Gly Asn
        115                 120                 125
Leu Gly Thr Ala Phe Leu His Tyr Asn Phe Thr Lys Asn Asn Asn Thr
    130                 135                 140
Lys Ile Ser Met Ala Phe Asp Ile Arg Glu Ser Lys Ile Gly Thr Glu
145                 150                 155                 160
Val Gly Gly Val Pro Val Tyr Asn Leu Asp Asp Leu Glu Gln His Val
                165                 170                 175
Lys Asp Glu Ser Val Ala Ile Leu Thr Val Pro Ala Val Ala Ala Gln
            180                 185                 190
Ser Ile Thr Asp Arg Leu Val Ala Leu Gly Ile Lys Gly Ile Leu Asn
    195                 200                 205
Phe Thr Pro Ala Arg Leu Asn Val Pro Glu His Ile Arg Ile His His
210                 215                 220
Ile Asp Leu Ala Val Glu Leu Gln Ser Leu Val Tyr Phe Leu Lys His
225                 230                 235                 240
Tyr Ser Val Leu Glu Glu Tyr Asn Ser Asp Asn Val Tyr Ile Met Ala
                245                 250                 255
Asp Lys Gln Lys Asn Gly Ile Lys Ala Asn Phe Lys Ile Arg His Asn
            260                 265                 270
Val Glu Asp Gly Ser Val Gln Leu Ala Asp His Tyr Gln Gln Asn Thr
        275                 280                 285
Pro Ile Gly Asp Gly Pro Val Leu Leu Pro Asp Asn His Tyr Leu Ser
    290                 295                 300
Phe Gln Ser Val Leu Ser Lys Asp Pro Asn Glu Lys Arg Asp His Met
305                 310                 315                 320
Val Leu Leu Glu Phe Val Thr Ala Ala Gly Ile Thr Leu Gly Met Asp
                325                 330                 335
Glu Leu Tyr Asn Val Asp Gly Ser Gly Gly Thr Gly Ser Lys Gly
            340                 345                 350
Glu Glu Leu Phe Thr Gly Val Val Pro Ile Leu Val Glu Leu Asp Gly
        355                 360                 365
Asp Val Asn Gly His Lys Phe Ser Val Ser Gly Glu Gly Glu Gly Asp
    370                 375                 380
Ala Thr Tyr Gly Lys Leu Thr Leu Lys Leu Ile Cys Thr Thr Gly Lys
385                 390                 395                 400
Leu Pro Val Pro Trp Pro Thr Leu Val Thr Thr Leu Gly Tyr Gly Leu
                405                 410                 415
```

```
Lys Cys Phe Ala Arg Tyr Pro Asp His Met Lys Gln His Asp Phe Phe
                420                 425                 430

Lys Ser Ala Met Pro Glu Gly Tyr Val Gln Glu Arg Thr Ile Phe Phe
            435                 440                 445

Lys Asp Asp Gly Asn Tyr Lys Thr Arg Ala Glu Val Lys Phe Glu Gly
        450                 455                 460

Asp Thr Leu Val Asn Arg Ile Glu Leu Lys Gly Ile Gly Phe Lys Glu
465                 470                 475                 480

Asp Gly Asn Ile Leu Gly His Lys Leu Glu Tyr Asn Gly Thr Met Thr
                485                 490                 495

Asp Val Ile Leu Ile Gly Val Gly Asn Leu Gly Thr Ala Phe Leu His
                500                 505                 510

Tyr Asn Phe Thr Lys Asn Asn Asn Thr Lys Ile Ser Met Ala Phe Asp
            515                 520                 525

Ile Arg Glu Ser Lys Ile Gly Thr Glu Val Gly Gly Val Pro Val Tyr
        530                 535                 540

Asn Leu Asp Asp Leu Glu Gln His Val Lys Asp Glu Ser Val Ala Ile
545                 550                 555                 560

Leu Thr Val Pro Ala Val Ala Ala Gln Ser Ile Thr Asp Arg Leu Val
                565                 570                 575

Ala Leu Gly Ile Lys Gly Ile Leu Asn Phe Thr Pro Ala Arg Leu Asn
                580                 585                 590

Val Pro Glu His Ile Arg Ile His His Ile Asp Leu Ala Val Glu Leu
            595                 600                 605

Gln Ser Leu Val Tyr Phe Leu Lys His Tyr Ser Val Leu Glu Glu Ile
    610                 615                 620

Glu Lys Leu
625

<210> SEQ ID NO 119
<211> LENGTH: 627
<212> TYPE: PRT
<213> ORGANISM: artificial sequence
<220> FEATURE:
<223> OTHER INFORMATION: Synthetic fluorescent sensor, mutant

<400> SEQUENCE: 119

Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

Pro Met Asn Lys Asp Gln Ser Lys Ile Pro Gln Ala Thr Ala Lys Arg
        35                  40                  45

Leu Pro Leu Tyr Tyr Arg Phe Leu Lys Asn Leu His Ala Ser Gly Lys
    50                  55                  60

Gln Arg Val Ser Ser Ala Glu Leu Ser Asp Ala Val Lys Val Asp Ser
65                  70                  75                  80

Ala Thr Ile Arg Arg Asp Phe Ser Tyr Phe Gly Ala Leu Gly Lys Lys
                85                  90                  95

Gly Tyr Gly Tyr Asn Val Asp Tyr Leu Leu Ser Phe Phe Arg Lys Thr
            100                 105                 110

Leu Asp Gln Asp Glu Met Thr Asp Val Ile Leu Ile Gly Val Gly Asn
        115                 120                 125

Leu Gly Thr Ala Phe Leu His Tyr Asn Phe Thr Lys Asn Asn Asn Thr
    130                 135                 140
```

```
Lys Ile Ser Met Ala Phe Asp Ile Glu Glu Ser Lys Ile Gly Thr Glu
145                 150                 155                 160

Val Gly Gly Val Pro Val Tyr Asn Leu Asp Leu Glu Gln His Val
            165                 170                 175

Lys Asp Glu Ser Val Ala Ile Leu Thr Val Pro Ala Val Ala Ala Gln
            180                 185                 190

Ser Ile Thr Asp Arg Leu Val Ala Leu Gly Ile Lys Gly Ile Leu Asn
            195                 200                 205

Phe Thr Pro Ala Arg Leu Asn Val Pro Glu His Ile Arg Ile His His
            210                 215                 220

Ile Asp Leu Ala Val Glu Leu Gln Ser Leu Val Tyr Phe Leu Lys His
225                 230                 235                 240

Tyr Ser Val Leu Glu Glu Tyr Asn Ser Asp Asn Val Tyr Ile Met Ala
                245                 250                 255

Asp Lys Gln Lys Asn Gly Ile Lys Ala Asn Phe Lys Ile Arg His Asn
            260                 265                 270

Val Glu Asp Gly Ser Val Gln Leu Ala Asp His Tyr Gln Gln Asn Thr
            275                 280                 285

Pro Ile Gly Asp Gly Pro Val Leu Leu Pro Asp Asn His Tyr Leu Ser
290                 295                 300

Phe Gln Ser Val Leu Ser Lys Asp Pro Asn Glu Lys Arg Asp His Met
305                 310                 315                 320

Val Leu Leu Glu Phe Val Thr Ala Ala Gly Ile Thr Leu Gly Met Asp
                325                 330                 335

Glu Leu Tyr Asn Val Asp Gly Gly Ser Gly Gly Thr Gly Ser Lys Gly
            340                 345                 350

Glu Glu Leu Phe Thr Gly Val Val Pro Ile Leu Val Glu Leu Asp Gly
            355                 360                 365

Asp Val Asn Gly His Lys Phe Ser Val Ser Gly Glu Gly Glu Gly Asp
            370                 375                 380

Ala Thr Tyr Gly Lys Leu Thr Leu Lys Leu Ile Cys Thr Thr Gly Lys
385                 390                 395                 400

Leu Pro Val Pro Trp Pro Thr Leu Val Thr Thr Leu Gly Tyr Gly Leu
                405                 410                 415

Lys Cys Phe Ala Arg Tyr Pro Asp His Met Lys Gln His Asp Phe Phe
            420                 425                 430

Lys Ser Ala Met Pro Glu Gly Tyr Val Gln Glu Arg Thr Ile Phe Phe
            435                 440                 445

Lys Asp Asp Gly Asn Tyr Lys Thr Arg Ala Glu Val Lys Phe Glu Gly
            450                 455                 460

Asp Thr Leu Val Asn Arg Ile Glu Leu Lys Gly Ile Gly Phe Lys Glu
465                 470                 475                 480

Asp Gly Asn Ile Leu Gly His Lys Leu Glu Tyr Asn Gly Thr Met Thr
            485                 490                 495

Asp Val Ile Leu Ile Gly Val Gly Asn Leu Gly Thr Ala Phe Leu His
                500                 505                 510

Tyr Asn Phe Thr Lys Asn Asn Thr Lys Ile Ser Met Ala Phe Asp
            515                 520                 525

Ile Glu Glu Ser Lys Ile Gly Thr Glu Val Gly Gly Val Pro Val Tyr
530                 535                 540

Asn Leu Asp Asp Leu Glu Gln His Val Lys Asp Glu Ser Val Ala Ile
545                 550                 555                 560
```

-continued

Leu Thr Val Pro Ala Val Ala Gln Ser Ile Thr Asp Arg Leu Val
              565             570                 575

Ala Leu Gly Ile Lys Gly Ile Leu Asn Phe Thr Pro Ala Arg Leu Asn
              580             585                 590

Val Pro Glu His Ile Arg Ile His His Ile Asp Leu Ala Val Glu Leu
              595             600                 605

Gln Ser Leu Val Tyr Phe Leu Lys His Tyr Ser Val Leu Glu Glu Ile
610             615                 620

Glu Lys Leu
625

<210> SEQ ID NO 120
<211> LENGTH: 627
<212> TYPE: PRT
<213> ORGANISM: artificial sequence
<220> FEATURE:
<223> OTHER INFORMATION: Synthetic fluorescent sensor, mutant

<400> SEQUENCE: 120

Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

Pro Met Asn Lys Asp Gln Ser Lys Ile Pro Gln Ala Thr Ala Lys Arg
        35                  40                  45

Leu Pro Leu Tyr Tyr Arg Phe Leu Lys Asn Leu His Ala Ser Gly Lys
    50                  55                  60

Gln Arg Val Ser Ser Ala Glu Leu Ser Asp Ala Val Lys Val Asp Ser
65                  70                  75                  80

Ala Thr Ile Arg Arg Asp Phe Ser Tyr Phe Gly Ala Leu Gly Lys Lys
                85                  90                  95

Gly Tyr Gly Tyr Asn Val Asp Tyr Leu Leu Ser Phe Phe Arg Lys Thr
            100                 105                 110

Leu Asp Gln Asp Glu Met Thr Asp Val Ile Leu Ile Gly Val Gly Asn
        115                 120                 125

Leu Gly Thr Ala Phe Leu His Tyr Asn Phe Thr Lys Asn Asn Asn Thr
    130                 135                 140

Lys Ile Ser Met Ala Phe Asp Ile Asp Glu Ser Lys Ile Gly Thr Glu
145                 150                 155                 160

Val Gly Gly Val Pro Val Tyr Asn Leu Asp Asp Leu Glu Gln His Val
                165                 170                 175

Lys Asp Glu Ser Val Ala Ile Leu Thr Val Pro Ala Val Ala Ala Gln
            180                 185                 190

Ser Ile Thr Asp Arg Leu Val Ala Leu Gly Ile Lys Gly Ile Leu Asn
        195                 200                 205

Phe Thr Pro Ala Arg Leu Asn Val Pro Glu His Ile Arg Ile His His
    210                 215                 220

Ile Asp Leu Ala Val Glu Leu Gln Ser Leu Val Tyr Phe Leu Lys His
225                 230                 235                 240

Tyr Ser Val Leu Glu Glu Tyr Asn Ser Asp Asn Val Tyr Ile Met Ala
                245                 250                 255

Asp Lys Gln Lys Asn Gly Ile Lys Ala Asn Phe Lys Ile Arg His Asn
            260                 265                 270

Val Glu Asp Gly Ser Val Gln Leu Ala Asp His Tyr Gln Gln Asn Thr
        275                 280                 285

```
Pro Ile Gly Asp Gly Pro Val Leu Leu Pro Asp Asn His Tyr Leu Ser
    290                 295                 300

Phe Gln Ser Val Leu Ser Lys Asp Pro Asn Glu Lys Arg Asp His Met
305                 310                 315                 320

Val Leu Leu Glu Phe Val Thr Ala Ala Gly Ile Thr Leu Gly Met Asp
                325                 330                 335

Glu Leu Tyr Asn Val Asp Gly Ser Gly Gly Thr Gly Ser Lys Gly
            340                 345                 350

Glu Glu Leu Phe Thr Gly Val Pro Ile Leu Val Glu Leu Asp Gly
            355                 360                 365

Asp Val Asn Gly His Lys Phe Ser Val Ser Gly Glu Gly Gly Asp
    370                 375                 380

Ala Thr Tyr Gly Lys Leu Thr Leu Lys Leu Ile Cys Thr Thr Gly Lys
385                 390                 395                 400

Leu Pro Val Pro Trp Pro Thr Leu Val Thr Thr Leu Gly Tyr Gly Leu
                405                 410                 415

Lys Cys Phe Ala Arg Tyr Pro Asp His Met Lys Gln His Asp Phe Phe
                420                 425                 430

Lys Ser Ala Met Pro Glu Gly Tyr Val Gln Glu Arg Thr Ile Phe Phe
            435                 440                 445

Lys Asp Asp Gly Asn Tyr Lys Thr Arg Ala Glu Val Lys Phe Glu Gly
450                 455                 460

Asp Thr Leu Val Asn Arg Ile Glu Leu Lys Gly Ile Gly Phe Lys Glu
465                 470                 475                 480

Asp Gly Asn Ile Leu Gly His Lys Leu Glu Tyr Asn Gly Thr Met Thr
                485                 490                 495

Asp Val Ile Leu Ile Gly Val Gly Asn Leu Gly Thr Ala Phe Leu His
                500                 505                 510

Tyr Asn Phe Thr Lys Asn Asn Thr Lys Ile Ser Met Ala Phe Asp
            515                 520                 525

Ile Asp Glu Ser Lys Ile Gly Thr Glu Val Gly Val Pro Val Tyr
530                 535                 540

Asn Leu Asp Asp Leu Glu Gln His Val Lys Asp Glu Ser Val Ala Ile
545                 550                 555                 560

Leu Thr Val Pro Ala Val Ala Ala Gln Ser Ile Thr Asp Arg Leu Val
                565                 570                 575

Ala Leu Gly Ile Lys Gly Ile Leu Asn Phe Thr Pro Ala Arg Leu Asn
                580                 585                 590

Val Pro Glu His Ile Arg Ile His His Ile Asp Leu Ala Val Glu Leu
                595                 600                 605

Gln Ser Leu Val Tyr Phe Leu Lys His Tyr Ser Val Leu Glu Glu Ile
    610                 615                 620

Glu Lys Leu
625

<210> SEQ ID NO 121
<211> LENGTH: 627
<212> TYPE: PRT
<213> ORGANISM: artificial sequence
<220> FEATURE:
<223> OTHER INFORMATION: Synthetic fluorescent sensor, mutant

<400> SEQUENCE: 121

Met Arg Gly Ser His His His His His His Gly Met Ala Ser Met Thr
1               5                   10                  15
```

```
Gly Gly Gln Gln Met Gly Arg Asp Leu Tyr Asp Asp Asp Lys Asp
            20                  25                  30

Pro Met Asn Lys Asp Gln Ser Lys Ile Pro Gln Ala Thr Ala Lys Arg
        35                  40                  45

Leu Pro Leu Tyr Tyr Arg Phe Leu Lys Asn Leu His Ala Ser Gly Lys
50                      55                  60

Gln Arg Val Ser Ser Ala Glu Leu Ser Asp Ala Val Lys Val Asp Ser
65                  70                  75                  80

Ala Thr Ile Arg Arg Asp Phe Ser Tyr Phe Gly Ala Leu Gly Lys Lys
                85                  90                  95

Gly Tyr Gly Tyr Asn Val Asp Tyr Leu Leu Ser Phe Phe Arg Lys Thr
                100                 105                 110

Leu Asp Gln Asp Glu Met Thr Asp Val Ile Leu Ile Gly Val Gly Asn
        115                 120                 125

Leu Gly Thr Ala Phe Leu His Tyr Asn Phe Thr Lys Asn Asn Asn Thr
130                 135                 140

Lys Ile Ser Met Ala Phe Asp Ile Asn Glu Ser Lys Ile Gly Thr Glu
145                 150                 155                 160

Val Gly Gly Val Pro Val Tyr Asn Leu Asp Asp Leu Glu Gln His Val
                165                 170                 175

Lys Asp Glu Ser Val Ala Ile Leu Thr Val Pro Ala Val Ala Ala Gln
        180                 185                 190

Ser Ile Thr Asp Arg Leu Val Ala Leu Gly Ile Lys Gly Ile Leu Asn
        195                 200                 205

Phe Thr Pro Ala Arg Leu Asn Val Pro Glu His Ile Arg Ile His His
210                 215                 220

Ile Asn Leu Ala Val Glu Leu Gln Ser Leu Val Tyr Phe Leu Lys His
225                 230                 235                 240

Tyr Ser Val Leu Glu Glu Tyr Asn Ser Asp Asn Val Tyr Ile Met Ala
                245                 250                 255

Asp Lys Gln Lys Asn Gly Ile Lys Ala Asn Phe Lys Ile Arg His Asn
        260                 265                 270

Val Glu Asp Gly Ser Val Gln Leu Ala Asp His Tyr Gln Gln Asn Thr
        275                 280                 285

Pro Ile Gly Asp Gly Pro Val Leu Leu Pro Asp Asn His Tyr Leu Ser
290                 295                 300

Phe Gln Ser Val Leu Ser Lys Asp Pro Asn Glu Lys Arg Asp His Met
305                 310                 315                 320

Val Leu Leu Glu Phe Val Thr Ala Ala Gly Ile Thr Leu Gly Met Asp
                325                 330                 335

Glu Leu Tyr Asn Val Asp Gly Ser Gly Gly Thr Gly Ser Lys Gly
        340                 345                 350

Glu Glu Leu Phe Thr Gly Val Val Pro Ile Leu Val Glu Leu Asp Gly
        355                 360                 365

Asp Val Asn Gly His Lys Phe Ser Val Ser Gly Glu Gly Glu Gly Asp
370                 375                 380

Ala Thr Tyr Gly Lys Leu Thr Leu Lys Leu Ile Cys Thr Thr Gly Lys
385                 390                 395                 400

Leu Pro Val Pro Trp Pro Thr Leu Val Thr Thr Leu Gly Tyr Gly Leu
                405                 410                 415

Lys Cys Phe Ala Arg Tyr Pro Asp His Met Lys Gln His Asp Phe Phe
        420                 425                 430

Lys Ser Ala Met Pro Glu Gly Tyr Val Gln Glu Arg Thr Ile Phe Phe
```

```
                435                 440                 445
Lys Asp Asp Gly Asn Tyr Lys Thr Arg Ala Glu Val Lys Phe Glu Gly
450                 455                 460

Asp Thr Leu Val Asn Arg Ile Glu Leu Lys Gly Ile Gly Phe Lys Glu
465                 470                 475                 480

Asp Gly Asn Ile Leu Gly His Lys Leu Glu Tyr Asn Gly Thr Met Thr
                485                 490                 495

Asp Val Ile Leu Ile Gly Val Gly Asn Leu Gly Thr Ala Phe Leu His
            500                 505                 510

Tyr Asn Phe Thr Lys Asn Asn Thr Lys Ile Ser Met Ala Phe Asp
        515                 520                 525

Ile Asn Glu Ser Lys Ile Gly Thr Glu Val Gly Gly Val Pro Val Tyr
530                 535                 540

Asn Leu Asp Asp Leu Glu Gln His Val Lys Asp Glu Ser Val Ala Ile
545                 550                 555                 560

Leu Thr Val Pro Ala Val Ala Ala Gln Ser Ile Thr Asp Arg Leu Val
                565                 570                 575

Ala Leu Gly Ile Lys Gly Ile Leu Asn Phe Thr Pro Ala Arg Leu Asn
            580                 585                 590

Val Pro Glu His Ile Arg Ile His His Ile Asn Leu Ala Val Glu Leu
        595                 600                 605

Gln Ser Leu Val Tyr Phe Leu Lys His Tyr Ser Val Leu Glu Glu Ile
610                 615                 620

Glu Lys Leu
625

<210> SEQ ID NO 122
<211> LENGTH: 627
<212> TYPE: PRT
<213> ORGANISM: artificial sequence
<220> FEATURE:
<223> OTHER INFORMATION: Synthetic fluorescent sensor, mutant

<400> SEQUENCE: 122

Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

Pro Met Asn Lys Asp Gln Ser Lys Ile Pro Gln Ala Thr Ala Lys Arg
            35                  40                  45

Leu Pro Leu Tyr Tyr Arg Phe Leu Lys Asn Leu His Ala Ser Gly Lys
        50                  55                  60

Gln Arg Val Ser Ser Ala Glu Leu Ser Asp Ala Val Lys Val Asp Ser
65                  70                  75                  80

Ala Thr Ile Arg Arg Asp Phe Ser Tyr Phe Gly Ala Leu Gly Lys Lys
                85                  90                  95

Gly Tyr Gly Tyr Asn Val Asp Tyr Leu Leu Ser Phe Phe Arg Lys Thr
            100                 105                 110

Leu Asp Gln Asp Glu Met Thr Asp Val Ile Leu Ile Gly Val Gly Asn
        115                 120                 125

Leu Gly Thr Ala Phe Leu His Tyr Asn Phe Thr Lys Asn Asn Asn Thr
    130                 135                 140

Lys Ile Ser Met Ala Phe Asp Ile Asn Glu Ser Lys Ile Gly Thr Glu
145                 150                 155                 160

Val Gly Gly Val Pro Val Tyr Asn Leu Asp Asp Leu Glu Gln His Val
```

```
                  165                 170                 175
Lys Asp Glu Ser Val Ala Ile Leu Thr Val Pro Ala Val Ala Gln
                180                 185                 190

Ser Ile Thr Asp Arg Leu Val Ala Leu Gly Ile Lys Gly Ile Leu Asn
                195                 200                 205

Phe Thr Pro Ala Arg Leu Asn Val Pro Glu His Ile Arg Ile His His
    210                 215                 220

Ile Lys Leu Ala Val Glu Leu Gln Ser Leu Val Tyr Phe Leu Lys His
225                 230                 235                 240

Tyr Ser Val Leu Glu Glu Tyr Asn Ser Asp Asn Val Tyr Ile Met Ala
                245                 250                 255

Asp Lys Gln Lys Asn Gly Ile Lys Ala Asn Phe Lys Ile Arg His Asn
                260                 265                 270

Val Glu Asp Gly Ser Val Gln Leu Ala Asp His Tyr Gln Gln Asn Thr
                275                 280                 285

Pro Ile Gly Asp Gly Pro Val Leu Leu Pro Asp Asn His Tyr Leu Ser
                290                 295                 300

Phe Gln Ser Val Leu Ser Lys Asp Pro Asn Glu Lys Arg Asp His Met
305                 310                 315                 320

Val Leu Leu Glu Phe Val Thr Ala Ala Gly Ile Thr Leu Gly Met Asp
                325                 330                 335

Glu Leu Tyr Asn Val Asp Gly Ser Gly Thr Gly Ser Lys Gly
                340                 345                 350

Glu Glu Leu Phe Thr Gly Val Val Pro Ile Leu Val Glu Leu Asp Gly
                355                 360                 365

Asp Val Asn Gly His Lys Phe Ser Val Ser Gly Glu Gly Glu Gly Asp
                370                 375                 380

Ala Thr Tyr Gly Lys Leu Thr Leu Lys Leu Ile Cys Thr Thr Gly Lys
385                 390                 395                 400

Leu Pro Val Pro Trp Pro Thr Leu Val Thr Thr Leu Gly Tyr Gly Leu
                405                 410                 415

Lys Cys Phe Ala Arg Tyr Pro Asp His Met Lys Gln His Asp Phe Phe
                420                 425                 430

Lys Ser Ala Met Pro Glu Gly Tyr Val Gln Glu Arg Thr Ile Phe Phe
                435                 440                 445

Lys Asp Asp Gly Asn Tyr Lys Thr Arg Ala Glu Val Lys Phe Glu Gly
                450                 455                 460

Asp Thr Leu Val Asn Arg Ile Glu Leu Lys Gly Ile Gly Phe Lys Glu
465                 470                 475                 480

Asp Gly Asn Ile Leu Gly His Lys Leu Glu Tyr Asn Gly Thr Met Thr
                485                 490                 495

Asp Val Ile Leu Ile Gly Val Gly Asn Leu Gly Thr Ala Phe Leu His
                500                 505                 510

Tyr Asn Phe Thr Lys Asn Asn Thr Lys Ile Ser Met Ala Phe Asp
                515                 520                 525

Ile Asn Glu Ser Lys Ile Gly Thr Glu Val Gly Val Pro Val Tyr
530                 535                 540

Asn Leu Asp Asp Leu Glu Gln His Val Lys Asp Glu Ser Val Ala Ile
545                 550                 555                 560

Leu Thr Val Pro Ala Val Ala Ala Gln Ser Ile Thr Asp Arg Leu Val
                565                 570                 575

Ala Leu Gly Ile Lys Gly Ile Leu Asn Phe Thr Pro Ala Arg Leu Asn
                580                 585                 590
```

Val Pro Glu His Ile Arg Ile His His Ile Lys Leu Ala Val Glu Leu
            595                 600                 605

Gln Ser Leu Val Tyr Phe Leu Lys His Tyr Ser Val Leu Glu Glu Ile
        610                 615                 620

Glu Lys Leu
625

<210> SEQ ID NO 123
<211> LENGTH: 627
<212> TYPE: PRT
<213> ORGANISM: artificial sequence
<220> FEATURE:
<223> OTHER INFORMATION: Synthetic fluorescent sensor, mutant

<400> SEQUENCE: 123

Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

Pro Met Asn Lys Asp Gln Ser Lys Ile Pro Gln Ala Thr Ala Lys Arg
        35                  40                  45

Leu Pro Leu Tyr Tyr Arg Phe Leu Lys Asn Leu His Ala Ser Gly Lys
    50                  55                  60

Gln Arg Val Ser Ser Ala Glu Leu Ser Asp Ala Val Lys Val Asp Ser
65                  70                  75                  80

Ala Thr Ile Arg Arg Asp Phe Ser Tyr Phe Gly Ala Leu Gly Lys Lys
                85                  90                  95

Gly Tyr Gly Tyr Asn Val Asp Tyr Leu Leu Ser Phe Phe Arg Lys Thr
            100                 105                 110

Leu Asp Gln Asp Glu Met Thr Asp Val Ile Leu Ile Gly Val Gly Asn
        115                 120                 125

Leu Gly Thr Ala Phe Leu His Tyr Asn Phe Thr Lys Asn Asn Asn Thr
    130                 135                 140

Lys Ile Ser Met Ala Phe Asp Ile Asn Glu Ser Lys Ile Gly Thr Glu
145                 150                 155                 160

Val Gly Gly Val Pro Val Tyr Asn Leu Asp Asp Leu Glu Gln His Val
                165                 170                 175

Lys Asp Glu Ser Val Ala Ile Leu Thr Val Pro Ala Val Ala Ala Gln
            180                 185                 190

Ser Ile Thr Asp Arg Leu Val Ala Leu Gly Ile Lys Gly Ile Leu Asn
        195                 200                 205

Phe Thr Pro Ala Arg Leu Asn Val Pro Glu His Ile Arg Ile His His
    210                 215                 220

Ile Asp Lys Ala Val Glu Leu Gln Ser Leu Val Tyr Phe Leu Lys His
225                 230                 235                 240

Tyr Ser Val Leu Glu Glu Tyr Asn Ser Asp Asn Val Tyr Ile Met Ala
                245                 250                 255

Asp Lys Gln Lys Asn Gly Ile Lys Ala Asn Phe Lys Ile Arg His Asn
            260                 265                 270

Val Glu Asp Gly Ser Val Gln Leu Ala Asp His Tyr Gln Gln Asn Thr
        275                 280                 285

Pro Ile Gly Asp Gly Pro Val Leu Leu Pro Asp Asn His Tyr Leu Ser
    290                 295                 300

Phe Gln Ser Val Leu Ser Lys Asp Pro Asn Glu Lys Arg Asp His Met
305                 310                 315                 320

Val Leu Leu Glu Phe Val Thr Ala Ala Gly Ile Thr Leu Gly Met Asp
                325                 330                 335

Glu Leu Tyr Asn Val Asp Gly Gly Ser Gly Thr Gly Ser Lys Gly
            340                 345                 350

Glu Glu Leu Phe Thr Gly Val Val Pro Ile Leu Val Glu Leu Asp Gly
            355                 360                 365

Asp Val Asn Gly His Lys Phe Ser Val Ser Gly Glu Gly Glu Gly Asp
            370                 375                 380

Ala Thr Tyr Gly Lys Leu Thr Leu Lys Leu Ile Cys Thr Thr Gly Lys
385                 390                 395                 400

Leu Pro Val Pro Trp Pro Thr Leu Val Thr Thr Leu Gly Tyr Gly Leu
                405                 410                 415

Lys Cys Phe Ala Arg Tyr Pro Asp His Met Lys Gln His Asp Phe Phe
                420                 425                 430

Lys Ser Ala Met Pro Glu Gly Tyr Val Gln Glu Arg Thr Ile Phe Phe
            435                 440                 445

Lys Asp Asp Gly Asn Tyr Lys Thr Arg Ala Glu Val Lys Phe Glu Gly
            450                 455                 460

Asp Thr Leu Val Asn Arg Ile Glu Leu Lys Gly Ile Gly Phe Lys Glu
465                 470                 475                 480

Asp Gly Asn Ile Leu Gly His Lys Leu Glu Tyr Asn Gly Thr Met Thr
                485                 490                 495

Asp Val Ile Leu Ile Gly Val Gly Asn Leu Gly Thr Ala Phe Leu His
                500                 505                 510

Tyr Asn Phe Thr Lys Asn Asn Thr Lys Ile Ser Met Ala Phe Asp
            515                 520                 525

Ile Asn Glu Ser Lys Ile Gly Thr Glu Val Gly Val Pro Val Tyr
            530                 535                 540

Asn Leu Asp Asp Leu Glu Gln His Val Lys Asp Glu Ser Val Ala Ile
545                 550                 555                 560

Leu Thr Val Pro Ala Val Ala Ala Gln Ser Ile Thr Asp Arg Leu Val
                565                 570                 575

Ala Leu Gly Ile Lys Gly Ile Leu Asn Phe Thr Pro Ala Arg Leu Asn
                580                 585                 590

Val Pro Glu His Ile Arg Ile His His Ile Asp Lys Ala Val Glu Leu
                595                 600                 605

Gln Ser Leu Val Tyr Phe Leu Lys His Tyr Ser Val Leu Glu Glu Ile
            610                 615                 620

Glu Lys Leu
625

<210> SEQ ID NO 124
<211> LENGTH: 627
<212> TYPE: PRT
<213> ORGANISM: artificial sequence
<220> FEATURE:
<223> OTHER INFORMATION: Synthetic fluorescent sensor, mutant

<400> SEQUENCE: 124

Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

Pro Met Asn Lys Asp Gln Ser Lys Ile Pro Gln Ala Thr Ala Lys Arg
            35                  40                  45

```
Leu Pro Leu Tyr Tyr Arg Phe Leu Lys Asn Leu His Ala Ser Gly Lys
    50                  55                  60

Gln Arg Val Ser Ser Ala Glu Leu Ser Asp Ala Val Lys Val Asp Ser
65                  70                  75                  80

Ala Thr Ile Arg Arg Asp Phe Ser Tyr Phe Gly Ala Leu Gly Lys Lys
                85                  90                  95

Gly Tyr Gly Tyr Asn Val Asp Tyr Leu Leu Ser Phe Phe Arg Lys Thr
            100                 105                 110

Leu Asp Gln Asp Glu Met Thr Asp Val Ile Leu Ile Gly Val Gly Asn
            115                 120                 125

Leu Gly Thr Ala Phe Leu His Tyr Asn Phe Thr Lys Asn Asn Asn Thr
        130                 135                 140

Lys Ile Ser Met Ala Phe Asp Ile Asn Glu Ser Lys Ile Gly Thr Glu
145                 150                 155                 160

Val Gly Gly Val Pro Val Tyr Asn Leu Asp Asp Leu Glu Gln His Val
                165                 170                 175

Lys Asp Glu Ser Val Ala Ile Leu Thr Val Pro Ala Val Ala Ala Gln
            180                 185                 190

Ser Ile Thr Asp Arg Leu Val Ala Leu Gly Ile Lys Gly Ile Leu Asn
        195                 200                 205

Phe Thr Pro Ala Arg Leu Asn Val Pro Glu His Ile Arg Ile His His
    210                 215                 220

Ile Asp Arg Ala Val Glu Leu Gln Ser Leu Val Tyr Phe Leu Lys His
225                 230                 235                 240

Tyr Ser Val Leu Glu Glu Tyr Asn Ser Asp Asn Val Tyr Ile Met Ala
                245                 250                 255

Asp Lys Gln Lys Asn Gly Ile Lys Ala Asn Phe Lys Ile Arg His Asn
            260                 265                 270

Val Glu Asp Gly Ser Val Gln Leu Ala Asp His Tyr Gln Gln Asn Thr
        275                 280                 285

Pro Ile Gly Asp Gly Pro Val Leu Leu Pro Asp Asn His Tyr Leu Ser
    290                 295                 300

Phe Gln Ser Val Leu Ser Lys Asp Pro Asn Glu Lys Arg Asp His Met
305                 310                 315                 320

Val Leu Leu Glu Phe Val Thr Ala Ala Gly Ile Thr Leu Gly Met Asp
                325                 330                 335

Glu Leu Tyr Asn Val Asp Gly Ser Gly Gly Thr Gly Ser Lys Gly
            340                 345                 350

Glu Glu Leu Phe Thr Gly Val Val Pro Ile Leu Val Glu Leu Asp Gly
        355                 360                 365

Asp Val Asn Gly His Lys Phe Ser Val Ser Gly Glu Gly Glu Gly Asp
    370                 375                 380

Ala Thr Tyr Gly Lys Leu Thr Leu Lys Leu Ile Cys Thr Thr Gly Lys
385                 390                 395                 400

Leu Pro Val Pro Trp Pro Thr Leu Val Thr Thr Leu Gly Tyr Gly Leu
                405                 410                 415

Lys Cys Phe Ala Arg Tyr Pro Asp His Met Lys Gln His Asp Phe Phe
            420                 425                 430

Lys Ser Ala Met Pro Glu Gly Tyr Val Gln Glu Arg Thr Ile Phe Phe
        435                 440                 445

Lys Asp Asp Gly Asn Tyr Lys Thr Arg Ala Glu Val Lys Phe Glu Gly
    450                 455                 460
```

```
Asp Thr Leu Val Asn Arg Ile Glu Leu Lys Gly Ile Gly Phe Lys Glu
465                 470                 475                 480

Asp Gly Asn Ile Leu Gly His Lys Leu Glu Tyr Asn Gly Thr Met Thr
                485                 490                 495

Asp Val Ile Leu Ile Gly Val Gly Asn Leu Gly Thr Ala Phe Leu His
                500                 505                 510

Tyr Asn Phe Thr Lys Asn Asn Asn Thr Lys Ile Ser Met Ala Phe Asp
                515                 520                 525

Ile Asn Glu Ser Lys Ile Gly Thr Glu Val Gly Val Pro Val Tyr
                530                 535                 540

Asn Leu Asp Asp Leu Glu Gln His Val Lys Asp Glu Ser Val Ala Ile
545                 550                 555                 560

Leu Thr Val Pro Ala Val Ala Ala Gln Ser Ile Thr Asp Arg Leu Val
                565                 570                 575

Ala Leu Gly Ile Lys Gly Ile Leu Asn Phe Thr Pro Ala Arg Leu Asn
                580                 585                 590

Val Pro Glu His Ile Arg Ile His Ile Asp Arg Ala Val Glu Leu
                595                 600                 605

Gln Ser Leu Val Tyr Phe Leu Lys His Tyr Ser Val Leu Glu Glu Ile
                610                 615                 620

Glu Lys Leu
625
```

<210> SEQ ID NO 125
<211> LENGTH: 627
<212> TYPE: PRT
<213> ORGANISM: artificial sequence
<220> FEATURE:
<223> OTHER INFORMATION: Synthetic fluorescent sensor, mutant

<400> SEQUENCE: 125

```
Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
                20                  25                  30

Pro Met Asn Lys Asp Gln Ser Lys Ile Pro Gln Ala Thr Ala Lys Arg
                35                  40                  45

Leu Pro Leu Tyr Tyr Arg Phe Leu Lys Asn Leu His Ala Ser Gly Lys
            50                  55                  60

Gln Arg Val Ser Ser Ala Glu Leu Ser Asp Ala Val Lys Val Asp Ser
65                  70                  75                  80

Ala Thr Ile Arg Arg Asp Phe Ser Tyr Phe Gly Ala Leu Gly Lys Lys
                85                  90                  95

Gly Tyr Gly Tyr Asn Val Asp Tyr Leu Leu Ser Phe Phe Arg Lys Thr
                100                 105                 110

Leu Asp Gln Asp Glu Met Thr Asp Val Ile Leu Ile Gly Val Gly Asn
            115                 120                 125

Leu Gly Thr Ala Phe Leu His Tyr Asn Phe Thr Lys Asn Asn Asn Thr
            130                 135                 140

Lys Ile Ser Met Ala Phe Asp Ile Asn Glu Ser Lys Ile Gly Thr Glu
145                 150                 155                 160

Val Gly Gly Val Pro Val Tyr Asn Leu Asp Asp Leu Glu Gln His Val
                165                 170                 175

Lys Asp Glu Ser Val Ala Ile Leu Thr Val Pro Ala Val Ala Ala Gln
            180                 185                 190
```

```
Ser Ile Thr Asp Arg Leu Val Ala Leu Gly Ile Lys Gly Ile Leu Asn
            195                 200                 205

Phe Thr Pro Ala Arg Leu Asn Val Pro Glu His Ile Arg Ile His His
        210                 215                 220

Ile Asp Glu Ala Val Glu Leu Gln Ser Leu Val Tyr Phe Leu Lys His
225                 230                 235                 240

Tyr Ser Val Leu Glu Glu Tyr Asn Ser Asp Asn Val Tyr Ile Met Ala
                245                 250                 255

Asp Lys Gln Lys Asn Gly Ile Lys Ala Asn Phe Lys Ile Arg His Asn
            260                 265                 270

Val Glu Asp Gly Ser Val Gln Leu Ala Asp His Tyr Gln Gln Asn Thr
        275                 280                 285

Pro Ile Gly Asp Gly Pro Val Leu Leu Pro Asp Asn His Tyr Leu Ser
290                 295                 300

Phe Gln Ser Val Leu Ser Lys Asp Pro Asn Glu Lys Arg Asp His Met
305                 310                 315                 320

Val Leu Leu Glu Phe Val Thr Ala Ala Gly Ile Thr Leu Gly Met Asp
                325                 330                 335

Glu Leu Tyr Asn Val Asp Gly Gly Ser Gly Gly Thr Gly Ser Lys Gly
            340                 345                 350

Glu Glu Leu Phe Thr Gly Val Val Pro Ile Leu Val Glu Leu Asp Gly
        355                 360                 365

Asp Val Asn Gly His Lys Phe Ser Val Ser Gly Glu Gly Glu Gly Asp
        370                 375                 380

Ala Thr Tyr Gly Lys Leu Thr Leu Lys Leu Ile Cys Thr Thr Gly Lys
385                 390                 395                 400

Leu Pro Val Pro Trp Pro Thr Leu Val Thr Thr Leu Gly Tyr Gly Leu
                405                 410                 415

Lys Cys Phe Ala Arg Tyr Pro Asp His Met Lys Gln His Asp Phe Phe
            420                 425                 430

Lys Ser Ala Met Pro Glu Gly Tyr Val Gln Glu Arg Thr Ile Phe Phe
        435                 440                 445

Lys Asp Asp Gly Asn Tyr Lys Thr Arg Ala Glu Val Lys Phe Glu Gly
450                 455                 460

Asp Thr Leu Val Asn Arg Ile Glu Leu Lys Gly Ile Gly Phe Lys Glu
465                 470                 475                 480

Asp Gly Asn Ile Leu Gly His Lys Leu Glu Tyr Asn Gly Thr Met Thr
                485                 490                 495

Asp Val Ile Leu Ile Gly Val Gly Asn Leu Gly Thr Ala Phe Leu His
            500                 505                 510

Tyr Asn Phe Thr Lys Asn Asn Thr Lys Ile Ser Met Ala Phe Asp
        515                 520                 525

Ile Asn Glu Ser Lys Ile Gly Thr Glu Val Gly Val Pro Val Tyr
530                 535                 540

Asn Leu Asp Asp Leu Glu Gln His Val Lys Asp Glu Ser Val Ala Ile
545                 550                 555                 560

Leu Thr Val Pro Ala Val Ala Ala Gln Ser Ile Thr Asp Arg Leu Val
                565                 570                 575

Ala Leu Gly Ile Lys Gly Ile Leu Asn Phe Thr Pro Ala Arg Leu Asn
            580                 585                 590

Val Pro Glu His Ile Arg Ile His His Ile Asp Glu Ala Val Glu Leu
        595                 600                 605

Gln Ser Leu Val Tyr Phe Leu Lys His Tyr Ser Val Leu Glu Glu Ile
```

Glu Lys Leu
625

<210> SEQ ID NO 126
<211> LENGTH: 630
<212> TYPE: PRT
<213> ORGANISM: artificial sequence
<220> FEATURE:
<223> OTHER INFORMATION: Synthetic fluorescent sensor, mutant

<400> SEQUENCE: 126

Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

Pro Met Asn Lys Asp Gln Ser Lys Ile Pro Gln Ala Thr Ala Lys Arg
        35                  40                  45

Leu Pro Leu Tyr Tyr Arg Phe Leu Lys Asn Leu His Ala Ser Gly Lys
    50                  55                  60

Gln Arg Val Ser Ser Ala Glu Leu Ser Asp Ala Val Lys Val Asp Ser
65                  70                  75                  80

Ala Thr Ile Arg Arg Asp Phe Ser Tyr Phe Gly Ala Leu Gly Lys Lys
                85                  90                  95

Gly Tyr Gly Tyr Asn Val Asp Tyr Leu Leu Ser Phe Phe Arg Lys Thr
            100                 105                 110

Leu Asp Gln Asp Glu Met Thr Asp Val Ile Leu Ile Gly Val Gly Asn
        115                 120                 125

Leu Gly Thr Ala Phe Leu His Tyr Asn Phe Thr Lys Asn Asn Asn Thr
    130                 135                 140

Lys Ile Ser Met Ala Phe Asp Ile Asn Glu Ser Lys Ile Gly Thr Glu
145                 150                 155                 160

Val Gly Gly Val Pro Val Tyr Asn Leu Asp Asp Leu Glu Gln His Val
                165                 170                 175

Lys Asp Glu Ser Val Ala Ile Leu Thr Val Pro Ala Val Ala Ala Gln
            180                 185                 190

Ser Ile Thr Asp Arg Leu Val Ala Leu Gly Ile Lys Gly Ile Leu Asn
        195                 200                 205

Phe Thr Pro Ala Arg Leu Asn Val Pro Glu His Ile Arg Ile His His
    210                 215                 220

Ile Asp Leu Ala Val Glu Leu Gln Ser Leu Val Tyr Phe Leu Lys His
225                 230                 235                 240

Tyr Ser Val Leu Glu Glu Ile Glu Thr Tyr Asn Ser Asp Asn Val Tyr
                245                 250                 255

Ile Met Ala Asp Lys Gln Lys Asn Gly Ile Lys Ala Asn Phe Lys Ile
            260                 265                 270

Arg His Asn Val Glu Asp Gly Ser Val Gln Leu Ala Asp His Tyr Gln
        275                 280                 285

Gln Asn Thr Pro Ile Gly Asp Gly Pro Val Leu Leu Pro Asp Asn His
    290                 295                 300

Tyr Leu Ser Phe Gln Ser Val Leu Ser Lys Asp Pro Asn Glu Lys Arg
305                 310                 315                 320

Asp His Met Val Leu Leu Glu Phe Val Thr Ala Ala Gly Ile Thr Leu
                325                 330                 335

Gly Met Asp Glu Leu Tyr Asn Val Asp Gly Gly Ser Gly Gly Thr Gly

-continued

```
                340             345             350
        Ser Lys Gly Glu Glu Leu Phe Thr Gly Val Pro Ile Leu Val Glu
                    355             360             365

Leu Asp Gly Asp Val Asn Gly His Lys Phe Ser Val Ser Gly Glu Gly
                    370             375             380

Glu Gly Asp Ala Thr Tyr Gly Lys Leu Thr Leu Lys Leu Ile Cys Thr
        385             390             395             400

Thr Gly Lys Leu Pro Val Pro Trp Pro Thr Leu Val Thr Thr Leu Gly
                        405             410             415

Tyr Gly Leu Lys Cys Phe Ala Arg Tyr Pro Asp His Met Lys Gln His
                    420             425             430

Asp Phe Phe Lys Ser Ala Met Pro Glu Gly Tyr Val Gln Glu Arg Thr
                    435             440             445

Ile Phe Phe Lys Asp Asp Gly Asn Tyr Lys Thr Arg Ala Glu Val Lys
                    450             455             460

Phe Glu Gly Asp Thr Leu Val Asn Arg Ile Glu Leu Lys Gly Ile Gly
        465             470             475             480

Phe Lys Glu Asp Gly Asn Ile Leu Gly His Lys Leu Glu Tyr Asn Gly
                        485             490             495

Thr Met Thr Asp Val Ile Leu Ile Gly Val Gly Asn Leu Gly Thr Ala
                    500             505             510

Phe Leu His Tyr Asn Phe Thr Lys Asn Asn Thr Lys Ile Ser Met
                    515             520             525

Ala Phe Asp Ile Asn Glu Ser Lys Ile Gly Thr Glu Val Gly Gly Val
                    530             535             540

Pro Val Tyr Asn Leu Asp Asp Leu Glu Gln His Val Lys Asp Glu Ser
        545             550             555             560

Val Ala Ile Leu Thr Val Pro Ala Val Ala Gln Ser Ile Thr Asp
                        565             570             575

Arg Leu Val Ala Leu Gly Ile Lys Gly Ile Leu Asn Phe Thr Pro Ala
                    580             585             590

Arg Leu Asn Val Pro Glu His Ile Arg Ile His His Ile Asp Leu Ala
                    595             600             605

Val Glu Leu Gln Ser Leu Val Tyr Phe Leu Lys His Tyr Ser Val Leu
                    610             615             620

Glu Glu Ile Glu Lys Leu
        625             630

<210> SEQ ID NO 127
<211> LENGTH: 463
<212> TYPE: PRT
<213> ORGANISM: artificial sequence
<220> FEATURE:
<223> OTHER INFORMATION: Synthetic fluorescent sensor, mutant

<400> SEQUENCE: 127

Met Lys Val Pro Glu Ala Ala Ile Ser Arg Leu Ile Thr Tyr Leu Arg
        1               5                   10                  15

Ile Leu Glu Glu Leu Glu Ala Gln Gly Val His Arg Thr Ser Ser Glu
                        20                  25                  30

Gln Leu Gly Glu Leu Ala Gln Val Thr Ala Phe Gln Val Arg Lys Asp
                    35                  40                  45

Leu Ser Tyr Phe Gly Ser Tyr Gly Thr Arg Gly Val Gly Tyr Thr Val
                50                  55                  60

Pro Val Leu Lys Arg Glu Leu Arg His Ile Leu Gly Leu Asn Arg Lys
```

```
                65                  70                  75                  80
        Trp Gly Leu Cys Ile Val Gly Met Gly Arg Leu Gly Ser Ala Leu Ala
                            85                  90                  95

Asp Tyr Pro Gly Phe Gly Glu Ser Phe Glu Leu Arg Gly Phe Phe Asp
                        100                 105                 110

Val Asp Pro Glu Lys Val Gly Arg Pro Val Arg Gly Val Ile Glu
                    115                 120                 125

His Val Asp Leu Leu Pro Gln Arg Val Pro Gly Arg Ile Glu Ile Ala
                130                 135                 140

Leu Leu Thr Val Pro Arg Glu Ala Ala Gln Lys Ala Ala Asp Leu Leu
        145                 150                 155                 160

Val Ala Ala Gly Ile Lys Gly Ile Leu Asn Phe Ala Pro Val Val Leu
                        165                 170                 175

Glu Val Pro Lys Glu Val Ala Val Glu Asn Val Asp Phe Ser Ala Gly
                    180                 185                 190

Tyr Asn Ser Asp Asn Val Tyr Ile Met Ala Asp Lys Gln Lys Asn Gly
                195                 200                 205

Ile Lys Ala Asn Phe Lys Ile Arg His Asn Val Glu Asp Gly Ser Val
            210                 215                 220

Gln Leu Ala Asp His Tyr Gln Gln Asn Thr Pro Ile Gly Asp Gly Pro
        225                 230                 235                 240

Val Leu Leu Pro Asp Asn His Tyr Leu Ser Phe Gln Ser Val Leu Ser
                        245                 250                 255

Lys Asp Pro Asn Glu Lys Arg Asp His Met Val Leu Leu Glu Phe Val
                    260                 265                 270

Thr Ala Ala Gly Ile Thr Leu Gly Met Asp Glu Leu Tyr Asn Val Asp
                275                 280                 285

Gly Gly Ser Gly Gly Thr Gly Ser Lys Gly Glu Glu Leu Phe Thr Gly
            290                 295                 300

Val Val Pro Ile Leu Val Glu Leu Asp Gly Asp Val Asn Gly His Lys
        305                 310                 315                 320

Phe Ser Val Ser Gly Glu Gly Glu Gly Asp Ala Thr Tyr Gly Lys Leu
                        325                 330                 335

Thr Leu Lys Leu Ile Cys Thr Thr Gly Lys Leu Pro Val Pro Trp Pro
                    340                 345                 350

Thr Leu Val Thr Thr Leu Gly Tyr Gly Leu Lys Cys Phe Ala Arg Tyr
                355                 360                 365

Pro Asp His Met Lys Gln His Asp Phe Phe Lys Ser Ala Met Pro Glu
            370                 375                 380

Gly Tyr Val Gln Glu Arg Thr Ile Phe Phe Lys Asp Asp Gly Asn Tyr
        385                 390                 395                 400

Lys Thr Arg Ala Glu Val Lys Phe Glu Gly Asp Thr Leu Val Asn Arg
                        405                 410                 415

Ile Glu Leu Lys Gly Ile Gly Phe Lys Glu Asp Gly Asn Ile Leu Gly
                    420                 425                 430

His Lys Leu Glu Tyr Asn Gly Thr Gly Leu Ala Gly Leu Thr Arg Leu
                435                 440                 445

Ser Phe Ala Ile Leu Asn Pro Lys Trp Arg Glu Glu Met Met Gly
            450                 455                 460

<210> SEQ ID NO 128
<211> LENGTH: 462
<212> TYPE: PRT
<213> ORGANISM: artificial sequence
```

<220> FEATURE:
<223> OTHER INFORMATION: Synthetic fluorescent sensor, mutant

<400> SEQUENCE: 128

```
Met Lys Val Pro Glu Ala Ala Ile Ser Arg Leu Ile Thr Tyr Leu Arg
1               5                   10                  15

Ile Leu Glu Glu Leu Glu Ala Gln Gly Val His Arg Thr Ser Ser Glu
            20                  25                  30

Gln Leu Gly Glu Leu Ala Gln Val Thr Ala Phe Gln Val Arg Lys Asp
        35                  40                  45

Leu Ser Tyr Phe Gly Ser Tyr Gly Thr Arg Gly Val Gly Tyr Thr Val
    50                  55                  60

Pro Val Leu Lys Arg Glu Leu Arg His Ile Leu Gly Leu Asn Arg Lys
65                  70                  75                  80

Trp Gly Leu Cys Ile Val Gly Met Gly Arg Leu Gly Ser Ala Leu Ala
                85                  90                  95

Asp Tyr Pro Gly Phe Gly Glu Ser Phe Glu Leu Arg Gly Phe Phe Asp
            100                 105                 110

Val Asp Pro Glu Lys Val Gly Arg Pro Val Arg Gly Val Ile Glu
        115                 120                 125

His Val Asp Leu Leu Pro Gln Arg Val Pro Gly Arg Ile Glu Ile Ala
    130                 135                 140

Leu Leu Thr Val Pro Arg Glu Ala Ala Gln Lys Ala Ala Asp Leu Leu
145                 150                 155                 160

Val Ala Ala Gly Ile Lys Gly Ile Leu Asn Phe Ala Pro Val Val Leu
                165                 170                 175

Glu Val Pro Lys Glu Val Ala Val Glu Asn Val Asp Phe Ala Gly Tyr
            180                 185                 190

Asn Ser Asp Asn Val Tyr Ile Met Ala Asp Lys Gln Lys Asn Gly Ile
        195                 200                 205

Lys Ala Asn Phe Lys Ile Arg His Asn Val Glu Asp Gly Ser Val Gln
    210                 215                 220

Leu Ala Asp His Tyr Gln Gln Asn Thr Pro Ile Gly Asp Gly Pro Val
225                 230                 235                 240

Leu Leu Pro Asp Asn His Tyr Leu Ser Phe Gln Ser Val Leu Ser Lys
                245                 250                 255

Asp Pro Asn Glu Lys Arg Asp His Met Val Leu Leu Glu Phe Val Thr
            260                 265                 270

Ala Ala Gly Ile Thr Leu Gly Met Asp Glu Leu Tyr Asn Val Asp Gly
        275                 280                 285

Gly Ser Gly Gly Thr Gly Ser Lys Gly Glu Glu Leu Phe Thr Gly Val
    290                 295                 300

Val Pro Ile Leu Val Glu Leu Asp Gly Asp Val Asn Gly His Lys Phe
305                 310                 315                 320

Ser Val Ser Gly Glu Gly Glu Gly Asp Ala Thr Tyr Gly Lys Leu Thr
                325                 330                 335

Leu Lys Leu Ile Cys Thr Thr Gly Lys Leu Pro Val Pro Trp Pro Thr
            340                 345                 350

Leu Val Thr Thr Leu Gly Tyr Gly Leu Lys Cys Phe Ala Arg Tyr Pro
        355                 360                 365

Asp His Met Lys Gln His Asp Phe Phe Lys Ser Ala Met Pro Glu Gly
    370                 375                 380

Tyr Val Gln Glu Arg Thr Ile Phe Phe Lys Asp Asp Gly Asn Tyr Lys
385                 390                 395                 400
```

```
Thr Arg Ala Glu Val Lys Phe Glu Gly Asp Thr Leu Val Asn Arg Ile
            405                 410                 415

Glu Leu Lys Gly Ile Gly Phe Lys Glu Asp Gly Asn Ile Leu Gly His
            420                 425                 430

Lys Leu Glu Tyr Asn Gly Thr Gly Leu Ala Gly Leu Thr Arg Leu Ser
            435                 440                 445

Phe Ala Ile Leu Asn Pro Lys Trp Arg Glu Glu Met Met Gly
450                 455                 460

<210> SEQ ID NO 129
<211> LENGTH: 461
<212> TYPE: PRT
<213> ORGANISM: artificial sequence
<220> FEATURE:
<223> OTHER INFORMATION: Synthetic fluorescent sensor, mutant

<400> SEQUENCE: 129

Met Lys Val Pro Glu Ala Ala Ile Ser Arg Leu Ile Thr Tyr Leu Arg
1               5                   10                  15

Ile Leu Glu Glu Leu Glu Ala Gln Gly Val His Arg Thr Ser Ser Glu
            20                  25                  30

Gln Leu Gly Glu Leu Ala Gln Val Thr Ala Phe Gln Val Arg Lys Asp
        35                  40                  45

Leu Ser Tyr Phe Gly Ser Tyr Gly Thr Arg Gly Val Gly Tyr Thr Val
    50                  55                  60

Pro Val Leu Lys Arg Glu Leu Arg His Ile Leu Gly Leu Asn Arg Lys
65                  70                  75                  80

Trp Gly Leu Cys Ile Val Gly Met Gly Arg Leu Gly Ser Ala Leu Ala
                85                  90                  95

Asp Tyr Pro Gly Phe Gly Glu Ser Phe Glu Leu Arg Gly Phe Phe Asp
            100                 105                 110

Val Asp Pro Glu Lys Val Gly Arg Pro Val Arg Gly Gly Val Ile Glu
        115                 120                 125

His Val Asp Leu Leu Pro Gln Arg Val Pro Gly Arg Ile Glu Ile Ala
    130                 135                 140

Leu Leu Thr Val Pro Arg Glu Ala Ala Gln Lys Ala Ala Asp Leu Leu
145                 150                 155                 160

Val Ala Ala Gly Ile Lys Gly Ile Leu Asn Phe Ala Pro Val Val Leu
                165                 170                 175

Glu Val Pro Lys Glu Val Ala Val Glu Asn Val Asp Phe Gly Tyr Asn
            180                 185                 190

Ser Asp Asn Val Tyr Ile Met Ala Asp Lys Gln Lys Asn Gly Ile Lys
        195                 200                 205

Ala Asn Phe Lys Ile Arg His Asn Val Glu Asp Gly Ser Val Gln Leu
    210                 215                 220

Ala Asp His Tyr Gln Gln Asn Thr Pro Ile Gly Asp Gly Pro Val Leu
225                 230                 235                 240

Leu Pro Asp Asn His Tyr Leu Ser Phe Gln Ser Val Leu Ser Lys Asp
                245                 250                 255

Pro Asn Glu Lys Arg Asp His Met Val Leu Leu Glu Phe Val Thr Ala
            260                 265                 270

Ala Gly Ile Thr Leu Gly Met Asp Glu Leu Tyr Asn Val Asp Gly Gly
        275                 280                 285

Ser Gly Gly Thr Gly Ser Lys Gly Glu Glu Leu Phe Thr Gly Val Val
    290                 295                 300
```

```
Pro Ile Leu Val Glu Leu Asp Gly Asp Val Asn Gly His Lys Phe Ser
305                 310                 315                 320

Val Ser Gly Glu Gly Glu Gly Asp Ala Thr Tyr Gly Lys Leu Thr Leu
            325                 330                 335

Lys Leu Ile Cys Thr Thr Gly Lys Leu Pro Val Pro Trp Pro Thr Leu
            340                 345                 350

Val Thr Thr Leu Gly Tyr Gly Leu Lys Cys Phe Ala Arg Tyr Pro Asp
            355                 360                 365

His Met Lys Gln His Asp Phe Phe Lys Ser Ala Met Pro Glu Gly Tyr
            370                 375                 380

Val Gln Glu Arg Thr Ile Phe Phe Lys Asp Asp Gly Asn Tyr Lys Thr
385                 390                 395                 400

Arg Ala Glu Val Lys Phe Glu Gly Asp Thr Leu Val Asn Arg Ile Glu
                405                 410                 415

Leu Lys Gly Ile Gly Phe Lys Glu Asp Gly Asn Ile Leu Gly His Lys
            420                 425                 430

Leu Glu Tyr Asn Gly Thr Gly Leu Ala Gly Leu Thr Arg Leu Ser Phe
            435                 440                 445

Ala Ile Leu Asn Pro Lys Trp Arg Glu Met Met Gly
            450                 455                 460

<210> SEQ ID NO 130
<211> LENGTH: 460
<212> TYPE: PRT
<213> ORGANISM: artificial sequence
<220> FEATURE:
<223> OTHER INFORMATION: Synthetic fluorescent sensor, mutant

<400> SEQUENCE: 130

Met Lys Val Pro Glu Ala Ala Ile Ser Arg Leu Ile Thr Tyr Leu Arg
1               5                   10                  15

Ile Leu Glu Glu Leu Glu Ala Gln Gly Val His Arg Thr Ser Ser Glu
            20                  25                  30

Gln Leu Gly Glu Leu Ala Gln Val Thr Ala Phe Gln Val Arg Lys Asp
        35                  40                  45

Leu Ser Tyr Phe Gly Ser Tyr Gly Thr Arg Gly Val Gly Tyr Thr Val
    50                  55                  60

Pro Val Leu Lys Arg Glu Leu Arg His Ile Leu Gly Leu Asn Arg Lys
65                  70                  75                  80

Trp Gly Leu Cys Ile Val Gly Met Gly Arg Leu Gly Ser Ala Leu Ala
            85                  90                  95

Asp Tyr Pro Gly Phe Gly Glu Ser Phe Glu Leu Arg Gly Phe Phe Asp
            100                 105                 110

Val Asp Pro Glu Lys Val Gly Arg Pro Val Arg Gly Val Ile Glu
            115                 120                 125

His Val Asp Leu Leu Pro Gln Arg Val Pro Gly Arg Ile Glu Ile Ala
            130                 135                 140

Leu Leu Thr Val Pro Arg Glu Ala Ala Gln Lys Ala Ala Asp Leu Leu
145                 150                 155                 160

Val Ala Ala Gly Ile Lys Gly Ile Leu Asn Phe Ala Pro Val Val Leu
                165                 170                 175

Glu Val Pro Lys Glu Val Ala Val Glu Asn Val Asp Phe Tyr Asn Ser
            180                 185                 190

Asp Asn Val Tyr Ile Met Ala Asp Lys Gln Lys Asn Gly Ile Lys Ala
            195                 200                 205
```

```
Asn Phe Lys Ile Arg His Asn Val Glu Asp Gly Ser Val Gln Leu Ala
            210                 215                 220

Asp His Tyr Gln Gln Asn Thr Pro Ile Gly Asp Gly Pro Val Leu Leu
225                 230                 235                 240

Pro Asp Asn His Tyr Leu Ser Phe Gln Ser Val Leu Ser Lys Asp Pro
                245                 250                 255

Asn Glu Lys Arg Asp His Met Val Leu Leu Glu Phe Val Thr Ala Ala
            260                 265                 270

Gly Ile Thr Leu Gly Met Asp Glu Leu Tyr Asn Val Asp Gly Gly Ser
            275                 280                 285

Gly Gly Thr Gly Ser Lys Gly Glu Glu Leu Phe Thr Gly Val Val Pro
            290                 295                 300

Ile Leu Val Glu Leu Asp Gly Asp Val Asn Gly His Lys Phe Ser Val
305                 310                 315                 320

Ser Gly Glu Gly Glu Gly Asp Ala Thr Tyr Gly Lys Leu Thr Leu Lys
                325                 330                 335

Leu Ile Cys Thr Thr Gly Lys Leu Pro Val Pro Trp Pro Thr Leu Val
            340                 345                 350

Thr Thr Leu Gly Tyr Gly Leu Lys Cys Phe Ala Arg Tyr Pro Asp His
            355                 360                 365

Met Lys Gln His Asp Phe Phe Lys Ser Ala Met Pro Glu Gly Tyr Val
            370                 375                 380

Gln Glu Arg Thr Ile Phe Phe Lys Asp Asp Gly Asn Tyr Lys Thr Arg
385                 390                 395                 400

Ala Glu Val Lys Phe Glu Gly Asp Thr Leu Val Asn Arg Ile Glu Leu
                405                 410                 415

Lys Gly Ile Gly Phe Lys Glu Asp Gly Asn Ile Leu Gly His Lys Leu
            420                 425                 430

Glu Tyr Asn Gly Thr Gly Leu Ala Gly Leu Thr Arg Leu Ser Phe Ala
            435                 440                 445

Ile Leu Asn Pro Lys Trp Arg Glu Glu Met Met Gly
450                 455                 460
```

<210> SEQ ID NO 131
<211> LENGTH: 462
<212> TYPE: PRT
<213> ORGANISM: artificial sequence
<220> FEATURE:
<223> OTHER INFORMATION: Synthetic fluorescent sensor, mutant

<400> SEQUENCE: 131

```
Met Lys Val Pro Glu Ala Ala Ile Ser Arg Leu Ile Thr Tyr Leu Arg
1               5                   10                  15

Ile Leu Glu Glu Leu Glu Ala Gln Gly Val His Arg Thr Ser Ser Glu
                20                  25                  30

Gln Leu Gly Glu Leu Ala Gln Val Thr Ala Phe Gln Val Arg Lys Asp
            35                  40                  45

Leu Ser Tyr Phe Gly Ser Tyr Gly Thr Arg Gly Val Gly Tyr Thr Val
        50                  55                  60

Pro Val Leu Lys Arg Glu Leu Arg His Ile Leu Gly Leu Asn Arg Lys
65                  70                  75                  80

Trp Gly Leu Cys Ile Val Gly Met Gly Arg Leu Gly Ser Ala Leu Ala
                85                  90                  95

Asp Tyr Pro Gly Phe Gly Glu Ser Phe Glu Leu Arg Gly Phe Phe Asp
                100                 105                 110
```

Val Asp Pro Glu Lys Val Gly Arg Pro Val Arg Gly Gly Val Ile Glu
            115                 120                 125

His Val Asp Leu Leu Pro Gln Arg Val Pro Gly Arg Ile Glu Ile Ala
        130                 135                 140

Leu Leu Thr Val Pro Arg Glu Ala Ala Gln Lys Ala Ala Asp Leu Leu
145                 150                 155                 160

Val Ala Ala Gly Ile Lys Gly Ile Leu Asn Phe Ala Pro Val Val Leu
                165                 170                 175

Glu Val Pro Lys Glu Val Ala Val Glu Asn Val Asp Phe Ser Ala Gly
            180                 185                 190

Tyr Asn Ser Asp Asn Val Tyr Ile Met Ala Asp Lys Gln Lys Asn Gly
        195                 200                 205

Ile Lys Ala Asn Phe Lys Ile Arg His Asn Val Glu Asp Gly Ser Val
210                 215                 220

Gln Leu Ala Asp His Tyr Gln Gln Asn Thr Pro Ile Gly Asp Gly Pro
225                 230                 235                 240

Val Leu Leu Pro Asp Asn His Tyr Leu Ser Phe Gln Ser Val Leu Ser
                245                 250                 255

Lys Asp Pro Asn Glu Lys Arg Asp His Met Val Leu Leu Glu Phe Val
            260                 265                 270

Thr Ala Ala Gly Ile Thr Leu Gly Met Asp Glu Leu Tyr Asn Val Asp
        275                 280                 285

Gly Gly Ser Gly Gly Thr Gly Ser Lys Gly Glu Glu Leu Phe Thr Gly
    290                 295                 300

Val Val Pro Ile Leu Val Glu Leu Asp Gly Asp Val Asn Gly His Lys
305                 310                 315                 320

Phe Ser Val Ser Gly Glu Gly Glu Gly Asp Ala Thr Tyr Gly Lys Leu
                325                 330                 335

Thr Leu Lys Leu Ile Cys Thr Thr Gly Lys Leu Pro Val Pro Trp Pro
            340                 345                 350

Thr Leu Val Thr Thr Leu Gly Tyr Gly Leu Lys Cys Phe Ala Arg Tyr
        355                 360                 365

Pro Asp His Met Lys Gln His Asp Phe Phe Lys Ser Ala Met Pro Glu
    370                 375                 380

Gly Tyr Val Gln Glu Arg Thr Ile Phe Phe Lys Asp Asp Gly Asn Tyr
385                 390                 395                 400

Lys Thr Arg Ala Glu Val Lys Phe Glu Gly Asp Thr Leu Val Asn Arg
                405                 410                 415

Ile Glu Leu Lys Gly Ile Gly Phe Lys Glu Asp Gly Asn Ile Leu Gly
            420                 425                 430

His Lys Leu Glu Tyr Asn Gly Thr Leu Ala Gly Leu Thr Arg Leu Ser
        435                 440                 445

Phe Ala Ile Leu Asn Pro Lys Trp Arg Glu Glu Met Met Gly
450                 455                 460

<210> SEQ ID NO 132
<211> LENGTH: 461
<212> TYPE: PRT
<213> ORGANISM: artificial sequence
<220> FEATURE:
<223> OTHER INFORMATION: Synthetic fluorescent sensor, mutant

<400> SEQUENCE: 132

Met Lys Val Pro Glu Ala Ala Ile Ser Arg Leu Ile Thr Tyr Leu Arg
1               5                   10                  15

```
Ile Leu Glu Glu Leu Glu Ala Gln Gly Val His Arg Thr Ser Ser Glu
                20                  25                  30

Gln Leu Gly Glu Leu Ala Gln Val Thr Ala Phe Gln Val Arg Lys Asp
            35                  40                  45

Leu Ser Tyr Phe Gly Ser Tyr Gly Thr Arg Gly Val Gly Tyr Thr Val
 50                  55                  60

Pro Val Leu Lys Arg Glu Leu Arg His Ile Leu Gly Leu Asn Arg Lys
 65                  70                  75                  80

Trp Gly Leu Cys Ile Val Gly Met Gly Arg Leu Gly Ser Ala Leu Ala
                85                  90                  95

Asp Tyr Pro Gly Phe Gly Glu Ser Phe Glu Leu Arg Gly Phe Phe Asp
            100                 105                 110

Val Asp Pro Glu Lys Val Gly Arg Pro Val Arg Gly Val Ile Glu
        115                 120                 125

His Val Asp Leu Leu Pro Gln Arg Val Pro Gly Arg Ile Glu Ile Ala
130                 135                 140

Leu Leu Thr Val Pro Arg Glu Ala Ala Gln Lys Ala Ala Asp Leu Leu
145                 150                 155                 160

Val Ala Ala Gly Ile Lys Gly Ile Leu Asn Phe Ala Pro Val Val Leu
                165                 170                 175

Glu Val Pro Lys Glu Val Ala Val Glu Asn Val Asp Phe Ser Ala Gly
            180                 185                 190

Tyr Asn Ser Asp Asn Val Tyr Ile Met Ala Asp Lys Gln Lys Asn Gly
        195                 200                 205

Ile Lys Ala Asn Phe Lys Ile Arg His Asn Val Glu Asp Gly Ser Val
        210                 215                 220

Gln Leu Ala Asp His Tyr Gln Gln Asn Thr Pro Ile Gly Asp Gly Pro
225                 230                 235                 240

Val Leu Leu Pro Asp Asn His Tyr Leu Ser Phe Gln Ser Val Leu Ser
                245                 250                 255

Lys Asp Pro Asn Glu Lys Arg Asp His Met Val Leu Leu Glu Phe Val
            260                 265                 270

Thr Ala Ala Gly Ile Thr Leu Gly Met Asp Glu Leu Tyr Asn Val Asp
        275                 280                 285

Gly Gly Ser Gly Gly Thr Gly Ser Lys Gly Glu Glu Leu Phe Thr Gly
        290                 295                 300

Val Val Pro Ile Leu Val Glu Leu Asp Gly Asp Val Asn Gly His Lys
305                 310                 315                 320

Phe Ser Val Ser Gly Glu Gly Glu Gly Asp Ala Thr Tyr Gly Lys Leu
                325                 330                 335

Thr Leu Lys Leu Ile Cys Thr Thr Gly Lys Leu Pro Val Pro Trp Pro
            340                 345                 350

Thr Leu Val Thr Thr Leu Gly Tyr Gly Leu Lys Cys Phe Ala Arg Tyr
        355                 360                 365

Pro Asp His Met Lys Gln His Asp Phe Phe Lys Ser Ala Met Pro Glu
        370                 375                 380

Gly Tyr Val Gln Glu Arg Thr Ile Phe Phe Lys Asp Asp Gly Asn Tyr
385                 390                 395                 400

Lys Thr Arg Ala Glu Val Lys Phe Glu Gly Asp Thr Leu Val Asn Arg
                405                 410                 415

Ile Glu Leu Lys Gly Ile Gly Phe Lys Glu Asp Gly Asn Ile Leu Gly
            420                 425                 430
```

His Lys Leu Glu Tyr Asn Gly Leu Ala Gly Leu Thr Arg Leu Ser Phe
            435                 440                 445

Ala Ile Leu Asn Pro Lys Trp Arg Glu Glu Met Met Gly
            450                 455                 460

<210> SEQ ID NO 133
<211> LENGTH: 460
<212> TYPE: PRT
<213> ORGANISM: artificial sequence
<220> FEATURE:
<223> OTHER INFORMATION: Synthetic fluorescent sensor, mutant

<400> SEQUENCE: 133

Met Lys Val Pro Glu Ala Ala Ile Ser Arg Leu Ile Thr Tyr Leu Arg
1               5                   10                  15

Ile Leu Glu Glu Leu Glu Ala Gln Gly Val His Arg Thr Ser Ser Glu
                20                  25                  30

Gln Leu Gly Glu Leu Ala Gln Val Thr Ala Phe Gln Val Arg Lys Asp
            35                  40                  45

Leu Ser Tyr Phe Gly Ser Tyr Gly Thr Arg Gly Val Gly Tyr Thr Val
    50                  55                  60

Pro Val Leu Lys Arg Glu Leu Arg His Ile Leu Gly Leu Asn Arg Lys
65                  70                  75                  80

Trp Gly Leu Cys Ile Val Gly Met Gly Arg Leu Gly Ser Ala Leu Ala
                85                  90                  95

Asp Tyr Pro Gly Phe Gly Glu Ser Phe Glu Leu Arg Gly Phe Phe Asp
                100                 105                 110

Val Asp Pro Glu Lys Val Gly Arg Pro Val Arg Gly Val Ile Glu
            115                 120                 125

His Val Asp Leu Leu Pro Gln Arg Val Pro Gly Arg Ile Glu Ile Ala
        130                 135                 140

Leu Leu Thr Val Pro Arg Glu Ala Ala Gln Lys Ala Ala Asp Leu Leu
145                 150                 155                 160

Val Ala Ala Gly Ile Lys Gly Ile Leu Asn Phe Ala Pro Val Val Leu
                165                 170                 175

Glu Val Pro Lys Glu Val Ala Val Glu Asn Val Asp Phe Ser Ala Gly
            180                 185                 190

Tyr Asn Ser Asp Asn Val Tyr Ile Met Ala Asp Lys Gln Lys Asn Gly
        195                 200                 205

Ile Lys Ala Asn Phe Lys Ile Arg His Asn Val Glu Asp Gly Ser Val
210                 215                 220

Gln Leu Ala Asp His Tyr Gln Gln Asn Thr Pro Ile Gly Asp Gly Pro
225                 230                 235                 240

Val Leu Leu Pro Asp Asn His Tyr Leu Ser Phe Gln Ser Val Leu Ser
                245                 250                 255

Lys Asp Pro Asn Glu Lys Arg Asp His Met Val Leu Leu Glu Phe Val
            260                 265                 270

Thr Ala Ala Gly Ile Thr Leu Gly Met Asp Glu Leu Tyr Asn Val Asp
        275                 280                 285

Gly Gly Ser Gly Gly Thr Gly Ser Lys Gly Glu Glu Leu Phe Thr Gly
    290                 295                 300

Val Val Pro Ile Leu Val Glu Leu Asp Gly Asp Val Asn Gly His Lys
305                 310                 315                 320

Phe Ser Val Ser Gly Glu Gly Glu Gly Asp Ala Thr Tyr Gly Lys Leu
                325                 330                 335

```
Thr Leu Lys Leu Ile Cys Thr Thr Gly Lys Leu Pro Val Pro Trp Pro
            340                 345                 350

Thr Leu Val Thr Thr Leu Gly Tyr Gly Leu Lys Cys Phe Ala Arg Tyr
            355                 360                 365

Pro Asp His Met Lys Gln His Asp Phe Phe Lys Ser Ala Met Pro Glu
370                 375                 380

Gly Tyr Val Gln Glu Arg Thr Ile Phe Phe Lys Asp Asp Gly Asn Tyr
385                 390                 395                 400

Lys Thr Arg Ala Glu Val Lys Phe Glu Gly Asp Thr Leu Val Asn Arg
                405                 410                 415

Ile Glu Leu Lys Gly Ile Gly Phe Lys Glu Asp Gly Asn Ile Leu Gly
            420                 425                 430

His Lys Leu Glu Tyr Asn Leu Ala Gly Leu Thr Arg Leu Ser Phe Ala
            435                 440                 445

Ile Leu Asn Pro Lys Trp Arg Glu Glu Met Met Gly
            450                 455                 460

<210> SEQ ID NO 134
<211> LENGTH: 461
<212> TYPE: PRT
<213> ORGANISM: artificial sequence
<220> FEATURE:
<223> OTHER INFORMATION: Synthetic fluorescent sensor, mutant

<400> SEQUENCE: 134

Met Lys Val Pro Glu Ala Ala Ile Ser Arg Leu Ile Thr Tyr Leu Arg
1               5                   10                  15

Ile Leu Glu Glu Leu Glu Ala Gln Gly Val His Arg Thr Ser Ser Glu
            20                  25                  30

Gln Leu Gly Glu Leu Ala Gln Val Thr Ala Phe Gln Val Arg Lys Asp
        35                  40                  45

Leu Ser Tyr Phe Gly Ser Tyr Gly Thr Arg Gly Val Gly Tyr Thr Val
    50                  55                  60

Pro Val Leu Lys Arg Glu Leu Arg His Ile Leu Gly Leu Asn Arg Lys
65                  70                  75                  80

Trp Gly Leu Cys Ile Val Gly Met Gly Arg Leu Gly Ser Ala Leu Ala
                85                  90                  95

Asp Tyr Pro Gly Phe Gly Glu Ser Phe Glu Leu Arg Gly Phe Phe Asp
            100                 105                 110

Val Asp Pro Glu Lys Val Gly Arg Pro Val Arg Gly Val Ile Glu
        115                 120                 125

His Val Asp Leu Leu Pro Gln Arg Val Pro Gly Arg Ile Glu Ile Ala
    130                 135                 140

Leu Leu Thr Val Pro Arg Glu Ala Ala Gln Lys Ala Ala Asp Leu Leu
145                 150                 155                 160

Val Ala Ala Gly Ile Lys Gly Ile Leu Asn Phe Ala Pro Val Val Leu
                165                 170                 175

Glu Val Pro Lys Glu Val Ala Val Glu Asn Val Asp Phe Ala Gly Tyr
            180                 185                 190

Asn Ser Asp Asn Val Tyr Ile Met Ala Asp Lys Gln Lys Asn Gly Ile
        195                 200                 205

Lys Ala Asn Phe Lys Ile Arg His Asn Val Glu Asp Gly Ser Val Gln
    210                 215                 220

Leu Ala Asp His Tyr Gln Gln Asn Thr Pro Ile Gly Asp Gly Pro Val
225                 230                 235                 240
```

```
Leu Leu Pro Asp Asn His Tyr Leu Ser Phe Gln Ser Val Leu Ser Lys
            245                 250                 255

Asp Pro Asn Glu Lys Arg Asp His Met Val Leu Leu Glu Phe Val Thr
        260                 265                 270

Ala Ala Gly Ile Thr Leu Gly Met Asp Glu Leu Tyr Asn Val Asp Gly
    275                 280                 285

Gly Ser Gly Gly Thr Gly Ser Lys Gly Glu Glu Leu Phe Thr Gly Val
290                 295                 300

Val Pro Ile Leu Val Glu Leu Asp Gly Asp Val Asn Gly His Lys Phe
305                 310                 315                 320

Ser Val Ser Gly Glu Gly Glu Gly Asp Ala Thr Tyr Gly Lys Leu Thr
                325                 330                 335

Leu Lys Leu Ile Cys Thr Thr Gly Lys Leu Pro Val Pro Trp Pro Thr
            340                 345                 350

Leu Val Thr Thr Leu Gly Tyr Gly Leu Lys Cys Phe Ala Arg Tyr Pro
        355                 360                 365

Asp His Met Lys Gln His Asp Phe Phe Lys Ser Ala Met Pro Glu Gly
    370                 375                 380

Tyr Val Gln Glu Arg Thr Ile Phe Phe Lys Asp Asp Gly Asn Tyr Lys
385                 390                 395                 400

Thr Arg Ala Glu Val Lys Phe Glu Gly Asp Thr Leu Val Asn Arg Ile
                405                 410                 415

Glu Leu Lys Gly Ile Gly Phe Lys Glu Asp Gly Asn Ile Leu Gly His
            420                 425                 430

Lys Leu Glu Tyr Asn Gly Thr Leu Ala Gly Leu Thr Arg Leu Ser Phe
        435                 440                 445

Ala Ile Leu Asn Pro Lys Trp Arg Glu Glu Met Met Gly
    450                 455                 460

<210> SEQ ID NO 135
<211> LENGTH: 460
<212> TYPE: PRT
<213> ORGANISM: artificial sequence
<220> FEATURE:
<223> OTHER INFORMATION: Synthetic fluorescent sensor, mutant

<400> SEQUENCE: 135

Met Lys Val Pro Glu Ala Ala Ile Ser Arg Leu Ile Thr Tyr Leu Arg
1               5                   10                  15

Ile Leu Glu Glu Leu Glu Ala Gln Gly Val His Arg Thr Ser Ser Glu
            20                  25                  30

Gln Leu Gly Glu Leu Ala Gln Val Thr Ala Phe Gln Val Arg Lys Asp
        35                  40                  45

Leu Ser Tyr Phe Gly Ser Tyr Gly Thr Arg Gly Val Gly Tyr Thr Val
    50                  55                  60

Pro Val Leu Lys Arg Glu Leu Arg His Ile Leu Gly Leu Asn Arg Lys
65                  70                  75                  80

Trp Gly Leu Cys Ile Val Gly Met Gly Arg Leu Gly Ser Ala Leu Ala
                85                  90                  95

Asp Tyr Pro Gly Phe Gly Glu Ser Phe Glu Leu Arg Gly Phe Phe Asp
            100                 105                 110

Val Asp Pro Glu Lys Val Gly Arg Pro Val Arg Gly Val Ile Glu
        115                 120                 125

His Val Asp Leu Leu Pro Gln Arg Val Pro Gly Arg Ile Glu Ile Ala
    130                 135                 140
```

```
Leu Leu Thr Val Pro Arg Glu Ala Ala Gln Lys Ala Ala Asp Leu Leu
145                 150                 155                 160

Val Ala Ala Gly Ile Lys Gly Ile Leu Asn Phe Ala Pro Val Val Leu
                165                 170                 175

Glu Val Pro Lys Glu Val Ala Val Glu Asn Val Asp Phe Gly Tyr Asn
            180                 185                 190

Ser Asp Asn Val Tyr Ile Met Ala Asp Lys Gln Lys Asn Gly Ile Lys
        195                 200                 205

Ala Asn Phe Lys Ile Arg His Asn Val Glu Asp Gly Ser Val Gln Leu
    210                 215                 220

Ala Asp His Tyr Gln Gln Asn Thr Pro Ile Gly Asp Gly Pro Val Leu
225                 230                 235                 240

Leu Pro Asp Asn His Tyr Leu Ser Phe Gln Ser Val Leu Ser Lys Asp
                245                 250                 255

Pro Asn Glu Lys Arg Asp His Met Val Leu Leu Glu Phe Val Thr Ala
            260                 265                 270

Ala Gly Ile Thr Leu Gly Met Asp Glu Leu Tyr Asn Val Asp Gly Gly
        275                 280                 285

Ser Gly Gly Thr Gly Ser Lys Gly Glu Glu Leu Phe Thr Gly Val Val
    290                 295                 300

Pro Ile Leu Val Glu Leu Asp Gly Asp Val Asn Gly His Lys Phe Ser
305                 310                 315                 320

Val Ser Gly Glu Gly Glu Gly Asp Ala Thr Tyr Gly Lys Leu Thr Leu
                325                 330                 335

Lys Leu Ile Cys Thr Thr Gly Lys Leu Pro Val Pro Trp Pro Thr Leu
            340                 345                 350

Val Thr Thr Leu Gly Tyr Gly Leu Lys Cys Phe Ala Arg Tyr Pro Asp
        355                 360                 365

His Met Lys Gln His Asp Phe Phe Lys Ser Ala Met Pro Glu Gly Tyr
    370                 375                 380

Val Gln Glu Arg Thr Ile Phe Phe Lys Asp Asp Gly Asn Tyr Lys Thr
385                 390                 395                 400

Arg Ala Glu Val Lys Phe Glu Gly Asp Thr Leu Val Asn Arg Ile Glu
                405                 410                 415

Leu Lys Gly Ile Gly Phe Lys Glu Asp Gly Asn Ile Leu Gly His Lys
            420                 425                 430

Leu Glu Tyr Asn Gly Thr Leu Ala Gly Leu Thr Arg Leu Ser Phe Ala
        435                 440                 445

Ile Leu Asn Pro Lys Trp Arg Glu Met Met Gly
    450                 455                 460

<210> SEQ ID NO 136
<211> LENGTH: 459
<212> TYPE: PRT
<213> ORGANISM: artificial sequence
<220> FEATURE:
<223> OTHER INFORMATION: Synthetic fluorescent sensor, mutant

<400> SEQUENCE: 136

Met Lys Val Pro Glu Ala Ala Ile Ser Arg Leu Ile Thr Tyr Leu Arg
1               5                   10                  15

Ile Leu Glu Glu Leu Glu Ala Gln Gly Val His Arg Thr Ser Ser Glu
                20                  25                  30

Gln Leu Gly Glu Leu Ala Gln Val Thr Ala Phe Gln Val Arg Lys Asp
        35                  40                  45
```

```
Leu Ser Tyr Phe Gly Ser Tyr Gly Thr Arg Gly Val Gly Tyr Thr Val
 50                  55                  60

Pro Val Leu Lys Arg Glu Leu Arg His Ile Leu Gly Leu Asn Arg Lys
 65                  70                  75                  80

Trp Gly Leu Cys Ile Val Gly Met Gly Arg Leu Gly Ser Ala Leu Ala
                 85                  90                  95

Asp Tyr Pro Gly Phe Gly Glu Ser Phe Glu Leu Arg Gly Phe Phe Asp
            100                 105                 110

Val Asp Pro Glu Lys Val Gly Arg Pro Val Arg Gly Val Ile Glu
            115                 120                 125

His Val Asp Leu Leu Pro Gln Arg Val Pro Gly Arg Ile Glu Ile Ala
130                 135                 140

Leu Leu Thr Val Pro Arg Glu Ala Ala Gln Lys Ala Ala Asp Leu Leu
145                 150                 155                 160

Val Ala Ala Gly Ile Lys Gly Ile Leu Asn Phe Ala Pro Val Val Leu
                165                 170                 175

Glu Val Pro Lys Glu Val Ala Val Glu Asn Val Asp Phe Tyr Asn Ser
            180                 185                 190

Asp Asn Val Tyr Ile Met Ala Asp Lys Gln Lys Asn Gly Ile Lys Ala
            195                 200                 205

Asn Phe Lys Ile Arg His Asn Val Glu Asp Gly Ser Val Gln Leu Ala
210                 215                 220

Asp His Tyr Gln Gln Asn Thr Pro Ile Gly Asp Gly Pro Val Leu Leu
225                 230                 235                 240

Pro Asp Asn His Tyr Leu Ser Phe Gln Ser Val Leu Ser Lys Asp Pro
            245                 250                 255

Asn Glu Lys Arg Asp His Met Val Leu Leu Glu Phe Val Thr Ala Ala
            260                 265                 270

Gly Ile Thr Leu Gly Met Asp Glu Leu Tyr Asn Val Asp Gly Gly Ser
                275                 280                 285

Gly Gly Thr Gly Ser Lys Gly Glu Glu Leu Phe Thr Gly Val Val Pro
290                 295                 300

Ile Leu Val Glu Leu Asp Gly Asp Val Asn Gly His Lys Phe Ser Val
305                 310                 315                 320

Ser Gly Glu Gly Glu Gly Asp Ala Thr Tyr Gly Lys Leu Thr Leu Lys
                325                 330                 335

Leu Ile Cys Thr Thr Gly Lys Leu Pro Val Pro Trp Pro Thr Leu Val
            340                 345                 350

Thr Thr Leu Gly Tyr Gly Leu Lys Cys Phe Ala Arg Tyr Pro Asp His
            355                 360                 365

Met Lys Gln His Asp Phe Phe Lys Ser Ala Met Pro Glu Gly Tyr Val
370                 375                 380

Gln Glu Arg Thr Ile Phe Phe Lys Asp Asp Gly Asn Tyr Lys Thr Arg
385                 390                 395                 400

Ala Glu Val Lys Phe Glu Gly Asp Thr Leu Val Asn Arg Ile Glu Leu
                405                 410                 415

Lys Gly Ile Gly Phe Lys Glu Asp Gly Asn Ile Leu Gly His Lys Leu
            420                 425                 430

Glu Tyr Asn Gly Thr Leu Ala Gly Leu Thr Arg Leu Ser Phe Ala Ile
            435                 440                 445

Leu Asn Pro Lys Trp Arg Glu Glu Met Met Gly
450                 455
```

```
<210> SEQ ID NO 137
<211> LENGTH: 460
<212> TYPE: PRT
<213> ORGANISM: artificial sequence
<220> FEATURE:
<223> OTHER INFORMATION: Synthetic fluorescent sensor, mutant

<400> SEQUENCE: 137
```

| | | | | | | | | | | | | | | | |
|---|---|---|---|---|---|---|---|---|---|---|---|---|---|---|---|
|Met|Lys|Val|Pro|Glu|Ala|Ala|Ile|Ser|Arg|Leu|Ile|Thr|Tyr|Leu|Arg|
|1| | | |5| | | | |10| | | | |15| |
|Ile|Leu|Glu|Glu|Leu|Glu|Ala|Gln|Gly|Val|His|Arg|Thr|Ser|Ser|Glu|
| | | |20| | | | |25| | | | |30| | |
|Gln|Leu|Gly|Glu|Leu|Ala|Gln|Val|Thr|Ala|Phe|Gln|Val|Arg|Lys|Asp|
| | |35| | | | |40| | | | |45| | | |
|Leu|Ser|Tyr|Phe|Gly|Ser|Tyr|Gly|Thr|Arg|Gly|Val|Gly|Tyr|Thr|Val|
| |50| | | | |55| | | | |60| | | | |
|Pro|Val|Leu|Lys|Arg|Glu|Leu|Arg|His|Ile|Leu|Gly|Leu|Asn|Arg|Lys|
|65| | | | |70| | | | |75| | | | |80| |
|Trp|Gly|Leu|Cys|Ile|Val|Gly|Met|Gly|Arg|Leu|Gly|Ser|Ala|Leu|Ala|
| | | | |85| | | | |90| | | | |95| | |
|Asp|Tyr|Pro|Gly|Phe|Gly|Glu|Ser|Phe|Glu|Leu|Arg|Gly|Phe|Phe|Asp|
| | | |100| | | | |105| | | | |110| | | |
|Val|Asp|Pro|Glu|Lys|Val|Gly|Arg|Pro|Val|Arg|Gly|Val|Ile|Glu|
| | |115| | | | |120| | | | |125| | | |
|His|Val|Asp|Leu|Leu|Pro|Gln|Arg|Val|Pro|Gly|Arg|Ile|Glu|Ile|Ala|
| |130| | | | |135| | | | |140| | | | |
|Leu|Leu|Thr|Val|Pro|Arg|Glu|Ala|Ala|Gln|Lys|Ala|Ala|Asp|Leu|Leu|
|145| | | | |150| | | | |155| | | | |160| |
|Val|Ala|Ala|Gly|Ile|Lys|Gly|Ile|Leu|Asn|Phe|Ala|Pro|Val|Val|Leu|
| | | | |165| | | | |170| | | | |175| | |
|Glu|Val|Pro|Lys|Glu|Val|Ala|Val|Glu|Asn|Val|Asp|Phe|Ala|Gly|Tyr|
| | | |180| | | | |185| | | | |190| | | |
|Asn|Ser|Asp|Asn|Val|Tyr|Ile|Met|Ala|Asp|Lys|Gln|Lys|Asn|Gly|Ile|
| | |195| | | | |200| | | | |205| | | | |
|Lys|Ala|Asn|Phe|Lys|Ile|Arg|His|Asn|Val|Glu|Asp|Gly|Ser|Val|Gln|
| |210| | | | |215| | | | |220| | | | |
|Leu|Ala|Asp|His|Tyr|Gln|Gln|Asn|Thr|Pro|Ile|Gly|Asp|Gly|Pro|Val|
|225| | | | |230| | | | |235| | | | |240| |
|Leu|Leu|Pro|Asp|Asn|His|Tyr|Leu|Ser|Phe|Gln|Ser|Val|Leu|Ser|Lys|
| | | |245| | | | |250| | | | |255| | | |
|Asp|Pro|Asn|Glu|Lys|Arg|Asp|His|Met|Val|Leu|Leu|Glu|Phe|Val|Thr|
| | |260| | | | |265| | | | |270| | | | |
|Ala|Ala|Gly|Ile|Thr|Leu|Gly|Met|Asp|Glu|Leu|Tyr|Asn|Val|Asp|Gly|
| |275| | | | |280| | | | |285| | | | |
|Gly|Ser|Gly|Gly|Thr|Gly|Ser|Lys|Gly|Glu|Glu|Leu|Phe|Thr|Gly|Val|
| |290| | | | |295| | | | |300| | | | |
|Val|Pro|Ile|Leu|Val|Glu|Leu|Asp|Gly|Asp|Val|Asn|Gly|His|Lys|Phe|
|305| | | | |310| | | | |315| | | | |320| |
|Ser|Val|Ser|Gly|Glu|Gly|Glu|Gly|Asp|Ala|Thr|Tyr|Gly|Lys|Leu|Thr|
| | | | |325| | | | |330| | | | |335| | |
|Leu|Lys|Leu|Ile|Cys|Thr|Thr|Gly|Lys|Leu|Pro|Val|Pro|Trp|Pro|Thr|
| | | |340| | | | |345| | | | |350| | | |
|Leu|Val|Thr|Thr|Leu|Gly|Tyr|Gly|Leu|Lys|Cys|Phe|Ala|Arg|Tyr|Pro|
| | |355| | | | |360| | | | |365| | | | |
|Asp|His|Met|Lys|Gln|His|Asp|Phe|Phe|Lys|Ser|Ala|Met|Pro|Glu|Gly|

```
                   370                 375                 380
Tyr Val Gln Glu Arg Thr Ile Phe Phe Lys Asp Asp Gly Asn Tyr Lys
385                 390                 395                 400

Thr Arg Ala Glu Val Lys Phe Glu Gly Asp Thr Leu Val Asn Arg Ile
                405                 410                 415

Glu Leu Lys Gly Ile Gly Phe Lys Glu Asp Gly Asn Ile Leu Gly His
            420                 425                 430

Lys Leu Glu Tyr Asn Gly Leu Ala Gly Leu Thr Arg Leu Ser Phe Ala
            435                 440                 445

Ile Leu Asn Pro Lys Trp Arg Glu Met Met Gly
    450                 455                 460

<210> SEQ ID NO 138
<211> LENGTH: 459
<212> TYPE: PRT
<213> ORGANISM: artificial sequence
<220> FEATURE:
<223> OTHER INFORMATION: Synthetic fluorescent sensor, mutant

<400> SEQUENCE: 138

Met Lys Val Pro Glu Ala Ala Ile Ser Arg Leu Ile Thr Tyr Leu Arg
1               5                   10                  15

Ile Leu Glu Glu Leu Glu Ala Gln Gly Val His Arg Thr Ser Ser Glu
                20                  25                  30

Gln Leu Gly Glu Leu Ala Gln Val Thr Ala Phe Gln Val Arg Lys Asp
            35                  40                  45

Leu Ser Tyr Phe Gly Ser Tyr Gly Thr Arg Gly Val Gly Tyr Thr Val
    50                  55                  60

Pro Val Leu Lys Arg Glu Leu Arg His Ile Leu Gly Leu Asn Arg Lys
65              70                  75                  80

Trp Gly Leu Cys Ile Val Gly Met Gly Arg Leu Gly Ser Ala Leu Ala
                85                  90                  95

Asp Tyr Pro Gly Phe Gly Glu Ser Phe Glu Leu Arg Gly Phe Phe Asp
            100                 105                 110

Val Asp Pro Glu Lys Val Gly Arg Pro Val Arg Gly Gly Val Ile Glu
        115                 120                 125

His Val Asp Leu Leu Pro Gln Arg Val Pro Gly Arg Ile Glu Ile Ala
    130                 135                 140

Leu Leu Thr Val Pro Arg Glu Ala Ala Gln Lys Ala Ala Asp Leu Leu
145                 150                 155                 160

Val Ala Ala Gly Ile Lys Gly Ile Leu Asn Phe Ala Pro Val Val Leu
                165                 170                 175

Glu Val Pro Lys Glu Val Ala Val Glu Asn Val Asp Phe Gly Tyr Asn
            180                 185                 190

Ser Asp Asn Val Tyr Ile Met Ala Asp Lys Gln Lys Asn Gly Ile Lys
        195                 200                 205

Ala Asn Phe Lys Ile Arg His Asn Val Glu Asp Gly Ser Val Gln Leu
    210                 215                 220

Ala Asp His Tyr Gln Gln Asn Thr Pro Ile Gly Asp Gly Pro Val Leu
225                 230                 235                 240

Leu Pro Asp Asn His Tyr Leu Ser Phe Gln Ser Val Leu Ser Lys Asp
                245                 250                 255

Pro Asn Glu Lys Arg Asp His Met Val Leu Leu Glu Phe Val Thr Ala
            260                 265                 270

Ala Gly Ile Thr Leu Gly Met Asp Glu Leu Tyr Asn Val Asp Gly Gly
```

```
            275                 280                 285
Ser Gly Gly Thr Gly Ser Lys Gly Glu Glu Leu Phe Thr Gly Val Val
            290                 295                 300
Pro Ile Leu Val Glu Leu Asp Gly Asp Val Asn Gly His Lys Phe Ser
305                 310                 315                 320
Val Ser Gly Glu Gly Glu Gly Asp Ala Thr Tyr Gly Lys Leu Thr Leu
            325                 330                 335
Lys Leu Ile Cys Thr Thr Gly Lys Leu Pro Val Pro Trp Pro Thr Leu
            340                 345                 350
Val Thr Thr Leu Gly Tyr Gly Leu Lys Cys Phe Ala Arg Tyr Pro Asp
            355                 360                 365
His Met Lys Gln His Asp Phe Phe Lys Ser Ala Met Pro Glu Gly Tyr
            370                 375                 380
Val Gln Glu Arg Thr Ile Phe Phe Lys Asp Asp Gly Asn Tyr Lys Thr
385                 390                 395                 400
Arg Ala Glu Val Lys Phe Glu Gly Asp Thr Leu Val Asn Arg Ile Glu
            405                 410                 415
Leu Lys Gly Ile Gly Phe Lys Glu Asp Gly Asn Ile Leu Gly His Lys
            420                 425                 430
Leu Glu Tyr Asn Gly Leu Ala Gly Leu Thr Arg Leu Ser Phe Ala Ile
            435                 440                 445
Leu Asn Pro Lys Trp Arg Glu Glu Met Met Gly
            450                 455

<210> SEQ ID NO 139
<211> LENGTH: 458
<212> TYPE: PRT
<213> ORGANISM: artificial sequence
<220> FEATURE:
<223> OTHER INFORMATION: Synthetic fluorescent sensor, mutant

<400> SEQUENCE: 139

Met Lys Val Pro Glu Ala Ala Ile Ser Arg Leu Ile Thr Tyr Leu Arg
1               5                   10                  15
Ile Leu Glu Glu Leu Glu Ala Gln Gly Val His Arg Thr Ser Ser Glu
            20                  25                  30
Gln Leu Gly Glu Leu Ala Gln Val Thr Ala Phe Gln Val Arg Lys Asp
        35                  40                  45
Leu Ser Tyr Phe Gly Ser Tyr Gly Thr Arg Gly Val Gly Tyr Thr Val
    50                  55                  60
Pro Val Leu Lys Arg Glu Leu Arg His Ile Leu Gly Leu Asn Arg Lys
65                  70                  75                  80
Trp Gly Leu Cys Ile Val Gly Met Gly Arg Leu Gly Ser Ala Leu Ala
            85                  90                  95
Asp Tyr Pro Gly Phe Gly Glu Ser Phe Glu Leu Arg Gly Phe Phe Asp
            100                 105                 110
Val Asp Pro Glu Lys Val Gly Arg Pro Val Arg Gly Gly Val Ile Glu
            115                 120                 125
His Val Asp Leu Leu Pro Gln Arg Val Pro Gly Arg Ile Glu Ile Ala
            130                 135                 140
Leu Leu Thr Val Pro Arg Glu Ala Ala Gln Lys Ala Ala Asp Leu Leu
145                 150                 155                 160
Val Ala Ala Gly Ile Lys Gly Ile Leu Asn Phe Ala Pro Val Val Leu
            165                 170                 175
Glu Val Pro Lys Glu Val Ala Val Glu Asn Val Asp Phe Tyr Asn Ser
```

```
                180             185              190
Asp Asn Val Tyr Ile Met Ala Asp Lys Gln Lys Asn Gly Ile Lys Ala
            195                 200             205
Asn Phe Lys Ile Arg His Asn Val Glu Asp Gly Ser Val Gln Leu Ala
            210                 215                 220
Asp His Tyr Gln Gln Asn Thr Pro Ile Gly Asp Gly Pro Val Leu Leu
225                 230                 235                 240
Pro Asp Asn His Tyr Leu Ser Phe Gln Ser Val Leu Ser Lys Asp Pro
                245                 250                 255
Asn Glu Lys Arg Asp His Met Val Leu Leu Glu Phe Val Thr Ala Ala
            260                 265                 270
Gly Ile Thr Leu Gly Met Asp Glu Leu Tyr Asn Val Asp Gly Gly Ser
            275                 280                 285
Gly Gly Thr Gly Ser Lys Gly Glu Glu Leu Phe Thr Gly Val Val Pro
            290                 295                 300
Ile Leu Val Glu Leu Asp Gly Asp Val Asn Gly His Lys Phe Ser Val
305                 310                 315                 320
Ser Gly Glu Gly Glu Gly Asp Ala Thr Tyr Gly Lys Leu Thr Leu Lys
                325                 330                 335
Leu Ile Cys Thr Thr Gly Lys Leu Pro Val Pro Trp Pro Thr Leu Val
            340                 345                 350
Thr Thr Leu Gly Tyr Gly Leu Lys Cys Phe Ala Arg Tyr Pro Asp His
            355                 360                 365
Met Lys Gln His Asp Phe Phe Lys Ser Ala Met Pro Glu Gly Tyr Val
            370                 375                 380
Gln Glu Arg Thr Ile Phe Phe Lys Asp Asp Gly Asn Tyr Lys Thr Arg
385                 390                 395                 400
Ala Glu Val Lys Phe Glu Gly Asp Thr Leu Val Asn Arg Ile Glu Leu
                405                 410                 415
Lys Gly Ile Gly Phe Lys Glu Asp Gly Asn Ile Leu Gly His Lys Leu
                420                 425                 430
Glu Tyr Asn Gly Leu Ala Gly Leu Thr Arg Leu Ser Phe Ala Ile Leu
            435                 440                 445
Asn Pro Lys Trp Arg Glu Glu Met Met Gly
            450                 455

<210> SEQ ID NO 140
<211> LENGTH: 459
<212> TYPE: PRT
<213> ORGANISM: artificial sequence
<220> FEATURE:
<223> OTHER INFORMATION: Synthetic fluorescent sensor, mutant

<400> SEQUENCE: 140

Met Lys Val Pro Glu Ala Ala Ile Ser Arg Leu Ile Thr Tyr Leu Arg
1               5                   10                  15
Ile Leu Glu Glu Leu Glu Ala Gln Gly Val His Arg Thr Ser Ser Glu
                20                  25                  30
Gln Leu Gly Glu Leu Ala Gln Val Thr Ala Phe Gln Val Arg Lys Asp
            35                  40                  45
Leu Ser Tyr Phe Gly Ser Tyr Gly Thr Arg Gly Val Gly Tyr Thr Val
        50                  55                  60
Pro Val Leu Lys Arg Glu Leu Arg His Ile Leu Gly Leu Asn Arg Lys
65                  70                  75                  80
Trp Gly Leu Cys Ile Val Gly Met Gly Arg Leu Gly Ser Ala Leu Ala
```

```
                        85                  90                  95
Asp Tyr Pro Gly Phe Gly Glu Ser Phe Glu Leu Arg Gly Phe Phe Asp
                    100                 105                 110

Val Asp Pro Glu Lys Val Gly Arg Pro Val Arg Gly Val Ile Glu
                115                 120                 125

His Val Asp Leu Leu Pro Gln Arg Val Pro Gly Arg Ile Glu Ile Ala
130                 135                 140

Leu Leu Thr Val Pro Arg Glu Ala Ala Gln Lys Ala Ala Asp Leu Leu
145                 150                 155                 160

Val Ala Ala Gly Ile Lys Gly Ile Leu Asn Phe Ala Pro Val Val Leu
                165                 170                 175

Glu Val Pro Lys Glu Val Ala Val Glu Asn Val Asp Phe Ala Gly Tyr
                180                 185                 190

Asn Ser Asp Asn Val Tyr Ile Met Ala Asp Lys Gln Lys Asn Gly Ile
                195                 200                 205

Lys Ala Asn Phe Lys Ile Arg His Asn Val Glu Asp Gly Ser Val Gln
                210                 215                 220

Leu Ala Asp His Tyr Gln Gln Asn Thr Pro Ile Gly Asp Gly Pro Val
225                 230                 235                 240

Leu Leu Pro Asp Asn His Tyr Leu Ser Phe Gln Ser Val Leu Ser Lys
                245                 250                 255

Asp Pro Asn Glu Lys Arg Asp His Met Val Leu Leu Glu Phe Val Thr
                260                 265                 270

Ala Ala Gly Ile Thr Leu Gly Met Asp Glu Leu Tyr Asn Val Asp Gly
                275                 280                 285

Gly Ser Gly Gly Thr Gly Ser Lys Gly Glu Glu Leu Phe Thr Gly Val
                290                 295                 300

Val Pro Ile Leu Val Glu Leu Asp Gly Asp Val Asn Gly His Lys Phe
305                 310                 315                 320

Ser Val Ser Gly Glu Gly Glu Gly Asp Ala Thr Tyr Gly Lys Leu Thr
                325                 330                 335

Leu Lys Leu Ile Cys Thr Thr Gly Lys Leu Pro Val Pro Trp Pro Thr
                340                 345                 350

Leu Val Thr Thr Leu Gly Tyr Gly Leu Lys Cys Phe Ala Arg Tyr Pro
                355                 360                 365

Asp His Met Lys Gln His Asp Phe Phe Lys Ser Ala Met Pro Glu Gly
                370                 375                 380

Tyr Val Gln Glu Arg Thr Ile Phe Phe Lys Asp Asp Gly Asn Tyr Lys
385                 390                 395                 400

Thr Arg Ala Glu Val Lys Phe Glu Gly Asp Thr Leu Val Asn Arg Ile
                405                 410                 415

Glu Leu Lys Gly Ile Gly Phe Lys Glu Asp Gly Asn Ile Leu Gly His
                420                 425                 430

Lys Leu Glu Tyr Asn Leu Ala Gly Leu Thr Arg Leu Ser Phe Ala Ile
                435                 440                 445

Leu Asn Pro Lys Trp Arg Glu Glu Met Met Gly
450                 455
```

<210> SEQ ID NO 141
<211> LENGTH: 458
<212> TYPE: PRT
<213> ORGANISM: artificial sequence
<220> FEATURE:
<223> OTHER INFORMATION: Synthetic fluorescent sensor, mutant

<400> SEQUENCE: 141

```
Met Lys Val Pro Glu Ala Ala Ile Ser Arg Leu Ile Thr Tyr Leu Arg
1               5                   10                  15

Ile Leu Glu Glu Leu Glu Ala Gln Gly Val His Arg Thr Ser Ser Glu
            20                  25                  30

Gln Leu Gly Glu Leu Ala Gln Val Thr Ala Phe Gln Val Arg Lys Asp
        35                  40                  45

Leu Ser Tyr Phe Gly Ser Tyr Gly Thr Arg Gly Val Gly Tyr Thr Val
    50                  55                  60

Pro Val Leu Lys Arg Glu Leu Arg His Ile Leu Gly Leu Asn Arg Lys
65                  70                  75                  80

Trp Gly Leu Cys Ile Val Gly Met Gly Arg Leu Gly Ser Ala Leu Ala
                85                  90                  95

Asp Tyr Pro Gly Phe Gly Glu Ser Phe Glu Leu Arg Gly Phe Phe Asp
            100                 105                 110

Val Asp Pro Glu Lys Val Gly Arg Pro Val Arg Gly Val Ile Glu
        115                 120                 125

His Val Asp Leu Leu Pro Gln Arg Val Pro Gly Arg Ile Glu Ile Ala
    130                 135                 140

Leu Leu Thr Val Pro Arg Glu Ala Ala Gln Lys Ala Ala Asp Leu Leu
145                 150                 155                 160

Val Ala Ala Gly Ile Lys Gly Ile Leu Asn Phe Ala Pro Val Val Leu
                165                 170                 175

Glu Val Pro Lys Glu Val Ala Val Glu Asn Val Asp Phe Gly Tyr Asn
            180                 185                 190

Ser Asp Asn Val Tyr Ile Met Ala Asp Lys Gln Lys Asn Gly Ile Lys
        195                 200                 205

Ala Asn Phe Lys Ile Arg His Asn Val Glu Asp Gly Ser Val Gln Leu
    210                 215                 220

Ala Asp His Tyr Gln Gln Asn Thr Pro Ile Gly Asp Gly Pro Val Leu
225                 230                 235                 240

Leu Pro Asp Asn His Tyr Leu Ser Phe Gln Ser Val Leu Ser Lys Asp
                245                 250                 255

Pro Asn Glu Lys Arg Asp His Met Val Leu Leu Glu Phe Val Thr Ala
            260                 265                 270

Ala Gly Ile Thr Leu Gly Met Asp Glu Leu Tyr Asn Val Asp Gly Gly
        275                 280                 285

Ser Gly Gly Thr Gly Ser Lys Gly Glu Glu Leu Phe Thr Gly Val Val
    290                 295                 300

Pro Ile Leu Val Glu Leu Asp Gly Asp Val Asn Gly His Lys Phe Ser
305                 310                 315                 320

Val Ser Gly Glu Gly Glu Gly Asp Ala Thr Tyr Gly Lys Leu Thr Leu
                325                 330                 335

Lys Leu Ile Cys Thr Thr Gly Lys Leu Pro Val Pro Trp Pro Thr Leu
            340                 345                 350

Val Thr Thr Leu Gly Tyr Gly Leu Lys Cys Phe Ala Arg Tyr Pro Asp
        355                 360                 365

His Met Lys Gln His Asp Phe Phe Lys Ser Ala Met Pro Glu Gly Tyr
    370                 375                 380

Val Gln Glu Arg Thr Ile Phe Phe Lys Asp Asp Gly Asn Tyr Lys Thr
385                 390                 395                 400

Arg Ala Glu Val Lys Phe Glu Gly Asp Thr Leu Val Asn Arg Ile Glu
                405                 410                 415
```

Leu Lys Gly Ile Gly Phe Lys Glu Asp Gly Asn Ile Leu Gly His Lys
            420                 425                 430

Leu Glu Tyr Asn Leu Ala Gly Leu Thr Arg Leu Ser Phe Ala Ile Leu
            435                 440                 445

Asn Pro Lys Trp Arg Glu Glu Met Met Gly
    450                 455

<210> SEQ ID NO 142
<211> LENGTH: 457
<212> TYPE: PRT
<213> ORGANISM: artificial sequence
<220> FEATURE:
<223> OTHER INFORMATION: Synthetic fluorescent sensor, mutant

<400> SEQUENCE: 142

Met Lys Val Pro Glu Ala Ala Ile Ser Arg Leu Ile Thr Tyr Leu Arg
1               5                   10                  15

Ile Leu Glu Glu Leu Glu Ala Gln Gly Val His Arg Thr Ser Ser Glu
            20                  25                  30

Gln Leu Gly Glu Leu Ala Gln Val Thr Ala Phe Gln Val Arg Lys Asp
        35                  40                  45

Leu Ser Tyr Phe Gly Ser Tyr Gly Thr Arg Gly Val Gly Tyr Thr Val
    50                  55                  60

Pro Val Leu Lys Arg Glu Leu Arg His Ile Leu Gly Leu Asn Arg Lys
65                  70                  75                  80

Trp Gly Leu Cys Ile Val Gly Met Gly Arg Leu Gly Ser Ala Leu Ala
                85                  90                  95

Asp Tyr Pro Gly Phe Gly Glu Ser Phe Glu Leu Arg Gly Phe Phe Asp
            100                 105                 110

Val Asp Pro Glu Lys Val Gly Arg Pro Val Arg Gly Gly Val Ile Glu
        115                 120                 125

His Val Asp Leu Leu Pro Gln Arg Val Pro Gly Arg Ile Glu Ile Ala
    130                 135                 140

Leu Leu Thr Val Pro Arg Glu Ala Ala Gln Lys Ala Ala Asp Leu Leu
145                 150                 155                 160

Val Ala Ala Gly Ile Lys Gly Ile Leu Asn Phe Ala Pro Val Val Leu
                165                 170                 175

Glu Val Pro Lys Glu Val Ala Val Glu Asn Val Asp Phe Tyr Asn Ser
            180                 185                 190

Asp Asn Val Tyr Ile Met Ala Asp Lys Gln Lys Asn Gly Ile Lys Ala
        195                 200                 205

Asn Phe Lys Ile Arg His Asn Val Glu Asp Gly Ser Val Gln Leu Ala
    210                 215                 220

Asp His Tyr Gln Gln Asn Thr Pro Ile Gly Asp Gly Pro Val Leu Leu
225                 230                 235                 240

Pro Asp Asn His Tyr Leu Ser Phe Gln Ser Val Leu Ser Lys Asp Pro
                245                 250                 255

Asn Glu Lys Arg Asp His Met Val Leu Leu Glu Phe Val Thr Ala Ala
            260                 265                 270

Gly Ile Thr Leu Gly Met Asp Glu Leu Tyr Asn Val Asp Gly Gly Ser
        275                 280                 285

Gly Gly Thr Gly Ser Lys Gly Glu Glu Leu Phe Thr Gly Val Val Pro
    290                 295                 300

Ile Leu Val Glu Leu Asp Gly Asp Val Asn Gly His Lys Phe Ser Val
305                 310                 315                 320

```
Ser Gly Glu Gly Glu Gly Asp Ala Thr Tyr Gly Lys Leu Thr Leu Lys
            325                 330                 335

Leu Ile Cys Thr Thr Gly Lys Leu Pro Val Pro Trp Pro Thr Leu Val
            340                 345                 350

Thr Thr Leu Gly Tyr Gly Leu Lys Cys Phe Ala Arg Tyr Pro Asp His
            355                 360                 365

Met Lys Gln His Asp Phe Phe Lys Ser Ala Met Pro Glu Gly Tyr Val
            370                 375                 380

Gln Glu Arg Thr Ile Phe Phe Lys Asp Asp Gly Asn Tyr Lys Thr Arg
385                 390                 395                 400

Ala Glu Val Lys Phe Glu Gly Asp Thr Leu Val Asn Arg Ile Glu Leu
            405                 410                 415

Lys Gly Ile Gly Phe Lys Glu Asp Gly Asn Ile Leu Gly His Lys Leu
            420                 425                 430

Glu Tyr Asn Leu Ala Gly Leu Thr Arg Leu Ser Phe Ala Ile Leu Asn
            435                 440                 445

Pro Lys Trp Arg Glu Glu Met Met Gly
        450                 455

<210> SEQ ID NO 143
<211> LENGTH: 387
<212> TYPE: PRT
<213> ORGANISM: artificial sequence
<220> FEATURE:
<223> OTHER INFORMATION: Synthetic fluorescent sensor, mutant

<400> SEQUENCE: 143

Met Asn Arg Lys Trp Gly Leu Cys Ile Val Gly Met Gly Arg Leu Gly
1               5                   10                  15

Ser Ala Leu Ala Asp Tyr Pro Gly Phe Gly Ser Phe Glu Leu Arg
            20                  25                  30

Gly Phe Phe Asp Val Asp Pro Glu Lys Val Gly Arg Pro Val Arg Gly
            35                  40                  45

Gly Val Ile Glu His Val Asp Leu Leu Pro Gln Arg Val Pro Gly Arg
            50                  55                  60

Ile Glu Ile Ala Leu Leu Thr Val Pro Arg Glu Ala Ala Gln Lys Ala
65                  70                  75                  80

Ala Asp Leu Leu Val Ala Ala Gly Ile Lys Gly Ile Leu Asn Phe Ala
            85                  90                  95

Pro Val Val Leu Glu Val Pro Lys Glu Val Ala Val Glu Asn Val Asp
            100                 105                 110

Phe Ser Ala Gly Tyr Asn Ser Asp Asn Val Tyr Ile Met Ala Asp Lys
            115                 120                 125

Gln Lys Asn Gly Ile Lys Ala Asn Phe Lys Ile Arg His Asn Val Glu
            130                 135                 140

Asp Gly Ser Val Gln Leu Ala Asp His Tyr Gln Gln Asn Thr Pro Ile
145                 150                 155                 160

Gly Asp Gly Pro Val Leu Leu Pro Asp Asn His Tyr Leu Ser Phe Gln
            165                 170                 175

Ser Val Leu Ser Lys Asp Pro Asn Glu Lys Arg Asp His Met Val Leu
            180                 185                 190

Leu Glu Phe Val Thr Ala Ala Gly Ile Thr Leu Gly Met Asp Glu Leu
            195                 200                 205

Tyr Asn Val Asp Gly Gly Ser Gly Gly Thr Gly Ser Lys Gly Glu Glu
            210                 215                 220
```

```
Leu Phe Thr Gly Val Val Pro Ile Leu Val Glu Leu Asp Gly Asp Val
225                 230                 235                 240

Asn Gly His Lys Phe Ser Val Ser Gly Glu Gly Glu Gly Asp Ala Thr
            245                 250                 255

Tyr Gly Lys Leu Thr Leu Lys Leu Ile Cys Thr Thr Gly Lys Leu Pro
        260                 265                 270

Val Pro Trp Pro Thr Leu Val Thr Thr Leu Gly Tyr Gly Leu Lys Cys
            275                 280                 285

Phe Ala Arg Tyr Pro Asp His Met Lys Gln His Asp Phe Phe Lys Ser
290                 295                 300

Ala Met Pro Glu Gly Tyr Val Gln Glu Arg Thr Ile Phe Phe Lys Asp
305                 310                 315                 320

Asp Gly Asn Tyr Lys Thr Arg Ala Glu Val Lys Phe Glu Gly Asp Thr
            325                 330                 335

Leu Val Asn Arg Ile Glu Leu Lys Gly Ile Gly Phe Lys Glu Asp Gly
                340                 345                 350

Asn Ile Leu Gly His Lys Leu Glu Tyr Asn Gly Thr Gly Leu Ala Gly
            355                 360                 365

Leu Thr Arg Leu Ser Phe Ala Ile Leu Asn Pro Lys Trp Arg Glu Glu
    370                 375                 380

Met Met Gly
385

<210> SEQ ID NO 144
<211> LENGTH: 386
<212> TYPE: PRT
<213> ORGANISM: artificial sequence
<220> FEATURE:
<223> OTHER INFORMATION: Synthetic fluorescent sensor, mutant

<400> SEQUENCE: 144

Met Asn Arg Lys Trp Gly Leu Cys Ile Val Gly Met Gly Arg Leu Gly
1               5                   10                  15

Ser Ala Leu Ala Asp Tyr Pro Gly Phe Gly Glu Ser Phe Glu Leu Arg
            20                  25                  30

Gly Phe Phe Asp Val Asp Pro Glu Lys Val Gly Arg Pro Val Arg Gly
        35                  40                  45

Gly Val Ile Glu His Val Asp Leu Leu Pro Gln Arg Val Pro Gly Arg
    50                  55                  60

Ile Glu Ile Ala Leu Leu Thr Val Pro Arg Glu Ala Ala Gln Lys Ala
65                  70                  75                  80

Ala Asp Leu Leu Val Ala Ala Gly Ile Lys Gly Ile Leu Asn Phe Ala
                85                  90                  95

Pro Val Val Leu Glu Val Pro Lys Glu Val Ala Val Glu Asn Val Asp
            100                 105                 110

Phe Ala Gly Tyr Asn Ser Asp Asn Val Tyr Ile Met Ala Asp Lys Gln
        115                 120                 125

Lys Asn Gly Ile Lys Ala Asn Phe Lys Ile Arg His Asn Val Glu Asp
    130                 135                 140

Gly Ser Val Gln Leu Ala Asp His Tyr Gln Gln Asn Thr Pro Ile Gly
145                 150                 155                 160

Asp Gly Pro Val Leu Leu Pro Asp Asn His Tyr Leu Ser Phe Gln Ser
                165                 170                 175

Val Leu Ser Lys Asp Pro Asn Glu Lys Arg Asp His Met Val Leu Leu
            180                 185                 190
```

```
Glu Phe Val Thr Ala Ala Gly Ile Thr Leu Gly Met Asp Glu Leu Tyr
            195                 200                 205

Asn Val Asp Gly Gly Ser Gly Thr Gly Ser Lys Gly Glu Glu Leu
    210                 215                 220

Phe Thr Gly Val Val Pro Ile Leu Val Glu Leu Asp Gly Asp Val Asn
225                 230                 235                 240

Gly His Lys Phe Ser Val Ser Gly Glu Gly Glu Gly Asp Ala Thr Tyr
                245                 250                 255

Gly Lys Leu Thr Leu Lys Leu Ile Cys Thr Thr Gly Lys Leu Pro Val
                260                 265                 270

Pro Trp Pro Thr Leu Val Thr Thr Leu Gly Tyr Gly Leu Lys Cys Phe
            275                 280                 285

Ala Arg Tyr Pro Asp His Met Lys Gln His Asp Phe Phe Lys Ser Ala
            290                 295                 300

Met Pro Glu Gly Tyr Val Gln Glu Arg Thr Ile Phe Phe Lys Asp Asp
305                 310                 315                 320

Gly Asn Tyr Lys Thr Arg Ala Glu Val Lys Phe Glu Gly Asp Thr Leu
                325                 330                 335

Val Asn Arg Ile Glu Leu Lys Gly Ile Gly Phe Lys Leu Asp Gly Asn
                340                 345                 350

Ile Leu Gly His Lys Leu Glu Tyr Asn Gly Thr Gly Leu Ala Gly Leu
            355                 360                 365

Thr Arg Leu Ser Phe Ala Ile Leu Asn Pro Lys Trp Arg Glu Glu Met
            370                 375                 380

Met Gly
385

<210> SEQ ID NO 145
<211> LENGTH: 385
<212> TYPE: PRT
<213> ORGANISM: artificial sequence
<220> FEATURE:
<223> OTHER INFORMATION: Synthetic fluorescent sensor, mutant

<400> SEQUENCE: 145

Met Asn Arg Lys Trp Gly Leu Cys Ile Val Gly Met Gly Arg Leu Gly
1               5                   10                  15

Ser Ala Leu Ala Asp Tyr Pro Gly Phe Gly Glu Ser Phe Glu Leu Arg
                20                  25                  30

Gly Phe Phe Asp Val Asp Pro Glu Lys Val Gly Arg Pro Val Arg Gly
            35                  40                  45

Gly Val Ile Glu His Val Asp Leu Leu Pro Gln Arg Val Pro Gly Arg
    50                  55                  60

Ile Glu Ile Ala Leu Leu Thr Val Pro Arg Glu Ala Ala Gln Lys Ala
65                  70                  75                  80

Ala Asp Leu Leu Val Ala Ala Gly Ile Lys Gly Ile Leu Asn Phe Ala
                85                  90                  95

Pro Val Val Leu Glu Val Pro Lys Glu Val Ala Val Glu Asn Val Asp
            100                 105                 110

Phe Gly Tyr Asn Ser Asp Asn Val Tyr Ile Met Ala Asp Lys Gln Lys
            115                 120                 125

Asn Gly Ile Lys Ala Asn Phe Lys Ile Arg His Asn Val Glu Asp Gly
    130                 135                 140

Ser Val Gln Leu Ala Asp His Tyr Gln Gln Asn Thr Pro Ile Gly Asp
145                 150                 155                 160
```

```
Gly Pro Val Leu Leu Pro Asp Asn His Tyr Leu Ser Phe Gln Ser Val
                165                 170                 175

Leu Ser Lys Asp Pro Asn Glu Lys Arg Asp His Met Val Leu Leu Glu
            180                 185                 190

Phe Val Thr Ala Ala Gly Ile Thr Leu Gly Met Asp Glu Leu Tyr Asn
        195                 200                 205

Val Asp Gly Gly Ser Gly Gly Thr Gly Ser Lys Gly Glu Glu Leu Phe
    210                 215                 220

Thr Gly Val Val Pro Ile Leu Val Glu Leu Asp Gly Asp Val Asn Gly
225                 230                 235                 240

His Lys Phe Ser Val Ser Gly Glu Gly Glu Gly Asp Ala Thr Tyr Gly
                245                 250                 255

Lys Leu Thr Leu Lys Leu Ile Cys Thr Thr Gly Lys Leu Pro Val Pro
            260                 265                 270

Trp Pro Thr Leu Val Thr Thr Leu Gly Tyr Gly Leu Lys Cys Phe Ala
        275                 280                 285

Arg Tyr Pro Asp His Met Lys Gln His Asp Phe Phe Lys Ser Ala Met
    290                 295                 300

Pro Glu Gly Tyr Val Gln Glu Arg Thr Ile Phe Phe Lys Asp Asp Gly
305                 310                 315                 320

Asn Tyr Lys Thr Arg Ala Glu Val Lys Phe Glu Gly Asp Thr Leu Val
                325                 330                 335

Asn Arg Ile Glu Leu Lys Gly Ile Gly Phe Lys Glu Asp Gly Asn Ile
            340                 345                 350

Leu Gly His Lys Leu Glu Tyr Asn Gly Thr Gly Leu Ala Gly Leu Thr
        355                 360                 365

Arg Leu Ser Phe Ala Ile Leu Asn Pro Lys Trp Arg Glu Glu Met Met
    370                 375                 380

Gly
385

<210> SEQ ID NO 146
<211> LENGTH: 384
<212> TYPE: PRT
<213> ORGANISM: artificial sequence
<220> FEATURE:
<223> OTHER INFORMATION: Synthetic fluorescent sensor, mutant

<400> SEQUENCE: 146

Met Asn Arg Lys Trp Gly Leu Cys Ile Val Gly Met Gly Arg Leu Gly
1               5                   10                  15

Ser Ala Leu Ala Asp Tyr Pro Gly Phe Gly Glu Ser Phe Glu Leu Arg
            20                  25                  30

Gly Phe Phe Asp Val Asp Pro Lys Val Gly Arg Pro Val Arg Gly
        35                  40                  45

Gly Val Ile Glu His Val Asp Leu Leu Pro Gln Arg Val Pro Gly Arg
    50                  55                  60

Ile Glu Ile Ala Leu Leu Thr Val Pro Arg Glu Ala Ala Gln Lys Ala
65                  70                  75                  80

Ala Asp Leu Leu Val Ala Ala Gly Ile Lys Gly Ile Leu Asn Phe Ala
                85                  90                  95

Pro Val Val Leu Glu Val Pro Lys Glu Val Ala Val Glu Asn Val Asp
            100                 105                 110

Phe Tyr Asn Ser Asp Asn Val Tyr Ile Met Ala Asp Lys Gln Lys Asn
        115                 120                 125
```

```
Gly Ile Lys Ala Asn Phe Lys Ile Arg His Asn Val Glu Asp Gly Ser
            130                 135                 140

Val Gln Leu Ala Asp His Tyr Gln Gln Asn Thr Pro Ile Gly Asp Gly
145                 150                 155                 160

Pro Val Leu Leu Pro Asp Asn His Tyr Leu Ser Phe Gln Ser Val Leu
                165                 170                 175

Ser Lys Asp Pro Asn Glu Lys Arg Asp His Met Val Leu Leu Glu Phe
            180                 185                 190

Val Thr Ala Ala Gly Ile Thr Leu Gly Met Asp Glu Leu Tyr Asn Val
        195                 200                 205

Asp Gly Gly Ser Gly Gly Thr Gly Ser Lys Gly Glu Glu Leu Phe Thr
    210                 215                 220

Gly Val Val Pro Ile Leu Val Glu Leu Asp Gly Asp Val Asn Gly His
225                 230                 235                 240

Lys Phe Ser Val Ser Gly Glu Gly Glu Gly Asp Ala Thr Tyr Gly Lys
                245                 250                 255

Leu Thr Leu Lys Leu Ile Cys Thr Thr Gly Lys Leu Pro Val Pro Trp
            260                 265                 270

Pro Thr Leu Val Thr Thr Leu Gly Tyr Gly Leu Lys Cys Phe Ala Arg
        275                 280                 285

Tyr Pro Asp His Met Lys Gln His Asp Phe Phe Lys Ser Ala Met Pro
    290                 295                 300

Glu Gly Tyr Val Gln Glu Arg Thr Ile Phe Phe Lys Asp Asp Gly Asn
305                 310                 315                 320

Tyr Lys Thr Arg Ala Glu Val Lys Phe Glu Gly Asp Thr Leu Val Asn
                325                 330                 335

Arg Ile Glu Leu Lys Gly Ile Gly Phe Lys Glu Asp Gly Asn Ile Leu
            340                 345                 350

Gly His Lys Leu Glu Tyr Asn Gly Thr Gly Leu Ala Gly Leu Thr Arg
        355                 360                 365

Leu Ser Phe Ala Ile Leu Asn Pro Lys Trp Arg Glu Glu Met Met Gly
    370                 375                 380

<210> SEQ ID NO 147
<211> LENGTH: 386
<212> TYPE: PRT
<213> ORGANISM: artificial sequence
<220> FEATURE:
<223> OTHER INFORMATION: Synthetic fluorescent sensor, mutant

<400> SEQUENCE: 147

Met Asn Arg Lys Trp Gly Leu Cys Ile Val Gly Met Gly Arg Leu Gly
1               5                   10                  15

Ser Ala Leu Ala Asp Tyr Pro Gly Phe Gly Glu Ser Phe Glu Leu Arg
            20                  25                  30

Gly Phe Phe Asp Val Asp Pro Glu Lys Val Gly Arg Pro Val Arg Gly
        35                  40                  45

Gly Val Ile Glu His Val Asp Leu Leu Pro Gln Arg Val Pro Gly Arg
    50                  55                  60

Ile Glu Ile Ala Leu Leu Thr Val Pro Arg Glu Ala Ala Gln Lys Ala
65                  70                  75                  80

Ala Asp Leu Leu Val Ala Ala Gly Ile Lys Gly Ile Leu Asn Phe Ala
                85                  90                  95

Pro Val Val Leu Glu Val Pro Lys Glu Val Ala Val Glu Asn Val Asp
            100                 105                 110
```

```
Phe Ser Ala Gly Tyr Asn Ser Asp Asn Val Tyr Ile Met Ala Asp Lys
            115                 120                 125

Gln Lys Asn Gly Ile Lys Ala Asn Phe Lys Ile Arg His Asn Val Glu
        130                 135                 140

Asp Gly Ser Val Gln Leu Ala Asp His Tyr Gln Gln Asn Thr Pro Ile
145                 150                 155                 160

Gly Asp Gly Pro Val Leu Leu Pro Asp Asn His Tyr Leu Ser Phe Gln
                165                 170                 175

Ser Val Leu Ser Lys Asp Pro Asn Glu Lys Arg Asp His Met Val Leu
                180                 185                 190

Leu Glu Phe Val Thr Ala Ala Gly Ile Thr Leu Gly Met Asp Glu Leu
            195                 200                 205

Tyr Asn Val Asp Gly Gly Ser Gly Gly Thr Gly Ser Lys Gly Glu Glu
            210                 215                 220

Leu Phe Thr Gly Val Val Pro Ile Leu Val Glu Leu Asp Gly Asp Val
225                 230                 235                 240

Asn Gly His Lys Phe Ser Val Ser Gly Glu Gly Gly Asp Ala Thr
                245                 250                 255

Tyr Gly Lys Leu Thr Leu Lys Leu Ile Cys Thr Thr Gly Lys Leu Pro
            260                 265                 270

Val Pro Trp Pro Thr Leu Val Thr Thr Leu Gly Tyr Gly Leu Lys Cys
            275                 280                 285

Phe Ala Arg Tyr Pro Asp His Met Lys Gln His Asp Phe Phe Lys Ser
            290                 295                 300

Ala Met Pro Glu Gly Tyr Val Gln Glu Arg Thr Ile Phe Phe Lys Asp
305                 310                 315                 320

Asp Gly Asn Tyr Lys Thr Arg Ala Glu Val Lys Phe Glu Gly Asp Thr
                325                 330                 335

Leu Val Asn Arg Ile Glu Leu Lys Gly Ile Gly Phe Lys Glu Asp Gly
                340                 345                 350

Asn Ile Leu Gly His Lys Leu Glu Tyr Asn Gly Thr Leu Ala Gly Leu
            355                 360                 365

Thr Arg Leu Ser Phe Ala Ile Leu Asn Pro Lys Trp Arg Glu Glu Met
        370                 375                 380

Met Gly
385

<210> SEQ ID NO 148
<211> LENGTH: 385
<212> TYPE: PRT
<213> ORGANISM: artificial sequence
<220> FEATURE:
<223> OTHER INFORMATION: Synthetic fluorescent sensor, mutant

<400> SEQUENCE: 148

Met Asn Arg Lys Trp Gly Leu Cys Ile Val Gly Met Gly Arg Leu Gly
1               5                   10                  15

Ser Ala Leu Ala Asp Tyr Pro Gly Phe Gly Glu Ser Phe Glu Leu Arg
            20                  25                  30

Gly Phe Phe Asp Val Asp Pro Glu Lys Val Gly Arg Pro Val Arg Gly
        35                  40                  45

Gly Val Ile Glu His Val Asp Leu Leu Pro Gln Arg Val Pro Gly Arg
    50                  55                  60

Ile Glu Ile Ala Leu Leu Thr Val Pro Arg Glu Ala Ala Gln Lys Ala
65                  70                  75                  80
```

```
Ala Asp Leu Leu Val Ala Ala Gly Ile Lys Gly Ile Leu Asn Phe Ala
                85                  90                  95

Pro Val Val Leu Glu Val Pro Lys Glu Val Ala Val Glu Asn Val Asp
            100                 105                 110

Phe Ser Ala Gly Tyr Asn Ser Asp Asn Val Tyr Ile Met Ala Asp Lys
        115                 120                 125

Gln Lys Asn Gly Ile Lys Ala Asn Phe Lys Ile Arg His Asn Val Glu
    130                 135                 140

Asp Gly Ser Val Gln Leu Ala Asp His Tyr Gln Gln Asn Thr Pro Ile
145                 150                 155                 160

Gly Asp Gly Pro Val Leu Leu Pro Asp Asn His Tyr Leu Ser Phe Gln
                165                 170                 175

Ser Val Leu Ser Lys Asp Pro Asn Glu Lys Arg Asp His Met Val Leu
            180                 185                 190

Leu Glu Phe Val Thr Ala Ala Gly Ile Thr Leu Gly Met Asp Glu Leu
        195                 200                 205

Tyr Asn Val Asp Gly Gly Ser Gly Gly Thr Gly Ser Lys Gly Glu Glu
    210                 215                 220

Leu Phe Thr Gly Val Val Pro Ile Leu Val Glu Leu Asp Gly Asp Val
225                 230                 235                 240

Asn Gly His Lys Phe Ser Val Ser Gly Glu Gly Glu Gly Asp Ala Thr
                245                 250                 255

Tyr Gly Lys Leu Thr Leu Lys Leu Ile Cys Thr Thr Gly Lys Leu Pro
            260                 265                 270

Val Pro Trp Pro Thr Leu Val Thr Thr Leu Gly Tyr Gly Leu Lys Cys
        275                 280                 285

Phe Ala Arg Tyr Pro Asp His Met Lys Gln His Asp Phe Phe Lys Ser
    290                 295                 300

Ala Met Pro Glu Gly Tyr Val Gln Glu Arg Thr Ile Phe Phe Lys Asp
305                 310                 315                 320

Asp Gly Asn Tyr Lys Thr Arg Ala Glu Val Lys Phe Glu Gly Asp Thr
                325                 330                 335

Leu Val Asn Arg Ile Glu Leu Lys Gly Ile Gly Phe Lys Glu Asp Gly
            340                 345                 350

Asn Ile Leu Gly His Lys Leu Glu Tyr Asn Gly Leu Ala Gly Leu Thr
        355                 360                 365

Arg Leu Ser Phe Ala Ile Leu Asn Pro Lys Trp Arg Glu Glu Met Met
    370                 375                 380

Gly
385

<210> SEQ ID NO 149
<211> LENGTH: 384
<212> TYPE: PRT
<213> ORGANISM: artificial sequence
<220> FEATURE:
<223> OTHER INFORMATION: Synthetic fluorescent sensor, mutant

<400> SEQUENCE: 149

Met Asn Arg Lys Trp Gly Leu Cys Ile Val Met Gly Arg Leu Gly
1               5                   10                  15

Ser Ala Leu Ala Asp Tyr Pro Gly Phe Gly Glu Ser Phe Glu Leu Arg
            20                  25                  30

Gly Phe Phe Asp Val Asp Pro Glu Lys Val Gly Arg Pro Val Arg Gly
        35                  40                  45
```

```
Gly Val Ile Glu His Val Asp Leu Leu Pro Gln Arg Val Pro Gly Arg
    50                  55                  60

Ile Glu Ile Ala Leu Leu Thr Val Pro Arg Glu Ala Ala Gln Lys Ala
65                  70                  75                  80

Ala Asp Leu Leu Val Ala Ala Gly Ile Lys Gly Ile Leu Asn Phe Ala
                85                  90                  95

Pro Val Val Leu Glu Val Pro Lys Glu Val Ala Val Glu Asn Val Asp
            100                 105                 110

Phe Ser Ala Gly Tyr Asn Ser Asp Asn Val Tyr Ile Met Ala Asp Lys
        115                 120                 125

Gln Lys Asn Gly Ile Lys Ala Asn Phe Lys Ile Arg His Asn Val Glu
    130                 135                 140

Asp Gly Ser Val Gln Leu Ala Asp His Tyr Gln Gln Asn Thr Pro Ile
145                 150                 155                 160

Gly Asp Gly Pro Val Leu Leu Pro Asp Asn His Tyr Leu Ser Phe Gln
                165                 170                 175

Ser Val Leu Ser Lys Asp Pro Asn Glu Lys Arg Asp His Met Val Leu
            180                 185                 190

Leu Glu Phe Val Thr Ala Ala Gly Ile Thr Leu Gly Met Asp Glu Leu
        195                 200                 205

Tyr Asn Val Asp Gly Gly Ser Gly Gly Thr Gly Ser Lys Gly Glu Glu
    210                 215                 220

Leu Phe Thr Gly Val Val Pro Ile Leu Val Glu Leu Asp Gly Asp Val
225                 230                 235                 240

Asn Gly His Lys Phe Ser Val Ser Gly Glu Gly Glu Gly Asp Ala Thr
                245                 250                 255

Tyr Gly Lys Leu Thr Leu Lys Leu Ile Cys Thr Thr Gly Lys Leu Pro
            260                 265                 270

Val Pro Trp Pro Thr Leu Val Thr Thr Leu Gly Tyr Gly Leu Lys Cys
        275                 280                 285

Phe Ala Arg Tyr Pro Asp His Met Lys Gln His Asp Phe Phe Lys Ser
    290                 295                 300

Ala Met Pro Glu Gly Tyr Val Gln Glu Arg Thr Ile Phe Phe Lys Asp
305                 310                 315                 320

Asp Gly Asn Tyr Lys Thr Arg Ala Glu Val Lys Phe Glu Gly Asp Thr
                325                 330                 335

Leu Val Asn Arg Ile Glu Leu Lys Gly Ile Gly Phe Lys Glu Asp Gly
            340                 345                 350

Asn Ile Leu Gly His Lys Leu Glu Tyr Asn Leu Ala Gly Leu Thr Arg
        355                 360                 365

Leu Ser Phe Ala Ile Leu Asn Pro Lys Trp Arg Glu Glu Met Met Gly
    370                 375                 380

<210> SEQ ID NO 150
<211> LENGTH: 385
<212> TYPE: PRT
<213> ORGANISM: artificial sequence
<220> FEATURE:
<223> OTHER INFORMATION: Synthetic fluorescent sensor, mutant

<400> SEQUENCE: 150

Met Asn Arg Lys Trp Gly Leu Cys Ile Val Gly Met Gly Arg Leu Gly
1               5                   10                  15

Ser Ala Leu Ala Asp Tyr Pro Gly Phe Gly Glu Ser Phe Glu Leu Arg
            20                  25                  30
```

Gly Phe Phe Asp Val Asp Pro Glu Lys Val Gly Arg Pro Val Arg Gly
            35                  40                  45

Gly Val Ile Glu His Val Asp Leu Leu Pro Gln Arg Val Pro Gly Arg
 50                  55                  60

Ile Glu Ile Ala Leu Leu Thr Val Pro Arg Glu Ala Ala Gln Lys Ala
 65                  70                  75                  80

Ala Asp Leu Leu Val Ala Ala Gly Ile Lys Gly Ile Leu Asn Phe Ala
                 85                  90                  95

Pro Val Val Leu Glu Val Pro Lys Glu Val Ala Val Glu Asn Val Asp
                100                 105                 110

Phe Ala Gly Tyr Asn Ser Asp Asn Val Tyr Ile Met Ala Asp Lys Gln
            115                 120                 125

Lys Asn Gly Ile Lys Ala Asn Phe Lys Ile Arg His Asn Val Glu Asp
    130                 135                 140

Gly Ser Val Gln Leu Ala Asp His Tyr Gln Gln Asn Thr Pro Ile Gly
145                 150                 155                 160

Asp Gly Pro Val Leu Leu Pro Asp Asn His Tyr Leu Ser Phe Gln Ser
                165                 170                 175

Val Leu Ser Lys Asp Pro Asn Glu Lys Arg Asp His Met Val Leu Leu
            180                 185                 190

Glu Phe Val Thr Ala Ala Gly Ile Thr Leu Gly Met Asp Glu Leu Tyr
        195                 200                 205

Asn Val Asp Gly Gly Ser Gly Gly Thr Gly Ser Lys Gly Glu Glu Leu
    210                 215                 220

Phe Thr Gly Val Val Pro Ile Leu Val Glu Leu Asp Gly Asp Val Asn
225                 230                 235                 240

Gly His Lys Phe Ser Val Ser Gly Glu Gly Glu Gly Asp Ala Thr Tyr
                245                 250                 255

Gly Lys Leu Thr Leu Lys Leu Ile Cys Thr Thr Gly Lys Leu Pro Val
            260                 265                 270

Pro Trp Pro Thr Leu Val Thr Thr Leu Gly Tyr Gly Leu Lys Cys Phe
        275                 280                 285

Ala Arg Tyr Pro Asp His Met Lys Gln His Asp Phe Phe Lys Ser Ala
    290                 295                 300

Met Pro Glu Gly Tyr Val Gln Glu Arg Thr Ile Phe Phe Lys Asp Asp
305                 310                 315                 320

Gly Asn Tyr Lys Thr Arg Ala Glu Val Lys Phe Glu Gly Asp Thr Leu
                325                 330                 335

Val Asn Arg Ile Glu Leu Lys Gly Ile Gly Phe Lys Glu Asp Gly Asn
            340                 345                 350

Ile Leu Gly His Lys Leu Glu Tyr Asn Gly Thr Leu Ala Gly Leu Thr
        355                 360                 365

Arg Leu Ser Phe Ala Ile Leu Asn Pro Lys Trp Arg Glu Glu Met Met
    370                 375                 380

Gly
385

<210> SEQ ID NO 151
<211> LENGTH: 384
<212> TYPE: PRT
<213> ORGANISM: artificial sequence
<220> FEATURE:
<223> OTHER INFORMATION: Synthetic fluorescent sensor, mutant

<400> SEQUENCE: 151

```
Met Asn Arg Lys Trp Gly Leu Cys Ile Val Gly Met Gly Arg Leu Gly
1               5                   10                  15

Ser Ala Leu Ala Asp Tyr Pro Gly Phe Gly Glu Ser Phe Glu Leu Arg
            20                  25                  30

Gly Phe Phe Asp Val Asp Pro Glu Lys Val Gly Arg Pro Val Arg Gly
        35                  40                  45

Gly Val Ile Glu His Val Asp Leu Leu Pro Gln Arg Val Pro Gly Arg
    50                  55                  60

Ile Glu Ile Ala Leu Leu Thr Val Pro Arg Glu Ala Ala Gln Lys Ala
65                  70                  75                  80

Ala Asp Leu Leu Val Ala Ala Gly Ile Lys Gly Ile Leu Asn Phe Ala
                85                  90                  95

Pro Val Val Leu Glu Val Pro Lys Glu Val Ala Val Glu Asn Val Asp
                100                 105                 110

Phe Gly Tyr Asn Ser Asp Asn Val Tyr Ile Met Ala Asp Lys Gln Lys
            115                 120                 125

Asn Gly Ile Lys Ala Asn Phe Lys Ile Arg His Asn Val Glu Asp Gly
        130                 135                 140

Ser Val Gln Leu Ala Asp His Tyr Gln Gln Asn Thr Pro Ile Gly Asp
145                 150                 155                 160

Gly Pro Val Leu Leu Pro Asp Asn His Tyr Leu Ser Phe Gln Ser Val
                165                 170                 175

Leu Ser Lys Asp Pro Asn Glu Lys Arg Asp His Met Val Leu Leu Glu
                180                 185                 190

Phe Val Thr Ala Ala Gly Ile Thr Leu Gly Met Asp Glu Leu Tyr Asn
            195                 200                 205

Val Asp Gly Gly Ser Gly Gly Thr Gly Ser Lys Gly Glu Glu Leu Phe
210                 215                 220

Thr Gly Val Val Pro Ile Leu Val Glu Leu Asp Gly Asp Val Asn Gly
225                 230                 235                 240

His Lys Phe Ser Val Ser Gly Glu Gly Glu Gly Asp Ala Thr Tyr Gly
                245                 250                 255

Lys Leu Thr Leu Lys Leu Ile Cys Thr Thr Gly Lys Leu Pro Val Pro
                260                 265                 270

Trp Pro Thr Leu Val Thr Thr Leu Gly Tyr Gly Leu Lys Cys Phe Ala
            275                 280                 285

Arg Tyr Pro Asp His Met Lys Gln His Asp Phe Phe Lys Ser Ala Met
        290                 295                 300

Pro Glu Gly Tyr Val Gln Glu Arg Thr Ile Phe Phe Lys Asp Asp Gly
305                 310                 315                 320

Asn Tyr Lys Thr Arg Ala Glu Val Lys Phe Glu Gly Asp Thr Leu Val
                325                 330                 335

Asn Arg Ile Glu Leu Lys Gly Ile Gly Phe Lys Glu Asp Gly Asn Ile
                340                 345                 350

Leu Gly His Lys Leu Glu Tyr Asn Gly Thr Leu Ala Gly Leu Thr Arg
            355                 360                 365

Leu Ser Phe Ala Ile Leu Asn Pro Lys Trp Arg Glu Glu Met Met Gly
370                 375                 380

<210> SEQ ID NO 152
<211> LENGTH: 383
<212> TYPE: PRT
<213> ORGANISM: artificial sequence
<220> FEATURE:
```

<223> OTHER INFORMATION: Synthetic fluorescent sensor, mutant

<400> SEQUENCE: 152

```
Met Asn Arg Lys Trp Gly Leu Cys Ile Val Gly Met Gly Arg Leu Gly
1               5                   10                  15

Ser Ala Leu Ala Asp Tyr Pro Gly Phe Gly Glu Ser Phe Glu Leu Arg
            20                  25                  30

Gly Phe Phe Asp Val Asp Pro Glu Lys Val Gly Arg Pro Val Arg Gly
        35                  40                  45

Gly Val Ile Glu His Val Asp Leu Leu Pro Gln Arg Val Pro Gly Arg
    50                  55                  60

Ile Glu Ile Ala Leu Leu Thr Val Pro Arg Glu Ala Ala Gln Lys Ala
65                  70                  75                  80

Ala Asp Leu Leu Val Ala Ala Gly Ile Lys Gly Ile Leu Asn Phe Ala
                85                  90                  95

Pro Val Val Leu Glu Val Pro Lys Glu Val Ala Val Glu Asn Val Asp
            100                 105                 110

Phe Tyr Asn Ser Asp Asn Val Tyr Ile Met Ala Asp Lys Gln Lys Asn
        115                 120                 125

Gly Ile Lys Ala Asn Phe Lys Ile Arg His Asn Val Glu Asp Gly Ser
    130                 135                 140

Val Gln Leu Ala Asp His Tyr Gln Gln Asn Thr Pro Ile Gly Asp Gly
145                 150                 155                 160

Pro Val Leu Leu Pro Asp Asn His Tyr Leu Ser Phe Gln Ser Val Leu
                165                 170                 175

Ser Lys Asp Pro Asn Glu Lys Arg Asp His Met Val Leu Leu Glu Phe
            180                 185                 190

Val Thr Ala Ala Gly Ile Thr Leu Gly Met Asp Glu Leu Tyr Asn Val
        195                 200                 205

Asp Gly Gly Ser Gly Gly Thr Gly Ser Lys Gly Glu Glu Leu Phe Thr
    210                 215                 220

Gly Val Val Pro Ile Leu Val Glu Leu Asp Gly Asp Val Asn Gly His
225                 230                 235                 240

Lys Phe Ser Val Ser Gly Glu Gly Glu Gly Asp Ala Thr Tyr Gly Lys
                245                 250                 255

Leu Thr Leu Lys Leu Ile Cys Thr Thr Gly Lys Leu Pro Val Pro Trp
            260                 265                 270

Pro Thr Leu Val Thr Thr Leu Gly Tyr Gly Leu Lys Cys Phe Ala Arg
        275                 280                 285

Tyr Pro Asp His Met Lys Gln His Asp Phe Phe Lys Ser Ala Met Pro
    290                 295                 300

Glu Gly Tyr Val Gln Glu Arg Thr Ile Phe Phe Lys Asp Asp Gly Asn
305                 310                 315                 320

Tyr Lys Thr Arg Ala Glu Val Lys Phe Glu Gly Asp Thr Leu Val Asn
                325                 330                 335

Arg Ile Glu Leu Lys Gly Ile Gly Phe Lys Glu Asp Gly Asn Ile Leu
            340                 345                 350

Gly His Lys Leu Glu Tyr Asn Gly Thr Leu Ala Gly Leu Thr Arg Leu
        355                 360                 365

Ser Phe Ala Ile Leu Asn Pro Lys Trp Arg Glu Glu Met Met Gly
    370                 375                 380
```

<210> SEQ ID NO 153
<211> LENGTH: 384

```
<212> TYPE: PRT
<213> ORGANISM: artificial sequence
<220> FEATURE:
<223> OTHER INFORMATION: Synthetic fluorescent sensor, mutant

<400> SEQUENCE: 153

Met Asn Arg Lys Trp Gly Leu Cys Ile Val Gly Met Gly Arg Leu Gly
1               5                   10                  15

Ser Ala Leu Ala Asp Tyr Pro Gly Phe Gly Glu Ser Phe Glu Leu Arg
            20                  25                  30

Gly Phe Phe Asp Val Asp Pro Glu Lys Val Gly Arg Pro Val Arg Gly
        35                  40                  45

Gly Val Ile Glu His Val Asp Leu Leu Pro Gln Arg Val Pro Gly Arg
    50                  55                  60

Ile Glu Ile Ala Leu Leu Thr Val Pro Arg Glu Ala Ala Gln Lys Ala
65                  70                  75                  80

Ala Asp Leu Leu Val Ala Ala Gly Ile Lys Gly Ile Leu Asn Phe Ala
                85                  90                  95

Pro Val Val Leu Glu Val Pro Lys Glu Val Ala Val Glu Asn Val Asp
            100                 105                 110

Phe Ala Gly Tyr Asn Ser Asp Asn Val Tyr Ile Met Ala Asp Lys Gln
        115                 120                 125

Lys Asn Gly Ile Lys Ala Asn Phe Lys Ile Arg His Asn Val Glu Asp
    130                 135                 140

Gly Ser Val Gln Leu Ala Asp His Tyr Gln Gln Asn Thr Pro Ile Gly
145                 150                 155                 160

Asp Gly Pro Val Leu Leu Pro Asp Asn His Tyr Leu Ser Phe Gln Ser
                165                 170                 175

Val Leu Ser Lys Asp Pro Asn Glu Lys Arg Asp His Met Val Leu Leu
            180                 185                 190

Glu Phe Val Thr Ala Ala Gly Ile Thr Leu Gly Met Asp Glu Leu Tyr
        195                 200                 205

Asn Val Asp Gly Gly Ser Gly Gly Thr Gly Ser Lys Gly Glu Glu Leu
    210                 215                 220

Phe Thr Gly Val Val Pro Ile Leu Val Glu Leu Asp Gly Asp Val Asn
225                 230                 235                 240

Gly His Lys Phe Ser Val Ser Gly Glu Gly Glu Gly Asp Ala Thr Tyr
                245                 250                 255

Gly Lys Leu Thr Leu Lys Leu Ile Cys Thr Thr Gly Lys Leu Pro Val
            260                 265                 270

Pro Trp Pro Thr Leu Val Thr Thr Leu Gly Tyr Gly Leu Lys Cys Phe
        275                 280                 285

Ala Arg Tyr Pro Asp His Met Lys Gln His Asp Phe Phe Lys Ser Ala
    290                 295                 300

Met Pro Glu Gly Tyr Val Gln Glu Arg Thr Ile Phe Phe Lys Asp Asp
305                 310                 315                 320

Gly Asn Tyr Lys Thr Arg Ala Glu Val Lys Phe Glu Gly Asp Thr Leu
                325                 330                 335

Val Asn Arg Ile Glu Leu Lys Gly Ile Gly Phe Lys Glu Asp Gly Asn
            340                 345                 350

Ile Leu Gly His Lys Leu Glu Tyr Asn Gly Leu Ala Gly Leu Thr Arg
        355                 360                 365

Leu Ser Phe Ala Ile Leu Asn Pro Lys Trp Arg Glu Glu Met Met Gly
    370                 375                 380
```

<210> SEQ ID NO 154
<211> LENGTH: 383
<212> TYPE: PRT
<213> ORGANISM: artificial sequence
<220> FEATURE:
<223> OTHER INFORMATION: Synthetic fluorescent sensor, mutant

<400> SEQUENCE: 154

```
Met Asn Arg Lys Trp Gly Leu Cys Ile Val Gly Met Gly Arg Leu Gly
1               5                   10                  15

Ser Ala Leu Ala Asp Tyr Pro Gly Phe Gly Glu Ser Phe Glu Leu Arg
            20                  25                  30

Gly Phe Phe Asp Val Asp Pro Glu Lys Val Gly Arg Pro Val Arg Gly
        35                  40                  45

Gly Val Ile Glu His Val Asp Leu Leu Pro Gln Arg Val Pro Gly Arg
    50                  55                  60

Ile Glu Ile Ala Leu Leu Thr Val Pro Arg Glu Ala Ala Gln Lys Ala
65                  70                  75                  80

Ala Asp Leu Leu Val Ala Ala Gly Ile Lys Gly Ile Leu Asn Phe Ala
                85                  90                  95

Pro Val Val Leu Glu Val Pro Lys Glu Val Ala Val Glu Asn Val Asp
            100                 105                 110

Phe Gly Tyr Asn Ser Asp Asn Val Tyr Ile Met Ala Asp Lys Gln Lys
        115                 120                 125

Asn Gly Ile Lys Ala Asn Phe Lys Ile Arg His Asn Val Glu Asp Gly
    130                 135                 140

Ser Val Gln Leu Ala Asp His Tyr Gln Gln Asn Thr Pro Ile Gly Asp
145                 150                 155                 160

Gly Pro Val Leu Leu Pro Asp Asn His Tyr Leu Ser Phe Gln Ser Val
                165                 170                 175

Leu Ser Lys Asp Pro Asn Glu Lys Arg Asp His Met Val Leu Leu Glu
            180                 185                 190

Phe Val Thr Ala Ala Gly Ile Thr Leu Gly Met Asp Glu Leu Tyr Asn
        195                 200                 205

Val Asp Gly Gly Ser Gly Gly Thr Gly Ser Lys Gly Glu Glu Leu Phe
    210                 215                 220

Thr Gly Val Val Pro Ile Leu Val Glu Leu Asp Gly Asp Val Asn Gly
225                 230                 235                 240

His Lys Phe Ser Val Ser Gly Glu Gly Glu Gly Asp Ala Thr Tyr Gly
                245                 250                 255

Lys Leu Thr Leu Lys Leu Ile Cys Thr Thr Gly Lys Leu Pro Val Pro
            260                 265                 270

Trp Pro Thr Leu Val Thr Thr Leu Gly Tyr Gly Leu Lys Cys Phe Ala
        275                 280                 285

Arg Tyr Pro Asp His Met Lys Gln His Asp Phe Phe Lys Ser Ala Met
    290                 295                 300

Pro Glu Gly Tyr Val Gln Glu Arg Thr Ile Phe Phe Lys Asp Asp Gly
305                 310                 315                 320

Asn Tyr Lys Thr Arg Ala Glu Val Lys Phe Glu Gly Asp Thr Leu Val
                325                 330                 335

Asn Arg Ile Glu Leu Lys Gly Ile Gly Phe Lys Glu Asp Gly Asn Ile
            340                 345                 350

Leu Gly His Lys Leu Glu Tyr Asn Gly Leu Ala Gly Leu Thr Arg Leu
        355                 360                 365
```

```
Ser Phe Ala Ile Leu Asn Pro Lys Trp Arg Glu Glu Met Met Gly
        370                 375                 380
```

<210> SEQ ID NO 155
<211> LENGTH: 382
<212> TYPE: PRT
<213> ORGANISM: artificial sequence
<220> FEATURE:
<223> OTHER INFORMATION: Synthetic fluorescent sensor, mutant

<400> SEQUENCE: 155

```
Met Asn Arg Lys Trp Gly Leu Cys Ile Val Gly Met Gly Arg Leu Gly
  1               5                  10                  15

Ser Ala Leu Ala Asp Tyr Pro Gly Phe Gly Glu Ser Phe Glu Leu Arg
             20                  25                  30

Gly Phe Phe Asp Val Asp Pro Glu Lys Val Gly Arg Pro Val Arg Gly
         35                  40                  45

Gly Val Ile Glu His Val Asp Leu Leu Pro Gln Arg Val Pro Gly Arg
     50                  55                  60

Ile Glu Ile Ala Leu Leu Thr Val Pro Arg Glu Ala Ala Gln Lys Ala
 65                  70                  75                  80

Ala Asp Leu Leu Val Ala Ala Gly Ile Lys Gly Ile Leu Asn Phe Ala
                 85                  90                  95

Pro Val Val Leu Glu Val Pro Lys Glu Val Ala Val Glu Asn Val Asp
            100                 105                 110

Phe Tyr Asn Ser Asp Asn Val Tyr Ile Met Ala Asp Lys Gln Lys Asn
        115                 120                 125

Gly Ile Lys Ala Asn Phe Lys Ile Arg His Asn Val Glu Asp Gly Ser
    130                 135                 140

Val Gln Leu Ala Asp His Tyr Gln Gln Asn Thr Pro Ile Gly Asp Gly
145                 150                 155                 160

Pro Val Leu Leu Pro Asp Asn His Tyr Leu Ser Phe Gln Ser Val Leu
                165                 170                 175

Ser Lys Asp Pro Asn Glu Lys Arg Asp His Met Val Leu Leu Glu Phe
            180                 185                 190

Val Thr Ala Ala Gly Ile Thr Leu Gly Met Asp Glu Leu Tyr Asn Val
        195                 200                 205

Asp Gly Gly Ser Gly Gly Thr Gly Ser Lys Gly Glu Glu Leu Phe Thr
    210                 215                 220

Gly Val Val Pro Ile Leu Val Glu Leu Asp Gly Asp Val Asn Gly His
225                 230                 235                 240

Lys Phe Ser Val Ser Gly Glu Gly Glu Gly Asp Ala Thr Tyr Gly Lys
                245                 250                 255

Leu Thr Leu Lys Leu Ile Cys Thr Thr Gly Lys Leu Pro Val Pro Trp
            260                 265                 270

Pro Thr Leu Val Thr Thr Leu Gly Tyr Gly Leu Lys Cys Phe Ala Arg
        275                 280                 285

Tyr Pro Asp His Met Lys Gln His Asp Phe Phe Lys Ser Ala Met Pro
    290                 295                 300

Glu Gly Tyr Val Gln Glu Arg Thr Ile Phe Phe Lys Asp Asp Gly Asn
305                 310                 315                 320

Tyr Lys Thr Arg Ala Glu Val Lys Phe Glu Gly Asp Thr Leu Val Asn
                325                 330                 335

Arg Ile Glu Leu Lys Gly Ile Gly Phe Lys Glu Asp Gly Asn Ile Leu
            340                 345                 350
```

```
Gly His Lys Leu Glu Tyr Asn Gly Leu Ala Gly Leu Thr Arg Leu Ser
            355                 360                 365

Phe Ala Ile Leu Asn Pro Lys Trp Arg Glu Glu Met Met Gly
        370                 375                 380

<210> SEQ ID NO 156
<211> LENGTH: 383
<212> TYPE: PRT
<213> ORGANISM: artificial sequence
<220> FEATURE:
<223> OTHER INFORMATION: Synthetic fluorescent sensor, mutant

<400> SEQUENCE: 156

Met Asn Arg Lys Trp Gly Leu Cys Ile Val Gly Met Gly Arg Leu Gly
1               5                   10                  15

Ser Ala Leu Ala Asp Tyr Pro Gly Phe Gly Glu Ser Phe Glu Leu Arg
            20                  25                  30

Gly Phe Phe Asp Val Asp Pro Glu Lys Val Gly Arg Pro Val Arg Gly
        35                  40                  45

Gly Val Ile Glu His Val Asp Leu Leu Pro Gln Arg Val Pro Gly Arg
    50                  55                  60

Ile Glu Ile Ala Leu Leu Thr Val Pro Arg Glu Ala Ala Gln Lys Ala
65                  70                  75                  80

Ala Asp Leu Leu Val Ala Ala Gly Ile Lys Gly Ile Leu Asn Phe Ala
                85                  90                  95

Pro Val Leu Glu Val Pro Lys Glu Val Ala Val Glu Asn Val Asp
            100                 105                 110

Phe Ala Gly Tyr Asn Ser Asp Asn Val Tyr Ile Met Ala Asp Lys Gln
        115                 120                 125

Lys Asn Gly Ile Lys Ala Asn Phe Lys Ile Arg His Asn Val Glu Asp
130                 135                 140

Gly Ser Val Gln Leu Ala Asp His Tyr Gln Gln Asn Thr Pro Ile Gly
145                 150                 155                 160

Asp Gly Pro Val Leu Leu Pro Asp Asn His Tyr Leu Ser Phe Gln Ser
                165                 170                 175

Val Leu Ser Lys Asp Pro Asn Glu Lys Arg Asp His Met Val Leu Leu
            180                 185                 190

Glu Phe Val Thr Ala Ala Gly Ile Thr Leu Gly Met Asp Glu Leu Tyr
        195                 200                 205

Asn Val Asp Gly Gly Ser Gly Gly Thr Gly Ser Lys Gly Glu Glu Leu
    210                 215                 220

Phe Thr Gly Val Val Pro Ile Leu Val Glu Leu Asp Gly Asp Val Asn
225                 230                 235                 240

Gly His Lys Phe Ser Val Ser Gly Glu Gly Glu Gly Asp Ala Thr Tyr
                245                 250                 255

Gly Lys Leu Thr Leu Lys Leu Ile Cys Thr Thr Gly Lys Leu Pro Val
            260                 265                 270

Pro Trp Pro Thr Leu Val Thr Thr Leu Gly Tyr Gly Leu Lys Cys Phe
        275                 280                 285

Ala Arg Tyr Pro Asp His Met Lys Gln His Asp Phe Phe Lys Ser Ala
    290                 295                 300

Met Pro Glu Gly Tyr Val Gln Glu Arg Thr Ile Phe Phe Lys Asp Asp
305                 310                 315                 320

Gly Asn Tyr Lys Thr Arg Ala Glu Val Lys Phe Glu Gly Asp Thr Leu
                325                 330                 335
```

```
Val Asn Arg Ile Glu Leu Lys Gly Ile Gly Phe Lys Glu Asp Gly Asn
            340                 345                 350

Ile Leu Gly His Lys Leu Glu Tyr Asn Leu Ala Gly Leu Thr Arg Leu
            355                 360                 365

Ser Phe Ala Ile Leu Asn Pro Lys Trp Arg Glu Glu Met Met Gly
            370                 375                 380

<210> SEQ ID NO 157
<211> LENGTH: 382
<212> TYPE: PRT
<213> ORGANISM: artificial sequence
<220> FEATURE:
<223> OTHER INFORMATION: Synthetic fluorescent sensor, mutant

<400> SEQUENCE: 157

Met Asn Arg Lys Trp Gly Leu Cys Ile Val Gly Met Gly Arg Leu Gly
1               5                   10                  15

Ser Ala Leu Ala Asp Tyr Pro Gly Phe Gly Glu Ser Phe Glu Leu Arg
            20                  25                  30

Gly Phe Phe Asp Val Asp Pro Glu Lys Val Gly Arg Pro Val Arg Gly
            35                  40                  45

Gly Val Ile Glu His Val Asp Leu Leu Pro Gln Arg Val Pro Gly Arg
        50                  55                  60

Ile Glu Ile Ala Leu Leu Thr Val Pro Arg Glu Ala Ala Gln Lys Ala
65                  70                  75                  80

Ala Asp Leu Leu Val Ala Ala Gly Ile Lys Gly Ile Leu Asn Phe Ala
            85                  90                  95

Pro Val Val Leu Glu Val Pro Lys Glu Val Ala Val Glu Asn Val Asp
            100                 105                 110

Phe Gly Tyr Asn Ser Asp Asn Val Tyr Ile Met Ala Asp Lys Gln Lys
            115                 120                 125

Asn Gly Ile Lys Ala Asn Phe Lys Ile Arg His Asn Val Glu Asp Gly
        130                 135                 140

Ser Val Gln Leu Ala Asp His Tyr Gln Gln Asn Thr Pro Ile Gly Asp
145                 150                 155                 160

Gly Pro Val Leu Leu Pro Asp Asn His Tyr Leu Ser Phe Gln Ser Val
            165                 170                 175

Leu Ser Lys Asp Pro Asn Glu Lys Arg Asp His Met Val Leu Leu Glu
            180                 185                 190

Phe Val Thr Ala Ala Gly Ile Thr Leu Gly Met Asp Glu Leu Tyr Asn
            195                 200                 205

Val Asp Gly Gly Ser Gly Gly Thr Gly Ser Lys Gly Glu Glu Leu Phe
        210                 215                 220

Thr Gly Val Val Pro Ile Leu Val Glu Leu Asp Gly Asp Val Asn Gly
225                 230                 235                 240

His Lys Phe Ser Val Ser Gly Glu Gly Glu Gly Asp Ala Thr Tyr Gly
            245                 250                 255

Lys Leu Thr Leu Lys Leu Ile Cys Thr Thr Gly Lys Leu Pro Val Pro
            260                 265                 270

Trp Pro Thr Leu Val Thr Thr Leu Gly Tyr Gly Leu Lys Cys Phe Ala
            275                 280                 285

Arg Tyr Pro Asp His Met Lys Gln His Asp Phe Phe Lys Ser Ala Met
            290                 295                 300

Pro Glu Gly Tyr Val Gln Glu Arg Thr Ile Phe Phe Lys Asp Asp Gly
305                 310                 315                 320
```

```
Asn Tyr Lys Thr Arg Ala Glu Val Lys Phe Glu Gly Asp Thr Leu Val
            325                 330                 335

Asn Arg Ile Glu Leu Lys Gly Ile Gly Phe Lys Glu Asp Gly Asn Ile
            340                 345                 350

Leu Gly His Lys Leu Glu Tyr Asn Leu Ala Gly Leu Thr Arg Leu Ser
            355                 360                 365

Phe Ala Ile Leu Asn Pro Lys Trp Arg Glu Glu Met Met Gly
            370                 375                 380
```

<210> SEQ ID NO 158
<211> LENGTH: 381
<212> TYPE: PRT
<213> ORGANISM: artificial sequence
<220> FEATURE:
<223> OTHER INFORMATION: Synthetic fluorescent sensor, mutant

<400> SEQUENCE: 158

```
Met Asn Arg Lys Trp Gly Leu Cys Ile Val Gly Met Gly Arg Leu Gly
1               5                   10                  15

Ser Ala Leu Ala Asp Tyr Pro Gly Phe Gly Glu Ser Phe Glu Leu Arg
            20                  25                  30

Gly Phe Phe Asp Val Asp Pro Glu Lys Val Gly Arg Pro Val Arg Gly
        35                  40                  45

Gly Val Ile Glu His Val Asp Leu Leu Pro Gln Arg Val Pro Gly Arg
    50                  55                  60

Ile Glu Ile Ala Leu Leu Thr Val Pro Arg Glu Ala Ala Gln Lys Ala
65                  70                  75                  80

Ala Asp Leu Leu Val Ala Ala Gly Ile Lys Gly Ile Leu Asn Phe Ala
                85                  90                  95

Pro Val Val Leu Glu Val Pro Lys Glu Val Ala Val Glu Asn Val Asp
            100                 105                 110

Phe Tyr Asn Ser Asp Asn Val Tyr Ile Met Ala Asp Lys Gln Lys Asn
        115                 120                 125

Gly Ile Lys Ala Asn Phe Lys Ile Arg His Asn Val Glu Asp Gly Ser
    130                 135                 140

Val Gln Leu Ala Asp His Tyr Gln Gln Asn Thr Pro Ile Gly Asp Gly
145                 150                 155                 160

Pro Val Leu Leu Pro Asp Asn His Tyr Leu Ser Phe Gln Ser Val Leu
                165                 170                 175

Ser Lys Asp Pro Asn Glu Lys Arg Asp His Met Val Leu Leu Glu Phe
            180                 185                 190

Val Thr Ala Ala Gly Ile Thr Leu Gly Met Asp Glu Leu Tyr Asn Val
        195                 200                 205

Asp Gly Gly Ser Gly Gly Thr Gly Ser Lys Gly Glu Glu Leu Phe Thr
    210                 215                 220

Gly Val Val Pro Ile Leu Val Glu Leu Asp Gly Asp Val Asn Gly His
225                 230                 235                 240

Lys Phe Ser Val Ser Gly Glu Gly Glu Gly Asp Ala Thr Tyr Gly Lys
                245                 250                 255

Leu Thr Leu Lys Leu Ile Cys Thr Thr Gly Lys Leu Pro Val Pro Trp
            260                 265                 270

Pro Thr Leu Val Thr Thr Leu Gly Tyr Gly Leu Lys Cys Phe Ala Arg
        275                 280                 285

Tyr Pro Asp His Met Lys Gln His Asp Phe Phe Lys Ser Ala Met Pro
    290                 295                 300
```

```
Glu Gly Tyr Val Gln Glu Arg Thr Ile Phe Phe Lys Asp Asp Gly Asn
305                 310                 315                 320

Tyr Lys Thr Arg Ala Glu Val Lys Phe Glu Gly Asp Thr Leu Val Asn
                325                 330                 335

Arg Ile Glu Leu Lys Gly Ile Gly Phe Lys Glu Asp Gly Asn Ile Leu
            340                 345                 350

Gly His Lys Leu Glu Tyr Asn Leu Ala Gly Leu Thr Arg Leu Ser Phe
        355                 360                 365

Ala Ile Leu Asn Pro Lys Trp Arg Glu Glu Met Met Gly
    370                 375                 380

<210> SEQ ID NO 159
<211> LENGTH: 629
<212> TYPE: PRT
<213> ORGANISM: artificial sequence
<220> FEATURE:
<223> OTHER INFORMATION: Synthetic fluorescent sensor, mutant

<400> SEQUENCE: 159

Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

Pro Met Asn Lys Asp Gln Ser Lys Ile Pro Gln Ala Thr Ala Lys Arg
        35                  40                  45

Leu Pro Leu Tyr Tyr Arg Phe Leu Lys Asn Leu His Ala Ser Gly Lys
    50                  55                  60

Gln Arg Val Ser Ser Ala Glu Leu Ser Asp Ala Val Lys Val Asp Ser
65                  70                  75                  80

Ala Thr Ile Arg Arg Asp Phe Ser Tyr Phe Gly Ala Leu Gly Lys Lys
                85                  90                  95

Gly Tyr Gly Tyr Asn Val Asp Tyr Leu Leu Ser Phe Phe Arg Lys Thr
            100                 105                 110

Leu Asp Gln Asp Glu Met Thr Asp Val Ile Leu Ile Gly Val Gly Asn
        115                 120                 125

Leu Gly Thr Ala Phe Leu His Tyr Asn Phe Thr Lys Asn Asn Asn Thr
    130                 135                 140

Lys Ile Ser Met Ala Phe Asp Ile Asn Glu Ser Lys Ile Gly Thr Glu
145                 150                 155                 160

Val Gly Gly Val Pro Val Tyr Asn Leu Asp Asp Leu Glu Gln His Val
                165                 170                 175

Lys Asp Glu Ser Val Ala Ile Leu Thr Val Pro Ala Val Ala Ala Gln
            180                 185                 190

Ser Ile Thr Asp Arg Leu Val Ala Leu Gly Ile Lys Gly Ile Leu Asn
        195                 200                 205

Phe Thr Pro Ala Arg Leu Asn Val Pro Glu His Ile Arg Ile His His
    210                 215                 220

Ile Asp Leu Ala Val Glu Leu Gln Ser Leu Val Tyr Phe Leu Lys His
225                 230                 235                 240

Tyr Ser Val Leu Glu Glu Ile Glu Tyr Asn Ser Asp Asn Val Tyr Ile
                245                 250                 255

Met Ala Asp Lys Gln Lys Asn Gly Ile Lys Ala Asn Phe Lys Ile Arg
            260                 265                 270

His Asn Val Glu Asp Gly Ser Val Gln Leu Ala Asp His Tyr Gln Gln
        275                 280                 285
```

-continued

```
Asn Thr Pro Ile Gly Asp Gly Pro Val Leu Leu Pro Asp Asn His Tyr
    290             295                 300
Leu Ser Phe Gln Ser Val Leu Ser Lys Asp Pro Asn Glu Lys Arg Asp
305             310                 315                 320
His Met Val Leu Leu Glu Phe Val Thr Ala Ala Gly Ile Thr Leu Gly
                325                 330                 335
Met Asp Glu Leu Tyr Asn Val Asp Gly Ser Gly Gly Thr Gly Ser
                340             345                 350
Lys Gly Glu Glu Leu Phe Thr Gly Val Val Pro Ile Leu Val Glu Leu
            355             360                 365
Asp Gly Asp Val Asn Gly His Lys Phe Ser Val Ser Gly Glu Gly Glu
    370                 375                 380
Gly Asp Ala Thr Tyr Gly Lys Leu Thr Leu Lys Leu Ile Cys Thr Thr
385                 390                 395                 400
Gly Lys Leu Pro Val Pro Trp Pro Thr Leu Val Thr Thr Leu Gly Tyr
                405                 410                 415
Gly Leu Lys Cys Phe Ala Arg Tyr Pro Asp His Met Lys Gln His Asp
                420                 425                 430
Phe Phe Lys Ser Ala Met Pro Glu Gly Tyr Val Gln Glu Arg Thr Ile
            435                 440                 445
Phe Phe Lys Asp Asp Gly Asn Tyr Lys Thr Arg Ala Glu Val Lys Phe
    450                 455                 460
Glu Gly Asp Thr Leu Val Asn Arg Ile Glu Leu Lys Gly Ile Gly Phe
465             470                 475                 480
Lys Glu Asp Gly Asn Ile Leu Gly His Lys Leu Glu Tyr Asn Gly Thr
                485                 490                 495
Met Thr Asp Val Ile Leu Ile Gly Val Gly Asn Leu Gly Thr Ala Phe
                500                 505                 510
Leu His Tyr Asn Phe Thr Lys Asn Asn Asn Thr Lys Ile Ser Met Ala
        515                 520                 525
Phe Asp Ile Asn Glu Ser Lys Ile Gly Thr Glu Val Gly Gly Val Pro
    530                 535                 540
Val Tyr Asn Leu Asp Asp Leu Glu Gln His Val Lys Asp Glu Ser Val
545                 550                 555                 560
Ala Ile Leu Thr Val Pro Ala Val Ala Ala Gln Ser Ile Thr Asp Arg
                565                 570                 575
Leu Val Ala Leu Gly Ile Lys Gly Ile Leu Asn Phe Thr Pro Ala Arg
                580             585                 590
Leu Asn Val Pro Glu His Ile Arg Ile His His Ile Asp Leu Ala Val
            595                 600                 605
Glu Leu Gln Ser Leu Val Tyr Phe Leu Lys His Tyr Ser Val Leu Glu
    610                 615                 620
Glu Ile Glu Lys Leu
625
```